(12) United States Patent
Shoichet et al.

(10) Patent No.: US 9,371,337 B2
(45) Date of Patent: Jun. 21, 2016

(54) β-LACTAMASE INHIBITORS

(71) Applicants: The Regents of the University of California, Oakland, CA (US); Universita' Degli Studi di Modena e Reggio Emilia, Modena (IT)

(72) Inventors: Brian K. Shoichet, San Francisco, CA (US); Fabio Prati, Reggio Emilia (IT); Emilia Caselli, Sassuolo (IT); Chiara Romagnoli, Modena (IT); Oliv Eidam, San Francisco, CA (US)

(73) Assignees: The Regents of the University of California, Oakland, CA (US); Universita' degli Studi di Modena e Reggio Emilia, Modena (IT)

( * ) Notice: Subject to any disclaimer, the term of this patent is extended or adjusted under 35 U.S.C. 154(b) by 0 days.

(21) Appl. No.: 14/252,347

(22) Filed: Apr. 14, 2014

(65) Prior Publication Data

US 2014/0315861 A1   Oct. 23, 2014

Related U.S. Application Data

(63) Continuation of application No. PCT/US2012/060117, filed on Oct. 12, 2012.

(60) Provisional application No. 61/547,576, filed on Oct. 14, 2011.

(51) Int. Cl.
| | |
|---|---|
| *C07F 5/02* | (2006.01) |
| *A61K 45/06* | (2006.01) |
| *A61K 31/43* | (2006.01) |
| *A61K 31/431* | (2006.01) |

(52) U.S. Cl.
CPC ............... *C07F 5/025* (2013.01); *A61K 31/43* (2013.01); *A61K 31/431* (2013.01); *A61K 45/06* (2013.01)

(58) Field of Classification Search
CPC ........ C07F 5/025; A61K 45/06; A61K 31/43; A61K 31/431
See application file for complete search history.

(56) References Cited

U.S. PATENT DOCUMENTS 7,271,186 B1   9/2007   Shoichet et al.

FOREIGN PATENT DOCUMENTS

| WO | WO-97/06172 A1 | 2/1997 | |
|---|---|---|---|
| WO | WO-99/42462 A1 | 8/1999 | |
| WO | WO-2004/018484 A1 | 3/2004 | |
| WO | WO 2010085797 A2 * | 7/2010 | ......... A61K 49/0002 |
| WO | WO-2010/130708 A1 | 11/2010 | |
| WO | WO-2010/130708 A9 | 11/2010 | |

OTHER PUBLICATIONS

Eidam et al., J. of Med. Chem. (2010), 53(21), p. 7852-63.*
Beadle, B.M. et al. (Mar. 2002). "Structural milestones in the reaction pathway of an amide hydrolase: substrate, acyl, and product complexes of cephalothin with AmpC β-lactamase," *Structure* 10(3):413-424.
Bebrone, C. et al. (Apr. 16, 2010). "Current challenges in antimicrobial chemotherapy: focus on β-lactamase inhibition," *Drugs* 70(6):651-679.
Bush, K. (Nov. 1999). "β-Lactamases of increasing clinical importance," *Curr Pharm Des* 5(11):839-845.
Caselli, E. et al. (Jan. 2001). "Energetic, structural, and antimicrobial analyses of beta-lactam side chain recognition β-lactamases," *Chem Biol* 8(1):17-31.
Drawz, S.M. et al. (Jan. 2010). "Three decades of β-lactamase inhibitors," *Clin Microbiol Rev* 23(1):160-201.
Eidam, O. et al. (Oct. 23, 2012). "Fragment-guided design of subnanomolar β-lactamase inhibitors active in vivo," *PNAS USA* 109(43):17448-17453.
Hercouet, A. et al. (2004). "Synthesis of New Boron Analogues of Cyclic Carboxylic α-Amino Acids Using Ring-Closing Metathesis Reactions," *Tetrahedron Letters* 45:8749-8751.
Jacoby, G.A. (Jan. 2009). "AmpC β-lactamases," *Clin Microbiol Rev* 22(1):161-182.
Lode, H.M. (Jul. 2008, e-published Jun. 6, 2008). "Rational antibiotic therapy and the position of ampicillin/sulbactam," *Int J Antimicrob Agents* 32(1):10-28.
Morandi, F. et al. (Jan. 22, 2003). "Nanomolar inhibitors of AmpC beta-lactamase," *J Am Chem Soc* 125(3):685-695.
Morandi, S. et al. (Feb. 1, 2008, e-published Nov. 7, 2007). "Structure-based optimization of cephalothin-analogue boronic acids as beta-lactamase inhibitors," *Bioorg Med Chem* 16(3):1195-1205.
Powers, R.A. et al. (Nov. 1999). "The complexed structure and antimicrobial activity of a non-β-lactam inhibitor of AmpC β-lactamase," *Protein Sci* 8(11):2330-2337.
Powers, R.A. et al. (Jul. 2002). "Structure-based discovery of a novel, noncovalent inhibitor of AmpC β-lactamase," *Structure* 10(7):1013-1023.
Schlapbach, A. et al. (2001). "(*E*)-α-Sulfonamidocrotylboronates as Reagents for the Stereoselective Homoaldol Synthesis," *Eur J Org Chem* 323-328.
Sheehan, J.C. et al. (1957). "The Synthesis of Substituted Penicillins and Simpler Structural Analogs. XII. 6-Benzylsulfonamidopenicillanic Acid," *J Am Chem Soc* 79:237-240.
Strynadka, N.C.J. et al. (Aug. 1996). "Structure-based design of a potent transition state analogue for TEM-1 β-lactamase," *Nature Structural Biology* 3(8):688-695.
Tan, Q. et al. (Apr. 15, 2010, e-published Feb. 19, 2010). "4,7-Dichloro benzothien-2-yl sulfonylaminomethyl boronic acid: first boronic acid-derived beta-lactamase inhibitor with class A, C, and D activity," *Bioorg Med Chem Lett* 20(8):2622-2624.
Walker, G. et al. (2003). "A Novel Preparation of 2-Naphthyl and 5-Benzo[B]thienyl Methanesulfonyl Chlorides," *Synthetic Communications* 33(4):627-632.

(Continued)

*Primary Examiner* — Yong Chu
(74) *Attorney, Agent, or Firm* — Mintz Levin Cohn Ferris Glovsky and Popeo, P.C.

(57) ABSTRACT

Disclosed herein inter alia are Boron containing compounds and methods for treating infections related to antibiotic resistant microorganisms.

13 Claims, 34 Drawing Sheets

(56) References Cited

OTHER PUBLICATIONS

Weston, G.S. et al. (Nov. 5, 1998). "Structure-based enhancement of boronic acidbased inhibitors of AmpC beta-lactamase," *J Med Chem* 41(23):4577-4586.

International Search Report mailed on Mar. 29, 2013, for PCT Application No. PCT/US2012/060117, filed Oct. 12, 2012, 4 pages.

Written Opinion mailed on Mar. 29, 2013, for PCT Application No. PCT/US2012/060117, filed Oct. 12, 2012, 4 pages.

\* cited by examiner

Scheme 1

Scheme 3

12a,b
a  X = H
b  X = COO$^t$Bu 13a,b 14a,b 15a,b

16  X = H
17  X = COOH

Compound CR190

IC$_{50}$ = 1.6 nM

K$_i$ = 200 pM

Compound CR 192

IC$_{50}$ = 0.4 nM

K$_i$ = 50 pM

β-LACTAMASE INHIBITORS

CROSS-REFERENCES TO RELATED APPLICATIONS

This application is a continuation of PCT Application No. PCT/US2012/060117, filed Oct. 12, 2012, which claims the benefit of U.S. Provisional Patent Application No. 61/547,576, filed Oct. 14, 2011, which are incorporated herein by reference in their entirety and for all purposes.

STATEMENT AS TO RIGHTS TO INVENTIONS MADE UNDER FEDERALLY SPONSORED RESEARCH AND DEVELOPMENT

This invention was made with government support under grant GM63815 awarded by the National Institutes of Health. The Government has certain rights in the invention.

BACKGROUND OF THE INVENTION

The expression of β-lactamases is the most common cause of resistance to β-lactam antibiotics (i.e. beta-lactam containing antibiotics), such as penicillins and cephalosporins. (Livermore, D. M., *Curr. Protein Pept. Sci.* 2009, 10, 397-400; Fisher, J. F. et al., *Chem. Rev.* 2005, 105, 395-424; Paterson, D. L. and Bonomo, R. A., *Clin. Microbiol. Rev.* 2005, 18, 657-686) β-Lactamases catalyze the hydrolysis of the critical β-lactam ring in β-lactam antibiotics, thereby inactivating them. (Wilke, M. S. et al., *Curr. Opin. Microbiol.* 2005, 8, 525-533) To overcome this problem, β-lactamase inhibitors, such as clavulanic acid or sulbactam, are co-administered with the primary β-lactam (FIG. 1). (Lode, H. M., *Int. J. Antimicrob. Agents* 2008, 32, 10-28; Drawz, S. M. and Bonomo, R. A., *Clin. Microbiol. Rev.* 2010, 23, 160-201) However, the active core of these inhibitors remains a β-lactam ring, enabling the rapid development of resistance. (Bebrone, C. et al., *Drugs* 2010, 70, 651-679) For example, AmpC, a class C β-lactamase expressed by many nosocomial pathogens, is not inhibited by clavulanic acid or sulbactam, leading to substantial problems in the clinic. (Bush, K., *Curr. Pharm. Des.* 1999, 5, 839-845; Jacoby, G. A., *Clin. Microbiol. Rev.* 2009, 22, 161-182)

Inhibitors of β-lactamases can be used in combination with primary β-lactam antibiotics to help overcome bacterial resistance to antibiotics. An example of one of three such now on the market is Amoxicillin/Clavulanate (Augmentin), widely used empirically to treat bacteria resistant to penicillin and first generation cephalosporins via the action of a class A β-lactamase, such as TEM-1. A liability of the β-lactamase inhibitor drug, clavulanate, is that resistant forms of TEM-1 have evolved that can hydrolyze it (IRTs such as TEM-30, for instance), and its use has promoted the spread of β-lactamases natively resistant to its actions (e.g., class C β-lactamases like AmpC, and the metalo-β-lactamases). Clavulanate affords no protection to cephalosporins clinically, and has never been combined, for instance, with the 3$^{rd}$ generation cephalosporins (e.g., ceftazidime), leaving these widely used drugs susceptible to the evolution of the extended spectrum β-lactamases (ESBLs). Provided herein are solutions to these and other problems in the art.

BRIEF SUMMARY OF THE INVENTION

In a first aspect, a compound is provided having the formula:

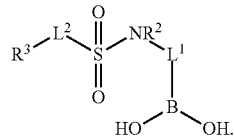

(I)

$L^1$ is a bond, substituted or unsubstituted alkylene, substituted or unsubstituted heteroalkylene, or substituted or unsubstituted arylene. $L^2$ is a bond, —NH—, —N($R^{L23a}$)—, substituted or unsubstituted alkylene or substituted or unsubstituted heteroalkylene. $R^2$ is hydrogen, substituted or unsubstituted $C_1$-$C_5$ alkyl, substituted or unsubstituted 2 to 5 membered heteroalkyl, substituted or unsubstituted $C_3$-$C_5$ cycloalkyl, substituted or unsubstituted 4 to 6 membered heterocycloalkyl, substituted or unsubstituted $C_6$-$C_{10}$ aryl, or substituted or unsubstituted 5 to 9 membered heteroaryl. $R^3$ is hydrogen, halogen, —$CX^a_3$, —CN, —$SO_2Cl$, —$SO_pR^{14}$, —$SO_qNR^{11}R^{12}$, —$NHNH_2$, —$ONR^{11}R^{12}$, —NHC=(O)$NHNH_2$, —NHC=(O)$NR^{11}R^{12}$, —N(O)$_r$, —$NR^{11}R^{12}$, —C(O)$R^{13}$, —C(O)—$OR^{13}$, —C(O)$NR^{11}R^{12}$, —$OR^{14}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{11}$, $R^{12}$, $R^{13}$, and $R^{14}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. The symbols q and r are independently 1 or 2. The symbol p is independently an integer from 0 to 4. The symbol $X^a$ is independently —Cl, —Br, —I, or —F.

In a second aspect, a compound is provided having any one of the formulas:

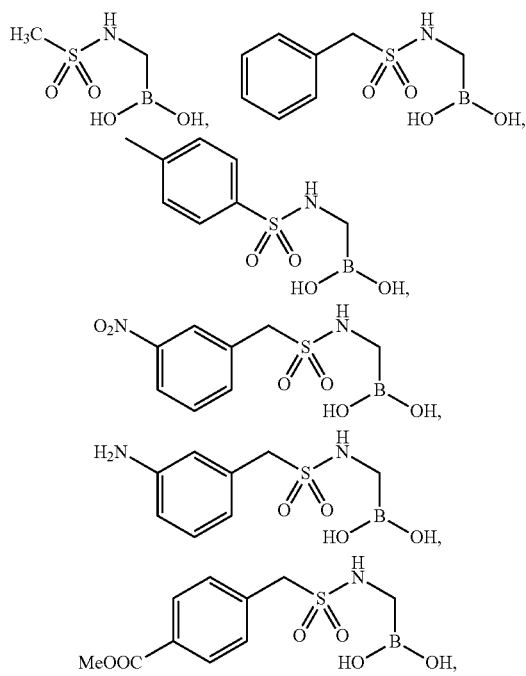

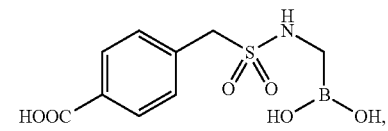
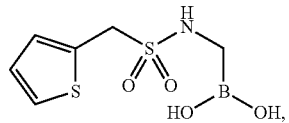
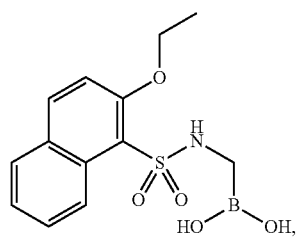
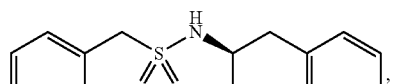
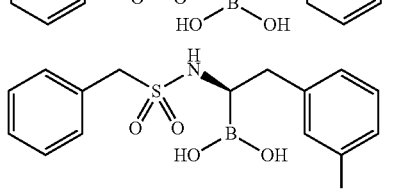
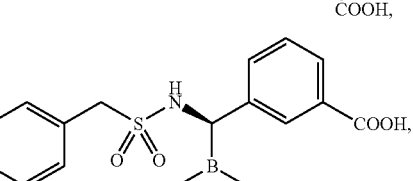
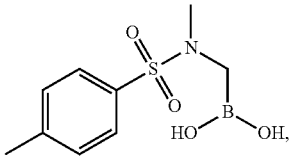
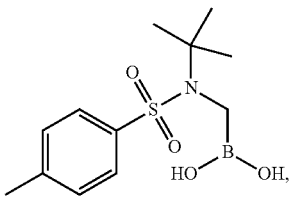
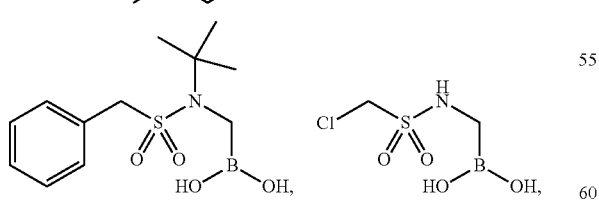
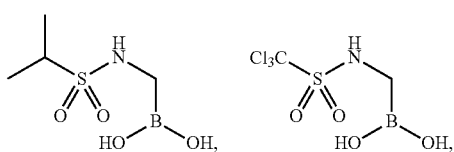
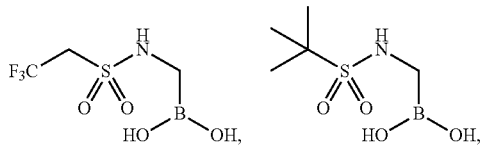
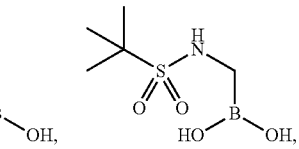
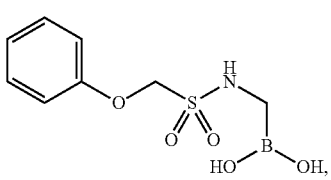
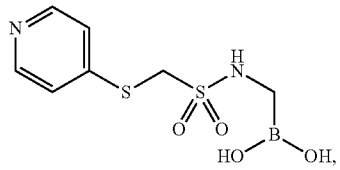
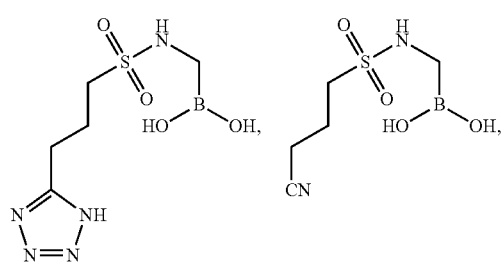
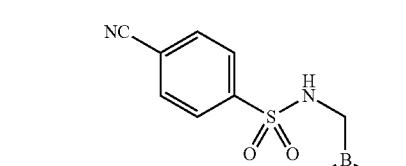
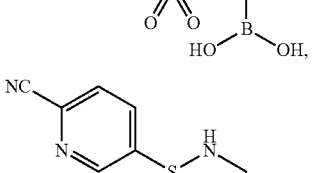
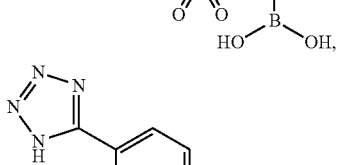
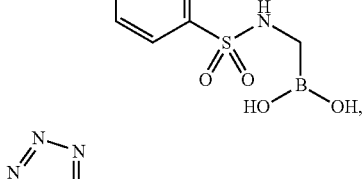
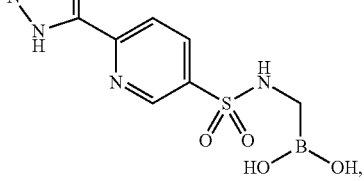

-continued
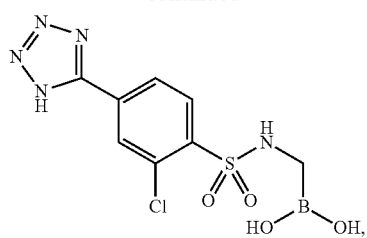
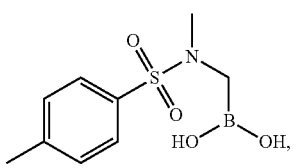
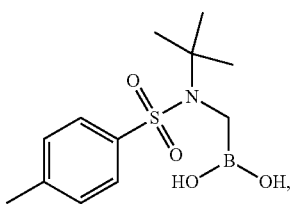
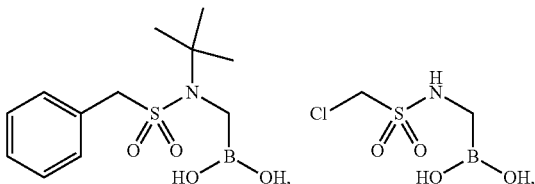
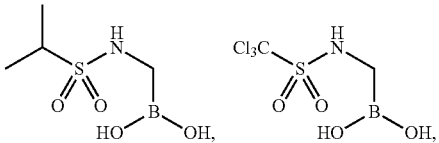
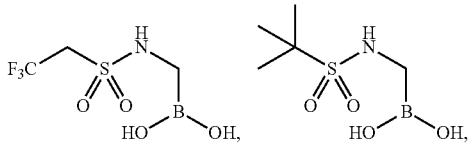
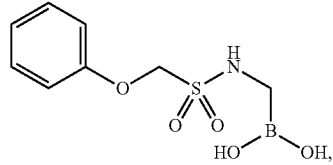
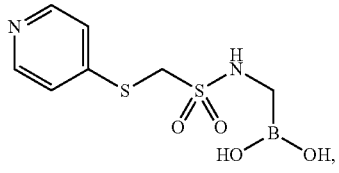
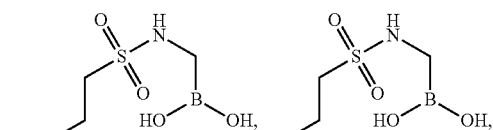
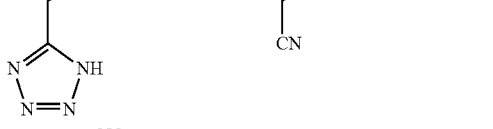
In a third aspect, a compound is provided having any one of the formulas:

-continued

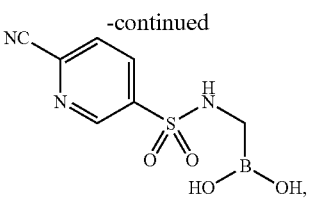
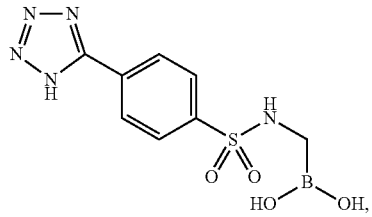
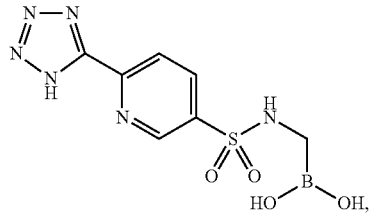
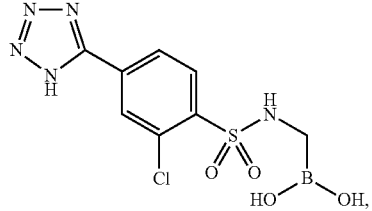
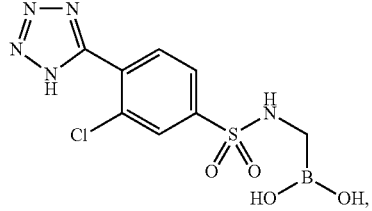
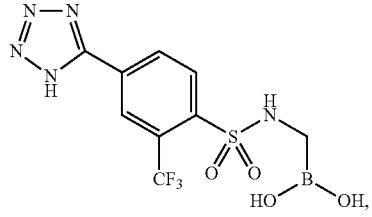
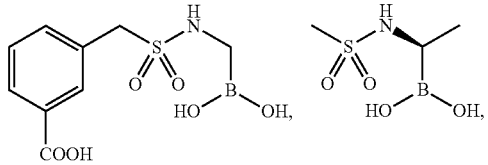
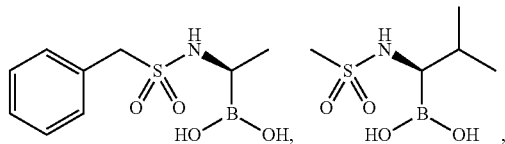
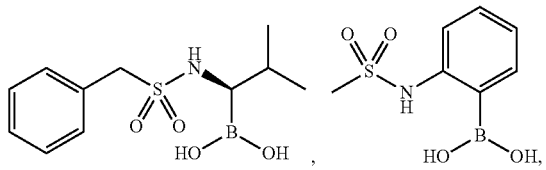

-continued

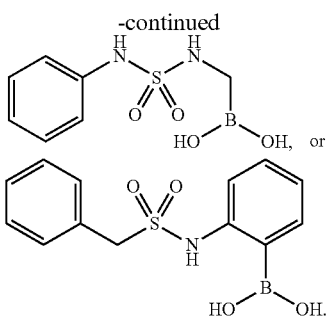
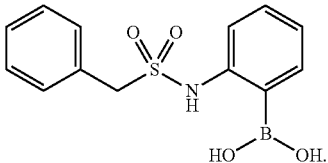

In a fourth aspect, a method of treating a disease in a patient in need of such treatment is provided. The method includes administering a therapeutically effective amount of a compound as described herein (e.g. Formula (I), (III), (V), (VII), (IX), (XI), (XIII), (XIV), (XVII), (XVIII), (XXIa), (XXIb), (XXIIIa), or (XXIIIb), including embodiments, or as described in the Example section below or as shown in Table 7).

In a fifth aspect, a method of inhibiting the growth of a bacterium in a patient is provided. The method includes administering a therapeutically effective amount of a compound as described herein (e.g. Formula (I), (III), (V), (VII), (IX), (XI), (XIII), (XIV), (XVII), (XVIII), (XXIa), (XXIb), (XXIIIa), or (XXIIIb), including embodiments, or as described in the Example section below or as shown in Table 7).

In a sixth aspect is a method of inhibiting the hydrolysis of a beta-lactam antibiotic by a bacterially expressed beta-lactamase in a patient is provided. The method includes administering an effective amount of a compound as described herein (e.g. Formula (I), (III), (V), (VII), (IX), (XI), (XIII), (XIV), (XVII), (XVIII), (XXIa), (XXIb), (XXIIIa), or (XXIIIb), including embodiments, or as described in the Example section below or as shown in Table 7).

In a seventh aspect, a method of reducing the therapeutically effective amount of an antibiotic necessary to treat a patient in need of such treatment is provided. The method includes administering an effective amount of a compound as described herein (e.g. Formula (I), (III), (V), (VII), (IX), (XI), (XIII), (XIV), (XVII), (XVIII), (XXIa), (XXIb), (XXIIIa), or (XXIIIb), including embodiments, or as described in the Example section below or as shown in Table 7).

In an eighth aspect, a kit is provided for treating a bacterial infectious disease including a compound as described herein (e.g. Formula (I), (III), (V), (VII), (IX), (XI), (XIII), (XIV), (XVII), (XVIII), (XXIa), (XXIb), (XXIIIa), or (XXIIIb), including embodiments, or as described in the Example section below or as shown in Table 7) and a beta-lactam containing antibiotic.

In a ninth aspect, a pharmaceutical composition is provided including a pharmaceutically acceptable excipient and a compound as described herein (e.g. Formula (I), (III), (V), (VII), (IX), (XI), (XIII), (XIV), (XVII), (XVIII), (XXIa), (XXIb), (XXIIIa), or (XXIIIb), including embodiments, or as described in the Example section below or as shown in Table 7).

In another aspect, a compound is provided having the formula:

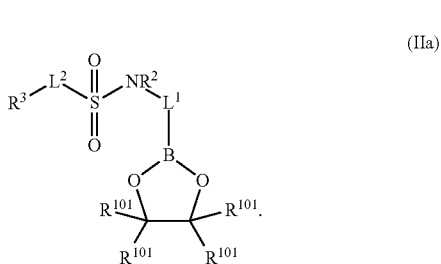

(IIa)

$L^1$, $L^2$, $R^2$, and $R^3$ are as described herein (e.g. Formula (I), (III), (V), (VII), (IX), (XI), (XIII), (XIV), (XVII), (XVIII), (XXIa), (XXIb), (XXIIIa), or (XXIIIb), including embodiments). $R^{101}$ is independently hydrogen, substituted or unsubstituted $C_1$-$C_{12}$ alkyl, substituted or unsubstituted $C_3$-$C_{12}$ cycloalkyl, or substituted or unsubstituted $C_6$-$C_{10}$ aryl. Two adjacent $R^{101}$ substituents are optionally joined to form a substituted or unsubstituted cycloalkyl, substituted or unsubstituted heterocycloalkyl, substituted or unsubstituted aryl, or substituted or unsubstituted heteroaryl.

DETAILED DESCRIPTION OF THE INVENTION

I. Definitions

Figure 1:
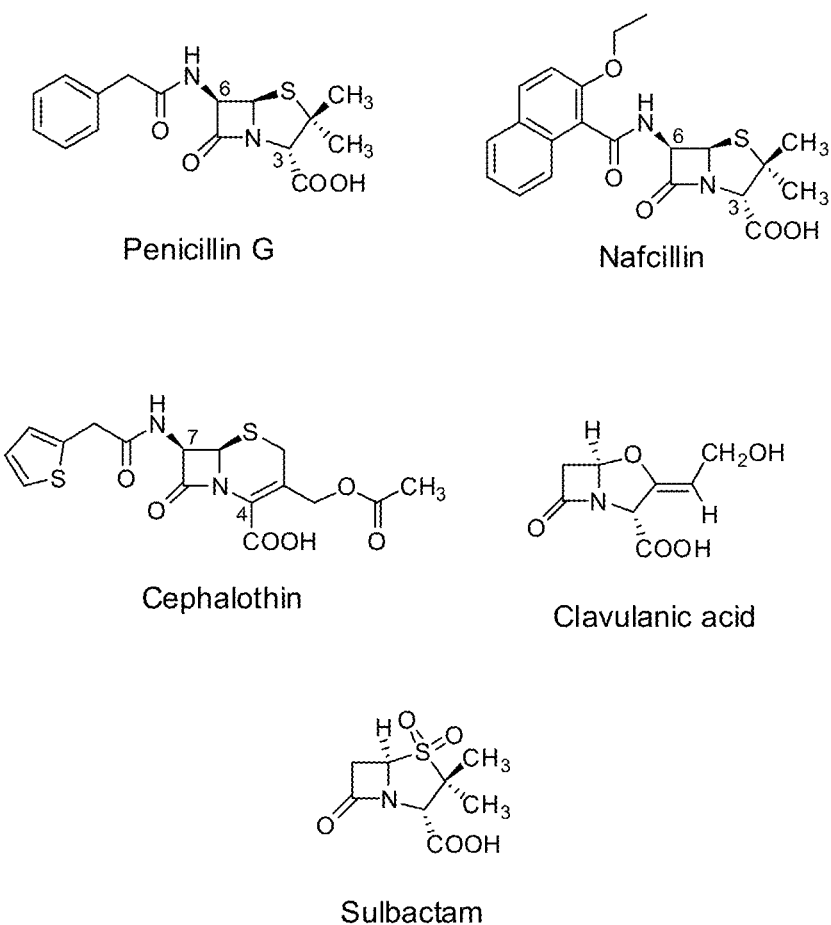
FIG. 1. Penicillin and cephalosporin antibiotics, and two clinically used β-lactamase inhibitors.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include di- and multivalent radicals, having the number of carbon atoms designated (i.e., $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom selected from the group consisting of O, N, P, Si, and S, and wherein the nitrogen and sulfur atoms may optionally be oxidized, and the nitrogen heteroatom may optionally be quaternized. The heteroatom(s) O, N, P, S, and Si may be placed at any interior position of the heteroalkyl group or at the position at which the alkyl group is attached to the remainder of the molecule. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH═CH—O—CH$_3$, —Si(CH$_3$)$_3$, —CH$_2$—CH═N—OCH$_3$, —CH═CH—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$.

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo(C$_1$-C$_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (e.g. from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, tetrazolyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively.

A fused ring heterocyloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substitutents described herein. A fused ring aryl refers to multiple rings fused together wherein at least one of the fused rings is an aryl ring. A fused ring heteroaryl refers to multiple rings fused together wherein at least one of the fused rings is a heteroaryl ring. A fused ring cycloalkyl refers to multiple rings fused together wherein at least one of the fused rings is a cycloalkyl ring. A fused ring heterocycloalkyl refers to multiple rings fused together wherein at least one of the fused rings is a heterocycloalkyl ring. Fused rings may be substituted or unsubstituted. Fused rings may be substituted with substituents selected from the possible substituents for non-fused ring groups (e.g. a fused ring aryl may have the same substituents that a non-fused aryl ring may have as substituents).

The term "oxo," as used herein, means an oxygen that is double bonded to a carbon atom.

The term "alkylsulfonyl," as used herein, means a moiety having the formula —S(O$_2$)—R', where R' is a substituted or unsubstituted alkyl group as defined above. R' may have a specified number of carbons (e.g., "C$_1$-C$_4$ alkylsulfonyl").

Each of the above terms (e.g., "alkyl," "heteroalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C=(O)NR"NR'"R"", —CN, —NO$_2$, in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound of the invention includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C=(O)NR"NR'"R"", —CN, —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R'", and R"" groups when more than one of these groups is present.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R'")$_d$—, where s and d are independently integers of from 0 to 3, and X' is —O—, —NR'—, —S—, —S(O)—, —S(O)$_2$—, or —S(O)$_2$NR'—. The substituents R, R', R", and R'" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), and silicon (Si).

A "substituent group," as used herein, means a group selected from the following moieties:

(A) —OH, —NH$_2$, —SH, —CN, —CF$_3$, —NO$_2$, Oxo, halogen, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:

(i) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected:

(a) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from: oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, each substituted or unsubstituted heterocycloalkyl is a substituted or unsubstituted 3 to 8 membered heterocycloalkyl, each substituted or unsubstituted aryl is a substituted or unsubstituted C$_6$-C$_{10}$ aryl, each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_3$-C$_7$ cycloalkyl, and each substituted or unsubstituted heterocycloalkyl is a substituted or unsubstituted 3 to 7 membered heterocycloalkyl, each substituted or unsubstituted aryl is a substituted or unsubstituted C$_6$-C$_{10}$ aryl, each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, each substituted or unsubstituted heterocycloalkyl is a substituted or unsubstituted 3 to 8 membered heterocycloalkyl, each substituted or unsubstituted aryl is a substituted or unsubstituted C$_6$-C$_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted C$_1$-C$_{20}$ alkylene, each substituted or unsubstituted heteroalkylene is a substituted or unsubstituted 2 to 20 membered heteroalkylene, each substituted or unsubstituted cycloalkylene is a substituted or unsubstituted C$_3$-C$_8$ cycloalkylene, each substituted or unsubstituted heterocycloalkylene is a substituted or unsubstituted 3 to 8 membered heterocycloalkylene, each substituted or unsubstituted arylene is a substituted or unsubstituted C$_6$-C$_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_3$-C$_7$ cycloalkyl, each substituted or unsubstituted heterocycloalkyl is a substituted or unsubstituted 3 to 7 membered heterocycloalkyl, each substituted or unsubstituted aryl is a substituted or unsubstituted C$_6$-C$_{10}$ aryl, and/or each substituted or unsubstituted heteroaryl is a substituted or unsubstituted 5 to 10 membered heteroaryl. In some embodiments, each substituted or unsubstituted alkylene is a substituted or unsubstituted C$_1$-C$_8$ alkylene, each substituted or unsubstituted heteroalkylene is a substituted or unsubstituted 2 to 8 membered heteroalkylene, each substituted or unsubstituted cycloalkylene is a substituted or unsubstituted C$_3$-C$_7$ cycloalkylene, each substituted or unsubstituted heterocycloalkylene is a substituted or unsubstituted 3 to 7 membered heterocycloalkylene, each substituted or unsubstituted arylene is a substituted or unsubstituted C$_6$-C$_{10}$ arylene, and/or each substituted or unsubstituted heteroarylene is a substituted or unsubstituted 5 to 10 membered heteroarylene. In some embodiments, the compound is a chemical species set forth in the Examples section below.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific compounds of the present invention contain both basic and acidic functionalities that allow the compounds to be converted into either base or acid addition salts.

Thus, the compounds of the present invention may exist as salts, such as with pharmaceutically acceptable acids. The present invention includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent. For example, boronic esters (e.g. pinocol esters or pinanediol esters) of the compounds described herein (e.g. Formula (I), (III), (V), (VII), (IX), (XI), (XIII), (XIV), (XVII), (XVIII), (XXIa), (XXIb), (XXIIIa), or (XXIIIb), including embodiments, or as described in the Example section below or as shown in Table 7) may be prodrugs of the compounds described herein if the boronic esters form compounds described herein (e.g. boronic acid forms of the boronic esters) when administered to a patient or when used in a method of treatment or other method described herein or when included in a kit, as described herein.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^{3}H$), iodine-125 ($^{125}I$), or carbon-14 ($^{14}C$). All isotopic variations of the compounds of the present invention, whether radioactive or not, are encompassed within the scope of the present invention.

The symbol "∿∿" denotes the point of attachment of a chemical moiety to the remainder of a molecule or chemical formula.

It should be noted that throughout the application that alternatives are written in Markush groups, for example, each substituent position in a compound that contains more than one possible substituent. It is specifically contemplated that each member of the Markush group should be considered separately, thereby comprising another embodiment, and the Markush group is not to be read as a single unit.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487-493 (1991) and Houghton et al., *Nature* 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication WO 93/20242), random bio-oligomers (e.g., PCT Publication No. WO 92/00091), benzodiazepines (e.g., U.S.

Pat. No. 5,288,514), diversomers such as hydantoins, benzodiazepines and dipeptides (Hobbs et al., *Proc. Nat. Acad. Sci. USA* 90:6909-6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217-9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology*, 14(3):309-314 (1996) and PCT/US96/10287), carbohydrate libraries (see, e.g., Liang et al., *Science,* 274:1520-1522 (1996) and U.S. Pat. No. 5,593,853). The methods above may be used to synthesize single molecular species or members of a chemical genus described herein.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls. Moreover, where a moiety is substituted with an R substituent, the group may be referred to as "R-substituted." Where a moiety is R-substituted, the moiety is substituted with at least one R substituent and each R substituent is optionally different. For example, where a moiety herein is $R^6$-substituted or unsubstituted alkyl, a plurality of $R^6$ substituents may be attached to the alkyl moiety wherein each $R^6$ substituent is optionally different. Where an R-substituted moiety is substituted with a plurality R substituents, each of the R-substituents may be differentiated herein using a prime symbol (') such as R', R", etc. For example, where a moiety is $R^6$-substituted or unsubstituted alkyl, and the moiety is substituted with a plurality of $R^6$ substituents, the plurality of $R^6$ substituents may be differentiated as $R^{6'}$, $R^{6''}$, $R^{6'''}$, etc. In some embodiments, the plurality of R substituents is 2. In some embodiments, the plurality of R substituents is 3. In some embodiments, the plurality of R substituents is 4. In some embodiments, the plurality of R substituents is 5. In some embodiments, the plurality of R substituents is 6. In some embodiments, the plurality of R substituents is 7. In some embodiments, the plurality of R substituents is 8. In some embodiments, the plurality of R substituents is 9. In some embodiments, the plurality of R substituents is 10. Some further examples of R groups that may be differentiated as R', R", etc. when present as a plurality of optionally different R groups are $R^1$, $R^4$, $R^5$, $R^6$, $R^7$, $R^8$, $R^9$, $R^{10}$, $R^{15}$, $R^{16}$, $R^{17}$, and $R^8$.

Description of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding to those skilled in the art thereby avoiding inherently unstable compounds.

A "boronic acid", as used herein, means a substituent with the structure —$B(OH)_2$. The term "boronic ester" is used according to its plain ordinary meaning and refers to a compound formed between a boronic acid and one or more alcohols (e.g. boronic acid pinacol ester or boronic acid pinanediol ester).

The term "cephalosporin" is used according to its plain ordinary meaning and refers to compounds that are derived from or related to 7-aminocephalosporanic acid, including modifications wherein functional groups or sidechains of the core 7-aminocephalosporanic acid group are modified or removed. The term "cephems" refers to the group of antibiotics comprising the cephalosporins and cephamycins.

The term "penicillin" is used according to its plain ordinary meaning and refers to compounds that are derived from or related to 6-aminopenicillanic acid, including modifications wherein functional groups or sidechains of the core 6-aminopenicillanic acid group are modified or removed.

The term "carbapenem" is used according to its plain ordingary meaning and refers to a class of beta lactam containing antibiotics including imipenem, meropenem, ertapenem, doripenem, panipenem, betamipron, biapenem, and tebipenem.

Cephalosporins are well known to be categorized into generations. When referring to a generation of cephalosporins herein, each generation is defined as commonly defined in the United States by medical practitioners or reference guides. "First generation cephalosporins" include Cefacetrile (cephacetrile), Cefadroxil (cefadroxyl; Duricef), Cephalexin (cephalexin; Keflex), Cefaloglycin (cephaloglycin), Cefalonium (cephalonium), Cefaloridine (cephaloradine), Cefalotin (cephalothin; Keflin), Cefapirin (cephapirin; Cefadryl), Cefatrizine, Cefazaflur, Cefazedone, Cefazolin (cephazolin; Ancef, Kefzol), Cefradine (cephradine; Velosef), Cefroxadine, Ceftezole. "Second generation cephalosporins" include Cefaclor (Ceclor, Distaclor, Keflor, Raniclor), Cefonicid (Monocid), Cefprozil (cefproxil; Cefzil), Cefuroxime (Zefu, Zinnat, Zinacef, Ceftin, Biofuroksym, Xorimax), Cefuzonam, Cefmetazole, Cefotetan, Cefoxitin. The following cephems are also sometimes grouped with second-generation cephalosporins: Carbacephems: loracarbef (Lorabid); Cephamycins: cefbuperazone, cefmetazole (Zefazone), cefminox, cefotetan (Cefotan), cefoxitin (Mefoxin). "Third generation cephalosporins" include Cefcapene, Cefdaloxime, Cefdinir (Zinir, Omnicef, Kefnir), Cefditoren, Cefetamet, Cefixime (Zifi, Suprax), Cefmenoxime, Cefodizime, Cefotaxime (Claforan), Cefovecin (Convenia), Cefpimizole, Cefpodoxime (Vantin, PECEF), Cefteram, Ceftibuten (Cedax), Ceftiofur, Ceftiolene, Ceftizoxime (Cefizox), Ceftriaxone (Rocephin), Cefoperazone (Cefobid), Ceftazidime (Fortum, Fortaz). The following cephems are also sometimes grouped with third-generation cephalosporins: Oxacephems: latamoxef (moxalactam). "Fourth generation cephalosporins" include Cefclidine, Cefepime (Maxipime), Cefluprenam, Cefoselis, Cefozopran, Cefpirome (Cefrom), Cefquinome, Oxacephems, flomoxef. "Fifth generation cephalosporins" include Ceftobiprole, Ceftaroline. Additional cephems include Cefaloram, Cefaparole, Cefcanel, Cefedrolor, Cefempidone, Cefetrizole, Cefivitril, Cefmatilen, Cefmepidium, Cefoxazole, Cefrotil, Cefsumide, Ceftioxide, Cefuracetime.

The terms "identical" or percent sequence "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site at ncbi.nlm.nih.gov/BLAST/ or the like). Such sequences are then said to be "substantially identical." This definition also refers to, or may be applied to, the compliment of a test sequence. The definition also includes sequences that have deletions and/or additions, as well as those that have substitutions. Employed algorithms can account for gaps and the like.

For sequence comparisons, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

An example of an algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. An oligomer comprising amino acid mimetics is a peptidomimetic. A peptidomimetic moiety is a monovalent peptidomimetic.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

An amino acid or nucleotide base "position" is denoted by a number that sequentially identifies each amino acid (or nucleotide base) in the reference sequence based on its position relative to the N-terminus (or 5'-end). Due to deletions, insertions, truncations, fusions, and the like that must be taken into account when determining an optimal alignment, in general the amino acid residue number in a test sequence determined by simply counting from the N-terminus will not necessarily be the same as the number of its corresponding position in the reference sequence. For example, in a case where a variant has a deletion relative to an aligned reference sequence, there will be no amino acid in the variant that corresponds to a position in the reference sequence at the site of deletion. Where there is an insertion in an aligned reference sequence, that insertion will not correspond to a numbered amino acid position in the reference sequence. In the case of truncations or fusions there can be stretches of amino acids in either the reference or aligned sequence that do not correspond to any amino acid in the corresponding sequence.

An amino acid residue in a protein "corresponds" to a given residue when it occupies the same essential structural position within the protein as the given residue. For example, a selected residue in a selected protein corresponds to Asn152 of *Escherichia coli* AmpC beta-lactamase when the selected residue occupies the same essential spatial or other structural relationship to other amino acids in the selected protein as Asn152 does with respect to the other residues in *Escherichia coli* AmpC beta-lactamase. Thus, if the selected protein is aligned for maximum homology with the *Escherichia coli* AmpC beta-lactamase protein, the position in the aligned selected protein that aligns with Asn152 is said to correspond to it. Instead of a primary sequence alignment, a three dimensional structural alignment can also be used, e.g., where the structure of the selected protein is aligned for maximum correspondence with the *Escherichia coli* AmpC beta-lactamase and the overall structures compared. In this case, an amino acid that occupies the same essential position as Asn152 in the structural model is said to correspond to the Asn152 residue.

The terms "treating" or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being, or improving the effectiveness of a method or compound administered to the patient for the purpose of treating the same disease (e.g. improving the effectiveness of an agent (e.g. antibiotic, antimicrobial, antibacterial) administered for treatment of a disease). The treatment or amelioration of symptoms can be based on objective or subjective parameters; including the results of a physical examination, neuropsychiatric exams, and/or a psychiatric evaluation. For example, the certain methods presented herein successfully treat infectious diseases by, without being limited by mechanism, decreasing the growth, survival, and/or replication of infectious agents (e.g. bacteria), decreasing the growth, survival, and/or replication of infectious agents (e.g. bacteria) resistant to one or more antibiotics (e.g. penicillins, cephalosporins, beta-lactam containing compounds, beta-lactam containing antibiotics/beta-lactam antibiotics), sensitizing infectious agents to one or more antibiotics (e.g. beta-lactam containing compounds or beta-lactam containing antibiotics/beta-lactam antibiotics), inhibiting bacterial cell wall synthesis, inhibiting beta-lactamase activity. The term "treating," and conjugations thereof, include prevention of an injury, pathology, condition, or disease.

The terms "antibiotic" and "antibacterial" are used according to their plain ordinary meaning, as would be understood by a medical professional, and refer to compounds that kill or slow the growth of bacteria. The term "antimicrobial" is used according to its plain ordinary meaning, as would be understood by a medical professional, and refers to compounds that kill or slow the growth of microbes (e.g. bacteria, viruses, fungi, certain parasites).

An "effective amount" is an amount sufficient to accomplish a stated purpose (e.g. achieve the effect for which it is administered, treat a disease, reduce enzyme activity, reduce one or more symptoms of a disease or condition, reduce the level of beta-lactamase activity, sensitize an infectious agent to a second therapeutic agent (e.g. antibiotic, beta-lactam containing compound, beta-lactam containing antibiotic/beta-lactam antibiotic, penicillin, cephalosporin). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist or compound required to decrease the activity of an enzyme (e.g. beta-lactamase) relative to the absence of the antagonist or compound. A "function disrupting amount," as used herein, refers to the amount of antagonist or compound required to disrupt the function of an enzyme or protein (e.g. beta-lactamase) relative to the absence of the antagonist or compound. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects.

"Contacting" is used in accordance with its plain ordinary meaning and refers to the process of allowing at least two distinct species (e.g. chemical compounds including biomolecules, proteins, or cells) to become sufficiently proximal to react, interact or physically touch. It should be appreciated, however, the resulting reaction product can be produced directly from a reaction between the added reagents or from an intermediate from one or more of the added reagents which can be produced in the reaction mixture.

The term "contacting" may include allowing two species to react, interact, or physically touch, wherein the two species may be a compound as described herein and a protein (e.g. beta-lactamase). In some embodiments, the protein may be an enzyme. In some embodiments, the enzyme may be a beta-lactamase. In some embodiments, the beta-lactamase may be a class A beta-lactamase). In some embodiments, the beta-lactamase may be a class B beta-lactamase). In some embodiments, the beta-lactamase may be a class C beta-lactamase). In some embodiments, the beta-lactamase may be a class D beta-lactamase). In some embodiments contacting includes allowing a compound described herein to interact with a protein or enzyme that promotes the hydrolysis of beta-lactam containing compounds. In some embodiments, contacting includes allowing a compound described herein to interact with an enzyme active site through specific amino acids (e.g. side chain atom or backbone atom). In some embodiments, contacting includes allowing a compound described herein to interact with an enzyme active site through specific amino acids identified through an x-ray crystal structure of the enzyme, or a similar or homologous enzyme, interacting with a substrate or compound described herein.

The terms "beta-lactamase" or "β-lactamase" or "beta-lactamase enzyme", are used interchangeably and according to their plain ordinary meaning and refer to an enzyme or enzymes that catalyze the hydrolysis of beta-lactam rings. Beta-lactamase enzymes include those enzymes identified by the Enzyme Commission number EC 3.5.2.6. Beta lactamases include the enzymes identified by the UniProt numbers P05193, AMPC_CITFR; P00811, AMPC_ECOLI; P05364, AMPC_ENTCL; Q48743, AMPC_LYSLA; P94958, AMPC_MORMO; O69773, AMPC_PROST; P24735, AMPC_PSEAE; P85302, AMPC_PSEFL; O05465, AMPC_PSYIM; P18539, AMPC_SERMA; P45460, AMPC_YEREN; Q9S424, BLA13_KLEPN; P67920, BLA1_ACTPL; Q44056, BLA1_AERHY; P10424, BLA1_BACCE; P28018, BLA1_BACMY; P0AD63, BLA1_ECOLX; P18251, BLA1_ENTCL; P67918, BLA1_HAEIF; P0AD64, BLA1_KLEPN; Q59514, BLA1_MORCA; P67919, BLA1_PASHA; P52700, BLA1_STEMA; Q03680, BLA1_STRCI; Q9S169, BLA24_ECOLX; Q9AHN9, BLA29_KLEPN; P10425, BLA2_BAC17; P04190, BLA2_BACCE; P0A9Z7, BLA2_ECOLX; P0A9Z8, BLA2_KLEPN; P0A9Z9, BLA2_KLEPO; P0AA00, BLA2_SALTY; P96465, BLA2_STEMA; P14560, BLA2_STRCI; Q93LM8, BLA34_ECOLX; P06548, BLA3_BACCE; P30896, BLA3_KLEPN; Q848S4, BLA46 KLEOX; P37323, BLA4_KLEPN; P0A3M1, BLA5 KLEPN; P0A3M2, BLA5_PSEAE; P96348, BLA6_KLEPN; O08337, BLA8_ECOLX; O08498, BLAB1_FLAME; Q9RB01, BLAB2_FLAME; Q9K303, BLAB3_FLAME; Q9XBN7, BLAB4_FLAME; Q9KJA9, BLAB5_FLAME; Q9KJB0, BLAB6_FLAME; Q9KJA8, BLAB7_FLAME; Q9KJA7, BLAB8 FLAME; P26918, BLAB_AERHY; P14488, BLAB_BACCE; P25910, BLAB_BACFR; P52664, BLAB_PROVU; P52699, BLAB_SERMA; Q44674, BLAC_BACAM; P00809, BLAC_BACCE; P00808, BLAC_BACLI; P39824, BLAC_BACSU; Q45726, BLAC_BACTU; P30898, BLAC_BACUN; P30899, BLAC_BACVU; P22390, BLAC_CITDI; P05192, BLAC_KLEPN; P0A5I7, BLAC_MYCBO; A5U493, BLAC_MYCTA; P0C5C1, BLAC_MYCTU; Q9EZQ7, BLAC_NOCAS; Q5YXD6, BLAC_NOCFA; Q06316, BLAC_NOCLA; P30897, BLAC_PROMI; P80298, BLAC_PROVU; P14171, BLAC_RHOCA; P80545, BLAC_SERFO; P00807, BLAC_STAAU; P14559, BLAC_STRAL; P10509, BLAC_STRAU; P35391, BLAC_STRBA; Q06650, BLAC_STRCE; P35392, BLAC_STRFR; P81173, BLAC_STRGR; P35393, BLAC_STRLA; Q01166, BLAC_YEREN; Q59517, BLAF_MYCFO; C7C422, BLAN1_KLEPN; P52663, BLAN_ENTCL; P52682, BLAN_SERMA; P62593, BLAT_ECOLX; Q48406, BLAT_KLEOX; P62594, BLAT_SALTI; P28585, BLC1_ECOLX; P74841, BLC2_SALTY; P37322, BLC3_PSEAE; Q51355, BLC4_PSEAE; O33807, BLC4_SALTY; O65975, BLC5_SALTY; O65976, BLC6_SALTY; P81781, BLC6_VIBCH; P37321, BLEI_PSEAE; Q848S6, BLKPC_KLEOX; Q9F663, BLKPC_KLEPN; Q00983, BLL1_PSEAE; P14489, BLO10_PSEAE; Q06778, BLO11_PSEAE; Q51574, BLO15_PSEAE; O07293, BLO18_PSEAE; Q9R976, BLO19_PSEAE; P13661, BLO1_ECOLX; P22391, BLO1_KLEOX; O84955, BLO20_PSEAE; P0A1V9, BLO2 ECOLX; P23954, BLO2_KLEOX; P0A1V8, BLO2_SALTY; Q51429, BLO3_PSEAE; Q00982, BLOS_PSEAE; P35695, BLO7_ECOLX; P0A3M4, BLO9_ENTAE; P0A3M3, BLO9_KLEPN; Q03170, BLP1_PSEAE; P16897, BLP4_PSEAE; Q47066, BLT1_ECOLX; O69395, BLT2_ECOLX; P0AEB2, DACA_ECOLI; Q9ZMM1, HCPA_HELPJ; O25001, HCPA_HELPY; O25103, HCPB_HELPY; Q9ZKB5, HCPC_HELPJ; O25728, HCPC_HELPY; Q9ZMSO, HCPD_HELPJ; O24968, HCPD_HELPY; Q9ZMJ9, HCPE_HELPJ; O25021, HCPE_HELPY; Q02940, PENA_BURM1; or P54427, YBXI_BACSU.

As defined herein, the term "inhibition", "inhibit", "inhibiting" and the like in reference to a protein-inhibitor (e.g. compound) interaction means negatively affecting (e.g. decreasing) the activity or function of the protein (e.g. decreasing the hydrolysis of beta-lactam containing antibiotics) relative to the activity or function of the protein in the absence of the inhibitor (e.g. compound). In some embodiments inhibition refers to reduction of a disease or symptoms of disease. In some embodiments, inhibition refers to a reduction in the presence of a disease-related agent (e.g. an infectious agent, infectious agent resistant to one or more antibiotics, bacterium, bacterium resistant to one or more antibiotics). Thus, inhibition includes, at least in part, partially or totally blocking stimulation, decreasing, preventing, or delaying activation, or inactivating, desensitizing, or down-regulating signal transduction or enzymatic activity or the amount of a protein. Similarly an "inhibitor" is a compound that inhibits bacterial survival, growth, or replication, e.g., by binding, partially or totally blocking, decreasing, preventing, delaying, inactivating, desensitizing, or down-regulating signal transduction or enzymatic activity (e.g. activity responsible for hydrolyzing beta-lactam containing compounds).

The term "modulator" refers to a composition that increases or decreases the level of a target molecule or the function of a target molecule (e.g. a target may be a beta-lactamase and the function in a disease state of a beta-lactamase, may be to hydrolyze therapeutic compounds such as for example beta-lactam containing antibiotics). In some embodiments, a beta-lactamase modulator is a compound that reduces the activity of a beta-lactamase. A beta-lactamase modulator may reduce an enzyme activity that results in a reduction of the amount of beta-lactamase activity and reduces the amount of hydrolyzed beta-lactam containing compounds or hydrolyzed beta-lactam containing antibiotics produced by beta-lactamases. In some embodiments, a beta-lactamase modulator is a compound that reduces the severity of one or more symptoms of a infectious disease.

"Patient" or "subject in need thereof" refers to a living organism suffering from or prone to a condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human.

"Disease" or "condition" refer to a state of being or health status of a patient or subject capable of being treated with the compounds or methods provided herein. In some embodiments, the disease is a disease related to (e.g. caused by) an infectious agent (e.g. bacteria) Examples of diseases, disorders, or conditions include, but are not limited to, infectious diseases, bacterial infectious diseases, nosocomial infections, nosocomial bacterial infections, ventilator associated pneumonias, bacterial blood stream infections, Cutaneous anthrax, Pulmonary anthrax, Gastrointestinal anthrax, Whooping cough, bacterial pneumonia, Lyme disease, Brucellosis, Acute enteritis, Community-acquired respiratory infection, Nongonococcal urethritis (NGU), Lymphogranuloma venereum (LGV), Trachoma, Inclusion conjunctivitis of the newborn (ICN), Psittacosis, Botulism, Pseudomembranous colitis, Gas gangrene, Acute food poisoning, Anaerobic cellulitis, Tetanus, Diphtheria, Nosocomial infections, Urinary tract infections (UTI), Diarrhea, Meningitis in infants, Traveller's diarrhea, Diarrhea in infants, Hemorrhagic colitis, Hemolytic-uremic syndrome, Tularemia, Bacterial meningitis, Upper respiratory tract infections, Pneumonia, bronchitis, Peptic ulcer, gastric carcinoma, gastric B-cell lymphoma, Legionnaire's Disease, Pontiac fever, Leptospirosis, Listeriosis, Leprosy (Hansen's disease), Tuberculosis, *Mycoplasma* pneumonia, Gonorrhea, Ophthalmia neonatorum, Septic arthritis, Meningococcal disease, Waterhouse-Friderichsen syndrome, *Pseudomonas* infection, Bacteremia, endocarditis, Rocky mountain spotted fever, Typhoid fever type salmonellosis (dysentery, colitis), Salmonellosis, gastroenteritis, enterocolitis, Bacillary dysentery/Shigellosis, Coagulase-positive staphylococcal infections, Impetigo, Acute infective endocarditis, Septicemia, Necrotizing pneumonia, Toxinoses, Toxic shock syndrome, Staphylococcal food poisoning, Cystitis, Meningitis, septicemia, Endometritis, Opportunistic infections, Acute bacterial pneumonia, Otitis media, sinusitis, Streptococcal pharyngitis, Scarlet fever, Rheumatic fever, erysipelas, Puerperal fever, Necrotizing fasciitis, Syphilis, Congenital syphilis, Cholera, Plague, Bubonic plague, Pneumonic plague, sepsis, Iraq war infection caused by *Acinetobacter baumannii* (i.e. Iraq war-related *Acinetobacter baumannii* infection), skin diseases or conditions, acne, *acne vulgaris*, keratosis pilaris, acne rosacea, harlequin ichthyosis, xeroderma pigmentosum, keratoses, eczema, rosacea, necrotizing fasciitis, tuberculosis, hospital-acquired pneumonia, gastroenteritis, or bacteremia.

As used herein, the term "infectious disease" refers to a disease or condition related to the presence of an organism (the agent or infectious agent) within or contacting the subject or patient. Examples include a bacterium, fungus, virus, or other microorganism. A "bacterial infectious disease" is an infectious disease wherein the organism is a bacterium. A "viral infectious disease" is an infectious disease wherein the organism is a virus. An "antibiotic resistant bacterial infectious disease" is an infectious disease wherein the organism is a bacterium resistant to one or more antibiotics effective in treating a disease caused by the non-antibiotic resistant strains of the bacterium. A "penicillin resistant bacterial infectious disease" is an antibiotic resistant bacterial infectious disease wherein the disease is not treated as effectively by a penicillin or penicillin-related compounds as a similar disease caused by a bacterial strain that is not penicillin resistant. A "cephalosporin resistant bacterial infectious disease" is an antibiotic resistant bacterial infectious disease wherein the disease is not treated as effectively by a cephalosporin or cephalosporin-related compounds as a similar disease caused by a bacterial strain that is not cephalosporin resistant. A "beta-lactam antibiotic resistant bacterial infectious disease" is a an antibiotic resistant bacterial infectious disease wherein the disease is not treated as effectively by beta-lactam containing antibiotics as a similar disease caused by a bacterial strain that is not beta-lactam antibiotic resistant. Examples of infectious diseases that may be treated with a compound or method described herein include nosocomial infections, bacteremia, Cutaneous anthrax, Pulmonary anthrax, Gastrointestinal anthrax, Whooping cough, bacterial pneumonia, bacteremia, Lyme disease, Brucellosis, Acute enteritis, Community-acquired respiratory infection, Nongonococcal urethritis (NGU), Lymphogranuloma venereum (LGV), Trachoma, Inclusion conjunctivitis of the newborn (ICN), Psittacosis, Botulism, Pseudomembranous colitis, Gas gangrene, Acute food poisoning, Anaerobic cellulitis, Tetanus, Diphtheria, Nosocomial infections, Urinary tract infections (UTI), Diarrhea, Meningitis in infants, Traveller's diarrhea, Diarrhea in infants, Hemorrhagic colitis, Hemolytic-uremic syndrome, Tularemia, Bacterial meningitis, Upper respiratory tract infections, Pneumonia, bronchitis, Peptic ulcer, gastric carcinoma, gastric B-cell lymphoma, Legionnaire's Disease, Pontiac fever, Leptospirosis, Listeriosis, Leprosy (Hansen's disease), Tuberculosis, *Mycoplasma* pneumonia, Gonorrhea, Ophthalmia neonatorum, Septic arthritis, Meningococcal disease, Waterhouse-Friderichsen syndrome, *Pseudomonas* infection, Bacteremia, endocarditis, Rocky mountain spotted fever, Typhoid fever type salmonellosis (dysentery, colitis), Salmonellosis, gastroenteritis, enterocolitis, Bacillary dysentery/Shigellosis, Coagulase-positive staphylococcal infections: Impetigo, Acute infective endocarditis, Septicemia, Necrotizing pneumonia, Toxinoses, Toxic shock syndrome, Staphylococcal food poisoning, Cystitis, Meningitis, septicemia, Endometritis, Opportunistic infections, Acute bacterial pneumonia, Otitis media, sinusitis, Streptococcal pharyngitis, Scarlet fever, Rheumatic fever, erysipelas, Puerperal fever, Necrotizing fasciitis, Syphilis, Congenital syphilis, Cholera, Plague, Bubonic plague, Pneumonic plague, Iraq war infection caused by *Acinetobacter baumannii* (i.e. Iraq war-related *Acinetobacter baumannii* infection), necrotizing fasciitis, tuberculosis, hospital-acquired pneumonia, gastroenteritis, or sepsis.

"Infectious agent" refers to an organism that is associated with (in or contacting) patients with an infectious disease but not in patients without the infectious disease and wherein contacting a patient without the infectious disease with the organism results in the patient having the infectious disease. In some embodiments, the infectious agent associated with a disease that may be treated by the compounds and/or methods described herein is a bacterium. In some embodiments, the bacteria is of a genera selected from *Stenotrophomonas, Clostridium, Acinetobacter, Bordetella, Borrelia, Brucella, Campylobacter, Chlamydia, Chlamydophila, Clostridium, Corynebacterium, Enterococcus, Escherichia, Francisella, Haemophilus, Helicobacter, Legionella, Leptospira, Listeria, Mycobacterium, Mycoplasma, Neisseria, Pseudomonas, Rickettsia, Salmonella, Shigella, Staphylococcus, Streptococcus, Treponema, Vibrio, Klebsiella, Enterobacter, Citrobacter,* or *Yersinia.* In some embodiments, the bacteria is selected from *Stenotrophomonas maltophilia, Clostridium difficile, Bacillus anthracis, Bordetella pertussis, Borrelia burgdorferi, Brucella abortus, Brucella canis, Brucella melitensis, Brucella suis, Campylobacter jejuni, Chlamydia pneumoniae, Chlamydia trachomatis, Chlamydophila psittaci, Clostridium botulinum, Clostridium difficile, Clostridium perfringens, Clostridium tetani, Corynebacterium diphtheriae, Enterococcus faecalis, Enterococcus faecium, Escherichia coli,* Enterotoxigenic *Escherichia coli* (ETEC), Enteropathogenic *E. coli, E. coli* O157:H7, *Fran-* cisella tularensis, Haemophilus influenzae, Helicobacter pylori, Legionella pneumophila, Leptospira interrogans, Listeria monocytogenes, Mycobacterium leprae, Mycobacterium tuberculosis, Mycoplasma pneumoniae, Neisseria gonorrhoeae, Neisseria meningitidis, Pseudomonas aeruginosa, Rickettsia rickettsii, Salmonella typhi, Salmonella typhimurium, Shigella sonnei, Staphylococcus aureus, Staphylococcus epidermidis, Staphylococcus saprophyticus, Streptococcus agalactiae, Streptococcus pneumoniae, Streptococcus pyogenes, Treponema pallidum, Vibrio cholerae, Klebsiella pneumoniae, Enterobacter cloacae, Citrobacter freundii, Acinetobacter baumannii, or Yersinia pestis. In some embodiments, the bacteria is gram negative. In some embodiments, the bacteria is gram positive.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine. and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

II. Compounds

In a first aspect, a compound is provided having the formula:

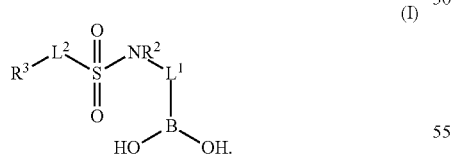
(I)

$L^1$ is a bond, substituted or unsubstituted alkylene, substituted or unsubstituted heteroalkylene, or substituted or unsubstituted arylene. $L^2$ is a bond, —NH—, —N($R^{L23a}$)—, substituted or unsubstituted alkylene or substituted or unsubstituted heteroalkylene. $R^2$ is hydrogen, halogen, substituted or unsubstituted $C_1$-$C_5$ alkyl, substituted or unsubstituted 2 to 5 membered heteroalkyl, substituted or unsubstituted $C_3$-$C_5$ cycloalkyl, substituted or unsubstituted 4 to 6 membered heterocycloalkyl, substituted or unsubstituted $C_6$-$C_{10}$ aryl, or substituted or unsubstituted 5 to 9 membered heteroaryl. $R^3$ is hydrogen, halogen, —$CX^a_3$, —CN, —$SO_2Cl$, —$SO_pR^{14}$, —$SO_qNR^{11}R^{12}$, —$NHNH_2$, —$ONR^{11}R^{12}$, —NHC=(O)$NHNH_2$, —NHC=(O)$NR^{11}R^{12}$, —N(O)$_r$, —$NR^{11}R^{12}$, —C(O)$R^{13}$, —C(O)—$OR^{13}$, —C(O)$NR^{11}R^{12}$, —$OR^{14}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{11}$, $R^{12}$, $R^{13}$, and $R^{14}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. The symbols q and r are independently 1 or 2. The symbol p is independently an integer from 0 to 4. The symbol $X^a$ is —Cl, —Br, —I, or —F. In some embodiments, if $L^1$ is unsubstituted methylene, $R^2$ is hydrogen, and $L^2$ is a bond then $R^3$ is not unsubstituted phenyl or

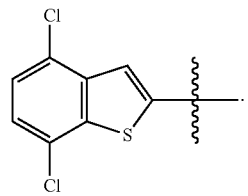 [SMILES: *c1cc2c(Cl)ccc(Cl)c2s1]

In some embodiments, the compound having Formula (I) is not

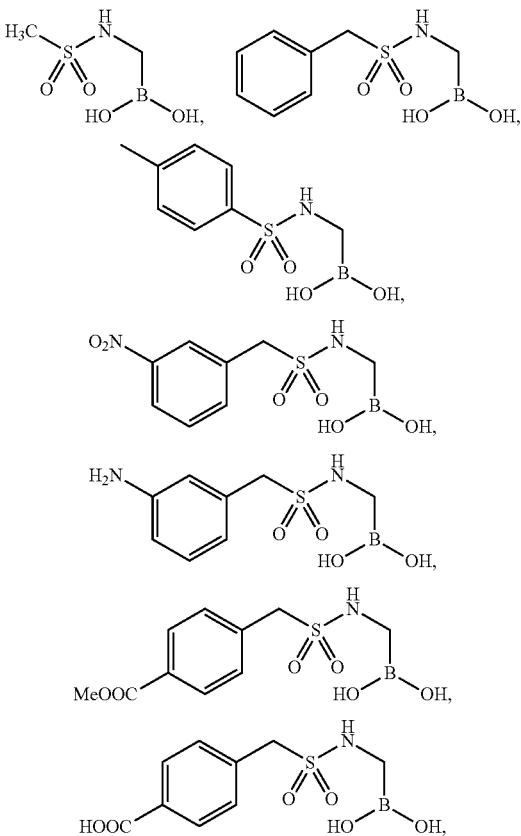

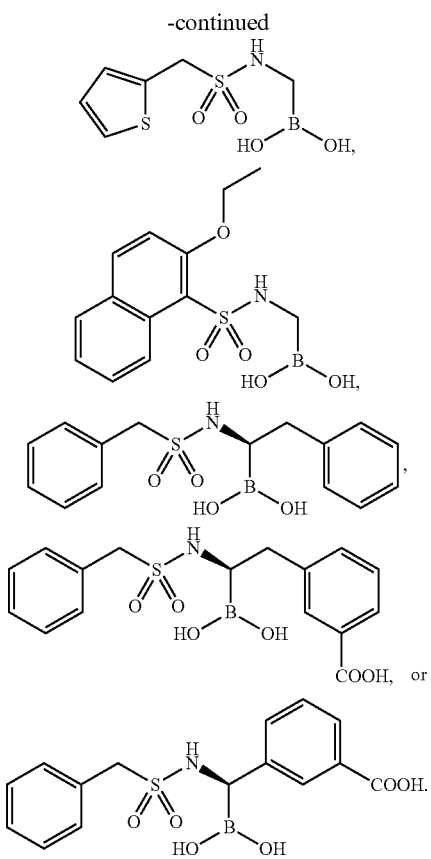

In some embodiments, the compound having formula (I) is not

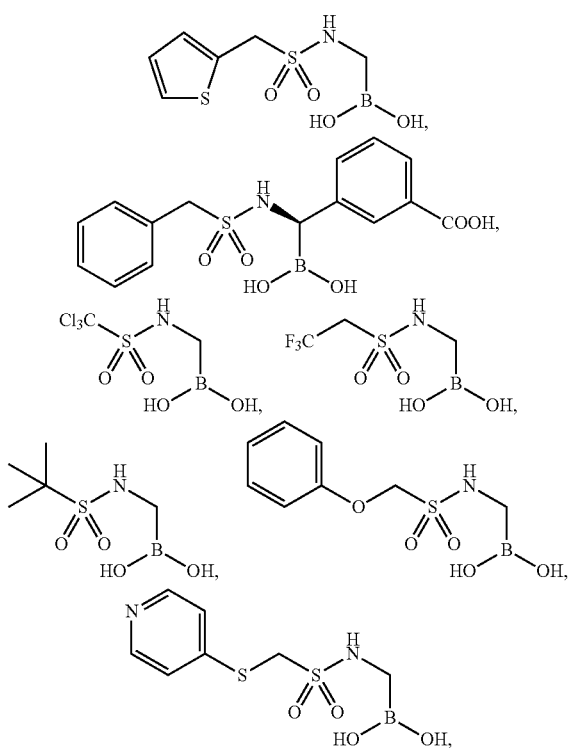

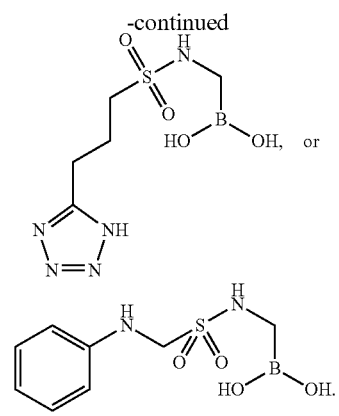

In some embodiments of the compounds described herein, wherein $L^1$ is unsubstituted methylene, $R^2$ is hydrogen, and $L^2$ is a bond, $R^3$ is not $R^{100}$ is independently hydrogen, halogen, —$CF_3$, —CN, —OH, —$NH_2$, —COOH, —$COOCH_3$, —$CONH_2$, —$NO_2$, —SH, —$SO_2Cl$, —$SO_3H$, —$SO_4H$, —$SO_2NH_2$, —$NHNH_2$, —$ONH_2$, —NHC═(O)$NHNH_2$, substituted or unsubstituted alkyl, substituted or unsubstituted 2 to 4 membered heteroalkyl, substituted or unsubstituted $C_4$-$C_8$ cycloalkyl, substituted or unsubstituted 4 to 8 membered heterocycloalkyl, substituted or unsubstituted aryl, or substituted or unsubstituted heteroaryl. The symbol aa is independently an integer from 1 to 4. In some embodiments, the symbol aa is independently an integer from 1 to 3. In some embodiments, the symbol aa is 1. In some embodiments, the symbol aa is 2. In some embodiments, the symbol aa is 3. In some embodiments, the symbol aa is 4.

In some embodiments, $R^{100}$ is halogen and the symbol aa is 2. In some embodiments, $R^{100}$ is independently halogen and the symbol aa is an integer from 1 to 4. In some embodiments, $R^{100}$ is independently —OH, —$NH_2$, —SH, or —$CF_3$ and the symbol aa is an integer from 1 to 4. In some embodiments, $R^{100}$ is independently unsubstituted $C_1$-$C_4$ alkyl and the symbol aa is an integer from 1 to 4. In some embodiments, $R^{100}$ is hydrogen.

In some embodiments of the compounds described herein, wherein $L^1$ is unsubstituted methylene, $R^2$ is hydrogen, and $L^2$ is a bond, $R^3$ is not substituted or unsubstituted benzothiophenyl. In some embodiments of the compounds described herein, wherein $L^1$ is unsubstituted methylene, $R^2$ is hydrogen, and $L^2$ is a bond, $R^3$ is not substituted or unsubstituted benzofuranyl. In some embodiments of the compounds described herein, wherein $L^1$ is unsubstituted methylene, $R^2$ is hydrogen, and $L^2$ is a bond, $R^3$ is not substituted or unsubstituted indolyl. In some embodiments of the compounds described herein, wherein $L^1$ is unsubstituted methylene, $R^2$ is hydrogen, and $L^2$ is a bond, $R^3$ is not substituted fused ring heteroaryl. In some embodiments of the compounds described herein, wherein $L^1$ is unsubstituted methylene, $R^2$ is hydrogen, and $L^2$ is a bond, $R^3$ is not unsubstituted fused ring heteroaryl. In some embodiments of the compounds described herein, wherein $L^1$ is unsubstituted methylene, $R^2$ is hydrogen, and $L^2$ is a bond, $R^3$ is not substituted heteroaryl. In some embodiments of the compounds described herein, wherein $L^1$ is unsubstituted methylene, $R^2$ is hydrogen, and $L^2$ is a bond, $R^3$ is not unsubstituted heteroaryl.

In some embodiments of the compounds described herein, wherein $L^1$ is unsubstituted methylene, $R^2$ is hydrogen, and $L^2$ is a bond, $R^3$ is not

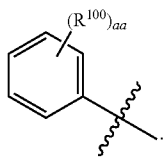

In some embodiments, $R^{100}$ is unsubstituted $C_1$-$C_4$ alkyl and the symbol aa is 1. In some embodiments, the symbol aa is 2. In some embodiments, the symbol aa is 3. In some embodiments, $R^{100}$ is unsubstituted $C_1$-$C_8$ alkyl. In some embodiments, $R^{100}$ is unsubstituted $C_1$-$C_{12}$ alkyl. In some embodiments, $R^{100}$ is unsubstituted $C_1$-$C_{20}$ alkyl. In some embodiments, $R^{100}$ is unsubstituted alkyl. In some embodiments, $R^{100}$ is independently —OH, —$NH_2$, —SH, or —$CF_3$. In some embodiments of the compounds described herein, wherein $L^1$ is unsubstituted methylene, $R^2$ is hydrogen, and $L^2$ is a bond, $R^3$ is not substituted phenyl. In some embodiments of the compounds described herein, if $L^1$ is unsubstituted methylene, $R^2$ is hydrogen, and $L^2$ is a bond, then $R^3$ is not unsubstituted phenyl.

In some embodiments of the compounds described herein, wherein $L^1$ is unsubstituted methylene, $R^2$ is hydrogen, and $L^2$ is a bond, $R^3$ is not unsubstituted $C_1$-$C_4$ alkyl. In some embodiments of the compounds described herein, wherein $L^1$ is unsubstituted methylene, $R^2$ is hydrogen, and $L^2$ is a bond, $R^3$ is not unsubstituted $C_1$-$C_8$ alkyl. In some embodiments of the compounds described herein, wherein $L^1$ is unsubstituted methylene, $R^2$ is hydrogen, and $L^2$ is a bond, $R^3$ is not unsubstituted $C_1$-$C_{12}$ alkyl. In some embodiments of the compounds described herein, wherein $L^1$ is unsubstituted methylene, $R^2$ is hydrogen, and $L^2$ is a bond, $R^3$ is not unsubstituted alkyl.

In some embodiments of the compounds described herein, wherein $L^1$ and $L^2$ are unsubstituted methylene and $R^2$ is hydrogen, $R^3$ is not

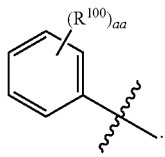

In some embodiments, $R^{100}$ is independently unsubstituted $C_1$-$C_4$ alkyl. —COOH, —$NH_2$, —$NO_2$, or —$COOCH_3$. In some embodiments, the symbol aa is 1. In some embodiments, the symbol aa is 2. In some embodiments, the symbol aa is 3. In some embodiments of the compounds described herein, wherein $L^1$ and $L^2$ are unsubstituted methylene and $R^2$ is hydrogen, $R^3$ is not substituted phenyl.

In some embodiments of the compounds described herein, wherein $L^1$ is unsubstituted methylene, $R^2$ is hydrogen, and $L^2$ is a bond, $R^3$ is not $C_1$-$C_4$ heteroalkyl substituted naphthyl. In some embodiments of the compounds described herein, wherein $L^1$ is unsubstituted methylene, $R^2$ is hydrogen, and $L^2$ is a bond, $R^3$ is not —O—($C_1$-$C_4$) alkyl substituted naphthyl. In some embodiments of the compounds described herein, wherein $L^1$ is unsubstituted methylene, $R^2$ is hydrogen, and $L^2$ is a bond, $R^3$ is not $C_1$-$C_4$ alkyl substituted naphthyl. In some embodiments of the compounds described herein, wherein $L^1$ is unsubstituted methylene, $R^2$ is hydrogen, and $L^2$ is a bond, $R^3$ is not unsubstituted naphthyl. In some embodiments of the compounds described herein, wherein $L^1$ and $L^2$ are unsubstituted methylene and $R^2$ is hydrogen, $R^3$ is not substituted thienyl. In some embodiments of the compounds described herein, wherein $L^1$ and $L^2$ are unsubstituted methylene and $R^2$ is hydrogen, $R^3$ is not unsubstituted furanyl. In some embodiments of the compounds described herein, wherein $L^1$ and $L^2$ are unsubstituted methylene and $R^2$ is hydrogen, $R^3$ is not substituted furanyl. In some embodiments of the compounds described herein, wherein $L^1$ and $L^2$ are unsubstituted methylene and $R^2$ is hydrogen, $R^3$ is not unsubstituted pyrrolyl. In some embodiments of the compounds described herein, wherein $L^1$ and $L^2$ are unsubstituted methylene and $R^2$ is hydrogen, $R^3$ is not substituted pyrrolyl. In some embodiments of the compounds described herein, wherein $L^1$ and $L^2$ are unsubstituted methylene and $R^2$ is hydrogen, $R^3$ is not unsubstituted 5 membered heteroaryl. In some embodiments of the compounds described herein, wherein $L^1$ and $L^2$ are unsubstituted methylene and $R^2$ is hydrogen, $R^3$ is not substituted 5 membered heteroaryl.

In some embodiments of the compounds described herein, wherein $L^2$ is unsubstituted methylene, $R^2$ is hydrogen, and $R^3$ is unsubstituted phenyl, $L^1$ is not

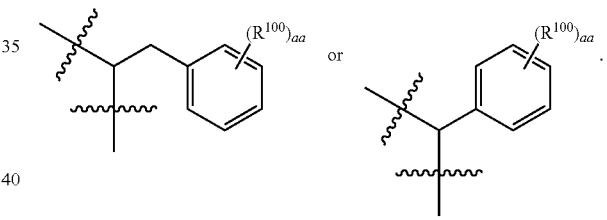

In some embodiments, $R^{100}$ is —COOH and the symbol aa is 1 to 3. In some embodiments $R^{100}$ is —$COOCH_3$. In some embodiments $R^{100}$ is unsubstituted $C_1$-$C_4$ alkyl. In some embodiments $R^{100}$ is unsubstituted 2 to 4 membered heteroalkyl. In some embodiments $R^{100}$ is substituted $C_1$-$C_4$ alkyl. In some embodiments $R^{100}$ is substituted 2 to 4 membered heteroalkyl. In some embodiments $R^{100}$ is independently —COOH, —$NH_2$, or —$NO_2$. In some embodiments the symbol aa is 1. In some embodiments, the symbol aa is 2. In some embodiments, the symbol aa is 3.

In some embodiments of the compounds described herein, wherein $L^2$ is unsubstituted methylene, $R^2$ is hydrogen, and $R^3$ is unsubstituted phenyl, $L^1$ is not

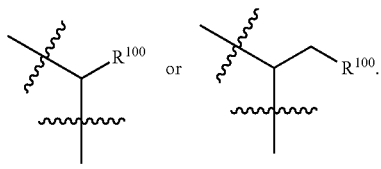

In some embodiments, $R^{100}$ is unsubstituted aryl. In some embodiments, $R^{100}$ is substituted aryl.

In some embodiments of a compound described herein (e.g. Formula (I), (III), (V), (VII), (IX), (XI), (XIII), (XIV), (XVII), (XVIII), (XXIa), (XXIb), (XXIIIa), or (XXIIIb), including embodiments), $L^1$ is unsubstituted $C_1$-$C_4$ alkylene. In some embodiments, $L^1$ is unsubstituted methylene. In some embodiments, $L^1$ is unsubstituted ethylene. In some embodiments, $L^1$ is unsubstituted phenylene. In some embodiments, $L^1$ is substituted $C_1$-$C_4$ alkylene. In some embodiments, $L^1$ is substituted methylene. In some embodiments, $L^1$ is substituted ethylene. In some embodiments, $L^1$ is substituted isopropylene. In some embodiments, $L^1$ is methylene substituted with unsubstituted $C_1$-$C_4$ alkyl. In some embodiments, $L^1$ is methylene substituted with methyl. In some embodiments, $L^1$ is methylene substituted with ethyl. In some embodiments, $L^1$ is methylene substituted with halogen. In some embodiments, $L^1$ is methylene substituted with —$CF_3$. In some embodiments, $L^1$ is methylene substituted with unsubstituted $C_3$-$C_5$ cycloalkyl. In some embodiments, $L^1$ is methylene substituted with cyclopropyl. In some embodiments, $L^1$ is methylene substituted with cyclobutyl. In some embodiments, $L^1$ is methylene substituted with cyclopentyl. In some embodiments, $L^1$ is methylene substituted with benzyl. In some embodiments, $L^1$ is ethylene substituted with benzyl. In some embodiments, $L^1$ is unsubstituted phenylene. In some embodiments, $L^1$ is substituted phenylene. In some embodiments, $L^1$ is an unsubstituted fused ring arylene. In some embodiments, $L^1$ is a substituted fused ring arylene. In some embodiments, $L^1$ is methylene substituted with halogen. In some embodiments, $L^1$ is $C_1$-$C_4$ alkylene substituted with halogen. In some embodiments, $L^1$ is methylene substituted with —Cl. In some embodiments, $L^1$ is $C_1$-$C_4$ alkylene substituted with —Cl. In some embodiments, $L^1$ is methylene substituted with —Br. In some embodiments, $L^1$ is $C_1$-$C_4$ alkylene substituted with —Cl. In some embodiments, $L^1$ is methylene substituted with —I. In some embodiments, $L^1$ is $C_1$-$C_4$ alkylene substituted with —I. In some embodiments, $L^1$ is methylene substituted with —F. In some embodiments, $L^1$ is $C_1$-$C_4$ alkylene substituted with —F. In some embodiments, $L^1$ is substituted with multiple substituents that are optionally different substituents. In some embodiments, $L^1$ is substituted with multiple substituents and each substituent is optional different. In some embodiments, $L^1$ is a bond.

In some embodiments of a compound described herein (e.g. Formula (I), (III), (V), (VII), (IX), (XI), (XIII), (XIV), (XVII), (XVIII), (XXIa), (XXIb), (XXIIIa), or (XXIIIb), including embodiments), $L^2$ is a bond. In some embodiments $L^2$ is —NH—. In some embodiments $L^2$ is —N($R^{L23a}$)—. In some embodiments $L^2$ is substituted or unsubstituted alkylene. In some embodiments $L^2$ is unsubstituted alkylene. In some embodiments $L^2$ is substituted alkylene. In some embodiments $L^2$ is unsubstituted $C_1$-$C_5$ alkylene. In some embodiments $L^2$ is substituted $C_1$-$C_5$ alkylene. In some embodiments $L^2$ is unsubstituted $C_1$-$C_3$ alkylene. In some embodiments $L^2$ is substituted $C_1$-$C_3$ alkylene. In some embodiments $L^2$ is unsubstituted n-propylene. In some embodiments $L^2$ is unsubstituted methylene. In some embodiments $L^2$ is unsubstituted ethylene. In some embodiments, $L^2$ is substituted with multiple substituents that are optionally different substituents.

In some embodiments of a compound described herein (e.g. Formula (I), (III), (V), (VII), (IX), (XI), (XIII), (XIV), (XVII), (XVIII), (XXIa), (XXIb), (XXIIIa), or (XXIIIb), including embodiments), the symbols q and r are independently 1. In some embodiments, the symbols q and r are independently 2. In some embodiments, the symbol p is independently 0. In some embodiments, the symbol p is independently 1. In some embodiments, the symbol p is independently 2. In some embodiments, the symbol p is independently 3. In some embodiments, the symbol p is independently 4.

In some embodiments, the symbol $X^a$ is —Cl. In some embodiments, the symbol $X^a$ is —Br. In some embodiments, the symbol $X^a$ is —I. In some embodiments, the symbol $X^a$ is —F.

In some embodiments of a compound described herein (e.g. Formula (I), (III), (V), (VII), (IX), (XI), (XIII), (XIV), (XVII), (XVIII), (XXIa), (XXIb), (XXIIIa), or (XXIIIb), including embodiments), $R^2$ is hydrogen. In some embodiments $R^2$ is halogen. In some embodiments $R^2$ is —Cl. In some embodiments $R^2$ is —Br. In some embodiments $R^2$ is —I. In some embodiments $R^2$ is —F. In some embodiments $R^2$ is substituted or unsubstituted $C_1$-$C_5$ alkyl, substituted or unsubstituted 2 to 5 membered heteroalkyl, substituted or unsubstituted $C_3$-$C_5$ cycloalkyl, substituted or unsubstituted 4 to 6 membered heterocycloalkyl. In some embodiments $R^2$ is substituted or unsubstituted $C_1$-$C_5$ alkyl or substituted or unsubstituted $C_3$-$C_5$ cycloalkyl. In some embodiments $R^2$ is unsubstituted $C_1$-$C_5$ alkyl or unsubstituted $C_3$-$C_5$ cycloalkyl. In some embodiments $R^2$ is unsubstituted $C_1$-$C_3$ alkyl. In some embodiments, $R^2$ is unsubstituted methyl. In some embodiments, $R^2$ is unsubstituted ethyl. In some embodiments, $R^2$ is unsubstituted n-propyl. In some embodiments, $R^2$ is unsubstituted isopropyl. In some embodiments, $R^2$ is unsubstituted cyclopropyl. In some embodiments, $R^2$ is unsubstituted cyclobutyl. In some embodiments, $R^2$ is unsubstituted cyclopentyl. In some embodiments, $R^2$ is unsubstituted t-butyl.

In some embodiments of a compound described herein (e.g. Formula (I), (III), (V), (VII), (IX), (XI), (XIII), (XIV), (XVII), (XVIII), (XXIa), (XXIb), (XXIIIa), or (XXIIIb), including embodiments), $R^3$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In some embodiments, $R^3$ is hydrogen. In some embodiments, $R^3$ is hydrogen, substituted or unsubstituted $C_1$-$C_5$ alkyl, substituted or unsubstituted 2 to 5 membered heteroalkyl, substituted or unsubstituted $C_3$-$C_5$ cycloalkyl, substituted or unsubstituted 4 to 6 membered heterocycloalkyl, substituted or unsubstituted $C_6$-$C_{10}$ aryl, or substituted or unsubstituted 5 to 9 membered heteroaryl. In some embodiments, $R^3$ is substituted or unsubstituted $C_6$-$C_{10}$ aryl. In some embodiments, $R^3$ is substituted or unsubstituted 5 to 9 membered heteroaryl. In some embodiments, $R^3$ is substituted or unsubstituted 5 to 6 membered heteroaryl. In some embodiments, $R^3$ is substituted or unsubstituted $C_1$-$C_5$ alkyl. In some embodiments, $R^3$ is substituted or unsubstituted 2 to 5 membered heteroalkyl. In some embodiments, $R^3$ is substituted or unsubstituted $C_3$-$C_5$ cycloalkyl. In some embodiments, $R^3$ is substituted or unsubstituted 4 to 6 membered heterocycloalkyl. In some embodiments, $R^3$ is halogen. In some embodiments, $R^3$ is independently —Cl. In some embodiments, $R^3$ is independently —Br. In some embodiments, $R^3$ is independently —I. In some embodiments, $R^3$ is independently —F. In some embodiments, $R^3$ is —$CX^a_3$. In some embodiments, $R^3$ is —$CCl_3$. In some embodiments, $R^3$ is —$CF_3$. In some embodiments, $R^3$ is substituted or unsubstituted phenyl. In some embodiments, $R^3$ is substituted phenyl. In some embodiments, $R^3$ is unsubstituted phenyl.

In some embodiments of a compound described herein (e.g. Formula (I), (III), (V), (VII), (IX), (XI), (XIII), (XIV), (XVII), (XVIII), (XXIa), (XXIb), (XXIIIa), or (XXIIIb), including embodiments), $R^{11}$, $R^{12}$, $R^{13}$, and $R^{14}$ are independently hydrogen, substituted or unsubstituted $C_1$-$C_5$ alkyl, substituted or unsubstituted 2 to 5 membered heteroalkyl, substituted or unsubstituted $C_3$-$C_5$ cycloalkyl, substituted or unsubstituted 4 to 6 membered heterocycloalkyl, substituted or unsubstituted $C_6$-$C_{10}$ aryl, or substituted or unsubstituted 5 to 9 membered heteroaryl. In some embodiments, $R^{11}$, $R^{12}$, $R^{13}$, and $R^{14}$ are independently hydrogen. In some embodiments, $R^{11}$, $R^{12}$, $R^{13}$, and $R^{14}$ are independently substituted or unsubstituted 2 to 5 membered heteroalkyl. In some embodiments, $R^{11}$, $R^{12}$, $R^{13}$, and $R^{14}$ are independently substituted or unsubstituted $C_3$-$C_5$ cycloalkyl. In some embodiments, $R^{11}$, $R^{12}$, $R^{13}$, and $R^{14}$ are independently substituted or unsubstituted 4 to 6 membered heterocycloalkyl. In some embodiments, $R^{11}$, $R^{12}$, $R^{13}$, and $R^{14}$ are independently substituted or unsubstituted $C_6$-$C_{10}$ aryl. In some embodiments, $R^{11}$, $R^{12}$, $R^{13}$, and $R^{14}$ are independently substituted or unsubstituted 5 to 9 membered heteroaryl. In some embodiments, $R^{11}$, $R^{12}$, $R^{13}$, and $R^{14}$ are independently substituted or unsubstituted 5 to 6 membered heteroaryl. In some embodiments, $R^{11}$, $R^{12}$, $R^{13}$, and $R^{14}$ are independently substituted or unsubstituted $C_6$ aryl.

In some embodiments of a compound described herein (e.g. Formula (I), including embodiments), the compound has the formula:

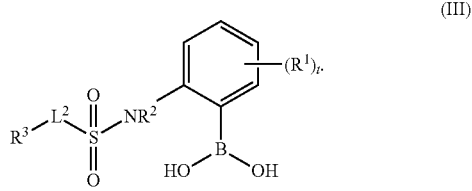

(III)

$L^2$, $R^2$, and $R^3$ are as described herein (e.g. Formula (I), including embodiments).

$R^1$ is independently hydrogen, halogen, —$CX_3$, —CN, —$SO_2Cl$, —$SO_nR^{10}$, —$SO_kNR^7R^8$, —$NHNH_2$, —$ONR^7R^8$, —NHC=(O)$NHNH_2$, —NHC=(O)$NR^7R^8$, —N(O)$_m$, —$NR^7R^8$, —C(O)$R^9$, —C(O)—$OR^9$, —C(O)$NR^7R^8$, —$OR^{10}$, substituted or unsubstituted $C_1$-$C_5$ alkyl, substituted or unsubstituted 2 to 5 membered heteroalkyl, substituted or unsubstituted $C_3$-$C_5$ cycloalkyl, substituted or unsubstituted 4 to 6 membered heterocycloalkyl, substituted or unsubstituted $C_6$-$C_{10}$ aryl, or substituted or unsubstituted 5 to 9 membered heteroaryl. Two adjacent $R^1$ substituents are optionally joined to form a substituted or unsubstituted cycloalkyl, substituted or unsubstituted heterocycloalkyl, substituted or unsubstituted aryl, or substituted or unsubstituted heteroaryl. $R^7$, $R^8$, $R^9$, and $R^{10}$ are independently hydrogen, substituted or unsubstituted $C_1$-$C_{20}$ alkyl, substituted or unsubstituted 2 to 20 membered heteroalkyl, substituted or unsubstituted $C_3$-$C_8$ cycloalkyl, substituted or unsubstituted 4 to 8 membered heterocycloalkyl, substituted or unsubstituted $C_6$-$C_{10}$ aryl, or substituted or unsubstituted 5 to 9 membered heteroaryl. The symbols k and m are independently 1 or 2. The symbols n and t are independently an integer from 0 to 4. The symbol X is —Cl, —Br, —I, or —F.

In some embodiments of a compound described herein (e.g. Formula (I), (III), (V), (VII), (IX), (XI), (XIII), (XIV), (XVII), (XVIII), (XXIa), (XXIb), (XXIIIa), or (XXIIIb), including embodiments), $R^1$ is independently hydrogen, substituted or unsubstituted $C_1$-$C_5$ alkyl, substituted or unsubstituted 2 to 5 membered heteroalkyl, substituted or unsubstituted $C_3$-$C_5$ cycloalkyl, substituted or unsubstituted 4 to 6 membered heterocycloalkyl, substituted or unsubstituted $C_6$-$C_{10}$ aryl, or substituted or unsubstituted 5 to 9 membered heteroaryl. In some embodiments, $R^1$ is independently hydrogen. In some embodiments, $R^1$ is independently substituted or unsubstituted $C_1$-$C_5$ alkyl or substituted or unsubstituted $C_3$-$C_5$ cycloalkyl. In some embodiments, $R^1$ is independently unsubstituted $C_1$-$C_5$ alkyl or unsubstituted $C_3$-$C_5$ cycloalkyl. In some embodiments, $R^1$ is independently unsubstituted methyl. In some embodiments, $R^1$ is independently unsubstituted ethyl. In some embodiments, $R^1$ is independently unsubstituted n-propyl. In some embodiments, $R^1$ is independently unsubstituted isopropyl. In some embodiments, $R^1$ is independently unsubstituted cyclopropyl. In some embodiments, $R^1$ is independently unsubstituted cyclobutyl. In some embodiments, $R^1$ is independently unsubstituted cyclopentyl. In some embodiments, $R^1$ is independently halogen. In some embodiments, $R^1$ is independently —COOH. In some embodiments, $R^1$ is independently —$CF_3$. In some embodiments, $R^1$ is independently —Cl. In some embodiments, $R^1$ is independently —Br. In some embodiments, $R^1$ is independently —I. In some embodiments, $R^1$ is independently —F. In some embodiments, $R^1$ is independently substituted or unsubstituted $C_6$ aryl. In some embodiments, $R^1$ is independently substituted or unsubstituted 5 to 6 membered heteroaryl. In some embodiments, $R^1$ is independently unsubstituted 5 to 6 membered heteroaryl. In some embodiments, $R^1$ is independently substituted 5 to 6 membered heteroaryl.

In some embodiments of a compound described herein (e.g. Formula (I), (III), (V), (VII), (IX), (XI), (XIII), (XIV), (XVII), (XVIII), (XXIa), (XXIb), (XXIIIa), or (XXIIIb), including embodiments), $R^7$, $R^8$, $R^9$, and $R^{10}$ are independently hydrogen, substituted or unsubstituted $C_1$-$C_5$ alkyl, substituted or unsubstituted 2 to 5 membered heteroalkyl, substituted or unsubstituted $C_3$-$C_5$ cycloalkyl, substituted or unsubstituted 4 to 6 membered heterocycloalkyl, substituted or unsubstituted $C_6$-$C_{10}$ aryl, or substituted or unsubstituted 5 to 9 membered heteroaryl. In some embodiments, $R^7$, $R^8$, $R^9$, and $R^{10}$ are independently hydrogen. In some embodiments, $R^7$, $R^8$, $R^9$, and $R^{10}$ are independently substituted or unsubstituted 2 to 5 membered heteroalkyl. In some embodiments, $R^7$, $R^8$, $R^9$, and $R^{10}$ are independently substituted or unsubstituted $C_3$-$C_5$ cycloalkyl. In some embodiments, $R^7$, $R^8$, $R^9$, and $R^{10}$ are independently substituted or unsubstituted 4 to 6 membered heterocycloalkyl. In some embodiments, $R^7$, $R^8$, $R^9$, and $R^{10}$ are independently substituted or unsubstituted $C_6$-$C_{10}$ aryl. In some embodiments, $R^7$, $R^8$, $R^9$, and $R^{10}$ are independently substituted or unsubstituted $C_6$ aryl. In some embodiments, $R^7$, $R^8$, $R^9$, and $R^{10}$ are independently substituted or unsubstituted 5 to 9 membered heteroaryl. In some embodiments, $R^7$, $R^8$, $R^9$, and $R^{10}$ are independently substituted or unsubstituted 5 to 6 membered heteroaryl.

In some embodiments of a compound described herein (e.g. Formula (I), (III), (V), (VII), (IX), (XI), (XIII), (XIV), (XVII), (XVIII), (XXIa), (XXIb), (XXIIIa), or (XXIIIb), including embodiments), the symbols k and m are independently 1. In some embodiments, the symbols k and m are independently 2. In some embodiments, the symbols n and t are independently 0. In some embodiments, the symbols n and t are independently 1. In some embodiments, the symbols n and t are independently 2. In some embodiments, the symbols n and t are independently 3. In some embodiments, the symbols n and t are independently 4. In some embodiments, X is independently —Cl. In some embodiments, X is independently —Br. In some embodiments, X is independently —I. In some embodiments, X is independently —F.

In some embodiments of a compound described herein (e.g. Formula (I) or (III), including embodiments), the compound has the formula:

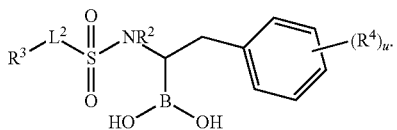

(V)

$L^2$, $R^2$, and $R^3$ are as described herein (e.g. Formula (I) or (III), including embodiments).

$R^4$ is independently hydrogen, halogen, —$CX_3$, —CN, —$SO_2Cl$, —$SO_nR^{10}$, —$SO_vNR^7R^8$, —$NHNH_2$, —$ONR^7R^8$, —NHC=(O)$NHNH_2$, —NHC=(O)$NR^7R^8$, —N(O)$_m$, —$NR^7R^8$, —C(O)$R^9$, —C(O)—$OR^9$, —C(O)$NR^7R^8$, —$OR^{10}$, substituted or unsubstituted $C_1$-$C_5$ alkyl, substituted or unsubstituted 2 to 5 membered heteroalkyl, substituted or unsubstituted $C_3$-$C_5$ cycloalkyl, substituted or unsubstituted 4 to 6 membered heterocycloalkyl, substituted or unsubstituted $C_6$-$C_{10}$ aryl, or substituted or unsubstituted 5 to 9 membered heteroaryl. Two adjacent $R^4$ substituents are optionally joined to form a substituted or unsubstituted cycloalkyl, substituted or unsubstituted heterocycloalkyl, substituted or unsubstituted aryl, or substituted or unsubstituted heteroaryl. The symbol u is independently an integer from 1 to 5.

In some embodiments of a compound described herein (e.g. Formula (I), (III), (V), (VII), (IX), (XI), (XIII), (XIV), (XVII), (XVIII), (XXIa), (XXIb), (XXIIIa), or (XXIIIb), including embodiments), $R^4$ is —COOH and u is 1. In some embodiments $R^4$ is meta substituted —COOH relative to the methylene and u is 1. In some embodiments $R^4$ is para substituted —COOH relative to the methylene and u is 1. In some embodiments, $R^4$ is independently hydrogen, substituted or unsubstituted $C_1$-$C_5$ alkyl, substituted or unsubstituted 2 to 5 membered heteroalkyl, substituted or unsubstituted $C_3$-$C_5$ cycloalkyl, substituted or unsubstituted 4 to 6 membered heterocycloalkyl, substituted or unsubstituted $C_6$-$C_{10}$ aryl, or substituted or unsubstituted 5 to 9 membered heteroaryl. In some embodiments, $R^4$ is independently halogen. In some embodiments, $R^4$ is independently —Cl. In some embodiments, $R^4$ is independently —Br. In some embodiments, $R^4$ is independently —I. In some embodiments, $R^4$ is independently —F. In some embodiments, $R^4$ is independently —$CF_3$.

In some embodiments of a compound described herein (e.g. Formula (I), (III) or (V), including embodiments), the symbol u is independently 1. In some embodiments, the symbol u is independently 2. In some embodiments, the symbol u is independently 3. In some embodiments, the symbol u is independently 4. In some embodiments, the symbol u is independently 5.

In some embodiments of a compound described herein (e.g. Formula (I), (III) or (V), including embodiments), the compound has the formula:

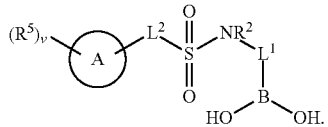

(VII)

$L^1$, $L^2$, and $R^2$ are as described herein (e.g. Formula (I), (III), or (V), including embodiments).

Ring A is unsubstituted cycloalkyl, unsubstituted heterocycloalkyl, unsubstituted aryl, or unsubstituted heteroaryl. $R^5$ is independently hydrogen, halogen, —$CX^a_3$, —CN, —$SO_2Cl$, —$SO_pR^{14}$, —$SO_qNR^{11}R^{12}$, —$NHNH_2$, —$ONR^{11}R^{12}$, —NHC=(O)$NHNH_2$, —NHC=(O)$NR^{11}R^{12}$, —N(O)$_r$, —$NR^{11}R^{12}$, —C(O)$R^{13}$, —C(O)—$OR^{13}$, —C(O)$NR^{11}R^{12}$, —$OR^{14}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. Two adjacent $R^5$ substituents are optionally joined to form a substituted or unsubstituted cycloalkyl, substituted or unsubstituted heterocycloalkyl, substituted or unsubstituted aryl, or substituted or unsubstituted heteroaryl. The symbol v is an integer from 0 to 7.

In some embodiments of a compound described herein (e.g. Formula (I), (III), (V), (VII), (IX), (XI), (XIII), (XIV), (XVII), (XVIII), (XXIa), (XXIb), (XXIIIa), or (XXIIIb), including embodiments), $R^5$ is independently hydrogen, substituted or unsubstituted $C_1$-$C_5$ alkyl, substituted or unsubstituted 2 to 5 membered heteroalkyl, substituted or unsubstituted $C_3$-$C_5$ cycloalkyl, substituted or unsubstituted 4 to 6 membered heterocycloalkyl, substituted or unsubstituted $C_6$-$C_{10}$ aryl, or substituted or unsubstituted 5 to 9 membered heteroaryl. In some embodiments, $R^5$ is independently hydrogen. In some embodiments, $R^5$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In some embodiments, $R^5$ is independently substituted or unsubstituted $C_6$-$C_{10}$ aryl. In some embodiments, $R^5$ is independently substituted or unsubstituted $C_6$ aryl. In some embodiments, $R^5$ is substituted or unsubstituted 5 to 9 membered heteroaryl. In some embodiments, $R^5$ is independently substituted or unsubstituted 5 to 6 membered heteroaryl. In some embodiments, $R^5$ is independently substituted 5 to 6 membered heteroaryl. In some embodiments, $R^5$ is independently unsubstituted 5 to 6 membered heteroaryl. In some embodiments, $R^5$ is independently substituted or unsubstituted $C_1$-$C_5$ alkyl. In some embodiments, $R^5$ is independently substituted or unsubstituted 2 to 5 membered heteroalkyl. In some embodiments, $R^5$ is independently substituted or unsubstituted $C_3$-$C_5$ cycloalkyl. In some embodiments, $R^5$ is independently substituted or unsubstituted 4 to 6 membered heterocycloalkyl. In some embodiments, $R^5$ is independently halogen. In some embodiments, $R^5$ is independently —Cl. In some embodiments, $R^5$ is independently —Br. In some embodiments, $R^5$ is independently —I. In some embodiments, $R^5$ is independently —F. In some embodiments, $R^5$ is independently —$CX^a_3$. In some embodiments, $R^5$ is —$CCl_3$. In some embodiments, $R^5$ is independently —$CF_3$. In some embodiments, $R^5$ is independently —$NH_2$. In some embodiments, $R^5$ is independently —OH. In some embodiments, $R^5$ is independently —COOH. In some embodiments, $R^5$ is independently —$NO_2$. In some embodiments, $R^5$ is independently —CN. In some embodiments, $R^5$ is independently —$COOCH_3$. In some embodiments, $R^5$ is independently —SH. In some embodiments, $R^5$ is independently —$SO_2Cl$.

In some embodiments of a compound described herein (e.g. Formula (I), (III), (V), (VII), (IX), (XI), (XIII), (XIV), (XVII), (XVIII), (XXIa), (XXIb), (XXIIIa), or (XXIIIb), including embodiments), the symbol v is independently an integer from 0 to 7. In some embodiments, the symbol v is independently an integer from 0 to 6. In some embodiments, the symbol v is independently an integer from 0 to 5. In some embodiments, the symbol v is independently an integer from 0 to 4. In some embodiments, the symbol v is independently an integer from 0 to 3. In some embodiments, the symbol v is independently an integer from 0 to 2. In some embodiments, the symbol v is independently an integer from 0 to 1. In some embodiments, the symbol v is independently 0. In some embodiments, the symbol v is independently 1. In some embodiments, the symbol v is independently 2. In some embodiments, the symbol v is independently 3. In some embodiments, the symbol v is independently 4. In some embodiments, the symbol v is independently 5. In some embodiments, the symbol v is independently 6. In some embodiments, the symbol v is independently 7.

In some embodiments of a compound described herein (e.g. Formula (I), (III), (V), (VII), or (IX), including embodiments), the ring A is independently unsubstituted aryl or unsubstituted heteroaryl. In some embodiments, ring A is independently unsubstituted heteroaryl. In some embodiments, ring A is independently unsubstituted aryl. In some embodiments, ring A is independently unsubstituted cycloalkyl or unsubstituted heterocycloalkyl. In some embodiments, ring A is independently unsubstituted cycloalkyl. In some embodiments, ring A is independently unsubstituted heterocycloalkyl. In some embodiments, ring A is independently unsubstituted $C_3$-$C_5$ cycloalkyl, unsubstituted 4 to 6 membered heterocycloalkyl, unsubstituted $C_6$-$C_{10}$ aryl, or unsubstituted 5 to 9 membered heteroaryl. In some embodiments, ring A is independently unsubstituted $C_6$-$C_{10}$ aryl. In some embodiments, ring A is independently unsubstituted $C_6$ aryl. In some embodiments, ring A is independently unsubstituted 5 to 9 membered heteroaryl. In some embodiments, ring A is independently unsubstituted 5 to 6 membered heteroaryl. In some embodiments, ring A is independently unsubstituted $C_4$-$C_8$ cycloalkyl. In some embodiments, ring A is independently unsubstituted 4 to 8 membered heterocycloalkyl. In some embodiments, ring A is independently unsubstituted $C_3$-$C_7$ cycloalkyl. In some embodiments, ring A is independently unsubstituted 3 to 7 membered heterocycloalkyl. In some embodiments, ring A is independently unsubstituted phenyl. In some embodiments, ring A is independently unsubstituted pyridyl. In some embodiments, ring A is independently unsubstituted thiophenyl. In some embodiments, ring A is independently unsubstituted thienyl. In some embodiments, ring A is independently unsubstituted tetrazolyl. In some embodiments, ring A is independently unsubstituted fused ring. In some embodiments, ring A is independently unsubstituted fused ring aryl. In some embodiments, ring A is independently unsubstituted fused ring heteroaryl.

In some embodiments, ring A is unsubstituted phenyl, unsubstituted naphthyl, unsubstituted pyridinyl, unsubstituted pyrimidinyl, unsubstituted thiophenyl, unsubstituted furanyl, unsubstituted indolyl, unsubstituted benzoxadiazolyl, unsubstituted benzodioxolyl, unsubstituted benzodioxanyl, unsubstituted thianaphthanyl, unsubstituted pyrrolopyridinyl, unsubstituted indazolyl, unsubstituted tetrahydronaphthalenyl, unsubstituted quinolinyl, unsubstituted quinoxalinyl, unsubstituted pyridopyrazinyl, unsubstituted quinazolinonyl, unsubstituted chromenonyl, unsubstituted benzoisoxazolyl, unsubstituted imidazopyridinyl, unsubstituted benzofuranyl, unsubstituted dihydro-benzofuranyl, unsubstituted dihydro-benzodioxinyl, unsubstituted benzoimidazolonyl, or unsubstituted benzothiophenyl.

In certain embodiments, ring A is unsubstituted pyrrolepyridinyl, unsubstituted quinolinyl, unsubstituted indazolyl, unsubstituted quinolinyl indolyl, or unsubstituted naphthyl.

Where Ring A is described above as a substituted monovalent cyclic substituent (e.g. cycloalkyl, heterocycloalkyl, aryl, or heteroaryl) it will be understood by one of ordinary skill in the art that ring A may alternatively be referred to as a divalent or multivalent cyclic substituent (e.g. as in formula IX)-using divalent or multivalent terms (e.g. cycloalkylene, hetercycloalkylene, arylene, or heteroarylene instead of cycloalkyl, heterocycloalkyl, aryl, or heteroaryl). Thus, divalent or multivalent forms of ring A may be variants of any of the substituted monovalent ring A possibilities.

In some embodiments of a compound described herein (e.g. Formula (I), (III), (V) or (VII), including embodiments), the compound has the formula:

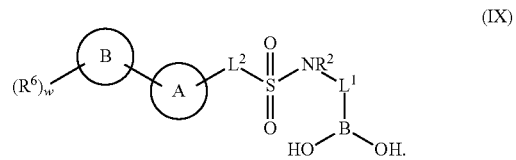

(IX)

$L^1$, $L^2$, ring A, and $R^2$ are as described herein (e.g. Formula (I), (III), (V), or (VII), including embodiments).

Ring B is independently unsubstituted cycloalkyl, unsubstituted heterocycloalkyl, unsubstituted aryl, or unsubstituted heteroaryl. $R^6$ is independently hydrogen, halogen, $-CX^{a1}{}_3$, $-CN$, $-SO_2Cl$, $-SO_{p1}R^{18}$, $-SO_{q1}NR^{15}R^{16}$, $-NHNH_2$, $-ONR^{15}R^{16}$, $-NHC=(O)NHNH_2$, $-NHC=(O)NR^{15}R^{16}$, $-N(O)_{r1}$, $-NR^{15}R^{16}$, $-C(O)R^{17}$, $-C(O)-OR^{17}$, $-C(O)NR^{15}R^{16}$, $-OR^{18}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. Two adjacent $R^6$ substituents are optionally joined to form a substituted or unsubstituted cycloalkyl, substituted or unsubstituted heterocycloalkyl, substituted or unsubstituted aryl, or substituted or unsubstituted heteroaryl. $R^{15}$, $R^{16}$, $R^{17}$, and $R^{18}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. The symbols q1 and r1 are independently 1 or 2. The symbol p1 is an integer from 0 to 4. The symbol $X^{a1}$ is $-Cl$, $-Br$, $-I$, or $-F$. The symbol w is an integer from 0 to 7.

In some embodiments of a compound described herein (e.g. Formula (I), (III), (V), (VII) or (IX), including embodiments), ring B is independently unsubstituted aryl or unsubstituted heteroaryl. In some embodiments, ring B is independently unsubstituted heteroaryl. In some embodiments, ring B is independently unsubstituted aryl. In some embodiments, ring B is independently unsubstituted cycloalkyl or unsubstituted heterocycloalkyl. In some embodiments, ring B is independently unsubstituted cycloalkyl. In some embodiments, ring B is independently unsubstituted heterocycloalkyl. In some embodiments, ring B is independently unsubstituted $C_3$-$C_5$ cycloalkyl, unsubstituted 4 to 6 membered heterocycloalkyl, unsubstituted $C_6$-$C_{10}$ aryl, or unsubstituted 5 to 9 membered heteroaryl. In some embodiments, ring B is independently unsubstituted $C_6$-$C_{10}$ aryl. In some embodiments, ring B is independently unsubstituted $C_6$ aryl. In some embodiments, ring B is independently unsubstituted 5 to 9 membered heteroaryl. In some embodiments, ring B is independently unsubstituted 5 to 6 membered heteroaryl. In some embodiments, ring B is independently unsubstituted $C_4$-$C_8$ cycloalkyl. In some embodiments, ring B is independently unsubstituted 4 to 8 membered heterocycloalkyl. In some embodiments, ring B is independently unsubstituted $C_3$-$C_7$ cycloalkyl. In some embodiments, ring B is independently unsubstituted 3 to 7 membered heterocycloalkyl. In some embodiments, ring B is independently unsubstituted phenyl. In some embodiments, ring B is independently unsubstituted pyridyl. In some embodiments, ring B is independently unsubstituted thiophenyl. In some embodiments, ring B is independently unsubstituted thienyl. In some embodiments, ring B is independently unsubstituted tetrazolyl. In some embodiments, ring B is independently unsubstituted fused ring. In some embodiments, ring B is independently unsubstituted fused ring aryl. In some embodiments, ring B is independently unsubstituted fused ring heteroaryl.

In some embodiments, the ring B is unsubstituted phenyl, unsubstituted naphthyl, unsubstituted pyridinyl, unsubstituted pyrimidinyl, unsubstituted thiophenyl, unsubstituted furanyl, unsubstituted indolyl, unsubstituted benzoxadiazolyl, unsubstituted benzodioxolyl, unsubstituted benzodioxanyl, unsubstituted thianaphthanyl, unsubstituted pyrrolopyridinyl, unsubstituted indazolyl, unsubstituted tetrahydronaphthalenyl, unsubstituted quinolinyl, unsubstituted quinoxalinyl, unsubstituted pyridopyrazinyl, unsubstituted quinazolinonyl, unsubstituted chromenonyl, unsubstituted benzoisoxazolyl, unsubstituted imidazopyridinyl, unsubstituted benzofuranyl, unsubstituted dihydro-benzofuranyl, unsubstituted dihydro-benzodioxinyl, unsubstituted benzoimidazolonyl, or unsubstituted benzothiophenyl.

In certain embodiments, ring B is unsubstituted pyrrolepyridinyl, unsubstituted quinolinyl, unsubstituted indazolyl, unsubstituted quinolinyl indolyl, or unsubstituted naphthyl.

In some embodiments of a compound described herein (e.g. Formula (I), (III), (V), (VII), (IX), (XI), (XIII), (XIV), (XVII), or (XVIII), including embodiments), $R^6$ is independently hydrogen, substituted or unsubstituted $C_1$-$C_5$ alkyl, substituted or unsubstituted 2 to 5 membered heteroalkyl, substituted or unsubstituted $C_3$-$C_5$ cycloalkyl, substituted or unsubstituted 4 to 6 membered heterocycloalkyl, substituted or unsubstituted $C_6$-$C_{10}$ aryl, or substituted or unsubstituted 5 to 9 membered heteroaryl. In some embodiments, $R^6$ is independently hydrogen. In some embodiments, $R^6$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In some embodiments, $R^6$ is independently substituted or unsubstituted $C_6$-$C_{10}$ aryl. In some embodiments, $R^6$ is independently substituted or unsubstituted 5 to 9 membered heteroaryl. In some embodiments, $R^6$ is independently substituted or unsubstituted 5 to 6 membered heteroaryl. In some embodiments, $R^6$ is independently substituted or unsubstituted $C_1$-$C_5$ alkyl. In some embodiments, $R^6$ is independently substituted or unsubstituted 2 to 5 membered heteroalkyl. In some embodiments, $R^6$ is independently substituted or unsubstituted $C_3$-$C_5$ cycloalkyl. In some embodiments, $R^6$ is independently substituted or unsubstituted 4 to 6 membered heterocycloalkyl. In some embodiments, $R^6$ is independently halogen. In some embodiments, $R^6$ is independently —Cl. In some embodiments, $R^6$ is independently —Br. In some embodiments, $R^6$ is independently —I. In some embodiments, $R^6$ is independently —F. In some embodiments, $R^6$ is independently —$CX^a_3$. In some embodiments, $R^6$ is independently —$CCl_3$. In some embodiments, $R^6$ is independently —$CF_3$. In some embodiments, $R^6$ is independently —$NH_2$. In some embodiments, $R^6$ is independently —OH. In some embodiments, $R^6$ is independently —COOH. In some embodiments, $R^6$ is independently —$NO_2$. In some embodiments, $R^6$ is independently —CN. In some embodiments, $R^6$ is independently —$COOCH_3$. In some embodiments, $R^6$ is independently —SH. In some embodiments, $R^6$ is independently —$SO_2Cl$.

In some embodiments of a compound described herein (e.g. Formula (I), (III), (V), (VII) or (IX), including embodiments), the symbol w is independently an integer from 0 to 6. In some embodiments, the symbol w is independently an integer from 0 to 5. In some embodiments, the symbol w is independently an integer from 0 to 4. In some embodiments, the symbol w is independently an integer from 0 to 3. In some embodiments, the symbol w is independently an integer from 0 to 2. In some embodiments, the symbol w is independently an integer from 0 to 1. In some embodiments, the symbol w is independently 0. In some embodiments, the symbol w is independently 1. In some embodiments, the symbol w is independently 2. In some embodiments, the symbol w is independently 3. In some embodiments, the symbol w is independently 4. In some embodiments, the symbol w is independently 5. In some embodiments, the symbol w is independently 6. In some embodiments, the symbol w is independently 7.

In some embodiments of a compound described herein (e.g. Formula (I), (III), (V), (VII), (IX), (XI), (XIII), (XIV), (XVII), or (XVIII), including embodiments), the symbols q1 and r1 are independently 1. In some embodiments, the symbols q1 and r1 are independently 2. In some embodiments, the symbol p1 is independently 0. In some embodiments, the symbol p1 is independently 1. In some embodiments, the symbol p1 is independently 2. In some embodiments, the symbol p1 is independently 3. In some embodiments, the symbol p1 is independently 4. In some embodiments, the symbol $X^{a1}$ is independently —Cl. In some embodiments, the symbol $X^{a1}$ is independently —Br. In some embodiments, the symbol $X^{a1}$ is independently —I. In some embodiments, the symbol $X^{a1}$ is independently —F.

In some embodiments of a compound described herein (e.g. Formula (I), (III), (V), (VII), (IX), (XI), (XIII), (XIV), (XVII), or (XVIII), including embodiments), $R^{15}$, $R^{16}$, $R^{17}$, and $R^{18}$ are independently hydrogen, substituted or unsubstituted $C_1$-$C_5$ alkyl, substituted or unsubstituted 2 to 5 membered heteroalkyl, substituted or unsubstituted $C_3$-$C_5$ cycloalkyl, substituted or unsubstituted 4 to 6 membered heterocycloalkyl, substituted or unsubstituted $C_6$-$C_{10}$ aryl, or substituted or unsubstituted 5 to 9 membered heteroaryl. In some embodiments, $R^{15}$, $R^{16}$, $R^{17}$, and $R^{18}$ are independently hydrogen. In some embodiments, $R^{15}$, $R^{16}$, $R^{17}$, and $R^{18}$ are independently substituted or unsubstituted 2 to 5 membered heteroalkyl. In some embodiments, $R^{15}$, $R^{16}$, $R^{17}$, and $R^{18}$ are independently substituted or unsubstituted $C_3$-$C_5$ cycloalkyl. In some embodiments, $R^{15}$, $R^{16}$, $R^{17}$, and $R^{18}$ are independently substituted or unsubstituted 4 to 6 membered heterocycloalkyl. In some embodiments, $R^{15}$, $R^{16}$, $R^{17}$, and $R^{18}$ are independently substituted or unsubstituted $C_6$-$C_{10}$ aryl. In some embodiments, $R^{15}$, $R^{16}$, $R^{17}$, and $R^{18}$ are independently substituted or unsubstituted $C_6$ aryl. In some embodiments, $R^{15}$, $R^{16}$, $R^{17}$, and $R^{18}$ are independently substituted or unsubstituted 5 to 9 membered heteroaryl. In some embodiments, $R^{15}$, $R^{16}$, $R^{17}$, and $R^{18}$ are independently substituted or unsubstituted 5 to 6 membered heteroaryl.

In some embodiments of a compound described herein (e.g. Formula (I), (III), (V) (VII), or (IX), including embodiments), the compound has the formula:

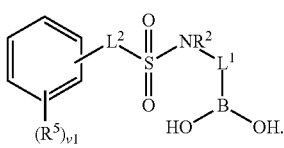 (XI)

$L^1$, $L^2$, $R^2$, and $R^5$ are as described herein (e.g. Formula (I), (III), (V), (VII), or (IX), including embodiments).

The symbol v1 is independently an integer from 0 to 5.

In some embodiments of a compound described herein (e.g. Formula (I), (III), (V), (VII), (IX), or (XI), including embodiments), the symbol v1 is independently an integer from 0 to 4. In some embodiments, the symbol v is independently an integer from 0 to 3. In some embodiments, the symbol v1 is independently an integer from 0 to 2. In some embodiments, the symbol v1 is independently an integer from 0 to 1. In some embodiments, the symbol v1 is independently 0. In some embodiments, the symbol v1 is independently 1. In some embodiments, the symbol v1 is independently 2. In some embodiments, the symbol v1 is independently 3. In some embodiments, the symbol v1 is independently 4. In some embodiments, the symbol v1 is independently 5.

In some embodiments of a compound described herein (e.g. Formula (I), (III), (V), (VII), (XI), or (XI), including embodiments), the compound has the formula:

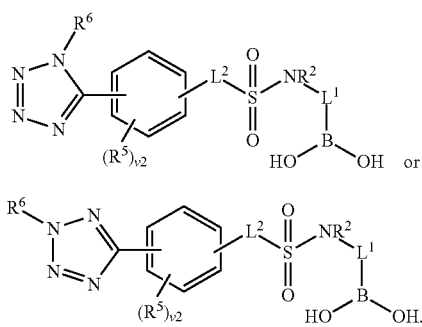
(XIII)

(XIV)

$L^1$, $L^2$, $R^2$, $R^5$, and $R^6$ are as described herein (e.g. Formula (I), (III), (V), (VII), (IX), or (XI), including embodiments). The symbol v2 is independently an integer from 0 to 4.

In some embodiments of a compound described herein (e.g. Formula (I), (III), (V), (VII), (IX), (XI), (XIII), (XIV), (XVII), or (XVIII), including embodiments), the symbol v2 is independently an integer from 0 to 3. In some embodiments, the symbol v2 is independently an integer from 0 to 2. In some embodiments, the symbol v2 is independently an integer from 0 to 1. In some embodiments, the symbol v2 is independently 0. In some embodiments, the symbol v2 is independently 1. In some embodiments, the symbol v2 is independently 2. In some embodiments, the symbol v2 is independently 3. In some embodiments, the symbol v2 is independently 4.

In some embodiments of a compound described herein (e.g. Formula (I), (III), (V), (VII), (IX), or (XI), including embodiments), the compound has the formula:

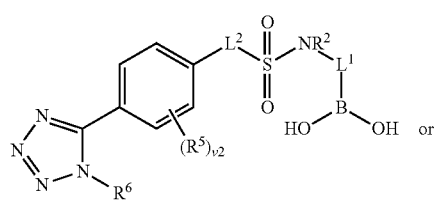
(XVII)

(XVIII)

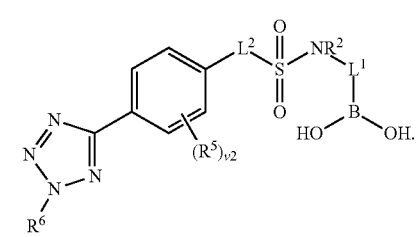

$L^1$, $L^2$, v2, $R^2$, $R^5$, and $R^6$ are as described herein (e.g. Formula (I), (III), (V), (VII), (IX), or (XI), including embodiments).

In some embodiments of a compound described herein (e.g. Formula (I), (III), (V), (VII), (IX), or (XI), including embodiments), the compound has the formula:

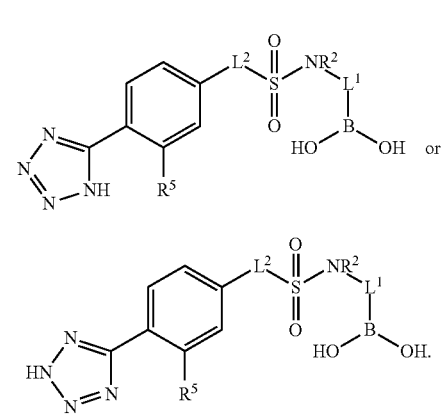
(XXIa)

(XXIb)

$L^1$, $L^2$, $R^2$, and $R^5$ are as described herein (e.g. Formula (I), (III), (V), (VII), (IX), or (XI), including embodiments).

In some embodiments of a compound described herein (e.g. Formula (I), (III), (V), (VII), (IX), or (XI), including embodiments), the compound has the formula:

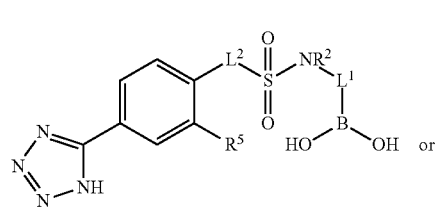
(XXIIIa)

or (XXIIIb)

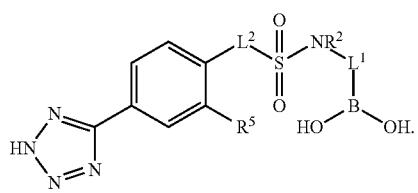

$L^1$, $L^2$, $R^2$, and $R^5$ are as described herein (e.g. Formula (I), (III), (V), (VII), (IX), or (XI), including embodiments).

In some embodiments of a compound described herein (e.g. Formula (I), (III), (V), (VII), (IX), (XI), (XIII), (XIV), (XVII), (XVIII), (XXIa), (XXIb), (XXIIIa), or (XXIIIb), including embodiments), $R^5$ is halogen. In some embodiments, $R^5$ is —Cl. In some embodiments, $R^5$ is —F. In some embodiments, $R^5$ is —I. In some embodiments, $R^5$ is —Br. In some embodiments, $R^5$ is —$CF_3$. In some embodiments, $R^5$ is —$CCl_3$.

In a second aspect, a compound is provided having any one of the formulas:

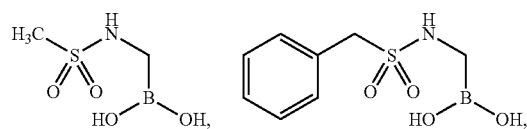
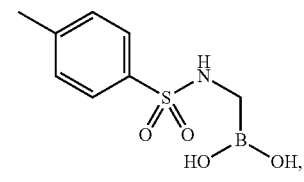
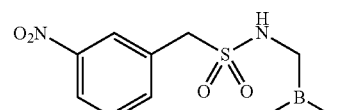
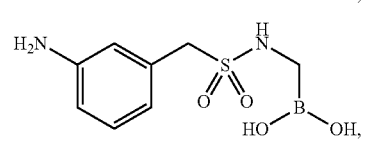
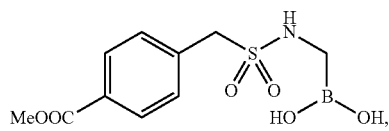
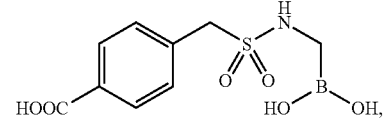
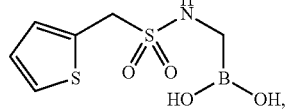
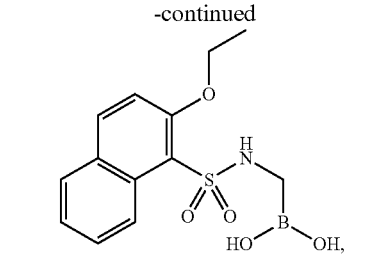
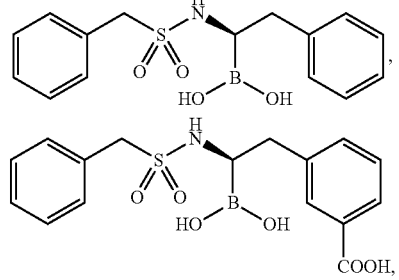
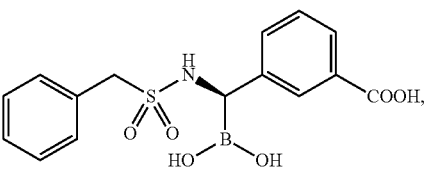
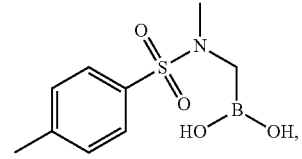
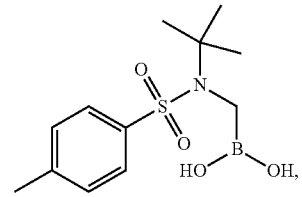
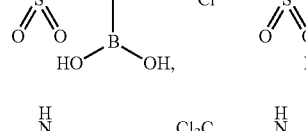
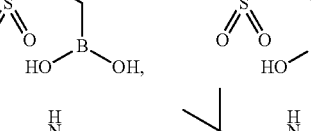
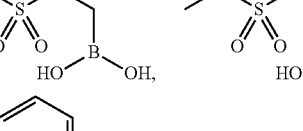
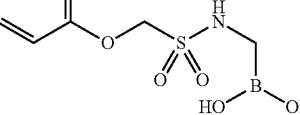

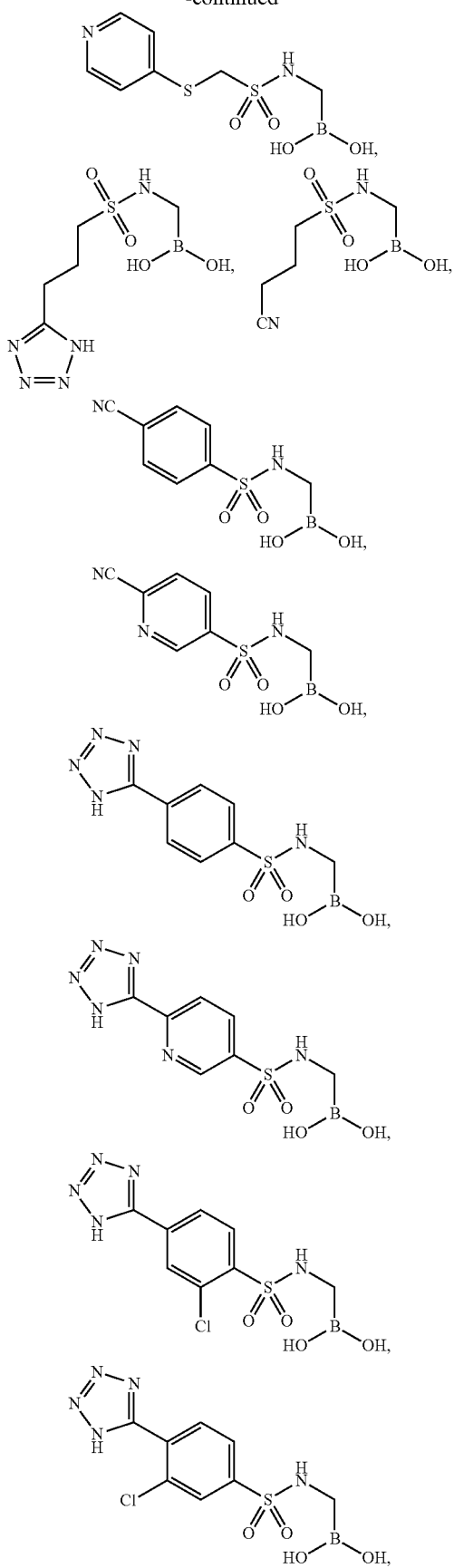
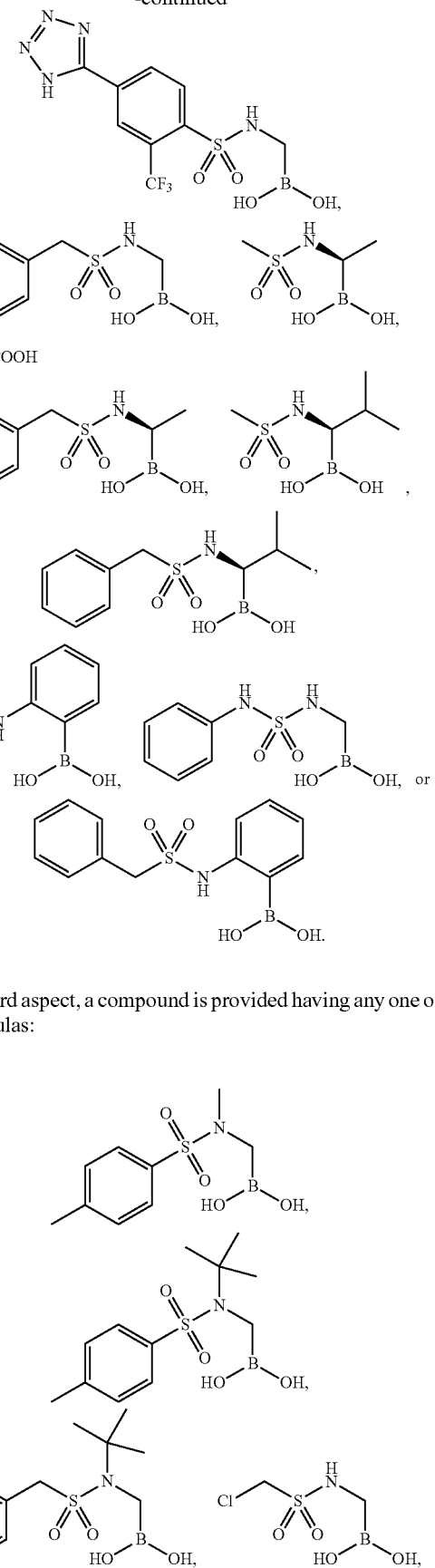
In a third aspect, a compound is provided having any one of the formulas:

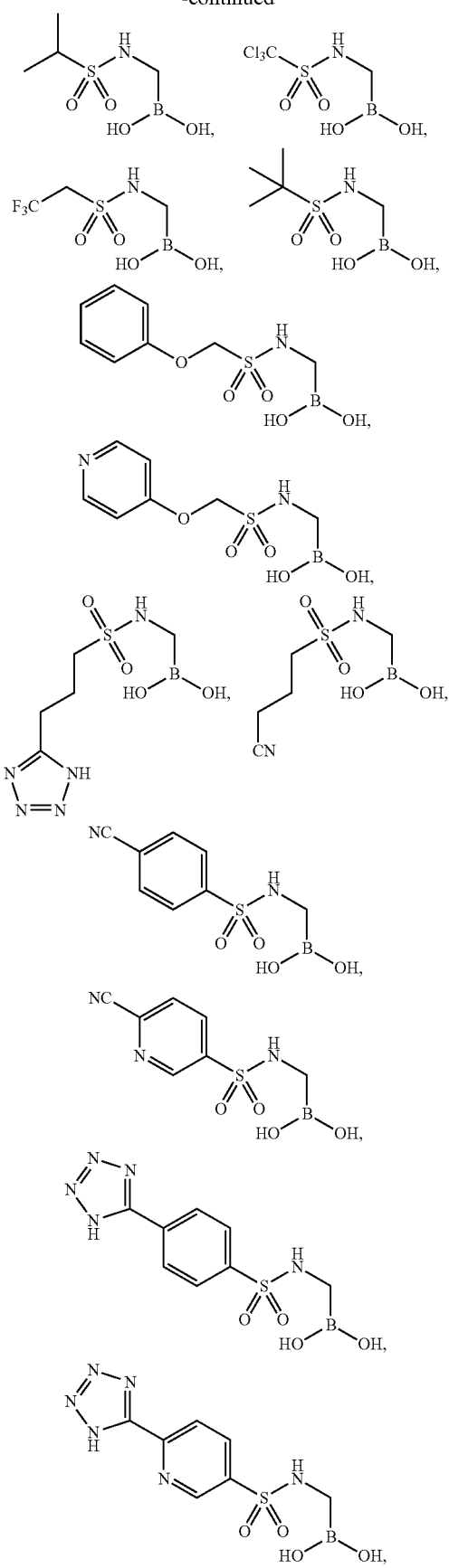
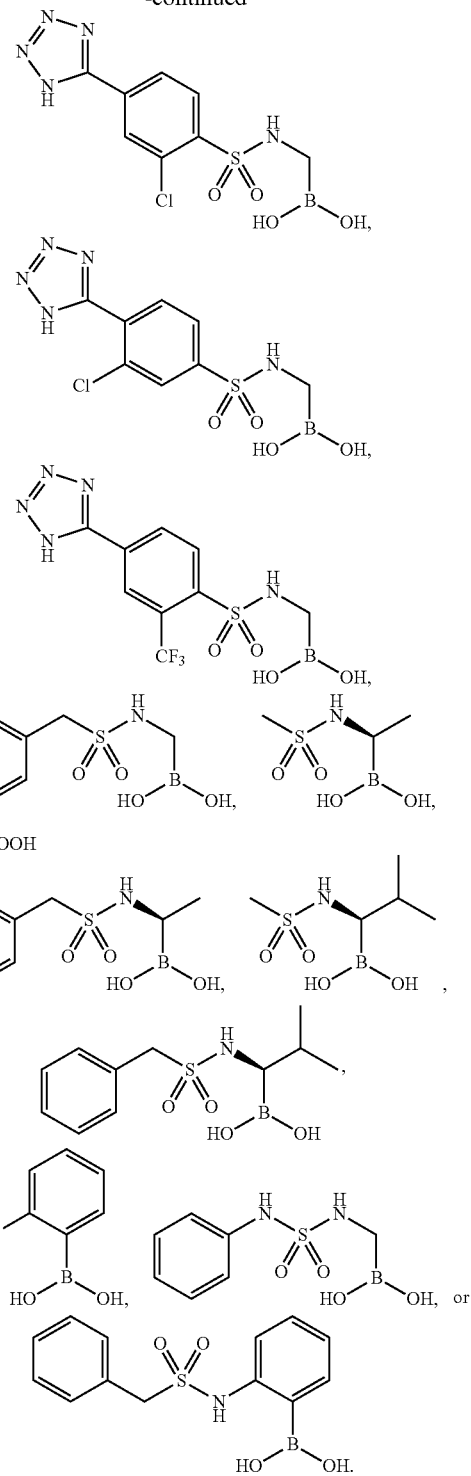

In some embodiments of a compound described herein (e.g. Formula (I), (III), (V), (VII), (IX), (XI), (XIII), (XIV), (XVII), (XVIII), (XXIa), (XXIb), (XXIIIa), or (XXIIIb), including embodiments), a boron of the compound (e.g. the boron atom shown in Formula (I), (III), (V), (VII), (IX), (XI), (XIII), (XIV), (XVII), (XVIII), (XXIa), (XXIb), (XXIIIa), or (XXIIIb)) contacts a sidechain of an amino acid of a bacterial beta-lactamase corresponding to *Escherichia coli* AmpC beta-lactamase amino acid Ser64. In some embodiments of a compound described herein (e.g. Formula (I), (III), (V), (VII), (IX), (XI), (XIII), (XIV), (XVII), (XVIII), (XXIa), (XXIb), (XXIIIa), or (XXIIIb), including embodiments) the compound contacts a sidechain of an amino acid of a bacterial beta-lactamase corresponding to *Escherichia coli* AmpC beta-lactamase amino acid Asn152. In some embodiments of a compound described herein (e.g. Formula (I), (III), (V), (VII), (IX), (XI), (XIII), (XIV), (XVII), (XVIII), (XXIa), (XXIb), (XXIIIa), or (XXIIIb), including embodiments) the compound contacts a backbone amide nitrogen of an amino acid of a bacterial beta-lactamase corresponding to *Escherichia coli* AmpC beta-lactamase amino acid Ser212 or Gly320. In some embodiments of a compound described herein (e.g. Formula (I), (III), (V), (VII), (IX), (XI), (XIII), (XIV), (XVII), (XVIII), (XXIa), (XXIb), (XXIIIa), or (XXIIIb), including embodiments) the compound contacts a backbone amide nitrogen of an amino acid of a bacterial beta-lactamase corresponding to *Escherichia coli* AmpC beta-lactamase amino acid Ser212. In some embodiments of a compound described herein (e.g. Formula (I), (III), (V), (VII), (IX), (XI), (XIII), (XIV), (XVII), (XVIII), (XXIa), (XXIb), (XXIIIa), or (XXIIIb), including embodiments) the compound contacts a backbone amide nitrogen of an amino acid of a bacterial beta-lactamase corresponding to *Escherichia coli* AmpC beta-lactamase amino acid Gly320. In some embodiments of a compound described herein (e.g. Formula (I), (III), (V), (VII), (IX), (XI), (XIII), (XIV), (XVII), (XVIII), (XXIa), (XXIb), (XXIIIa), or (XXIIIb), including embodiments), a boron of the compound (e.g. the boron atom shown in Formula (I), (III), (V), (VII), (IX), (XI), (XIII), (XIV), (XVII), (XVIII), (XXIa), (XXIb), (XXIIIa), or (XXIIIb)) contacts a sidechain of an amino acid of a bacterial beta-lactamase corresponding to *Escherichia coli* AmpC beta-lactamase amino acid Ser64; the compound contacts a sidechain of an amino acid of the bacterial beta-lactamase corresponding to *Escherichia coli* AmpC beta-lactamase amino acid Asn152; and the compound contacts a backbone amide nitrogen of an amino acid of the bacterial beta-lactamase corresponding to *Escherichia coli* AmpC beta-lactamase amino acid Ser212 and/or Gly320.

In some embodiments of a compound described herein (e.g. Formula (I), (III), (V), (VII), (IX), (XI), (XIII), (XIV), (XVII), (XVIII), (XXIa), (XXIb), (XXIIIa), or (XXIIIb), including embodiments) the compound contacts a sidechain of an amino acid of a bacterial beta-lactamase corresponding to *Escherichia coli* AmpC beta-lactamase amino acid Tyr221. In some embodiments of a compound described herein (e.g. Formula (I), (III), (V), (VII), (IX), (XI), (XIII), (XIV), (XVII), (XVIII), (XXIa), (XXIb), (XXIIIa), or (XXIIIb), including embodiments) the compound contacts a sidechain of an amino acid of a bacterial beta-lactamase corresponding to *Escherichia coli* AmpC beta-lactamase amino acid Tyr150. In some embodiments of a compound described herein (e.g. Formula (I), (III), (V), (VII), (IX), (XI), (XIII), (XIV), (XVII), (XVIII), (XXIa), (XXIb), (XXIIIa), or (XXIIIb), including embodiments) the compound contacts a backbone amide nitrogen of an amino acid of a bacterial beta-lactamase corresponding to *Escherichia coli* AmpC beta-lactamase amino acid Ser64. In some embodiments of a compound described herein (e.g. Formula (I), (III), (V), (VII), (IX), (XI), (XIII), (XIV), (XVII), (XVIII), (XXIa), (XXIb), (XXIIIa), or (XXIIIb), including embodiments) the compound contacts a backbone amide nitrogen of an amino acid of a bacterial beta-lactamase corresponding to *Escherichia coli* AmpC beta-lactamase amino acid Ala318. In some embodiments of a compound described herein (e.g. Formula (I), (III), (V), (VII), (IX), (XI), (XIII), (XIV), (XVII), (XVIII), (XXIa), (XXIb), (XXIIIa), or (XXIIIb), including embodiments) the compound contacts an amino acid of a bacterial beta-lactamase corresponding to *Escherichia coli* AmpC beta-lactamase amino acid Lys67.

In some embodiments of a compound described herein (e.g. Formula (I), (III), (V), (VII), (IX), (XI), (XIII), (XIV), (XVII), (XVIII), (XXIa), (XXIb), (XXIIIa), or (XXIIIb), including embodiments), the compound inhibits the activity of a bacterial beta-lactamase. In some embodiments, the bacterial beta-lactamase is expressed by a bacterium selected from *Stenotrophomonas maltophilia, Clostridium difficile, Bacillus anthracis, Bordetella pertussis, Borrelia burgdorferi, Brucella abortus, Brucella canis, Brucella melitensis, Brucella suis, Campylobacter jejuni, Chlamydia pneumoniae, Chlamydia trachomatis, Chlamydophila psittaci, Clostridium botulinum, Clostridium difficile, Clostridium perfringens, Clostridium tetani, Corynebacterium diphtheriae, Enterococcus faecalis, Enterococcus faecium, Escherichia coli*, Enterotoxigenic *Escherichia coli* (ETEC), Enteropathogenic *E. coli, E. coli* O157:H7, *Francisella tularensis, Haemophilus influenzae, Helicobacter pylori, Legionella pneumophila, Leptospira interrogans, Listeria monocytogenes, Mycobacterium leprae, Mycobacterium tuberculosis, Mycoplasma pneumoniae, Neisseria gonorrhoeae, Neisseria meningitidis, Pseudomonas aeruginosa, Rickettsia rickettsii, Salmonella typhi, Salmonella typhimurium, Shigella sonnei, Staphylococcus aureus, Staphylococcus epidermidis, Staphylococcus saprophyticus, Streptococcus agalactiae, Streptococcus pneumoniae, Streptococcus pyogenes, Treponema pallidum, Vibrio cholerae, Klebsiella pneumoniae, Enterobacter cloacae, Citrobacter freundii, Acinetobacter baumannii*, or *Yersinia pestis*. In some embodiments, the bacterial beta-lactamase is expressed by a bacterium that is gram negative. In some embodiments, the bacterial beta-lactamase is expressed by a bacterium that is gram positive.

In some embodiments of the compounds provided herein, $R^1$ is hydrogen, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)NHNH_2, $R^{20}$-substituted or unsubstituted $C_1$-$C_5$ alkyl, $R^{20}$-substituted or unsubstituted 2 to 5 membered heteroalkyl, $R^{20}$-substituted or unsubstituted $C_3$-$C_5$ cycloalkyl, $R^{20}$-substituted or unsubstituted 4 to 6 membered heterocycloalkyl, $R^{20}$-substituted or unsubstituted $C_6$-$C_{10}$ aryl, or $R^{20}$-substituted or unsubstituted 5 to 9 membered heteroaryl.

$R^{20}$ is independently halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)NHNH_2, $R^{21}$-substituted or unsubstituted alkyl, $R^{21}$-substituted or unsubstituted heteroalkyl, $R^{21}$-substituted or unsubstituted cycloalkyl, $R^{21}$-substituted or unsubstituted heterocycloalkyl, $R^{21}$-substituted or unsubstituted aryl, or $R^{21}$ substituted or unsubstituted heteroaryl.

$R^{21}$ is independently halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)NHNH_2, $R^{22}$-substituted or unsubstituted alkyl, $R^{22}$-substituted or unsubstituted heteroalkyl, $R^{22}$-substituted or unsubstituted cycloalkyl, $R^{22}$-substituted or unsubstituted heterocycloalkyl, $R^{22}$-substituted or unsubstituted aryl, or $R^{22}$-substituted or unsubstituted heteroaryl.

In some embodiments of the compounds provided herein, $R^2$ is hydrogen, halogen, $R^{23}$-substituted or unsubstituted $C_1$-$C_5$ alkyl, $R^{23}$-substituted or unsubstituted 2 to 5 membered heteroalkyl, $R^{23}$-substituted or unsubstituted $C_3$-$C_5$ cycloalkyl, $R^{23}$-substituted or unsubstituted 4 to 6 membered heterocycloalkyl, $R^{23}$-substituted or unsubstituted $C_6$-$C_{10}$ aryl, or $R^{23}$-substituted or unsubstituted 5 to 9 membered heteroaryl.

$R^{23}$ is independently halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, $R^{24}$-substituted or unsubstituted alkyl, $R^{24}$-substituted or unsubstituted heteroalkyl, $R^{24}$-substituted or unsubstituted cycloalkyl, $R^{24}$-substituted or unsubstituted heterocycloalkyl, $R^{24}$-substituted or unsubstituted aryl, or $R^{24}$ substituted or unsubstituted heteroaryl.

$R^{24}$ is independently halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, $R^{25}$-substituted or unsubstituted alkyl, $R^{25}$-substituted or unsubstituted heteroalkyl, $R^{25}$-substituted or unsubstituted cycloalkyl, $R^{25}$-substituted or unsubstituted heterocycloalkyl, $R^{25}$-substituted or unsubstituted aryl, or $R^{25}$ substituted or unsubstituted heteroaryl.

In some embodiments of the compounds provided herein, $R^3$ is hydrogen, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, $R^{26}$-substituted or unsubstituted alkyl, $R^{26}$-substituted or unsubstituted heteroalkyl, $R^{26}$-substituted or unsubstituted cycloalkyl, $R^{26}$-substituted or unsubstituted heterocycloalkyl, $R^{26}$-substituted or unsubstituted aryl, or $R^{26}$-substituted or unsubstituted heteroaryl.

$R^{26}$ is independently halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, $R^{27}$-substituted or unsubstituted alkyl, $R^{27}$-substituted or unsubstituted heteroalkyl, $R^{27}$-substituted or unsubstituted cycloalkyl, $R^{27}$ substituted or unsubstituted heterocycloalkyl, $R^{27}$-substituted or unsubstituted aryl, or $R^{27}$-substituted or unsubstituted heteroaryl.

$R^{27}$ is independently halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, $R^{28}$-substituted or unsubstituted alkyl, $R^{28}$-substituted or unsubstituted heteroalkyl, $R^{28}$-substituted or unsubstituted cycloalkyl, $R^{28}$-substituted or unsubstituted heterocycloalkyl, $R^{28}$-substituted or unsubstituted aryl, or $R^{28}$-substituted or unsubstituted heteroaryl.

In some embodiments of the compounds provided herein, $R^4$ is hydrogen, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —C(O)$OCH_3$, $R^{29}$-substituted or unsubstituted $C_1$-$C_5$ alky, $R^{29}$-substituted or unsubstituted 2 to 5 membered heteroalkyl, $R^{29}$-substituted or unsubstituted $C_3$-$C_5$ cycloalkyl, $R^{29}$-substituted or unsubstituted 4 to 6 membered heterocycloalkyl, $R^{29}$-substituted or unsubstituted $C_6$-$C_{10}$ aryl, or $R^{29}$-substituted or unsubstituted 5 to 9 membered heteroaryl.

$R^{29}$ is independently halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, $R^{30}$-substituted or unsubstituted alkyl, $R^{30}$-substituted or unsubstituted heteroalkyl, $R^{30}$-substituted or unsubstituted cycloalkyl, $R^{30}$ substituted or unsubstituted heterocycloalkyl, $R^{30}$-substituted or unsubstituted aryl, or $R^{30}$-substituted or unsubstituted heteroaryl.

$R^{30}$ is independently halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, $R^{31}$-substituted or unsubstituted alkyl, $R^{31}$-substituted or unsubstituted heteroalkyl, $R^{31}$-substituted or unsubstituted cycloalkyl, $R^{31}$-substituted or unsubstituted heterocycloalkyl, $R^{31}$-substituted or unsubstituted aryl, or $R^{31}$-substituted or unsubstituted heteroaryl.

In some embodiments of the compounds provided herein, $R^5$ is hydrogen, halogen, —$CF_3$, —$CCl_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —C(O)$OCH_3$, $R^{32}$-substituted or unsubstituted alkyl, $R^{32}$-substituted or unsubstituted heteroalkyl, $R^{32}$-substituted or unsubstituted cycloalkyl, $R^{32}$-substituted or unsubstituted heterocycloalkyl, $R^{32}$-substituted or unsubstituted aryl, or $R^{32}$-substituted or unsubstituted heteroaryl.

$R^{32}$ is independently halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, $R^{33}$-substituted or unsubstituted alkyl, $R^{33}$-substituted or unsubstituted heteroalkyl, $R^{33}$-substituted or unsubstituted cycloalkyl, $R^{33}$ substituted or unsubstituted heterocycloalkyl, $R^{33}$-substituted or unsubstituted aryl, or $R^{33}$-substituted or unsubstituted heteroaryl.

$R^{33}$ is independently halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, $R^{34}$-substituted or unsubstituted alkyl, $R^{34}$-substituted or unsubstituted heteroalkyl, $R^{34}$-substituted or unsubstituted cycloalkyl, $R^{34}$-substituted or unsubstituted heterocycloalkyl, $R^{34}$-substituted or unsubstituted aryl, or $R^{34}$-substituted or unsubstituted heteroaryl.

In some embodiments of the compounds provided herein, $R^6$ is hydrogen, halogen, —$CF_3$, —$CCl_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —C(O)$OCH_3$, $R^{35}$-substituted or unsubstituted alkyl, $R^{35}$-substituted or unsubstituted heteroalkyl, $R^{35}$-substituted or unsubstituted cycloalkyl, $R^{35}$-substituted or unsubstituted heterocycloalkyl, $R^{35}$-substituted or unsubstituted aryl, or $R^{35}$-substituted or unsubstituted heteroaryl.

$R^{35}$ is independently halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, $R^{36}$-substituted or unsubstituted alkyl, $R^{36}$-substituted or unsubstituted heteroalkyl, $R^{36}$-substituted or unsubstituted cycloalkyl, $R^{36}$ substituted or unsubstituted heterocycloalkyl, $R^{36}$-substituted or unsubstituted aryl, or $R^{36}$-substituted or unsubstituted heteroaryl.

$R^{36}$ is independently halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, $R^{37}$-substituted or unsubstituted alkyl, $R^{37}$-substituted or unsubstituted heteroalkyl, $R^{37}$-substituted or unsubstituted cycloalkyl, $R^{37}$-substituted or unsubstituted heterocycloalkyl, $R^{37}$-substituted or unsubstituted aryl, or $R^{37}$-substituted or unsubstituted heteroaryl.

In some embodiments of the compounds provided herein, $R^7$ is hydrogen, $R^{38}$-substituted or unsubstituted $C_1$-$C_{20}$ alkyl, $R^{38}$-substituted or unsubstituted 2 to 20 membered heteroalkyl, $R^{38}$-substituted or unsubstituted $C_3$-$C_8$ cycloalkyl, $R^{38}$-substituted or unsubstituted 4 to 8 membered heterocycloalkyl, $R^{38}$-substituted or unsubstituted $C_6$-$C_{10}$ aryl, or $R^{38}$-substituted or unsubstituted 5 to 9 membered heteroaryl.

$R^{38}$ is independently halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC═(O)NHNH$_2$, R$^{39}$-substituted or unsubstituted alkyl, R$^{39}$-substituted or unsubstituted heteroalkyl, R$^{39}$-substituted or unsubstituted cycloalkyl, R$^{39}$ substituted or unsubstituted heterocycloalkyl, R$^{39}$-substituted or unsubstituted aryl, or R$^{39}$-substituted or unsubstituted heteroaryl.

R$^{39}$ is independently halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC═(O)NHNH$_2$, R$^{40}$-substituted or unsubstituted alkyl, R$^{40}$-substituted or unsubstituted heteroalkyl, R$^{40}$-substituted or unsubstituted cycloalkyl, R$^{40}$-substituted or unsubstituted heterocycloalkyl, R$^{40}$-substituted or unsubstituted aryl, or R$^{40}$-substituted or unsubstituted heteroaryl.

In some embodiments of the compounds provided herein, R$^8$ is hydrogen, R$^{41}$-substituted or unsubstituted C$_1$-C$_{20}$ alkyl, R$^{41}$-substituted or unsubstituted 2 to 20 membered heteroalkyl, R$^{41}$-substituted or unsubstituted C$_3$-C$_8$ cycloalkyl, R$^{41}$-substituted or unsubstituted 4 to 8 membered heterocycloalkyl, R$^{41}$-substituted or unsubstituted C$_6$-C$_{10}$ aryl, or R$^{41}$-substituted or unsubstituted 5 to 9 membered heteroaryl.

R$^{41}$ is independently halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC═(O)NHNH$_2$, R$^{42}$-substituted or unsubstituted alkyl, R$^{42}$-substituted or unsubstituted heteroalkyl, R$^{42}$-substituted or unsubstituted cycloalkyl, R$^{42}$ substituted or unsubstituted heterocycloalkyl, R$^{42}$-substituted or unsubstituted aryl, or R$^{42}$-substituted or unsubstituted heteroaryl.

R$^{42}$ is independently halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC═(O)NHNH$_2$, R$^{43}$-substituted or unsubstituted alkyl, R$^{43}$-substituted or unsubstituted heteroalkyl, R$^{43}$-substituted or unsubstituted cycloalkyl, R$^{43}$-substituted or unsubstituted heterocycloalkyl, R$^{43}$-substituted or unsubstituted aryl, or R$^{43}$-substituted or unsubstituted heteroaryl.

In some embodiments of the compounds provided herein, R$^9$ is hydrogen, R$^{44}$-substituted or unsubstituted C$_1$-C$_{20}$ alkyl, R$^{44}$-substituted or unsubstituted 2 to 20 membered heteroalkyl, R$^{44}$-substituted or unsubstituted C$_3$-C$_8$ cycloalkyl, R$^{44}$-substituted or unsubstituted 4 to 8 membered heterocycloalkyl, R$^{44}$-substituted or unsubstituted C$_6$-C$_{10}$ aryl, or R$^{44}$-substituted or unsubstituted 5 to 9 membered heteroaryl.

R$^{44}$ is independently halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC═(O)NHNH$_2$, R$^{45}$-substituted or unsubstituted alkyl, R$^{45}$-substituted or unsubstituted heteroalkyl, R$^{45}$-substituted or unsubstituted cycloalkyl, R$^{45}$ substituted or unsubstituted heterocycloalkyl, R$^{45}$-substituted or unsubstituted aryl, or R$^{45}$-substituted or unsubstituted heteroaryl.

R$^{45}$ is independently halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC═(O)NHNH$_2$, R$^{46}$-substituted or unsubstituted alkyl, R$^{46}$-substituted or unsubstituted heteroalkyl, R$^{46}$-substituted or unsubstituted cycloalkyl, R$^{46}$-substituted or unsubstituted heterocycloalkyl, R$^{46}$-substituted or unsubstituted aryl, or R$^{46}$-substituted or unsubstituted heteroaryl.

In some embodiments of the compounds provided herein, R$^{10}$ is hydrogen, R$^{47}$-substituted or unsubstituted C$_1$-C$_{20}$ alkyl, R$^{47}$-substituted or unsubstituted 2 to 20 membered heteroalkyl, R$^{47}$-substituted or unsubstituted C$_3$-C$_8$ cycloalkyl, R$^{47}$-substituted or unsubstituted 4 to 8 membered heterocycloalkyl, R$^{47}$-substituted or unsubstituted C$_6$-C$_{10}$ aryl, or R$^{47}$-substituted or unsubstituted 5 to 9 membered heteroaryl.

R$^{47}$ is independently halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC═(O)NHNH$_2$, R$^{48}$-substituted or unsubstituted alkyl, R$^{48}$-substituted or unsubstituted heteroalkyl, R$^{48}$-substituted or unsubstituted cycloalkyl, R$^{48}$ substituted or unsubstituted heterocycloalkyl, R$^{48}$-substituted or unsubstituted aryl, or R$^{48}$-substituted or unsubstituted heteroaryl.

R$^{48}$ is independently halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC═(O)NHNH$_2$, R$^{49}$-substituted or unsubstituted alkyl, R$^{49}$-substituted or unsubstituted heteroalkyl, R$^{49}$-substituted or unsubstituted cycloalkyl, R$^{49}$-substituted or unsubstituted heterocycloalkyl, R$^{49}$-substituted or unsubstituted aryl, or R$^{49}$-substituted or unsubstituted heteroaryl.

In some embodiments of the compounds provided herein, R$^{11}$ is hydrogen, R$^{50}$-substituted or unsubstituted alkyl, R$^{50}$-substituted or unsubstituted heteroalkyl, R$^{50}$-substituted or unsubstituted cycloalkyl, R$^{50}$-substituted or unsubstituted heterocycloalkyl, R$^{50}$-substituted or unsubstituted aryl, or R$^{50}$-substituted or unsubstituted heteroaryl.

R$^{50}$ is independently halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC═(O)NHNH$_2$, R$^{51}$-substituted or unsubstituted alkyl, R$^{51}$-substituted or unsubstituted heteroalkyl, R$^{51}$-substituted or unsubstituted cycloalkyl, R$^{51}$ substituted or unsubstituted heterocycloalkyl, R$^{51}$-substituted or unsubstituted aryl, or R$^{51}$-substituted or unsubstituted heteroaryl.

R$^{51}$ is independently halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC═(O)NHNH$_2$, R$^{52}$-substituted or unsubstituted alkyl, R$^{52}$-substituted or unsubstituted heteroalkyl, R$^{52}$-substituted or unsubstituted cycloalkyl, R$^{52}$-substituted or unsubstituted heterocycloalkyl, R$^{52}$-substituted or unsubstituted aryl, or R$^{52}$-substituted or unsubstituted heteroaryl.

In some embodiments of the compounds provided herein, R$^{12}$ is hydrogen, R$^{53}$-substituted or unsubstituted alkyl, R$^{53}$-substituted or unsubstituted heteroalkyl, R$^{53}$-substituted or unsubstituted cycloalkyl, R$^{53}$-substituted or unsubstituted heterocycloalkyl, R$^{53}$-substituted or unsubstituted aryl, or R$^{53}$-substituted or unsubstituted heteroaryl.

R$^{53}$ is independently halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC═(O)NHNH$_2$, R$^{54}$-substituted or unsubstituted alkyl, R$^{54}$-substituted or unsubstituted heteroalkyl, R$^{54}$-substituted or unsubstituted cycloalkyl, R$^{54}$ substituted or unsubstituted heterocycloalkyl, R$^{54}$-substituted or unsubstituted aryl, or R$^{54}$-substituted or unsubstituted heteroaryl.

R$^{54}$ is independently halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC═(O)NHNH$_2$, R$^{55}$-substituted or unsubstituted alkyl, R$^{55}$-substituted or unsubstituted heteroalkyl, R$^{55}$-substituted or unsubstituted cycloalkyl, R$^{55}$-substituted or unsubstituted heterocycloalkyl, R$^{55}$-substituted or unsubstituted aryl, or R$^{55}$-substituted or unsubstituted heteroaryl.

In some embodiments of the compounds provided herein, R$^{13}$ is hydrogen, R$^{56}$-substituted or unsubstituted alkyl, R$^{56}$-substituted or unsubstituted heteroalkyl, R$^{56}$-substituted or unsubstituted cycloalkyl, R$^{56}$-substituted or unsubstituted heterocycloalkyl, $R^{56}$-substituted or unsubstituted aryl, or $R^{56}$-substituted or unsubstituted heteroaryl.

$R^{56}$ is independently halogen, $-CF_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $R^{57}$-substituted or unsubstituted alkyl, $R^{57}$-substituted or unsubstituted heteroalkyl, $R^{57}$-substituted or unsubstituted cycloalkyl, $R^{57}$ substituted or unsubstituted heterocycloalkyl, $R^{57}$-substituted or unsubstituted aryl, or $R^{57}$-substituted or unsubstituted heteroaryl.

$R^{57}$ is independently halogen, $-CF_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $R^{58}$-substituted or unsubstituted alkyl, $R^{58}$-substituted or unsubstituted heteroalkyl, $R^{58}$-substituted or unsubstituted cycloalkyl, $R^{58}$-substituted or unsubstituted heterocycloalkyl, $R^{58}$-substituted or unsubstituted aryl, or $R^{58}$-substituted or unsubstituted heteroaryl.

In another embodiment of the compounds provided herein, $R^{14}$ is hydrogen, $R^{59}$-substituted or unsubstituted alkyl, $R^{59}$-substituted or unsubstituted heteroalkyl, $R^{59}$-substituted or unsubstituted cycloalkyl, $R^{59}$-substituted or unsubstituted heterocycloalkyl, $R^{59}$-substituted or unsubstituted aryl, or $R^{59}$-substituted or unsubstituted heteroaryl.

$R^{59}$ is independently halogen, $-CF_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $R^{60}$-substituted or unsubstituted alkyl, $R^{60}$-substituted or unsubstituted heteroalkyl, $R^{60}$-substituted or unsubstituted cycloalkyl, $R^{60}$-substituted or unsubstituted heterocycloalkyl, $R^{60}$-substituted or unsubstituted aryl, or $R^{60}$-substituted or unsubstituted heteroaryl.

$R^{60}$ independently is halogen, $-CF_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $R^{61}$-substituted or unsubstituted alkyl, $R^{61}$-substituted or unsubstituted heteroalkyl, $R^{61}$-substituted or unsubstituted cycloalkyl, $R^{61}$-substituted or unsubstituted heterocycloalkyl, $R^{61}$-substituted or unsubstituted aryl, or $R^{61}$-substituted or unsubstituted heteroaryl.

In a further embodiment of the compounds provided herein, $R^{15}$ is hydrogen, $R^{62}$-substituted or unsubstituted alkyl, $R^{62}$-substituted or unsubstituted heteroalkyl, $R^{62}$-substituted or unsubstituted cycloalkyl, $R^{62}$-substituted or unsubstituted heterocycloalkyl, $R^{62}$-substituted or unsubstituted aryl, or $R^{62}$-substituted or unsubstituted heteroaryl.

$R^{62}$ is independently halogen, $-CF_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $R^{63}$-substituted or unsubstituted alkyl, $R^{63}$-substituted or unsubstituted heteroalkyl, $R^{63}$-substituted or unsubstituted cycloalkyl, $R^{63}$-substituted or unsubstituted heterocycloalkyl, $R^{63}$-substituted or unsubstituted aryl, or $R^{63}$-substituted or unsubstituted heteroaryl.

$R^{63}$ independently is halogen, $-CF_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $R^{64}$-substituted or unsubstituted alkyl, $R^{64}$-substituted or unsubstituted heteroalkyl, $R^{64}$-substituted or unsubstituted cycloalkyl, $R^{64}$-substituted or unsubstituted heterocycloalkyl, $R^{64}$-substituted or unsubstituted aryl, or $R^{64}$-substituted or unsubstituted heteroaryl.

In some embodiments of the compounds provided herein, $R^{16}$ is independently hydrogen, $R^{65}$-substituted or unsubstituted alkyl, $R^{65}$-substituted or unsubstituted heteroalkyl, $R^{65}$-substituted or unsubstituted cycloalkyl, $R^{65}$-substituted or unsubstituted heterocycloalkyl, $R^{65}$-substituted or unsubstituted aryl, or $R^{65}$-substituted or unsubstituted heteroaryl.

$R^{65}$ is independently halogen, $-CF_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $R^{66}$-substituted or unsubstituted alkyl, $R^{66}$-substituted or unsubstituted heteroalkyl, $R^{66}$-substituted or unsubstituted cycloalkyl, $R^{66}$-substituted or unsubstituted heterocycloalkyl, $R^{66}$-substituted or unsubstituted aryl, or $R^{66}$-substituted or unsubstituted heteroaryl.

$R^{66}$ is independently halogen, $-CF_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $R^{67}$-substituted or unsubstituted alkyl, $R^{67}$-substituted or unsubstituted heteroalkyl, $R^{67}$-substituted or unsubstituted cycloalkyl, $R^{67}$-substituted or unsubstituted heterocycloalkyl, $R^{67}$-substituted or unsubstituted aryl, or $R^{67}$-substituted or unsubstituted heteroaryl.

In some embodiments of the compounds provided herein, $R^{17}$ is independently hydrogen, $R^{68}$-substituted or unsubstituted alkyl, $R^{68}$-substituted or unsubstituted heteroalkyl, $R^{68}$-substituted or unsubstituted cycloalkyl, $R^{68}$-substituted or unsubstituted heterocycloalkyl, $R^{68}$-substituted or unsubstituted aryl, or $R^{68}$-substituted or unsubstituted heteroaryl.

$R^{68}$ is independently halogen, $-CF_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $R^{69}$-substituted or unsubstituted alkyl, $R^{69}$-substituted or unsubstituted heteroalkyl, $R^{69}$-substituted or unsubstituted cycloalkyl, $R^{69}$-substituted or unsubstituted heterocycloalkyl, $R^{69}$-substituted or unsubstituted aryl, or $R^{69}$-substituted or unsubstituted heteroaryl.

$R^{69}$ is independently halogen, $-CF_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $R^{70}$-substituted or unsubstituted alkyl, $R^{70}$-substituted or unsubstituted heteroalkyl, $R^{70}$-substituted or unsubstituted cycloalkyl, $R^{70}$-substituted or unsubstituted heterocycloalkyl, $R^{70}$-substituted or unsubstituted aryl, or $R^{70}$-substituted or unsubstituted heteroaryl.

In some embodiments of the compounds provided herein, $R^{18}$ is hydrogen, $R^{71}$-substituted or unsubstituted alkyl, $R^{71}$-substituted or unsubstituted heteroalkyl, $R^{71}$-substituted or unsubstituted cycloalkyl, $R^{71}$-substituted or unsubstituted heterocycloalkyl, $R^{71}$-substituted or unsubstituted aryl, or $R^{71}$-substituted or unsubstituted heteroaryl.

$R^{71}$ is independently halogen, $-CF_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $R^{72}$-substituted or unsubstituted alkyl, $R^{72}$-substituted or unsubstituted heteroalkyl, $R^{72}$-substituted or unsubstituted cycloalkyl, $R^{72}$ substituted or unsubstituted heterocycloalkyl, $R^{72}$-substituted or unsubstituted aryl, or $R^{72}$-substituted or unsubstituted heteroaryl.

$R^{72}$ is independently halogen, $-CF_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $R^{73}$-substituted or unsubstituted alkyl, $R^{73}$-substituted or unsubstituted heteroalkyl, $R^{73}$-substituted or unsubstituted cycloalkyl, $R^{73}$-substituted or unsubstituted heterocycloalkyl, $R^{73}$-substituted or unsubstituted aryl, or $R^{73}$-substituted or unsubstituted heteroaryl.

In some embodiments of the compounds provided herein, $R^{22}$, $R^{25}$, $R^{28}$, $R^{31}$, $R^{34}$, $R^{37}$, $R^{40}$, $R^{43}$, $R^{46}$, $R^{49}$, $R^{52}$, $R^{55}$, $R^{58}$, $R^{61}, R^{64}, R^{67}, R^{70}, R^{73}$, are independently hydrogen, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC$=$(O)NHNH_2$, unsubstituted alkyl, unsubstituted heteroalkyl, unsubstituted cycloalkyl, unsubstituted heterocycloalkyl, unsubstituted aryl, or unsubstituted heteroaryl.

In some embodiments of the compounds provided herein, $L^1$ is $R^{L20}$-substituted or unsubstituted alkylene, $R^{L20}$-substituted or unsubstituted heteroalkylene, or $R^{L20}$-substituted or unsubstituted arylene.

$R^{L20}$ is independently halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC$=$(O)NHNH_2$, $R^{L21}$-substituted or unsubstituted alkyl, $R^{L21}$-substituted or unsubstituted heteroalkyl, $R^{L21}$-substituted or unsubstituted cycloalkyl, $R^{L21}$-substituted or unsubstituted heterocycloalkyl, $R^{L21}$-substituted or unsubstituted aryl, or $R^{L21}$-substituted or unsubstituted heteroaryl.

$R^{L21}$ is independently halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC$=$(O)NHNH_2$, $R^{L22}$-substituted or unsubstituted alkyl, $R^{L22}$-substituted or unsubstituted heteroalkyl, $R^{L22}$-substituted or unsubstituted cycloalkyl, $R^{L22}$-substituted or unsubstituted heterocycloalkyl, $R^{L22}$-substituted or unsubstituted aryl, or $R^{L22}$-substituted or unsubstituted heteroaryl.

In some embodiments of the compounds provided herein, $L^2$ is a bond, —NH—, —$N(R^{L23a})$—, $R^{L23}$-substituted or unsubstituted alkylene, or $R^{L23}$-substituted or unsubstituted heteroalkylene.

$R^{L23}$ is independently halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC$=$(O)NHNH_2$, $R^{L24}$-substituted or unsubstituted alkyl, $R^{L24}$-substituted or unsubstituted heteroalkyl, $R^{L24}$-substituted or unsubstituted cycloalkyl, $R^{L24}$-substituted or unsubstituted heterocycloalkyl, $R^{L24}$-substituted or unsubstituted aryl, or $R^{L24}$-substituted or unsubstituted heteroaryl.

$R^{L23a}$ is independently halogen, —$CF_3$, —COOH, —$CONH_2$, $R^{L24}$-substituted or unsubstituted alkyl, $R^{L24}$-substituted or unsubstituted heteroalkyl, $R^{L24}$-substituted or unsubstituted cycloalkyl, $R^{L24}$-substituted or unsubstituted heterocycloalkyl, $R^{L24}$-substituted or unsubstituted aryl, or $R^{L24}$ substituted or unsubstituted heteroaryl.

$R^{L24}$ is independently halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC$=$(O)NHNH_2$, $R^{L25}$-substituted or unsubstituted alkyl, $R^{L25}$-substituted or unsubstituted heteroalkyl, $R^{L25}$-substituted or unsubstituted cycloalkyl, $R^{L25}$-substituted or unsubstituted heterocycloalkyl, $R^{L25}$-substituted or unsubstituted aryl, or $R^{L25}$-substituted or unsubstituted heteroaryl.

In some embodiments of the compounds provided herein, $R^{L22}$ and $R^{L25}$ are independently hydrogen, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC$=$(O)NHNH_2$, unsubstituted alkyl, unsubstituted heteroalkyl, unsubstituted cycloalkyl, unsubstituted heterocycloalkyl, unsubstituted aryl, or unsubstituted heteroaryl.

In some embodiments, the compound is any one of the compounds in the Examples section below, FIG. 5, FIG. 6, Sulfonamide boronic acids column of Table 1, Table 5, Table 7, or Table 8.

In some embodiments, the present compounds are not subject to degradation by β-lactamases, to which they are chemically inert, or upregulation of these enzymes, unlike a classical β-lactam-based inhibitor, like clavulanate.

In some embodiments, the new sulfonamide boronic acids derived from the conversion of the canonical carboxamide retain substantial inhibition activity against β-lactamases. In other embodiments, they rescue antibiotic resistance when used in combination with third generation antibiotics in bacterial cell cultures. In other embodiments the geometry of the inhibitors provided herein scramble the SAR observed in the analog carboxamides.

A favorable change in the SAR was observed for the smaller compounds of this study. The most substantial change in activity was observed for compound 3, which has a $K_i$ of 789 nM against AmpC. Its exact carboxamide analog 3c is 23-fold less potent (18.5 µM). The high affinity of 3 corresponds to a ligand efficiency of 0.91, placing it among the most efficient of enzyme inhibitors. Given the simplicity of this inhibitor, it seems clear that its improved affinity can be attributed to the advantages of the sulfonamide versus the carboxamide group in the AmpC site—this in turn may reflect the improved hydrogen bonds in this site owing to differences in polarity and geometry. This advantage was maintained during the SAR development among the smaller sulfonamide analogs, with potency improving 11-fold in compound 4 ($K_i$ 70 nM) and by another three-fold in compound 9 ($K_i$ 25 nM). The X-ray complexes of these inhibitors underscore the favorable hydrogen bonds made between them and canonical recognition residues.

We observed another change in the SAR when we tested compounds 16 and 17, having a benzyl and m-carboxybenzyl as $R_2$ group, respectively. In the carboxamide boronic acids, adding a m-carboxybenzyl improved affinity eight-fold from compound 10c to 17c. In our sulfonamide series, the same modification (compound 4 to 17) leads to a six-fold drop in potency. In the structure of the AmpC/17 complex, the sulfonamide hydrogen bonds have been completely disrupted and rearranged versus those made by 4 and 9 (FIG. 5E). To understand the flip of the sulfonamide, we modeled compound 17 in the conformation observed for compound 4 (FIG. 5F). The protein-inhibitor interactions in this model looked quite reasonable, but the ligand internal interactions were strained, with the distance of the aliphatic carbon in the m-carboxybenzyl group very close to one of the sulfonamide oxygens (3.0 Å). We reasoned that internal 1,5 repulsion between those two atoms could force the reorientation of the sulfonamide. We therefore calculated internal energies for both the model and the crystal structure of compound 17 using the semi-empirical QM method AMSOL.[41] The internal energy of the ligand alone in the crystal structure conformation (−90.89 kcal/mol) was substantially lower than the internal energy of the modeled ligand (−55.08 kcal/mol), consistent with the internal strain hypothesis.

The unexpected SAR of these inhibitors suggests that we cannot simply adopt lessons learned from earlier carboxamide series. Perhaps the most encouraging observation to emerge is that sulfonamide boronic acids with small side chains are very active against AmpC and can substantially reverse antibiotic resistance in bacterial cell culture.

In another aspect, a compound is provided having the formula:

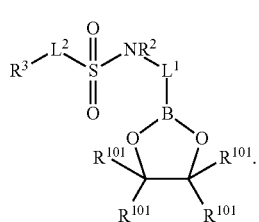
(IIa)

$L^1$, $L^2$, $R^2$, and $R^3$ are as described herein (e.g. Formula (I), (III), (V), (VII), (IX), (XI), (XIII), (XIV), (XVII), (XVIII), (XXIa), (XXIb), (XXIIIa), or (XXIIIb), including embodiments).

$R^{101}$ is independently hydrogen, substituted or unsubstituted $C_1$-$C_{12}$ alkyl, substituted or unsubstituted $C_3$-$C_{12}$ cycloalkyl, or substituted or unsubstituted $C_6$-$C_{10}$ aryl. Two adjacent $R^{101}$ substituents are optionally joined to form a substituted or unsubstituted cycloalkyl, substituted or unsubstituted heterocycloalkyl, substituted or unsubstituted aryl, or substituted or unsubstituted heteroaryl.

In some embodiments of the compound of Formula (IIa), the compound has a Formula selected from:

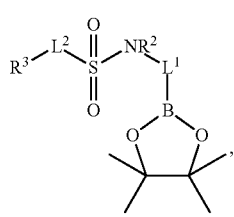
(IIb)

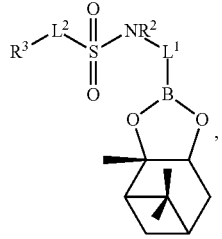
(IIc)

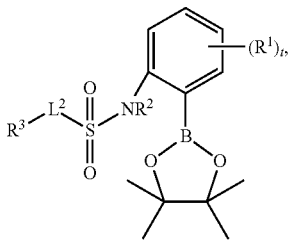
(IVa)

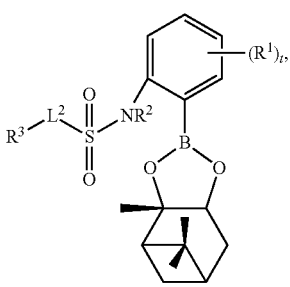
(IVb)

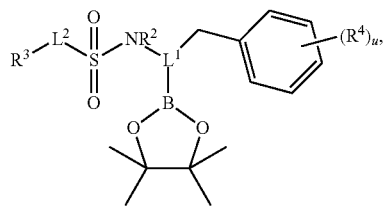
(VIa)

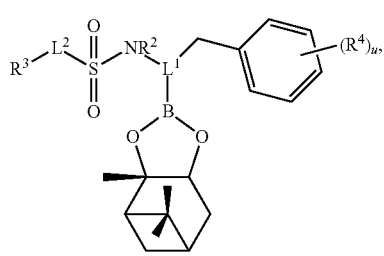
(VIb)

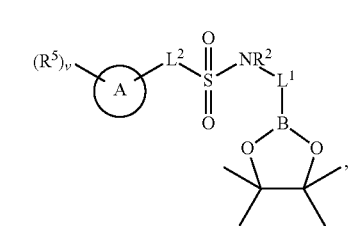
(VIIIa)

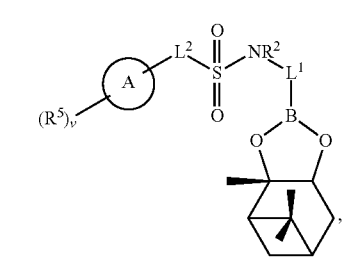
(VIIIb)

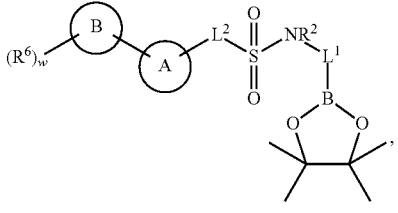
(Xa)

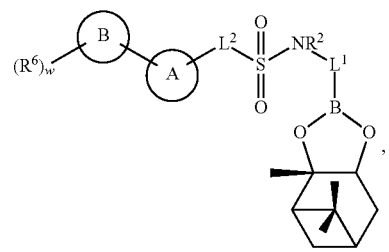
(Xb)

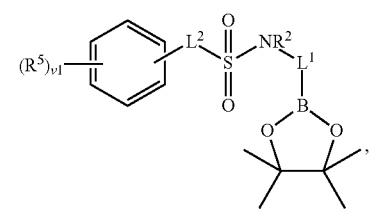
(XIIa)

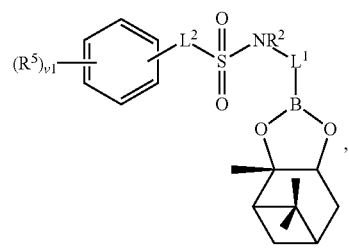
(XIIb)
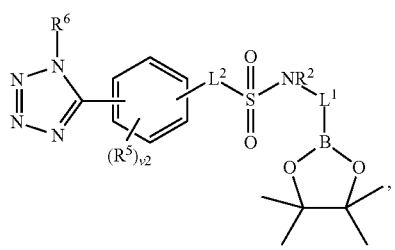
(XVa)
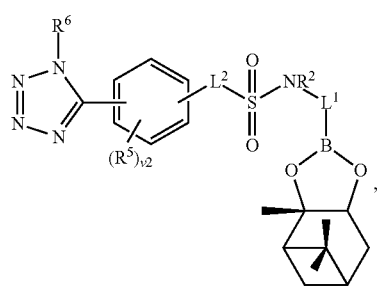
(XVb)
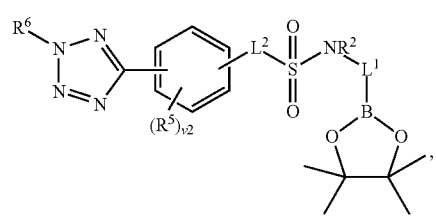
(XVIa)
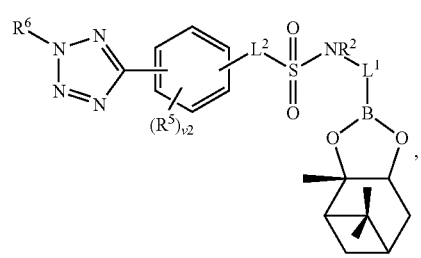
(XVIb)
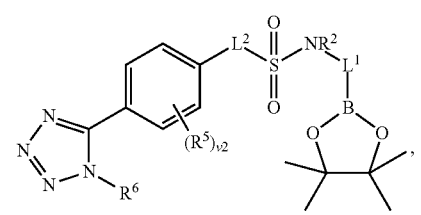
(XIXa)
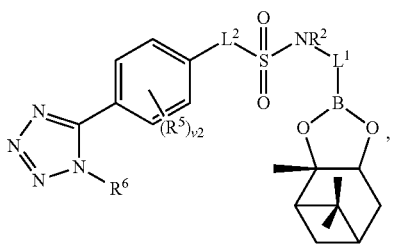
(XIXb)
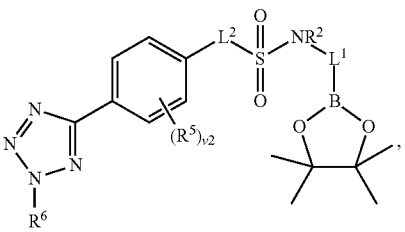
(XXa)
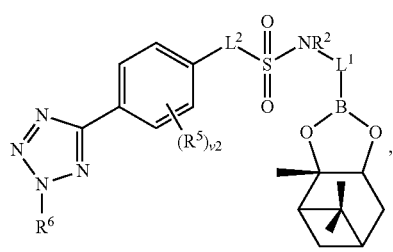
(XXb)
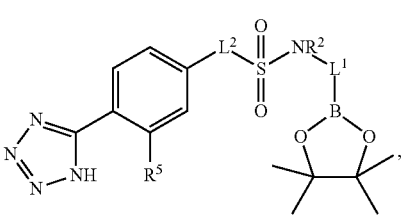
(XXIIa)
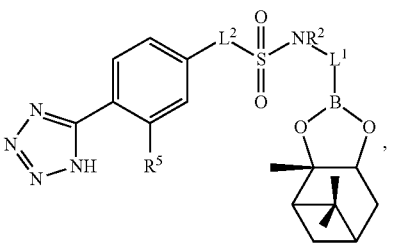
(XXIIb)
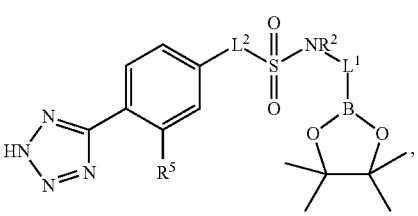
(XXIIc)

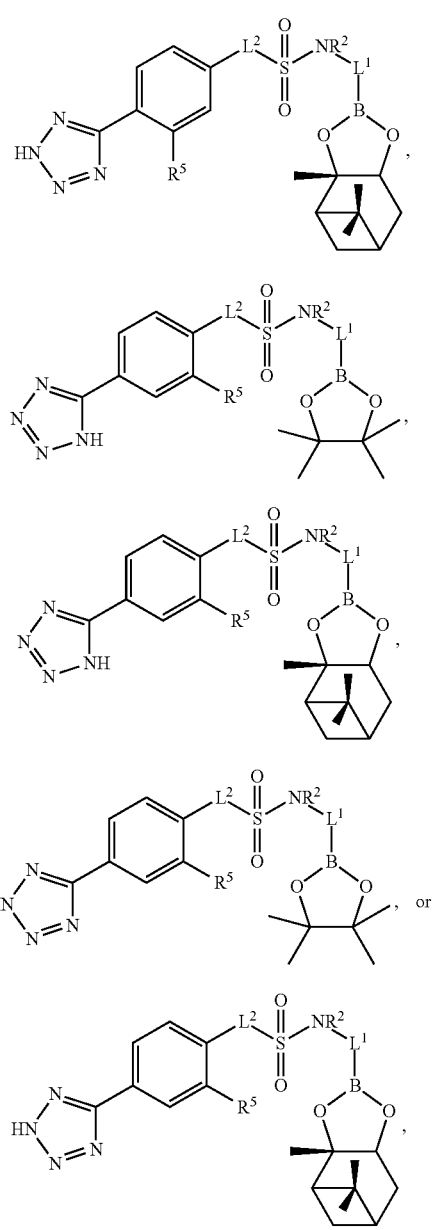

wherein $L^1$, $L^2$, t, u, v, v1, v2, w, ring A, ring B, $R^1$, $R^2$, $R^3$, $R^4$, $R^5$, and $R^6$ are as described herein (e.g. Formula (I), (III), (V), (VII), (IX), or (XI), including embodiments).

III. Methods of Treatment

In a fourth aspect, a method of treating a disease in a patient in need of such treatment is provided, the method includes administering a therapeutically effective amount of a compound as described herein (e.g. Formula (I), (III), (V), (VII), (IX), (XI), (XIII), (XIV), (XVII), (XVIII), (XXIa), (XXIb), (XXIIIa), or (XXIIIb), including embodiments, or as described in the Example section below or as shown in Table 7). In some embodiments, the disease is an infectious disease. In some embodiments, the disease is an infectious disease mediated by a bacterium. In some embodiments, the disease is an infectious disease caused by a bacterium. In some embodiments, the disease is a bacterial infectious disease. In further embodiments, the bacterium is resistant to an antibiotic. In further embodiments, the antibiotic is a beta-lactam containing antibiotic. In some embodiments of the method of treating a disease, the bacterium is a gram negative bacterium. In some embodiments of the method of treating a disease, the bacterium is a gram positive bacterium. In some embodiments of the method of treating a disease in a patient in need of such treatment, the method includes administering a therapeutically effective amount of a compound as described herein (e.g. Formula (I), (III), (V), (VII), (IX), (XI), (XIII), (XIV), (XVII), (XVIII), (XXIa), (XXIb), (XXIIIa), or (XXIIIb), including embodiments, or as described in the Example section below or as shown in Table 7), wherein the compound is selected from a set of compounds having the Formula (IIa), (IIb), (IIc), (IVa), (IVb), (VIa), (VIb), (VIIIa), (VIIIb), (Xa), (Xb), (XIIa), (XIIb), (XVa), (XVb), (XVIa), (XVIb), (XIXa), (XIXb), (XXa), (XXb), (XXIIa), (XXIIb), (XXIIc), (XXIId), (XXIVa) (XXIVb), (XXIVc) or (XXIVd), including embodiments.

In further embodiments of the method of treating a disease, the genera of the bacterium is selected from *Stenotrophomonas, Clostridium, Acinetobacter, Bordetella, Borrelia, Brucella, Campylobacter, Chlamydia, Chlamydophila, Clostridium, Corynebacterium, Enterococcus, Escherichia, Francisella, Haemophilus, Helicobacter, Legionella, Leptospira, Listeria, Mycobacterium, Mycoplasma, Neisseria, Pseudomonas, Rickettsia, Salmonella, Shigella, Staphylococcus, Streptococcus, Treponema, Vibrio, Klebsiella, Enterobacter, Citrobacter*, or *Yersinia*. In further embodiments of the method of treating a disease, the bacteria is selected from *Stenotrophomonas maltophilia, Clostridium difficile, Bacillus anthracis, Bordetella pertussis, Borrelia burgdorferi, Brucella abortus, Brucella canis, Brucella melitensis, Brucella suis, Campylobacter jejuni, Chlamydia pneumoniae, Chlamydia trachomatis, Chlamydophila psittaci, Clostridium botulinum, Clostridium difficile, Clostridium perfringens, Clostridium tetani, Corynebacterium diphtheriae, Enterococcus faecalis, Enterococcus faecium, Escherichia coli*, Enterotoxigenic *Escherichia coli* (ETEC), Enteropathogenic *E. coli, E. coli* O157:H7, *Francisella tularensis, Haemophilus influenzae, Helicobacter pylori, Legionella pneumophila, Leptospira interrogans, Listeria monocytogenes, Mycobacterium leprae, Mycobacterium tuberculosis, Mycoplasma pneumoniae, Neisseria gonorrhoeae, Neisseria meningitidis, Pseudomonas aeruginosa, Rickettsia rickettsii, Salmonella typhi, Salmonella typhimurium, Shigella sonnei, Staphylococcus aureus, Staphylococcus epidermidis, Staphylococcus saprophyticus, Streptococcus agalactiae, Streptococcus pneumoniae, Streptococcus pyogenes, Treponema pallidum, Klebsiella pneumoniae, Enterobacter cloacae, Citrobacter freundii, Vibrio cholerae, Acinetobacter baumannii*, or *Yersinia pestis*. In further embodiments of the method of treating a disease, the bacteria is selected from a beta-lactam antibiotic resistant strain of *Stenotrophomonas maltophilia, Clostridium difficile, Bacillus anthracis, Bordetella pertussis, Borrelia burgdorferi, Brucella abortus, Brucella canis, Brucella melitensis, Brucella suis, Campylobacter jejuni, Chlamydia pneumoniae, Chlamydia trachomatis, Chlamydophila psittaci, Clostridium botulinum, Clostridium difficile, Clostridium perfringens, Clostridium tetani, Corynebacterium diphtheriae, Enterococcus faecalis, Enterococcus faecium, Escherichia coli*, Enterotoxigenic *Escherichia coli* (ETEC), Enteropathogenic *E. coli, E. coli* O157:H7, *Francisella tularensis, Haemophilus influenzae, Helicobacter pylori, Legionella pneumophila, Leptospira interrogans, Listeria monocytogenes, Mycobacterium leprae, Mycobacterium tuberculosis,*

*Mycoplasma pneumoniae, Neisseria gonorrhoeae, Neisseria meningitidis, Pseudomonas aeruginosa, Rickettsia rickettsii, Salmonella typhi, Salmonella typhimurium, Shigella sonnei, Staphylococcus aureus, Staphylococcus epidermidis, Staphylococcus saprophyticus, Streptococcus agalactiae, Streptococcus pneumoniae, Streptococcus pyogenes, Treponema pallidum, Vibrio cholerae, Klebsiella pneumoniae, Enterobacter cloacae, Citrobacter freundii, Acinetobacter baumannii* or *Yersinia pestis*. In some embodiments of the method of treating a disease, the disease is selected from Cutaneous anthrax, Pulmonary anthrax, Gastrointestinal anthrax, Whooping cough, bacterial pneumonia, Lyme disease, Brucellosis, Acute enteritis, Community-acquired respiratory infection, Nongonococcal urethritis (NGU), Lymphogranuloma venereum (LGV), Trachoma, Inclusion conjunctivitis of the newborn (ICN), Psittacosis, Botulism, Pseudomembranous colitis, Gas gangrene, Acute food poisoning, Anaerobic cellulitis, Tetanus, Diphtheria, Nosocomial infections, Urinary tract infections (UTI), Diarrhea, Meningitis in infants, Traveller's diarrhea, Diarrhea in infants, Hemorrhagic colitis, Hemolytic-uremic syndrome, Tularemia, Bacterial meningitis, Upper respiratory tract infections, Pneumonia, bronchitis, Peptic ulcer, gastric carcinoma, gastric B-cell lymphoma, Legionnaire's Disease, Pontiac fever, Leptospirosis, Listeriosis, Leprosy (Hansen's disease), Tuberculosis, *Mycoplasma* pneumonia, Gonorrhea, Ophthalmia neonatorum, Septic arthritis, Meningococcal disease, Waterhouse-Friderichsen syndrome, *Pseudomonas* infection, Bacteremia, endocarditis, Rocky mountain spotted fever, Typhoid fever type salmonellosis (dysentery, colitis), Salmonellosis, gastroenteritis, enterocolitis, Bacillary dysentery/Shigellosis, Coagulase-positive staphylococcal infections: Impetigo, Acute infective endocarditis, Septicemia, Necrotizing pneumonia, Toxinoses, Toxic shock syndrome, Staphylococcal food poisoning, Cystitis, Meningitis, septicemia, Endometritis, Opportunistic infections, Acute bacterial pneumonia, Otitis media, sinusitis, Streptococcal pharyngitis, Scarlet fever, Rheumatic fever, erysipelas, Puerperal fever, Necrotizing fasciitis, Syphilis, Congenital syphilis, Cholera, Plague, Bubonic plague, Pneumonic plague, Iraq war infection caused by *Acinetobacter baumannii* (i.e. Iraq war-related *Acinetobacter baumannii* infection), necrotizing fasciitis, tuberculosis, hospital-acquired pneumonia, gastroenteritis, nosocomial infection, bacteremia, or sepsis. In some embodiments of the method of treating a disease, the disease is a nosocomial infection. In some embodiments of the method of treating a disease, the disease is ventilator associated pneumonia. In some embodiments of the method of treating a disease, the disease is bacteremia.

In some embodiments of the method of treating a disease, a compound as described herein (e.g. Formula (I), (III), (V), (VII), (IX), (XI), (XIII), (XIV), (XVII), (XVIII), (XXIa), (XXIb), (XXIIIa), or (XXIIIb), including embodiments, or as described in the Example section below or as shown in Table 7), is co-administered with an antibiotic. In some embodiments, the antibiotic is a beta-lactam containing antibiotic. In some embodiments, the antibiotic is a cephalosporin. In some embodiments, the cephalosporin is a first generation cephalosporin. In some embodiments, the cephalosporin is a second generation cephalosporin. In some embodiments, the cephalosporin is a third generation cephalosporin. In some embodiments, the cephalosporin is a fourth generation cephalosporin. In some embodiments, the cephalosporin is a fifth generation cephalosporin. In some embodiments, the cephalosporin is a sixth generation cephalosporin. In some embodiments, the antibiotic is a penicillin. In some embodiments, the antibiotic is a carbapenem.

In a fifth aspect, a method of inhibiting the growth of a bacterium in a patient is provided, the method includes administering a therapeutically effective amount of a compound as described herein (e.g. Formula (I), (III), (V), (VII), (IX), (XI), (XIII), (XIV), (XVII), (XVIII), (XXIa), (XXIb), (XXIIIa), or (XXIIIb), including embodiments, or as described in the Example section below or as shown in Table 7). In some embodiments of the method of inhibiting the growth of a bacterium in a patient, the bacterium is killed. In some embodiments of the method of inhibiting the growth of a bacterium in a patient, replication of the bacterium is slowed. In some embodiments of the method of inhibiting the growth of a bacterium in a patient, the bacterium is a gram negative bacterium. In some embodiments of the method of inhibiting the growth of a bacterium in a patient, the bacterium is a gram positive bacterium. In some embodiments of the method of inhibiting the growth of a bacterium in a patient, the method includes administering a therapeutically effective amount of a compound as described herein (e.g. Formula (I), (III), (V), (VII), (IX), (XI), (XIII), (XIV), (XVII), (XVIII), (XXIa), (XXIb), (XXIIIa), or (XXIIIb), including embodiments, or as described in the Example section below or as shown in Table 7), wherein the compound is selected from a set of compounds having the Formula (IIa), (IIb), (IIc), (IVa), (IVb), (VIa), (VIb), (VIIIa), (VIIIb), (Xa), (Xb), (XIIa), (XIIb), (XVa), (XVb), (XVIa), (XVIb), (XIXa), (XIXb), (XXa), (XXb), (XXIIa), (XXIIb), (XXIIc), (XXIId), (XXIVa) (XXIVb), (XXIVc) or (XXIVd), including embodiments.

In further embodiments of the method of inhibiting the growth of a bacterium in a patient, the genera of the bacterium is selected from *Stenotrophomonas, Clostridium, Acinetobacter, Bordetella, Borrelia, Brucella, Campylobacter, Chlamydia, Chlamydophila, Clostridium, Corynebacterium, Enterococcus, Escherichia, Francisella, Haemophilus, Helicobacter, Legionella, Leptospira, Listeria, Mycobacterium, Mycoplasma, Neisseria, Pseudomonas, Rickettsia, Salmonella, Shigella, Staphylococcus, Streptococcus, Treponema, Vibrio, Klebsiella, Enterobacter, Citrobacter*, or *Yersinia*. In further embodiments of the method of inhibiting the growth of a bacterium in a patient, the bacteria is selected from *Stenotrophomonas maltophilia, Clostridium difficile, Bacillus anthracis, Bordetella pertussis, Borrelia burgdorferi, Brucella abortus, Brucella canis, Brucella melitensis, Brucella suis, Campylobacter jejuni, Chlamydia pneumoniae, Chlamydia trachomatis, Chlamydophila psittaci, Clostridium botulinum, Clostridium difficile, Clostridium perfringens, Clostridium tetani, Corynebacterium diphtheriae, Enterococcus faecalis, Enterococcus faecium, Escherichia coli*, Enterotoxigenic *Escherichia coli* (ETEC), Enteropathogenic *E. coli, E. coli* O157:H7, *Francisella tularensis, Haemophilus influenzae, Helicobacter pylori, Legionella pneumophila, Leptospira interrogans, Listeria monocytogenes, Mycobacterium leprae, Mycobacterium tuberculosis, Mycoplasma pneumoniae, Neisseria gonorrhoeae, Neisseria meningitidis, Pseudomonas aeruginosa, Rickettsia rickettsii, Salmonella typhi, Salmonella typhimurium, Shigella sonnei, Staphylococcus aureus, Staphylococcus epidermidis, Staphylococcus saprophyticus, Streptococcus agalactiae, Streptococcus pneumoniae, Streptococcus pyogenes, Treponema pallidum, Vibrio cholerae, Klebsiella pneumoniae, Enterobacter cloacae, Citrobacter freundii, Acinetobacter baumannii*, or *Yersinia pestis*. In further embodiments of the method of inhibiting the growth of a bacterium in a patient, the bacteria is selected from a beta-lactam antibiotic resistant strain of *Stenotrophomonas maltophilia, Clostridium difficile, Bacillus anthracis, Bordetella pertussis, Borrelia burgdor-* feri, *Brucella abortus*, *Brucella canis*, *Brucella melitensis*, *Brucella suis*, *Campylobacter jejuni*, *Chlamydia pneumoniae*, *Chlamydia trachomatis*, *Chlamydophila psittaci*, *Clostridium botulinum*, *Clostridium difficile*, *Clostridium perfringens*, *Clostridium tetani*, *Corynebacterium diphtheriae*, *Enterococcus faecalis*, *Enterococcus faecium*, *Escherichia coli*, Enterotoxigenic *Escherichia coli* (ETEC), Enteropathogenic *E. coli*, *E. coli* O157:H7, *Francisella tularensis*, *Haemophilus influenzae*, *Helicobacter pylori*, *Legionella pneumophila*, *Leptospira interrogans*, *Listeria monocytogenes*, *Mycobacterium leprae*, *Mycobacterium tuberculosis*, *Mycoplasma pneumoniae*, *Neisseria gonorrhoeae*, *Neisseria meningitidis*, *Pseudomonas aeruginosa*, *Rickettsia rickettsii*, *Salmonella typhi*, *Salmonella typhimurium*, *Shigella sonnei*, *Staphylococcus aureus*, *Staphylococcus epidermidis*, *Staphylococcus saprophyticus*, *Streptococcus agalactiae*, *Streptococcus pneumoniae*, *Streptococcus pyogenes*, *Treponema pallidum*, *Vibrio cholerae*, *Klebsiella pneumoniae*, *Enterobacter cloacae*, *Citrobacter freundii*, *Acinetobacter baumannii*, or *Yersinia pestis*.

In a sixth aspect, a method of inhibiting the hydrolysis of a beta-lactam antibiotic by a bacterially expressed beta-lactamase in a patient is provided, the method includes administering an effective amount of a compound as described herein (e.g. Formula (I), (III), (V), (VII), (IX), (XI), (XIII), (XIV), (XVII), (XVIII), (XXIa), (XXIb), (XXIIIa), or (XXIIIb), including embodiments, or as described in the Example section below or as shown in Table 7). In some embodiments of the method of inhibiting the hydrolysis of a beta-lactam antibiotic by a bacterially expressed beta-lactamase in a patient, the bacterium is a gram negative bacterium. In some embodiments of the method of inhibiting the hydrolysis of a beta-lactam antibiotic by a bacterially expressed beta-lactamase in a patient, the bacterium is a gram positive bacterium. In some embodiments of the method of inhibiting the hydrolysis of a beta-lactam antibiotic by a bacterially expressed beta-lactamase in a patient, the method includes administering an effective amount of a compound as described herein (e.g. Formula (I), (III), (V), (VII), (IX), (XI), (XIII), (XIV), (XVII), (XVIII), (XXIa), (XXIb), (XXIIIa), or (XXIIIb), including embodiments, or as described in the Example section below or as shown in Table 7), wherein the compound is selected from a set of compounds having the Formula (IIa), (IIb), (IIc), (IVa), (IVb), (VIa), (VIb), (VIIIa), (VIIIb), (Xa), (Xb), (XIIa), (XIIb), (XVa), (XVb), (XVIa), (XVIb), (XIXa), (XIXb), (XXa), (XXb), (XXIIa), (XXIIb), (XXIIc), (XXIId), (XXIVa) (XXIVb), (XXIVc) or (XXIVd), including embodiments.

In further embodiments of the method of inhibiting the hydrolysis of a beta-lactam antibiotic by a bacterially expressed beta-lactamase in a patient, the genera of the bacterium is selected from *Stenotrophomonas*, *Clostridium*, *Acinetobacter*, *Bordetella*, *Borrelia*, *Brucella*, *Campylobacter*, *Chlamydia*, *Chlamydophila*, *Clostridium*, *Corynebacterium*, *Enterococcus*, *Escherichia*, *Francisella*, *Haemophilus*, *Helicobacter*, *Legionella*, *Leptospira*, *Listeria*, *Mycobacterium*, *Mycoplasma*, *Neisseria*, *Pseudomonas*, *Rickettsia*, *Salmonella*, *Shigella*, *Staphylococcus*, *Streptococcus*, *Treponema*, *Vibrio*, *Klebsiella*, *Enterobacter*, *Citrobacter*, or *Yersinia*. In further embodiments of the method of inhibiting the hydrolysis of a beta-lactam antibiotic by a bacterially expressed beta-lactamase in a patient, the bacteria is selected from *Stenotrophomonas maltophilia*, *Clostridium difficile*, *Bacillus anthracis*, *Bordetella pertussis*, *Borrelia burgdorferi*, *Brucella abortus*, *Brucella canis*, *Brucella melitensis*, *Brucella suis*, *Campylobacter jejuni*, *Chlamydia pneumoniae*, *Chlamydia trachomatis*, *Chlamydophila psittaci*, *Clostridium botulinum*, *Clostridium difficile*, *Clostridium perfringens*, *Clostridium tetani*, *Corynebacterium diphtheriae*, *Enterococcus faecalis*, *Enterococcus faecium*, *Escherichia coli*, Enterotoxigenic *Escherichia coli* (ETEC), Enteropathogenic *E. coli*, *E. coli* O157:H7, *Francisella tularensis*, *Haemophilus influenzae*, *Helicobacter pylori*, *Legionella pneumophila*, *Leptospira interrogans*, *Listeria monocytogenes*, *Mycobacterium leprae*, *Mycobacterium tuberculosis*, *Mycoplasma pneumoniae*, *Neisseria gonorrhoeae*, *Neisseria meningitidis*, *Pseudomonas aeruginosa*, *Rickettsia rickettsii*, *Salmonella typhi*, *Salmonella typhimurium*, *Shigella sonnei*, *Staphylococcus aureus*, *Staphylococcus epidermidis*, *Staphylococcus saprophyticus*, *Streptococcus agalactiae*, *Streptococcus pneumoniae*, *Streptococcus pyogenes*, *Treponema pallidum*, *Vibrio cholerae*, *Klebsiella pneumoniae*, *Enterobacter cloacae*, *Citrobacter freundii*, *Acinetobacter baumannii*, or *Yersinia pestis*. In further embodiments of the method of inhibiting the hydrolysis of a beta-lactam antibiotic by a bacterially expressed beta-lactamase in a patient, the bacteria is selected from a beta-lactam antibiotic resistant strain of *Stenotrophomonas maltophilia*, *Clostridium difficile*, *Bacillus anthracis*, *Bordetella pertussis*, *Borrelia burgdorferi*, *Brucella abortus*, *Brucella canis*, *Brucella melitensis*, *Brucella suis*, *Campylobacter jejuni*, *Chlamydia pneumoniae*, *Chlamydia trachomatis*, *Chlamydophila psittaci*, *Clostridium botulinum*, *Clostridium difficile*, *Clostridium perfringens*, *Clostridium tetani*, *Corynebacterium diphtheriae*, *Enterococcus faecalis*, *Enterococcus faecium*, *Escherichia coli*, Enterotoxigenic *Escherichia coli* (ETEC), Enteropathogenic *E. coli*, *E. coli* O157:H7, *Francisella tularensis*, *Haemophilus influenzae*, *Helicobacter pylori*, *Legionella pneumophila*, *Leptospira interrogans*, *Listeria monocytogenes*, *Mycobacterium leprae*, *Mycobacterium tuberculosis*, *Mycoplasma pneumoniae*, *Neisseria gonorrhoeae*, *Neisseria meningitidis*, *Pseudomonas aeruginosa*, *Rickettsia rickettsii*, *Salmonella typhi*, *Salmonella typhimurium*, *Shigella sonnei*, *Staphylococcus aureus*, *Staphylococcus epidermidis*, *Staphylococcus saprophyticus*, *Streptococcus agalactiae*, *Streptococcus pneumoniae*, *Streptococcus pyogenes*, *Treponema pallidum*, *Vibrio cholerae*, *Klebsiella pneumoniae*, *Enterobacter cloacae*, *Citrobacter freundii*, *Acinetobacter baumannii*, or *Yersinia pestis*. In some embodiments of the method of inhibiting the hydrolysis of a beta-lactam antibiotic by a bacterially expressed beta-lactamase in a patient, the beta-lactamase is a Class A beta-lactamase. In some embodiments of the method of inhibiting the hydrolysis of a beta-lactam antibiotic by a bacterially expressed beta-lactamase in a patient, the beta-lactamase is a Class B beta-lactamase. In some embodiments of the method of inhibiting the hydrolysis of a beta-lactam antibiotic by a bacterially expressed beta-lactamase in a patient, the beta-lactamase is a Class C beta-lactamase. In some embodiments of the method of inhibiting the hydrolysis of a beta-lactam antibiotic by a bacterially expressed beta-lactamase in a patient, the beta-lactamase is a Class D beta-lactamase.

In a seventh aspect, a method of reducing the therapeutically effective amount of an antibiotic necessary to treat a patient in need of such treatment is provided, the method includes administering an effective amount of a compound as described herein (e.g. Formula (I), (III), (V), (VII), (IX), (XI), (XIII), (XIV), (XVII), (XVIII), (XXIa), (XXIb), (XXIIIa), or (XXIIIb), including embodiments, or as described in the Example section below or as shown in Table 7). In some embodiments, the antibiotic is a penicillin. In some embodiments, the antibiotic is a cephalosporin. In some embodiments, the antibiotic is a cephamycin. In some embodiments, the antibiotic is a first-generation cephalosporin. In some embodiments, the antibiotic is a second-generation cephalosporin. In some embodiments, the antibiotic is a third-generation cephalosporin. In some embodiments, the b antibiotic is a fourth-generation cephalosporin. In some embodiments, the antibiotic is a fifth-generation cephalosporin. In some embodiments, the antibiotic is a sixth-generation cephalosporin. In some embodiments of the method of reducing the therapeutically effective amount of an antibiotic necessary to treat a patient in need of such treatment, the method includes administering an effective amount of a compound as described herein (e.g. Formula (I), (III), (V), (VII), (IX), (XI), (XIII), (XIV), (XVII), (XVIII), (XXIa), (XXIb), (XXIIIa), or (XXIIIb), including embodiments, or as described in the Example section below or as shown in Table 7), wherein the compound is selected from a set of compounds having the Formula (IIa), (IIb), (IIc), (IVa), (IVb), (VIa), (VIb), (VIIIa), (VIIIb), (Xa), (Xb), (XIIa), (XIIb), (XVa), (XVb), (XVIa), (XVIb), (XIXa), (XIXb), (XXa), (XXb), (XXIIa), (XXIIb), (XXIIc), (XXIId), (XXIVa) (XXIVb), (XXIVc) or (XXIVd), including embodiments.

In some embodiments of a method of reducing the therapeutically effective amount of an antibiotic necessary to treat a patient in need of such treatment, the antibiotic is selected from Cefacetrile (cephacetrile), Cefadroxil (cefadroxyl; Duricef), Cephalexin (cephalexin; Keflex), Cefaloglycin (cephaloglycin), Cefalonium (cephalonium), Cefaloridine (cephaloradine), Cefalotin (cephalothin; Keflin), Cefapirin (cephapirin; Cefadryl), Cefatrizine, Cefazaflur, Cefazedone, Cefazolin (cephazolin; Ancef, Kefzol), Cefradine (cephradine; Velosef), Cefroxadine, Ceftezole, Cefaclor (Ceclor, Distaclor, Keflor, Raniclor), Cefonicid (Monocid), Cefprozil (cefproxil; Cefzil), Cefuroxime (Zefu, Zinnat, Zinacef, Ceftin, Biofuroksym, Xorimax), Cefuzonam, Cefmetazole, Cefotetan, Cefoxitin, Carbacephems, loracarbef (Lorabid); Cephamycins: cefbuperazone, cefmetazole (Zefazone), cefminox, cefotetan (Cefotan), cefoxitin (Mefoxin), Cefcapene, Cefdaloxime, Cefdinir (Zinir, Omnicef, Kefnir), Cefditoren, Cefetamet, Cefixime (Zifi, Suprax), Cefmenoxime, Cefodizime, Cefotaxime (Claforan), Cefovecin (Convenia), Cefpimizole, Cefpodoxime (Vantin, PECEF), Cefteram, Ceftibuten (Cedax), Ceftiofur, Ceftiolene, Ceftizoxime (Cefizox), Ceftriaxone (Rocephin), Cefoperazone (Cefobid), Ceftazidime (Fortum, Fortaz), Oxacephems: latamoxef (moxalactam), Cefclidine, Cefepime (Maxipime), Cefluprenam, Cefoselis, Cefozopran, Cefpirome (Cefrom), Cefquinome, Oxacephems, flomoxef, Ceftobiprole, Ceftaroline, Cefaloram, Cefaparole, Cefcanel, Cefedrolor, Cefempidone, Cefetrizole, Cefivitril, Cefmatilen, Cefmepidium, Cefoxazole, Cefrotil, Cefsumide, Ceftioxide, or Cefuracetime.

In some embodiments of a method of treating a disease in a patient, reducing the therapeutically effective amount of an antibiotic necessary to treat a patient in need of such treatment, inhibiting the hydrolysis of a beta-lactam antibiotic by a bacterially expressed beta-lactamase in a patient, or inhibiting the growth of a bacterium in a patient, as described herein, the method further includes administering a beta-lactam antibiotic to the patient. In some embodiments, the beta-lactam antibiotic is a penicillin. In some embodiments, the beta-lactam antibiotic is a cephalosporin. In some embodiments, the beta-lactam antibiotic is a cephamycin. In some embodiments, the beta-lactam antibiotic is a first-generation cephalosporin. In some embodiments, the beta-lactam antibiotic is a second-generation cephalosporin. In some embodiments, the beta-lactam antibiotic is a third-generation cephalosporin. In some embodiments, the beta-lactam antibiotic is a fourth-generation cephalosporin. In some embodiments, the beta-lactam antibiotic is a fifth-generation cephalosporin. In some embodiments, the beta-lactam antibiotic is a sixth-generation cephalosporin. In some embodiments, the antibiotic is selected from Cefacetrile (cephacetrile), Cefadroxil (cefadroxyl; Duricef), Cephalexin (cephalexin; Keflex), Cefaloglycin (cephaloglycin), Cefalonium (cephalonium), Cefaloridine (cephaloradine), Cefalotin (cephalothin; Keflin), Cefapirin (cephapirin; Cefadryl), Cefatrizine, Cefazaflur, Cefazedone, Cefazolin (cephazolin; Ancef, Kefzol), Cefradine (cephradine; Velosef), Cefroxadine, Ceftezole, Cefaclor (Ceclor, Distaclor, Keflor, Raniclor), Cefonicid (Monocid), Cefprozil (cefproxil; Cefzil), Cefuroxime (Zefu, Zinnat, Zinacef, Ceftin, Biofuroksym, Xorimax), Cefuzonam, Cefmetazole, Cefotetan, Cefoxitin, Carbacephems, loracarbef (Lorabid); Cephamycins: cefbuperazone, cefmetazole (Zefazone), cefminox, cefotetan (Cefotan), cefoxitin (Mefoxin), Cefcapene, Cefdaloxime, Cefdinir (Zinir, Omnicef, Kefnir), Cefditoren, Cefetamet, Cefixime (Zifi, Suprax), Cefmenoxime, Cefodizime, Cefotaxime (Claforan), Cefovecin (Convenia), Cefpimizole, Cefpodoxime (Vantin, PECEF), Cefteram, Ceftibuten (Cedax), Ceftiofur, Ceftiolene, Ceftizoxime (Cefizox), Ceftriaxone (Rocephin), Cefoperazone (Cefobid), Ceftazidime (Fortum, Fortaz), Oxacephems: latamoxef (moxalactam), Cefclidine, Cefepime (Maxipime), Cefluprenam, Cefoselis, Cefozopran, Cefpirome (Cefrom), Cefquinome, Oxacephems, flomoxef, Ceftobiprole, Ceftaroline, Cefaloram, Cefaparole, Cefcanel, Cefedrolor, Cefempidone, Cefetrizole, Cefivitril, Cefmatilen, Cefmepidium, Cefoxazole, Cefrotil, Cefsumide, Ceftioxide, or Cefuracetime.

In an eighth aspect, a kit is provided for treating a bacterial infectious disease including a compound as described herein (e.g. Formula (I), (III), (V), (VII), (IX), (XI), (XIII), (XIV), (XVII), (XVIII), (XXIa), (XXIb), (XXIIIa), or (XXIIIb), including embodiments, or as described in the Example section below or as shown in Table 7) and a beta-lactam containing antibiotic. In some embodiments of the kit for treating a bacterial infectious disease, the beta-lactam containing antibiotic is a penicillin. In some embodiments of the kit for treating a bacterial infectious disease, the beta-lactam containing antibiotic is a cephalosporin. In some embodiments, the beta-lactam antibiotic is selected from Cefacetrile (cephacetrile), Cefadroxil (cefadroxyl; Duricef), Cephalexin (cephalexin; Keflex), Cefaloglycin (cephaloglycin), Cefalonium (cephalonium), Cefaloridine (cephaloradine), Cefalotin (cephalothin; Keflin), Cefapirin (cephapirin; Cefadryl), Cefatrizine, Cefazaflur, Cefazedone, Cefazolin (cephazolin; Ancef, Kefzol), Cefradine (cephradine; Velosef), Cefroxadine, Ceftezole, Cefaclor (Ceclor, Distaclor, Keflor, Raniclor), Cefonicid (Monocid), Cefprozil (cefproxil; Cefzil), Cefuroxime (Zefu, Zinnat, Zinacef, Ceftin, Biofuroksym, Xorimax), Cefuzonam, Cefmetazole, Cefotetan, Cefoxitin, Carbacephems, loracarbef (Lorabid); Cephamycins: cefbuperazone, cefmetazole (Zefazone), cefminox, cefotetan (Cefotan), cefoxitin (Mefoxin), Cefcapene, Cefdaloxime, Cefdinir (Zinir, Omnicef, Kefnir), Cefditoren, Cefetamet, Cefixime (Zifi, Suprax), Cefmenoxime, Cefodizime, Cefotaxime (Claforan), Cefovecin (Convenia), Cefpimizole, Cefpodoxime (Vantin, PECEF), Cefteram, Ceftibuten (Cedax), Ceftiofur, Ceftiolene, Ceftizoxime (Cefizox), Ceftriaxone (Rocephin), Cefoperazone (Cefobid), Ceftazidime (Fortum, Fortaz), Oxacephems: latamoxef (moxalactam), Cefclidine, Cefepime (Maxipime), Cefluprenam, Cefoselis, Cefozopran, Cefpirome (Cefrom), Cefquinome, Oxacephems, flomoxef, Ceftobiprole, Ceftaroline. Additional cephems include Cefaloram, Cefaparole, Cefcanel, Cefedrolor, Cefempidone, Cefetrizole, Cefivitril, Cefmatilen, Cefmepidium, Cefoxazole, Cefrotil, Cefsumide, Ceftioxide, or Cefuracetime. In some embodiments of the kit for treating a bacterial infectious disease including a compound as described herein (e.g. Formula (I), (III), (V), (VII), (IX), (XI), (XIII), (XIV), (XVII), (XVIII), (XXIa), (XXIb), (XXIIIa), or (XXIIIb), including embodiments, or as described in the Example section below or as shown in Table 7) and a beta-lactam containing antibiotic, the compound is selected from a set of compounds having the Formula (IIa), (IIb), (IIc), (IVa), (IVb), (VIa), (VIb), (VIIIa), (VIIIb), (Xa), (Xb), (XIIa), (XIIb), (XVa), (XVb), (XVIa), (XVIb), (XIXa), (XIXb), (XXa), (XXb), (XXIIa), (XXIIb), (XXIIc), (XXIId), (XXIVa) (XXIVb), (XXIVc) or (XXIVd), including embodiments.

IV. Pharmaceutical Compositions

In a ninth aspect, a pharmaceutical composition is provided including a pharmaceutically acceptable excipient and a compound as described herein (e.g. Formula (I), (III), (V), (VII), (IX), (XI), (XIII), (XIV), (XVII), (XVIII), (XXIa), (XXIb), (XXIIIa), or (XXIIIb), including embodiments). In some embodiments of the pharmaceutical composition, the compound has Formula (XXIa) or (XXIb), including embodiments. In some embodiments of the pharmaceutical composition, the compound has Formula (XXIIIa) or (XXIIIb), including embodiments. In some embodiments of the pharmaceutical composition, the compound is a compound described in the Examples section below or shown in Table 7. In some embodiments, the pharmaceutical composition includes an antibiotic. In some embodiments, the antibiotic is a beta-lactam containing antibiotic. In some embodiments, the antibiotic is a penicillin. In some embodiments, the antibiotic is a cephalosporin. In some embodiments, the antibiotic is a cephamycin. In some embodiments, the antibiotic is a first-generation cephalosporin. In some embodiments, the antibiotic is a second-generation cephalosporin. In some embodiments, the antibiotic is a third-generation cephalosporin. In some embodiments, the antibiotic is a fourth-generation cephalosporin. In some embodiments, the antibiotic is a fifth-generation cephalosporin. In some embodiments, the antibiotic is a sixth-generation cephalosporin. In some embodiments of the pharmaceutical composition including a pharmaceutically acceptable excipient and a compound as described herein (e.g. Formula (I), (III), (V), (VII), (IX), (XI), (XIII), (XIV), (XVII), (XVIII), (XXIa), (XXIb), (XXIIIa), or (XXIIIb), including embodiments, or as described in the Example section below or as shown in Table 7), wherein the compound is selected from a set of compounds having the Formula (IIa), (IIb), (IIc), (IVa), (IVb), (VIa), (VIb), (VIIIa), (VIIIb), (Xa), (Xb), (XIIa), (XIIb), (XVa), (XVb), (XVIa), (XVIb), (XIXa), (XIXb), (XXa), (XXb), (XXIIa), (XXIIb), (XXIIc), (XXIId), (XXIVa) (XXIVb), (XXIVc) or (XXIVd), including embodiments.

In some embodiments of a pharmaceutical composition, the antibiotic is selected from Cefacetrile (cephacetrile), Cefadroxil (cefadroxyl; Duricef), Cephalexin (cephalexin; Keflex), Cefaloglycin (cephaloglycin), Cefalonium (cephalonium), Cefaloridine (cephaloradine), Cefalotin (cephalothin; Keflin), Cefapirin (cephapirin; Cefadryl), Cefatrizine, Cefazaflur, Cefazedone, Cefazolin (cephazolin; Ancef, Kefzol), Cefradine (cephradine; Velosef), Cefroxadine, Ceftezole, Cefaclor (Ceclor, Distaclor, Keflor, Raniclor), Cefonicid (Monocid), Cefprozil (cefproxil; Cefzil), Cefuroxime (Zefu, Zinnat, Zinacef, Ceftin, Biofuroksym, Xorimax), Cefuzonam, Cefmetazole, Cefotetan, Cefoxitin, Carbacephems, loracarbef (Lorabid); Cephamycins: cefbuperazone, cefmetazole (Zefazone), cefminox, cefotetan (Cefotan), cefoxitin (Mefoxin), Cefcapene, Cefdaloxime, Cefdinir (Zinir, Omnicef, Kefnir), Cefditoren, Cefetamet, Cefixime (Zifi, Suprax), Cefmenoxime, Cefodizime, Cefotaxime (Claforan), Cefovecin (Convenia), Cefpimizole, Cefpodoxime (Vantin, PECEF), Cefteram, Ceftibuten (Cedax), Ceftiofur, Ceftiolene, Ceftizoxime (Cefizox), Ceftriaxone (Rocephin), Cefoperazone (Cefobid), Ceftazidime (Fortum, Fortaz), Oxacephems: latamoxef (moxalactam), Cefclidine, Cefepime (Maxipime), Cefluprenam, Cefoselis, Cefozopran, Cefpirome (Cefrom), Cefquinome, Oxacephems, flomoxef, Ceftobiprole, Ceftaroline, Cefaloram, Cefaparole, Cefcanel, Cefedrolor, Cefempidone, Cefetrizole, Cefivitril, Cefmatilen, Cefmepidium, Cefoxazole, Cefrotil, Cefsumide, Ceftioxide, or Cefuracetime.

The pharmaceutical compositions include optical isomers, diastereomers, or pharmaceutically acceptable salts of the modulators disclosed herein. The compound included in the pharmaceutical composition may be covalently attached to a carrier moiety, as described above. Alternatively, the compound included in the pharmaceutical composition is not covalently linked to a carrier moiety.

The compounds of the invention can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation).

The compounds of the present invention can be prepared and administered in a wide variety of oral, parenteral and topical dosage forms. Oral preparations include tablets, pills, powder, dragees, capsules, liquids, lozenges, cachets, gels, syrups, slurries, suspensions, etc., suitable for ingestion by the patient. The compounds of the present invention can also be administered by injection, that is, intravenously, intramuscularly, intracutaneously, subcutaneously, intraduodenally, or intraperitoneally. Also, the compounds described herein can be administered by inhalation, for example, intranasally. Additionally, the compounds of the present invention can be administered transdermally. It is also envisioned that multiple routes of administration (e.g., intramuscular, oral, transdermal) can be used to administer the compounds of the invention. Accordingly, the present invention also provides pharmaceutical compositions comprising a pharmaceutically acceptable excipient and one or more compounds of the invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substance, that may also act as diluents, flavoring agents, binders, preservatives, tablet disintegrating agents, or an encapsulating material.

In powders, the carrier is a finely divided solid in a mixture with the finely divided active component (e.g. a compound provided herein. In tablets, the active component is mixed with the carrier having the necessary binding properties in suitable proportions and compacted in the shape and size desired. The powders and tablets preferably contain from 5% to 70% of the active compound.

Suitable solid excipients include, but are not limited to, magnesium carbonate; magnesium stearate; talc; pectin; dextrin; starch; tragacanth; a low melting wax; cocoa butter; carbohydrates; sugars including, but not limited to, lactose, sucrose, mannitol, or sorbitol, starch from corn, wheat, rice, potato, or other plants; cellulose such as methyl cellulose, hydroxypropylmethyl-cellulose, or sodium carboxymethylcellulose; and gums including arabic and tragacanth; as well as proteins including, but not limited to, gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations of the invention can also be used orally using, for example, push-fit capsules made of gelatin, as well as soft, sealed capsules made of gelatin and a coating such as glycerol or sorbitol.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

When parenteral application is needed or desired, particularly suitable admixtures for the compounds of the invention are injectable, sterile solutions, preferably oily or aqueous solutions, as well as suspensions, emulsions, or implants, including suppositories. In particular, carriers for parenteral administration include aqueous solutions of dextrose, saline, pure water, ethanol, glycerol, propylene glycol, peanut oil, sesame oil, polyoxyethylene-block polymers, and the like. Ampules are convenient unit dosages. The compounds of the invention can also be incorporated into liposomes or administered via transdermal pumps or patches. Pharmaceutical admixtures suitable for use in the present invention are well-known to those of skill in the art and are described, for example, in Pharmaceutical Sciences (17th Ed., Mack Pub. Co., Easton, Pa.) and WO 96/05309, the teachings of both of which are hereby incorporated by reference.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Also included are solid form preparations that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

Oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, *J. Pharmacol. Exp. Ther.* 281:93-102, 1997. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg, more typically 1.0 mg to 1000 mg, most typically 10 mg to 500 mg, according to the particular application and the potency of the active component. The composition can, if desired, also contain other compatible therapeutic agents.

Some compounds may have limited solubility in water and therefore may require a surfactant or other appropriate co-solvent in the composition. Such co-solvents include: Polysorbate 20, 60 and 80; Pluronic F-68, F-84 and P-103; cyclodextrin; polyoxyl 35 castor oil; or other agents known to those skilled in the art. Such co-solvents are typically employed at a level between about 0.01% and about 2% by weight.

Viscosity greater than that of simple aqueous solutions may be desirable to decrease variability in dispensing the formulations, to decrease physical separation of components of a suspension or emulsion of formulation and/or otherwise to improve the formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, combinations of the foregoing, and other agents known to those skilled in the art. Such agents are typically employed at a level between about 0.01% and about 2% by weight. Determination of acceptable amounts of any of the above adjuvants is readily ascertained by one skilled in the art.

The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes.

Pharmaceutical compositions provided by the present invention include compositions wherein the active ingredient is contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., modulating the activity of a target molecule (e.g. beta-lactamase, class A beta-lactamase, class B beta-lactamase, class C beta-lactamase, or class D beta-lactamase), and/or reducing, eliminating, or slowing the progression of disease symptoms. Determination of a therapeutically effective amount of a compound of the invention is well within the capabilities of those skilled in the art, especially in light of the detailed disclosure herein.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated (e.g., infectious disease, bacterial infectious disease, antibiotic resistant bacterial infectious disease), kind of concurrent treatment, complications from the disease being treated or other health-related problems. Other therapeutic regimens or agents can be used in conjunction with the methods and compounds of Applicants' invention. Adjustment and manipulation of established dosages (e.g., frequency and duration) are well within the ability of those skilled in the art.

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. In one embodiment, the dosage range is 0.001% to 10% w/v. In another embodiment, the dosage range is 0.1% to 5% w/v.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

The ratio between toxicity and therapeutic effect for a particular compound is its therapeutic index and can be expressed as the ratio between $LD_{50}$ (the amount of compound lethal in 50% of the population) and $ED_{50}$ (the amount of compound effective in 50% of the population). Compounds that exhibit high therapeutic indices are preferred. Therapeutic index data obtained from cell culture assays and/or animal studies can be used in formulating a range of dosages for use in humans. The dosage of such compounds preferably lies within a range of plasma concentrations that include the $ED_{50}$ with little or no toxicity. The dosage may vary within this range depending upon the dosage form employed and the route of administration utilized. See, e.g. Fingl et al., In: THE PHARMACOLOGICAL BASIS OF THERAPEUTICS, Ch. 1, p. 1, 1975. The exact formulation, route of administration and dosage can be chosen by the individual physician in view of the patient's condition and the particular method in which the compound is used.

V. Administration

The compositions of the present invention can be delivered by transdermally, by a topical route, formulated as applicator sticks, solutions, suspensions, emulsions, gels, creams, ointments, pastes, jellies, paints, powders, and aerosols.

The compositions of the present invention can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). Both transdermal and intradermal routes afford constant delivery for weeks or months.

The pharmaceutical compositions of the present invention can be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preparation may be a lyophilized powder in 1 mM-50 mM histidine, 0.1%-2% sucrose, 2%-7% mannitol at a pH range of 4.5 to 5.5, that is combined with buffer prior to use.

In another embodiment, the compositions of the present invention are useful for parenteral administration, such as intravenous (IV) administration or administration into a body cavity or lumen of an organ. The formulations for administration will commonly comprise a solution of the compositions of the present invention dissolved in a pharmaceutically acceptable carrier. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of the compositions of the present invention in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

In another embodiment, the formulations of the compositions of the present invention can be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989).

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The compounds described herein can be used in combination with one another, with other active agents known to be useful in treating an infectious disease (antibiotic, penicillin, cephalosporin, beta-lactam containing antibiotic), or with adjunctive agents that may not be effective alone, but may contribute to the efficacy of the active agent.

In some embodiments, co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents (compound as described herein and a beta-lactam containing antibiotic). In other embodiments, the active agents can be formulated separately. In another embodiment, the active and/or adjunctive agents may be linked or conjugated to one another.

VI. Additional Embodiments

1. A compound having the formula:

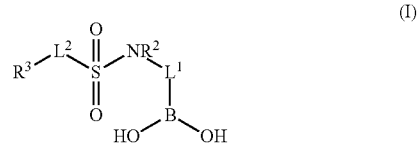

(I)

wherein, $L^1$ is substituted or unsubstituted alkylene, substituted or unsubstituted heteroalkylene, or substituted or unsubstituted arylene; $L^2$ is a bond, substituted or unsubstituted alkylene or substituted or unsubstituted heteroalkylene; $R^2$ is hydrogen, substituted or unsubstituted $C_1$-$C_5$ alkyl, substituted or unsubstituted 2 to 5 membered heteroalkyl, substituted or unsubstituted $C_3$-$C_5$ cycloalkyl, substituted or unsubstituted 4 to 6 membered heterocycloalkyl, substituted or unsubstituted $C_6$-$C_{10}$ aryl, or substituted or unsubstituted 5 to 9 membered heteroaryl; $R^3$ is hydrogen, halogen, $-CX^a_3$, $-CN$, $-SO_2Cl$, $-SO_pR^{14}$, $-SO_qNR^{11}R^{12}$, $-NHNH_2$, $-ONR^{11}R^{12}$, $-NHC=(O)NHNH_2$, $-NHC=(O)NR^{11}R^{12}$, $-N(O)_r$, $-NR^{11}R^{12}$, $-C(O)R^{13}$, $-C(O)-OR^{13}$, $-C(O)NR^{11}R^{12}$, $-OR^{14}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{11}$, $R^{12}$, $R^{13}$, and $R^{14}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; q and r are independently 1 or 2; p is independently an integer from 0 to 4; $X^a$ is $-Cl$, $-Br$, $-I$, or $-F$; with the proviso that if $L^1$ is unsubstituted methylene, $R^2$ is hydrogen, and $L^2$ is a bond then $R^3$ is not unsubstituted phenyl or

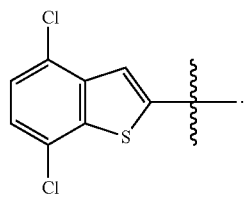 [SMILES: *c1cc2c(Cl)ccc(Cl)c2s1]

2. The compound of embodiment 1, with the proviso that the compound is not:

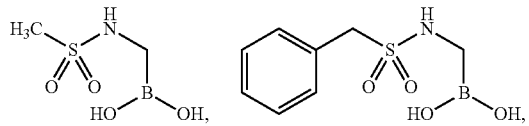

-continued

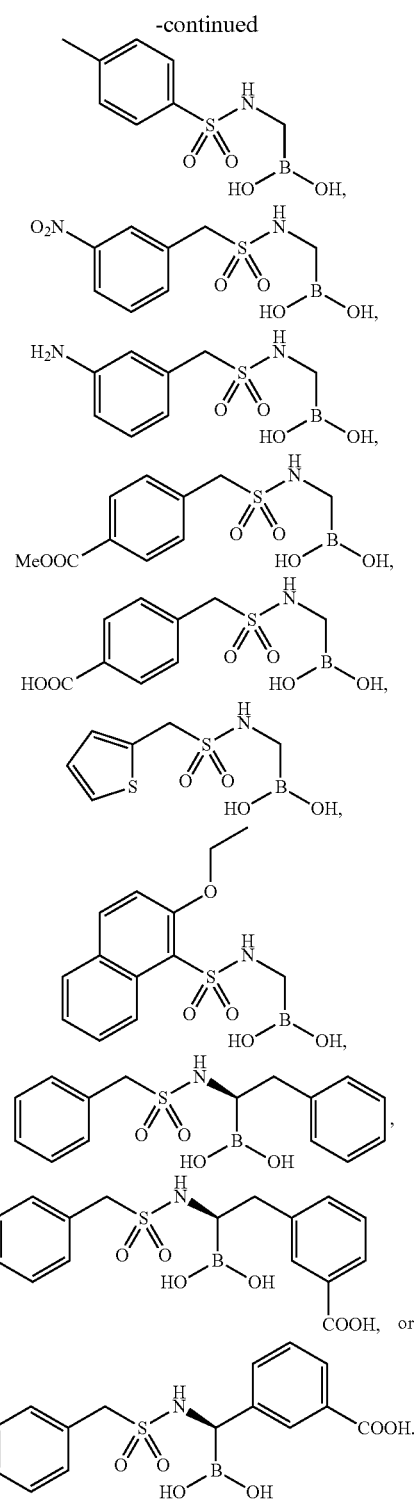

3. The compound of any one of embodiments 1 to 2, wherein $L^1$ is unsubstituted $(C_1$-$C_4)$alkylene.

4. The compound of any one of embodiments 1 to 3, wherein $L^1$ is unsubstituted methylene.

5. The compound of any one of embodiments 1 to 3, wherein $L^1$ is unsubstituted ethylene.

6. The compound of any one of embodiments 1 to 3, wherein $L^1$ is unsubstituted phenylene.

7. The compound of embodiment 1, having the formula:

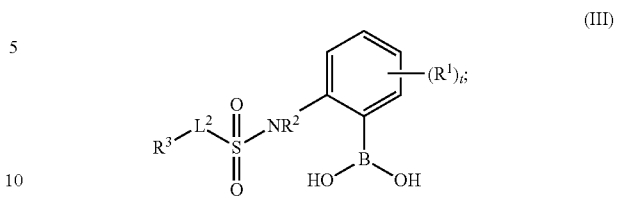

wherein, $R^1$ is independently hydrogen, halogen, —$CX_3$, —CN, —$SO_2Cl$, —$SO_nR^{10}$, —$SO_kNR^7R^8$, —$NHNH_2$, —$ONR^7R^8$, —$NHC$=(O)$NHNH_2$, —$NHC$=(O)$NR^7R^8$, —$N(O)_m$, —$NR^7R^8$, —C(O)$R^9$, —C(O)—$OR^9$, —C(O)$NR^7R^8$, —$OR^{10}$, substituted or unsubstituted $C_1$-$C_5$ alkyl, substituted or unsubstituted 2 to 5 membered heteroalkyl, substituted or unsubstituted $C_3$-$C_5$ cycloalkyl, substituted or unsubstituted 4 to 6 membered heterocycloalkyl, substituted or unsubstituted $C_6$-$C_{10}$ aryl, or substituted or unsubstituted 5 to 9 membered heteroaryl; wherein two adjacent $R^1$ substituents are optionally joined to form a substituted or unsubstituted cycloalkyl, substituted or unsubstituted heterocycloalkyl, substituted or unsubstituted aryl, or substituted or unsubstituted heteroaryl; $R^7$, $R^8$, $R^9$, and $R^{10}$ are independently hydrogen, substituted or unsubstituted $C_1$-$C_{20}$ alkyl, substituted or unsubstituted 2 to 20 membered heteroalkyl, substituted or unsubstituted $C_3$-$C_8$ cycloalkyl, substituted or unsubstituted 4 to 8 membered heterocycloalkyl, substituted or unsubstituted $C_6$-$C_{10}$ aryl, or substituted or unsubstituted 5 to 9 membered heteroaryl; k and m are independently 1 or 2; n and t are independently an integer from 0 to 4; X is —Cl, —Br, —I, or —F.

8. The compound of any one of embodiments 1 to 7, wherein $R^2$ is hydrogen.

9. The compound of any one of embodiments 1 to 7, wherein $R^2$ is substituted or unsubstituted $C_1$-$C_5$ alkyl, substituted or unsubstituted 2 to 5 membered heteroalkyl, substituted or unsubstituted $C_3$-$C_5$ cycloalkyl, substituted or unsubstituted 4 to 6 membered heterocycloalkyl.

10. The compound of any one of embodiments 1 to 7, wherein $R^2$ is substituted or unsubstituted $C_1$-$C_5$ alkyl or substituted or unsubstituted $C_3$-$C_5$ cycloalkyl.

11. The compound of any one of embodiments 1 to 7, wherein $R^2$ is unsubstituted $C_1$-$C_5$ alkyl or unsubstituted $C_3$-$C_5$ cycloalkyl.

12. The compound of any one of embodiments 1 to 7, wherein $R^2$ is unsubstituted $C_1$-$C_3$ alkyl.

13. The compound of any one of embodiments 1 to 7, wherein $R^2$ is unsubstituted methyl.

14. The compound of any one of embodiments 1 to 7, wherein $R^2$ is unsubstituted t-butyl.

15. The compound of any one of embodiments 1 to 14, wherein $L^2$ is a bond.

16. The compound of any one of embodiments 1 to 14, wherein $L^2$ is substituted or unsubstituted alkylene.

17. The compound of any one of embodiments 1 to 14, wherein $L^2$ is unsubstituted alkylene.

18. The compound of any one of embodiments 1 to 14, wherein $L^2$ is unsubstituted $C_1$-$C_3$ alkylene.

19. The compound of any one of embodiments 1 to 14, wherein $L^2$ is unsubstituted n-propylene.

20. The compound of any one of embodiments 1 to 14, wherein $L^2$ is unsubstituted methylene.

21. The compound of any one of embodiments 1 to 20, wherein $R^3$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

22. The compound of any one of embodiments 1 to 20, having the formula:

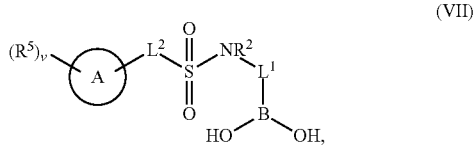

(VII)

wherein ring A is substituted or unsubstituted cycloalkyl, substituted or unsubstituted heterocycloalkyl, substituted or unsubstituted aryl, or substituted or unsubstituted heteroaryl; $R^5$ is independently hydrogen, halogen, $—CX^a{}_3$, $—CN$, $—SO_2Cl$, $—SO_pR^{14}$, $—SO_qNR^{11}R^{12}$, $—NHNH_2$, $—ONR^{11}R^{12}$, $—NHC=(O)NHNH_2$, $—NHC=(O)NR^{11}R^{12}$, $—N(O)_r$, $—NR^{11}R^{12}$, $—C(O)R^{13}$, $—C(O)OR^{13}$, $—C(O)NR^{11}R^{12}$, $—OR^{14}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; wherein two adjacent $R^5$ substituents are optionally joined to form a substituted or unsubstituted cycloalkyl, substituted or unsubstituted heterocycloalkyl, substituted or unsubstituted aryl, or substituted or unsubstituted heteroaryl; v is an integer from 0 to 7.

23. The compound of any one of embodiments 1 to 20, having the formula:

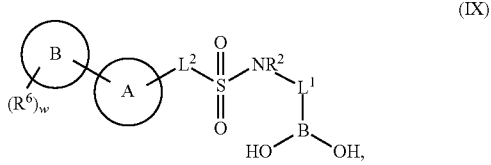

(IX)

wherein ring A is independently substituted or unsubstituted cycloalkylene, substituted or unsubstituted heterocycloalkylene, substituted or unsubstituted arylene, or substituted or unsubstituted heteroarylene; wherein ring B is independently substituted or unsubstituted cycloalkyl, substituted or unsubstituted heterocycloalkyl, substituted or unsubstituted aryl, or substituted or unsubstituted heteroaryl; $R^6$ is independently hydrogen, halogen, $—CX^{a1}{}_3$, $—CN$, $—SO_2Cl$, $—SO_{p1}R^{18}$, $—SO_{q1}NR^{15}R^{16}$, $—NHNH_2$, $—ONR^{15}R^{16}$, $—NHC=(O)NHNH_2$, $—NHC=(O)NR^{15}R^{16}$, $—N(O)_{r1}$, $—NR^{15}R^{16}$, $—C(O)R^{17}$, $—C(O)—OR^{17}$, $—C(O)NR^{15}R^{16}$, $—OR^{18}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; wherein two adjacent $R^6$ substituents are optionally joined to form a substituted or unsubstituted cycloalkyl, substituted or unsubstituted heterocycloalkyl, substituted or unsubstituted aryl, or substituted or unsubstituted heteroaryl; $R^{15}$, $R^{16}$, $R^{17}$, and $R^{18}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; q1 and r1 are independently 1 or 2; p1 is an integer from 0 to 4; $X^{a1}$ is $—Cl$, $—Br$, $—I$, or $—F$; w is an integer from 0 to 7.

24. The compound of embodiment 23, wherein ring B is substituted or unsubstituted aryl or substituted or unsubstituted heteroaryl.

25. The compound of embodiment 23, wherein ring B is substituted or unsubstituted heteroaryl.

26. The compound of embodiment 23, wherein ring B is unsubstituted heteroaryl.

27. The compound of embodiment 23, wherein ring B is substituted heteroaryl.

28. The compound of embodiment 23, wherein ring B is substituted aryl.

29. The compound of embodiment 23, wherein ring B is unsubstituted aryl.

30. The compound of any one of embodiments 22 to 29, wherein ring A is substituted or unsubstituted aryl or substituted or unsubstituted heteroaryl.

31. The compound of any one of embodiments 22 to 29, wherein ring A is substituted aryl or substituted heteroaryl.

32. The compound of any one of embodiments 22 to 29, wherein ring A is substituted aryl.

33. The compound of any one of embodiments 22 to 29, wherein ring A is substituted heteroaryl.

34. The compound of any one of embodiments 22 to 29, wherein ring A is substituted phenyl.

35. The compound of any one of embodiments 22 to 29, wherein ring A is substituted pyridinyl.

36. The compound of any one of embodiments 22 to 29, wherein ring A is substituted thiophenyl.

37. The compound of any one of embodiments 22 to 29, wherein ring A is unsubstituted thiophenyl.

38. The compound of any one of embodiments 1 to 37, having the formula:

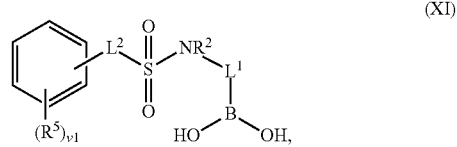

(XI)

wherein, $R^5$ is independently hydrogen, halogen, $—CX^a{}_3$, $—CN$, $—SO_2Cl$, $—SO_pR^{14}$, $—SO_qNR^{11}R^{12}$, $—NHNH_2$, $—ONR^{11}R^{12}$, $—NHC=(O)NHNH_2$, $—NHC=(O)NR^{11}R^{12}$, $—N(O)_r$, $—NR^{11}R^{12}$, $—C(O)R^{13}$, $—C(O)OR^{13}$, $—C(O)NR^{11}R^{12}$, $—OR^{14}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; wherein two adjacent $R^5$ substituents are optionally joined to form a substituted or unsubstituted cycloalkyl, substituted or unsubstituted heterocycloalkyl, substituted or unsubstituted aryl, or substituted or unsubstituted heteroaryl; v1 is an integer from 0 to 5.

39. The compound of any one of embodiments 1 to 38, having the formula:

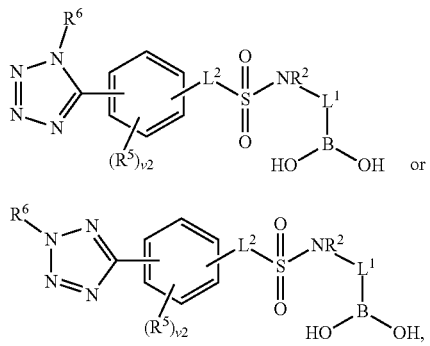

(XIII)

(XIV)

wherein, R⁵ is independently hydrogen, halogen, —CX$^a_3$, —CN, —SO$_2$Cl, —SO$_p$R$^{14}$, —SO$_q$NR$^{11}$R$^{12}$, —NHNH$_2$, —ONR$^{11}$R$^{12}$, —NHC=(O)NHNH$_2$, —NHC=(O)NR$^{11}$R$^{12}$, —N(O)$_r$, —NR$^{11}$R$^{12}$, —C(O)R$^{13}$, —C(O)—OR$^{13}$, —C(O)NR$^{11}$R$^{12}$, —OR$^{14}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; wherein two adjacent R⁵ substituents are optionally joined to form a substituted or unsubstituted cycloalkyl, substituted or unsubstituted heterocycloalkyl, substituted or unsubstituted aryl, or substituted or unsubstituted heteroaryl; R⁶ is independently hydrogen, halogen, —CX$^{a1}_3$, —CN, —C(O)R$^{17}$, —C(O)—OR$^{17}$, —C(O)NR$^{15}$R$^{16}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{15}$, R$^{16}$, and R$^{17}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; X$^{a1}$ is —Cl, —Br, —I, or —F; v2 is an integer from 0 to 4.

40. The compound of any one of embodiments 1 to 39, having the formula:

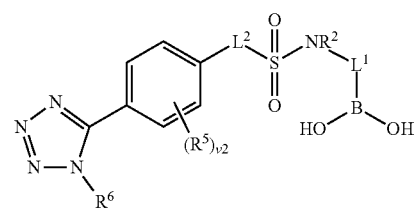

(XVII)

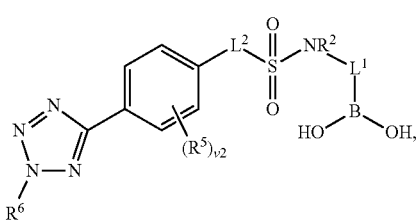

(XVIII)

wherein, R⁵ is independently hydrogen, halogen, —CX$^a_3$, —CN, —SO$_2$Cl, —SO$_p$R$^{14}$, —SO$_q$NR$^{11}$R$^{12}$, —NHNH$_2$, —ONR$^{11}$R$^{12}$, —NHC=(O)NHNH$_2$, —NHC=(O)NR$^{11}$R$^{12}$, —N(O)$_r$, —NR$^{11}$R$^{12}$, —C(O)R$^{13}$, —C(O)—OR$^{13}$, —C(O)NR$^{11}$R$^{12}$, —OR$^{14}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; wherein two adjacent R⁵ substituents are optionally joined to form a substituted or unsubstituted cycloalkyl, substituted or unsubstituted heterocycloalkyl, substituted or unsubstituted aryl, or substituted or unsubstituted heteroaryl; R⁶ is independently hydrogen, halogen, —CX$^{a1}_3$, —CN, —C(O)R$^{17}$, —C(O)—OR$^{17}$, —C(O)NR$^{15}$R$^{16}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{15}$, R$^{16}$, and R$^{17}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; X$^{a1}$ is —Cl, —Br, —I, or —F; v2 is an integer from 0 to 4.

41. The compound of any one of embodiments 1 to 40, having the formula:

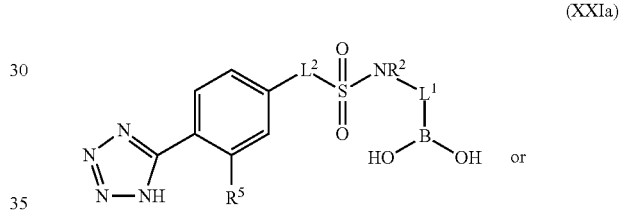

(XXIa)

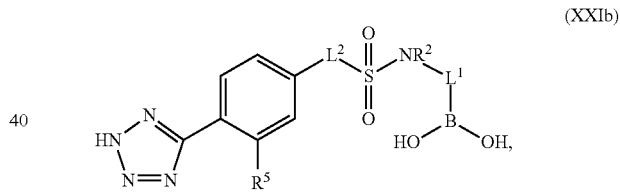

(XXIb)

wherein, R⁵ is independently hydrogen, halogen, —CX$^a_3$, —CN, —SO$_2$Cl, —SO$_p$R$^{14}$, —SO$_q$NR$^{11}$R$^{12}$, —NHNH$_2$, —ONR$^{11}$R$^{12}$, —NHC=(O)NHNH$_2$, —NHC=(O)NR$^{11}$R$^{12}$, —N(O)$_r$, —NR$^{11}$R$^{12}$, —C(O)R$^{13}$, —C(O)—OR$^{13}$, —C(O)NR$^{11}$R$^{12}$, —OR$^{14}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

42. The compound of any one of embodiments 1 to 40, having the formula:

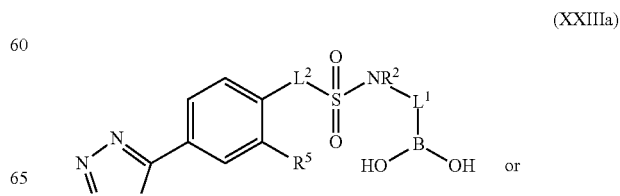

(XXIIIa)

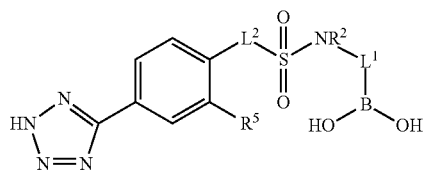

(XXIIIb)

wherein, $R^5$ is independently hydrogen, halogen, $-CX^a_3$, $-CN$, $-SO_2Cl$, $-SO_pR^{14}$, $-SO_qNR^{11}R^{12}$, $-NHNH_2$, $-ONR^{11}R^{12}$, $-NHC=(O)NHNH_2$, $-NHC=(O)NR^{11}R^{12}$, $-N(O)_r$, $-NR^{11}R^{12}$, $-C(O)R^{13}$, $-C(O)-OR^{13}$, $-C(O)NR^{11}R^{12}$, $-OR^{14}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

43. The compound of any one of embodiments 22 to 42, wherein $R^5$ is halogen.
44. The compound of any one of embodiments 22 to 42, wherein $R^5$ is $-Cl$.
45. The compound of any one of embodiments 22 to 42, wherein $R^5$ is $-F$.
46. The compound of any one of embodiments 22 to 42, wherein $R^5$ is $-I$.
47. The compound of any one of embodiments 22 to 42, wherein $R^5$ is $-Br$.
48. The compound of any one of embodiments 22 to 42, wherein $R^5$ is $-CF_3$.
49. The compound of any one of embodiments 22 to 42, wherein $R^5$ is $-CCl_3$.
50. A compound selected from

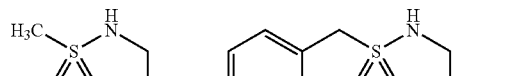
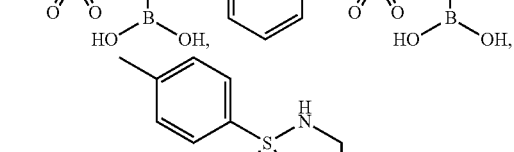
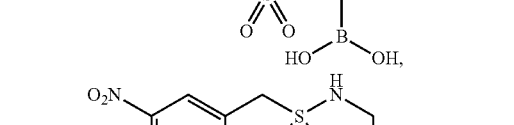
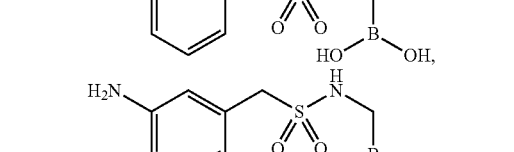
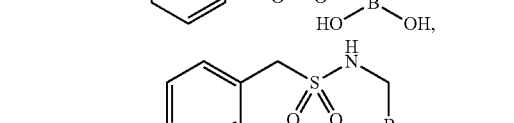
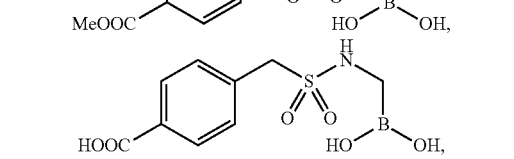

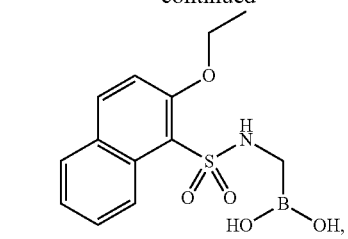
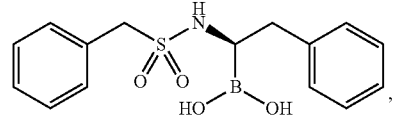
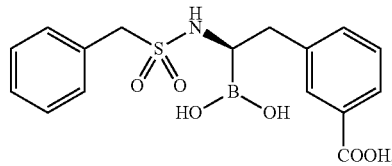
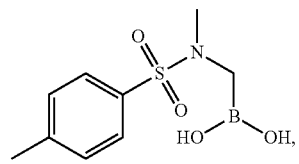
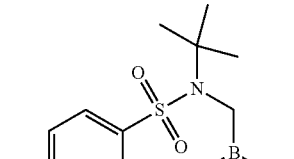
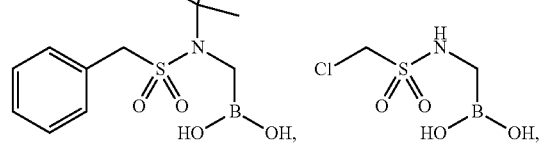
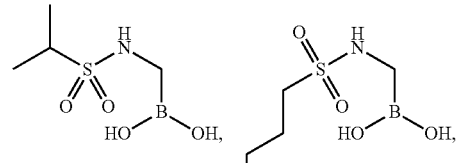
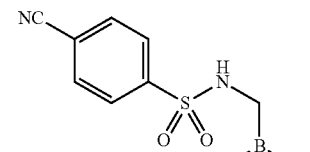
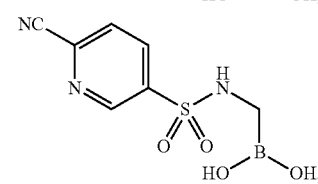

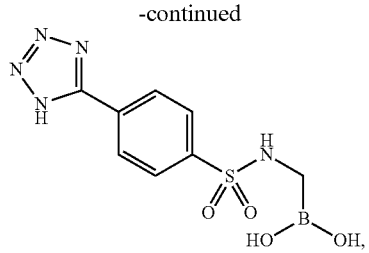
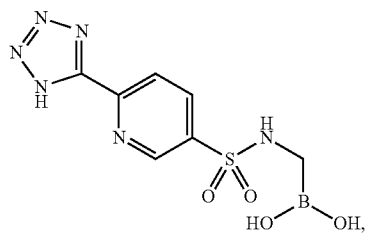
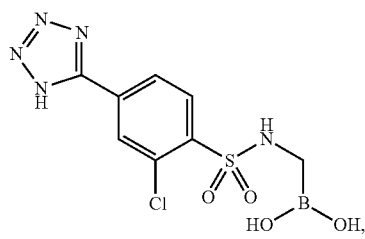
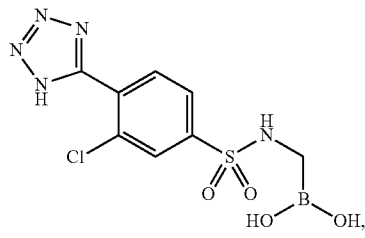
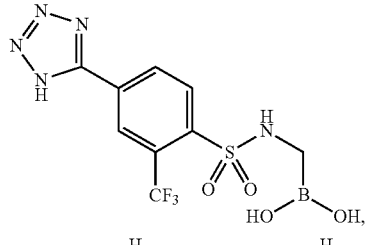
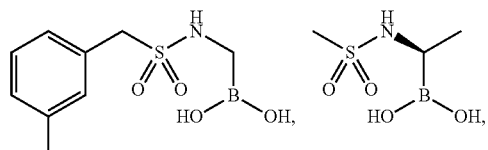
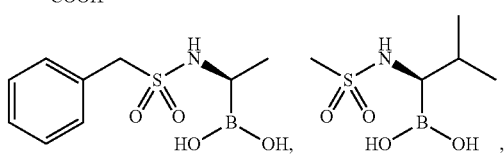
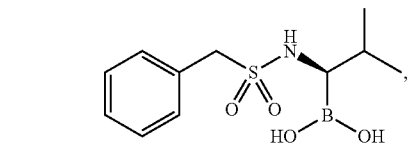
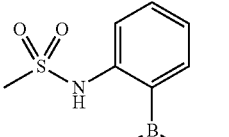
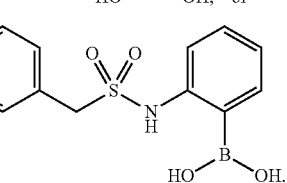
51. A compound selected from
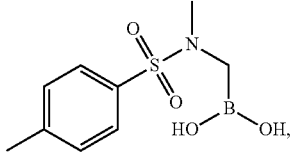
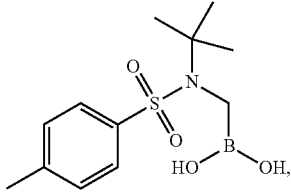
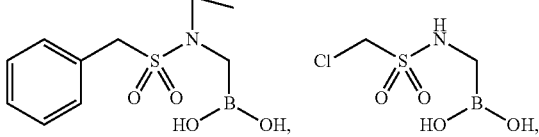
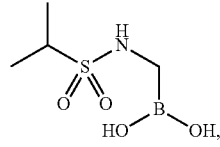
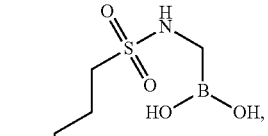
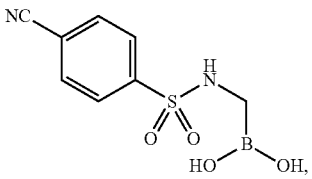
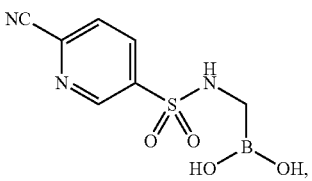

-continued

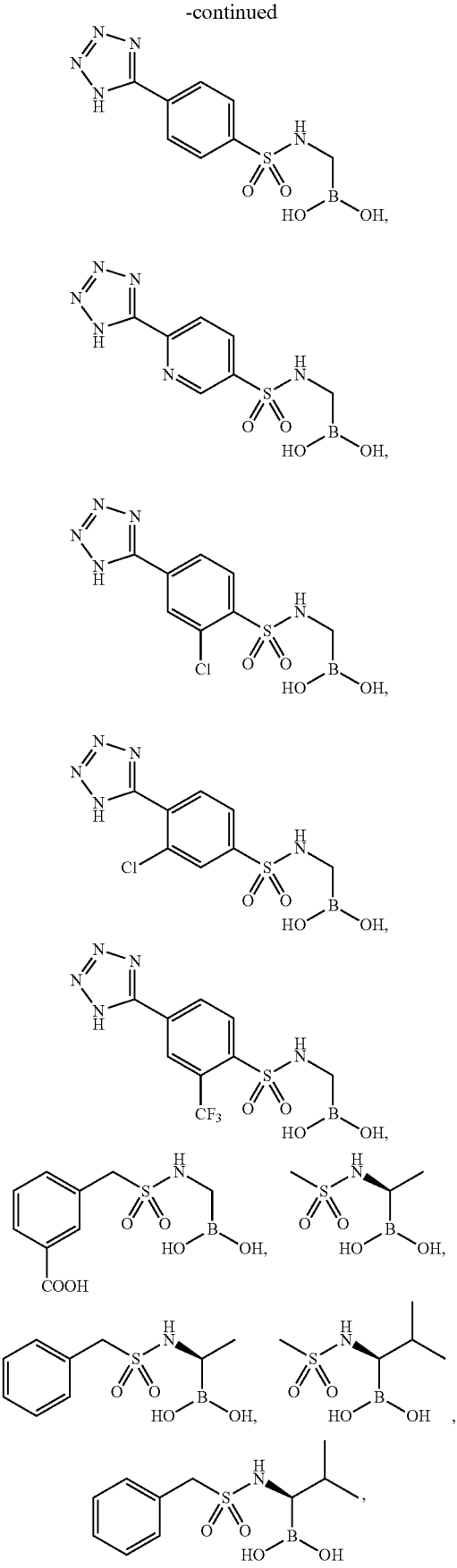

52. A compound of any one of embodiments 1 to 51, wherein, a boron of said compound contacts a sidechain of an amino acid of a bacterial beta-lactamase corresponding to *Escherichia coli* AmpC beta-lactamase amino acid Ser64; said compound contacts a sidechain of an amino acid of said bacterial beta-lactamase corresponding to *Escherichia coli* AmpC beta-lactamase amino acid Asn152; and said compound contacts a backbone amide nitrogen of an amino acid of said bacterial beta-lactamase corresponding to *Escherichia coli* AmpC beta-lactamase amino acid Ser212 or Gly320.

53. A compound of embodiment 52, wherein said compound inhibits the activity of said bacterial beta-lactamase.

54. A pharmaceutical composition comprising a pharmaceutically acceptable excipient and a compound of any one of embodiments 1 to 53.

55. A method of treating a disease in a patient in need of such treatment, said method comprising administering a therapeutically effective amount of a compound of any one of embodiments 1 to 53.

56. The method of embodiment 55, wherein the disease is an infectious disease mediated by a bacterium.

57. The method of embodiment 56, wherein the bacterium is resistant to an antibiotic.

58. The method of embodiment 57, wherein the antibiotic is a beta-lactam antibiotic.

59. A method of inhibiting the growth of a bacterium in a patient, said method comprising administering a therapeutically effective amount of a compound of any one of embodiments 1 to 53.

60. The method of any one of embodiments 55 to 59, wherein the bacterium is a gram negative bacterium.

61. The method of any one of embodiments 55 to 59, wherein the bacterium is a gram positive bacterium.

62. A method of inhibiting the hydrolysis of a beta-lactam antibiotic by a bacterially expressed beta-lactamase in a patient, said method comprising administering an effective amount of a compound of any one of embodiments 1 to 53.

63. A method of reducing the therapeutically effective amount of an antibiotic necessary to treat a patient in need of such treatment, said method comprising administering an effective amount of a compound of any one of embodiments 1 to 53.

64. The method of any one of embodiments 55 to 63, further comprising administering a beta-lactam antibiotic to said patient.

65. The method of embodiment 64, wherein the beta-lactam antibiotic is a penicillin.

66. The method of embodiment 64, wherein the beta-lactam antibiotic is a cephalosporin.

67. The method of embodiment 64, wherein the beta-lactam antibiotic is a cephamycin.

68. The method of embodiment 64, wherein the beta-lactam antibiotic is a first-generation cephalosporin.

69. The method of embodiment 64, wherein the beta-lactam antibiotic is a second-generation cephalosporin.

70. The method of embodiment 64, wherein the beta-lactam antibiotic is a third-generation cephalosporin.

71. The method of embodiment 64, wherein the beta-lactam antibiotic is a fourth-generation cephalosporin.

72. The method of embodiment 64, wherein the beta-lactam antibiotic is a fifth-generation cephalosporin.

73. The method of embodiment 64, wherein the beta-lactam antibiotic is a sixth-generation cephalosporin.

74. A kit for treating a bacterial infectious disease comprising a compound of any one of embodiments 1 to 53 and a beta-lactam containing antibiotic.

75. The kit of embodiment 74, wherein the beta-lactam containing antibiotic is a penicillin.

76. The kit of embodiment 74, wherein the beta-lactam containing antibiotic is a cephalosporin.

VII. Examples

A. Example 1

Experimental Overview

Figure 2:
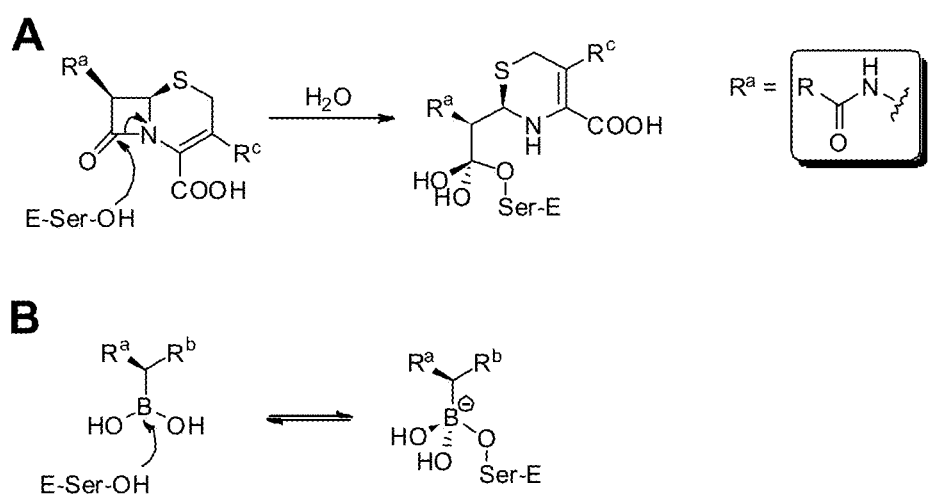
FIG. 2. Boronic acids as transition-state analogs. A) Hydrolytic attack on the β-lactam ring of a cephalosporin and formation of the high-energy intermediate. B) Binding of β-lactamase to a boronic acid and formation of a transition-state analog.

Boronic acids are transition-state analogs that lack the β-lactam recognition motif and are distinct enough chemically to evade pre-evolved resistance mechanisms. (Powers, R. A. et al., *Protein Sci.* 1999, 8, 2330-2337; Weston, G. S. et al., *J. Med. Chem.* 1998, 41, 4577-4586; Caselli, E. et al., *Chem. Biol.* 2001, 8, 17-31) They form rapidly dative reversible covalent bonds with the active site serine, forming a tetrahedral adduct, mimicking the high-energy intermediate of β-lactams along the β-lactamase reaction coordinate (FIG. 2). (Beadle, B. M. et al., *Structure* 2002, 10, 413-424)

We found that acylglycyl boronic acids bearing side chains characteristic of penicillins and cephalosporins ($R^a$ group in FIG. 2A) have $K_i$ values as low as 20 nM against AmpC. (Caselli, E. et al., *Chem. Biol.* 2001, 8, 17-31) Using a structure-based drug design approach, we designed m-carboxyphenyl boronic acids having a negatively charged group in a position corresponding to the C4 of cephalosporins, such as cephalothin (FIG. 1). (Morandi, F. et al., *J. Am. Chem. Soc.* 2003, 125, 685-695; Morandi, S. et al., *Bioorg. Med. Chem.* 2008, 16, 1195-1205) Compound 18c has a $K_i$ value of 1 nM, improving potency up to 300-fold compared to the corresponding acylglycyl boronic acid 10c (Table 1).

Figure 3:
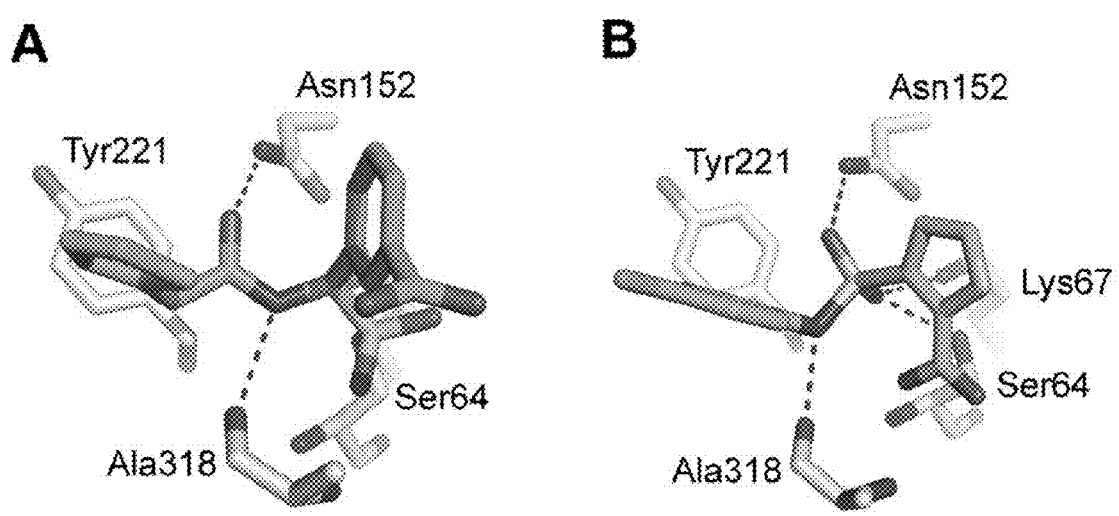
FIG. 3. Inspiration for sulfonamide boronic acids. A) The carboxamide of boronic acid 18c (Table 1) hydrogen bonds with Asn152 and Ala318 of AmpC β-lactamase (PDB code 1MXO). Carbon atoms of inhibitor colored light gray, oxygens dark gray, nitrogens dark gray, sulfur dark gray, boron atom dark gray. B) The sulfonamide of a non-covalent β-lactamase inhibitor hydrogen bonds with Asn152, Ala318, Ser64 and Lys67 (PDB code 1L2S). Carbon atoms of inhibitor colored light gray, oxygens dark gray, nitrogens dark gray, sulfur dark gray, chloride dark gray.

In the crystal structure of the AmpC/18c complex, the oxygen atom of the carboxamide forms a hydrogen bond with Asn152, a conserved residue in the AmpC active site, while the carboxamide nitrogen hydrogen bonds with the backbone carbonyl of Ala318, a residue that contributes to the enzyme's oxyanion hole (FIG. 3A). In an unrelated series of non-covalent β-lactamase inhibitors, discovered by molecular docking, a sulfonamide group is similarly positioned and makes the same interactions (FIG. 3B). (Powers, R. A. et al., *Structure* 2002, 10, 1013-1023)

Figure 4:
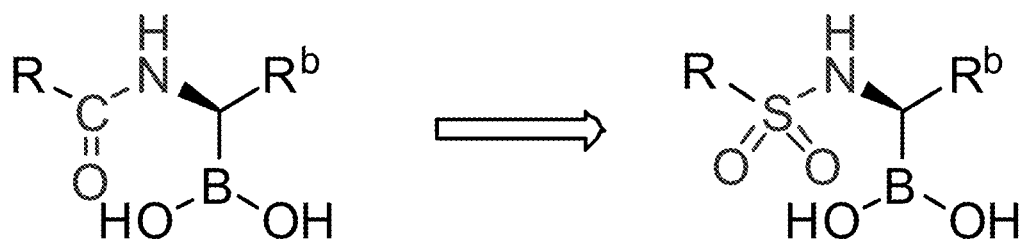
FIG. 4. Scheme 1. The conversion of carboxamide boronic acids into sulfonamide boronic acids.

It therefore seemed interesting to replace the ubiquitous carboxamide, present in the $R^a$ side chain of both β-lactams and their boronic acid mimics, by a sulfonamide (FIG. 4, Scheme 1). Whereas sulfonamide replacements for carboxamides date back to the seminal synthetic work of Sheehan in the 1950s, (Sheehan, J. C. and Hoff, D. R., *J. Am. Chem. Soc.* 1957, 79, 237-240) these derivatives were never used clinically.

We investigated a series of sulfonamide boronic acids that resulted from the merging of two unrelated AmpC β-lactamase inhibitor series. The new boronic acids differed in the replacement of the canonical carboxamide, found in all penicillin and cephalosporin antibiotics, with a sulfonamide. Whereas this change appears modest, it converts a planar amide into a tetrahedral sulfonamide. These compounds have no precedence among either transition-state analog or β-lactam-based inhibitors of β-lactamase. These compounds have significantly changed SAR compared to earlier compounds, often in unexpected ways. Surprisingly, these sulfonamides had a highly distinct structure-activity relationship from the previously explored carboxamides, high ligand efficiencies (up to 0.91), $K_i$ values down to 25 nM and up to 23 times better for smaller analogs. Conversely, $K_i$ values were 10 to 20 times worse for some larger molecules than in the carboxamide congener series. X-ray crystal structures (1.6-1.8 Å) of AmpC with three of the new sulfonamides suggest that this altered structure-activity relationship results from the different geometry and polarity of the sulfonamide versus the carboxamide. The most potent inhibitor reversed β-lactamase-mediated resistance to third generation cephalosporins, lowering their minimum inhibitory concentrations up to 32-fold in cell culture.

For example, the two compounds shown immediately below have activities that are much better than would have been predicted from previous amide compounds.

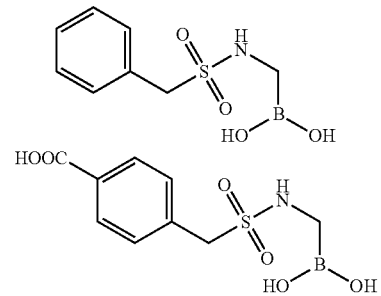

Figure 9:
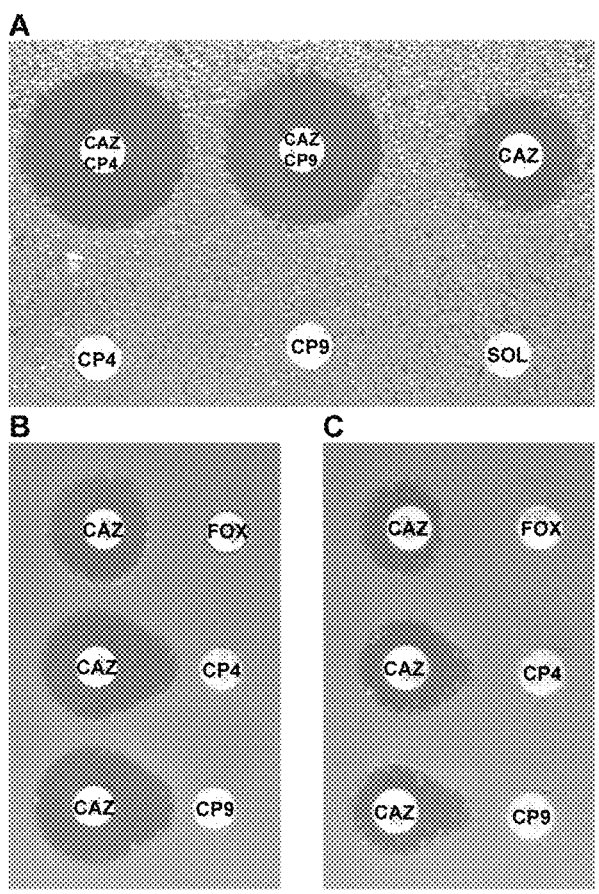
FIG. 9. Inhibition of bacterial growth and potentiation effect. A) Activity of compounds 4 (CP4) and 9 (CP9) in combination with ceftazidime (CAZ) and alone against a Klebsiella pneumoniae strain producing AmpC β-lactamase. Solvent (SOL):DMSO/Water 1:1. B) Potentiation of β-lactamase inhibition in an E. cloacae strain in which ampC gene expression is inducible by β-lactam antibiotics, such as cefoxitin (FOX). C) Potentiation of β-lactamase inhibition in a Klebsiella pneumoniae isolate producing the inducible class C enzyme DHA-1.
Figure 10:
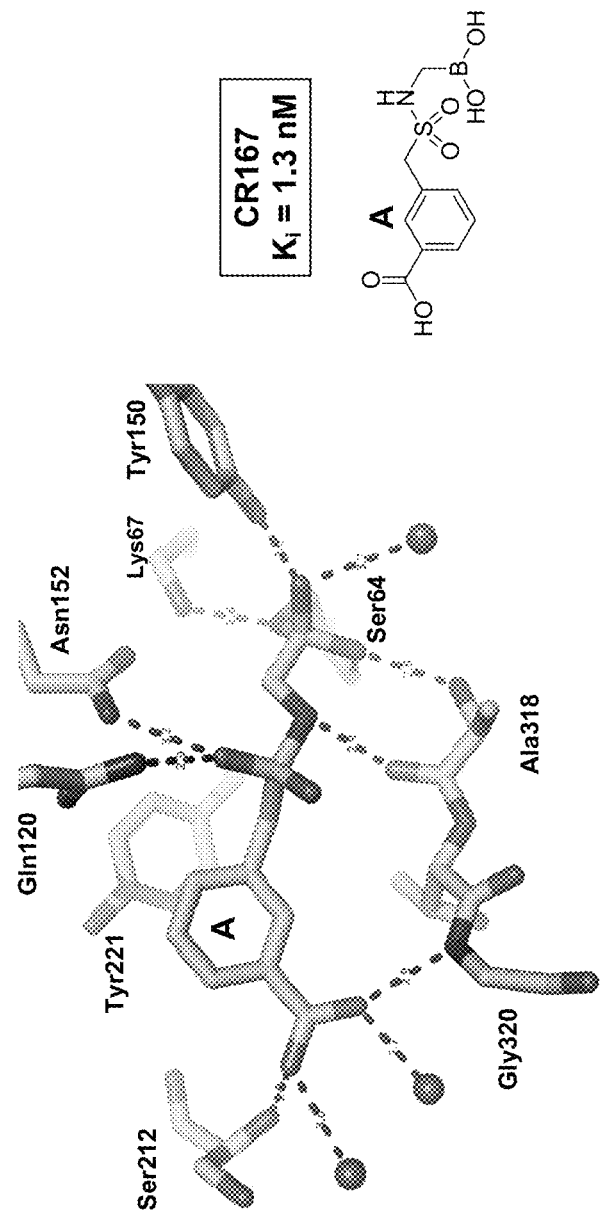
FIG. 10. CR167: Hydrogen bonding with distal site (Ser212 and Gly320). Boronic acid is covalently bound to Ser64 and hydrogen bonds with Lys67, Tyr150 and Ala318. Sulfonamide oxygen hydrogen bonds with Asn152 and Gln120. Benzyl makes parallel displaced pi-pi stacking interactions with Tyr221. Carboxylate hydrogen bonds with main chain amides of Ser212 and Gly320 and two waters. Light Gray:carbon. Medium Gray. Dark Gray: Nitrogen. Spheres: Water. Gray dashes: H-bonds, Off-white dashes: Halogen bonds, Black dashes.
Figure 11:
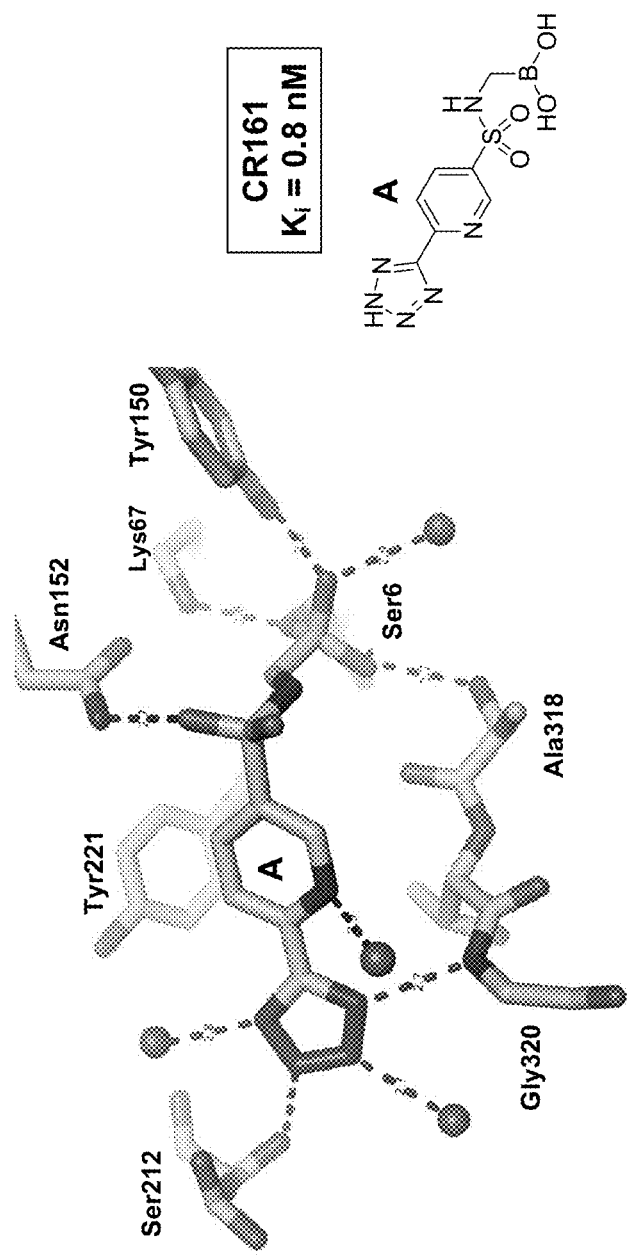
FIG. 11. CR161: Hydrogen bonding with distal site (Ser212 and Gly320). Boronic acid is covalently bound to Ser64 and hydrogen bonds with Lys67, Tyr150. Sulfonamide oxygen forms a short hydrogen bond with Asn152 (2.7 Å). Pyridine ring makes T-shaped pi-pi stacking interactions (70° angle) with Tyr221 and H-bonds water. Tetrazole hydrogen bonds with main chain amides of Ser212 and Gly320 and two waters. Light Gray:carbon. Medium Gray. Dark Gray: Nitrogen. Spheres: Water. Gray dashes: H-bonds, Off-white dashes: Halogen bonds, Black dashes.
Figure 12:
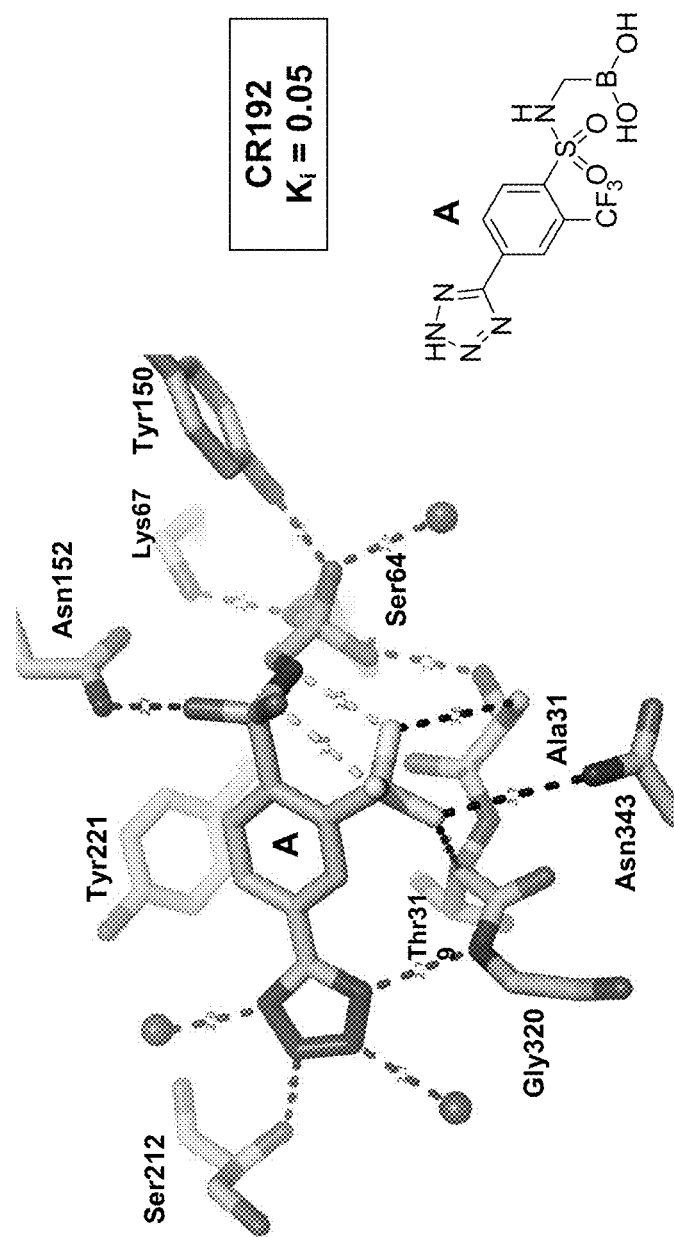
FIG. 12. CR192: Additional van der Waals contacts may explain gain in affinity. The trifluoromethyl derivative CR192 binds like CR161, but makes additional inter- and intramolecular van der Waals contacts: Intermolecular: with Ala318, Thr319 and Asn343. Intramolecular: with nitrogen and oxygen of sulfonamide. Light Gray:carbon. Medium Gray. Dark Gray: Nitrogen. Spheres: Water. Gray dashes: H-bonds, Off-white dashes: Halogen bonds, Black dashes.
Figure 13:
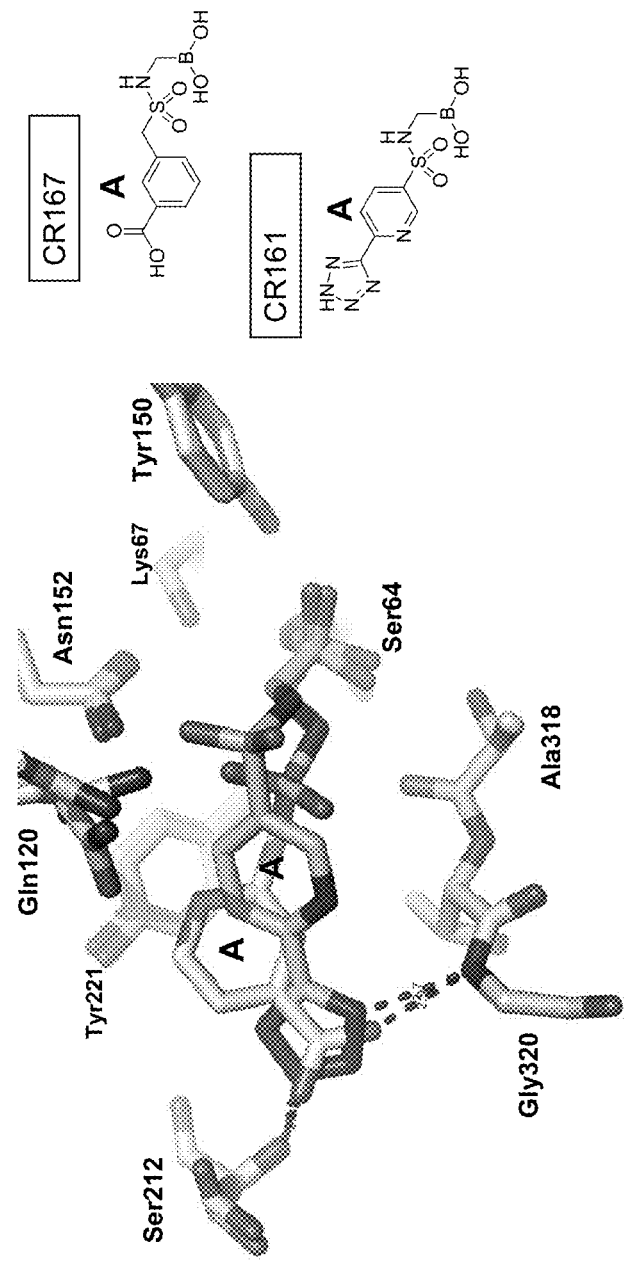
FIG. 13. Carboxylate and tetrazole compounds both contact the distal site but also have different interactions. VdW contacts. Common: interactions around Ser64 and hydrogen bonds with Ser212 and Gly320. Different: Sulfonamide interactions, aromatic interactions. Comparison suggests that charged groups may be linked by other ring systems. Different substituents of A ring may yield more potent inhibitors. Alkylation/halogenation of sulfonamide nitrogen and carbon next to boron may yield additional potent inhibitors. Light Gray:carbon. Medium Gray. Dark Gray: Nitrogen. Spheres: Water. Gray dashes: H-bonds, Off-white dashes: Halogen bonds, Black dashes.
Figure 14:
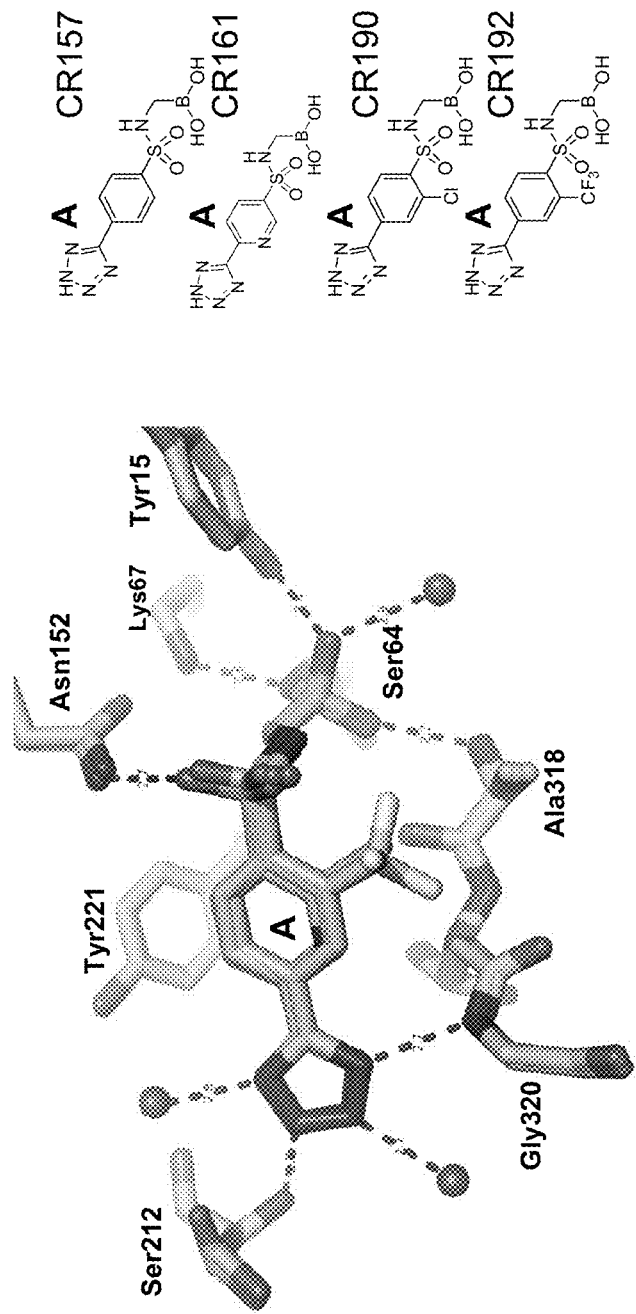
FIG. 14. All tetrazole structures look very similar. Superposition of CR157, CR161, CR190 and CR192 shows that all 4 structures look very similar. Light Gray:carbon. Medium Gray. Dark Gray: Nitrogen. Spheres: Water. Gray dashes: H-bonds, Off-white dashes: Halogen bonds, Black dashes.

The new sulfonamide class has been shown to have substantial activity in cell culture. This may be shown both by disk diffusion (FIG. 9) and by classical MIC determination (Table 3 and 6)

We synthesized multiple sulfonamide boronic acids and tested their inhibition of AmpC β-lactamase. Among them are many different R groups including the penicillin G and nafcillin side chains. We found that the simplest of these new sulfonamides were unexpectedly very potent ($K_i$ values in the 25 nM range), over 23 times more than their carboxamide analogs, and that the SAR of this series differed completely from what was observed in the carboxamide series. To understand these differences, we determined X-ray structures of three inhibitors in complex with AmpC. Finally, we investigated the efficacy of some of the more potent inhibitors to reverse antibiotic resistance in bacterial cell cultures.

B. Example 2

Compound Design

The geometry and electronic properties of a sulfonamide are quite different from a carboxamide and we were interested in how this substitution would affect affinity (FIG. 4, Scheme 1). First, we explored the sulfonamide substitution with a methyl alone as the $R^a$ group. Since this compound was unexpectedly potent against AmpC, we then synthesized and tested sulfonamide boronic acids with many more elaborate $R^a$ groups (FIG. 2, Table 1). We also synthesized molecules with a benzyl and m-carboxybenzyl groups as $R^b$ substituents.

Figure 20:
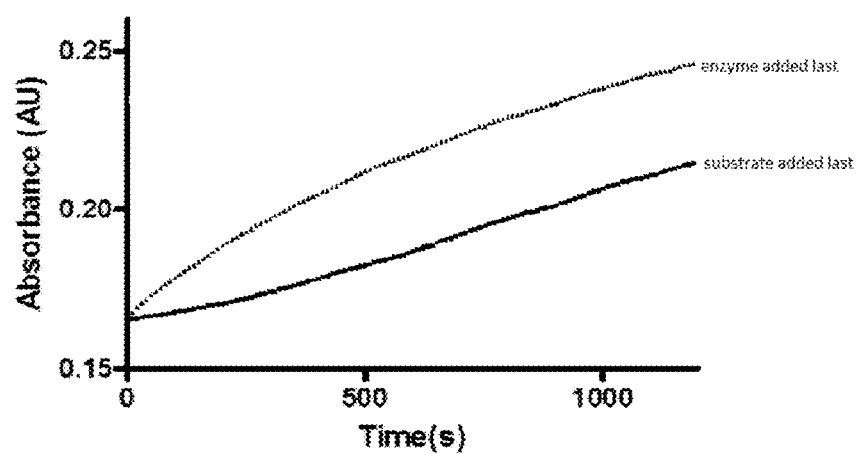
FIG. 20. Incubation effect due to slow inhibitor off-rates. Depicted are the rates of substrate hydrolysis in the presence of 500 pM inhibitor CR192. The lower curve (■) shows an increasing rate of substrate hydrolysis over time after pre-incubation of AmpC with CR192 for 5 minutes prior to adding substrate. The upper curve (▲) shows a decrease in the substrate hydrolysis rate over time when reaction was initiated with the enzyme: this is because the enzyme active site is initially unoccupied by the inhibitor. The rates (eg. slope) converge after reaching equilibrium (after ~10-15 minutes in this example). Conditions: 50 pM AmpC, 120 M CENTA, 500 pM inhibitor CR192.

$K_i$ values of the new boronic acids CR167, CR157, and CR161, were determined from $IC_{50}$ curves, and competition with the AmpC substrate CENTA was confirmed by full Lineweaver-Burk analysis, as described (Weston G S, et al. (1998), J Med Chem 41:4577-4586). All were competitive inhibitors with $K_i$ values ranging from 0.8 to 1.3 nM, an improvement of 20- to 30-fold relative to the lead CR107 (Table 8). Whereas CR107 had no measurable time dependence to its activity, all three of the new inhibitors exhibited an incubation effect owing to slow off-rates, as suggested by enzyme incubation and dilution experiments (FIG. 20) (Morrison J F & Walsh C T (1988), Adv Enzymol Relat Areas Mol Biol 61:201-301).

Figure 15:
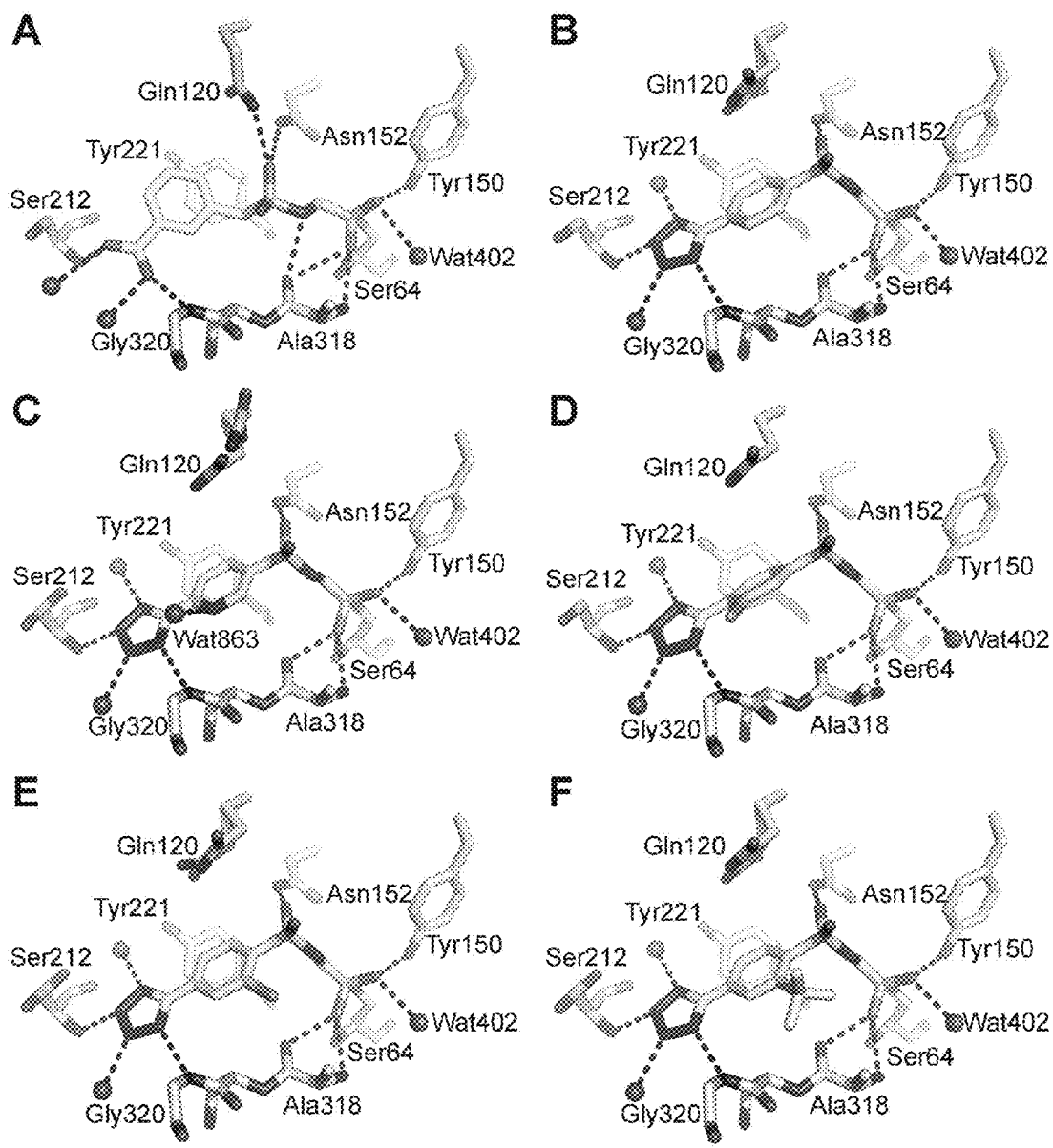
FIG. 15. X-ray structures of the new sulfonamide boronic acids bound to AmpC. AmpC carbon atoms depicted in grey, ligand carbons in light gray, oxygens dark gray, nitrogens dark gray, sulfurs light gray, borons light gray, chlorides in medium gray, fluorides in light gray. Dashes represent hydrogen bonds, water molecules are represented by red spheres. (A) AmpC/CR167. (B) AmpC/CR157. (C) AmpC/CR161. (D) AmpC/CR191. (E) AmpC/CR190. (F) AmpC/CR192.
Figure 16:
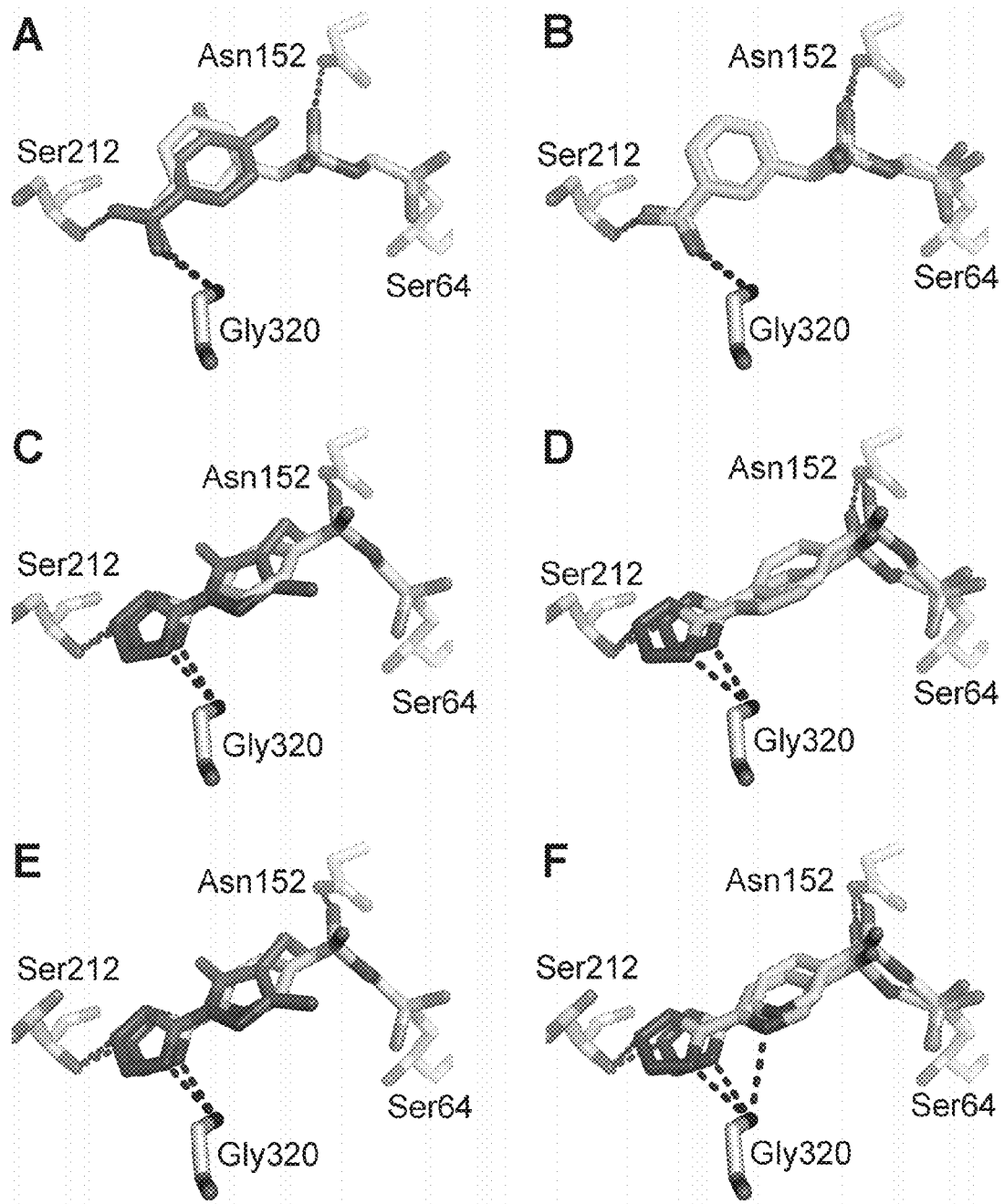
FIG. 16. X-ray structures of the new compounds superposed on the fragments and on the initial models. Carbon atoms of new ligands depicted in light gray, carbons of fragments in medium gray, carbons of models in light gray, carbons of AmpC residues in grey. Dashes represent hydrogen bonds. (A) CR167 and 4-amino-3-hydroxybenzoate. (B) CR167 and model of CR167. (C) CR157 and 5-(4-ethyl-3-methyl-5-oxo-2,5-dihydro-1H-pyrazol-1-yl)tetrazol-2-ide. (D) CR157 and model of CR157. (E) CR161 and 5-(4-ethyl-3-methyl-5-oxo-2,5-dihydro-1H-pyrazol-1-yl)tetrazol-2-ide. (F) CR161 and model of CR161.
Figure 21:
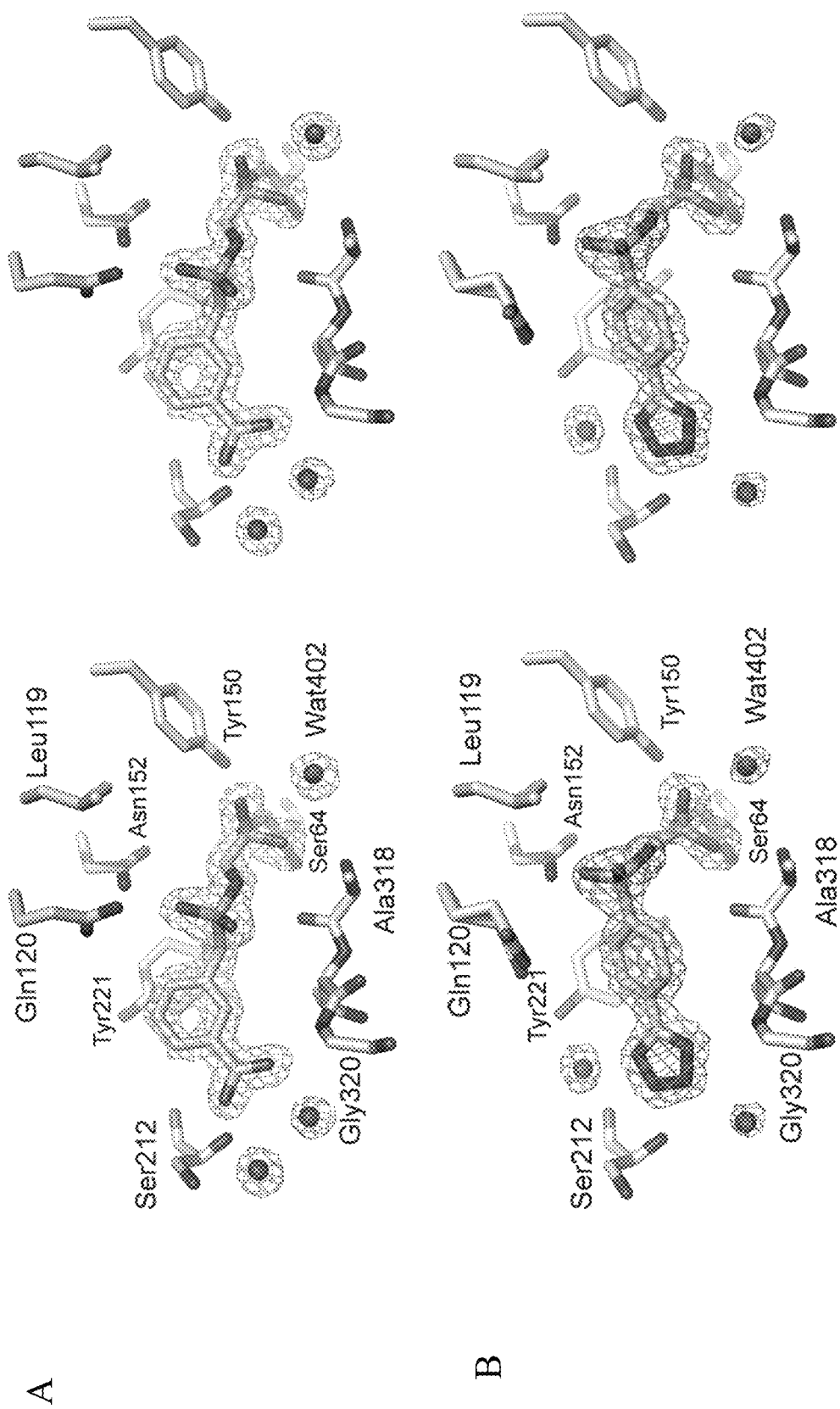
FIG. 21. Stereoviews of electron density difference maps. $F_o$-$F_c$ density maps from early stages of refinement are depicted for ligands and selected water molecules. Maps are contoured at 3σ level except for CR70, where density is contoured at 2.5σ level. Figures were prepared with PyMOL (www.pymol.org), carbons in light gray, oxygens dark gray, nitrogens dark gray, sulfurs light gray, borons light gray, chlorides in medium gray, fluorides in light gray. (A) AmpC/CR167; (B) AmpC/CR157; (C) AmpC/CR161; (D) AmpC/CR191; (E) AmpC/CR190; (F) AmpC/CR192; (G) AmpC/CR70.
Figure 21:
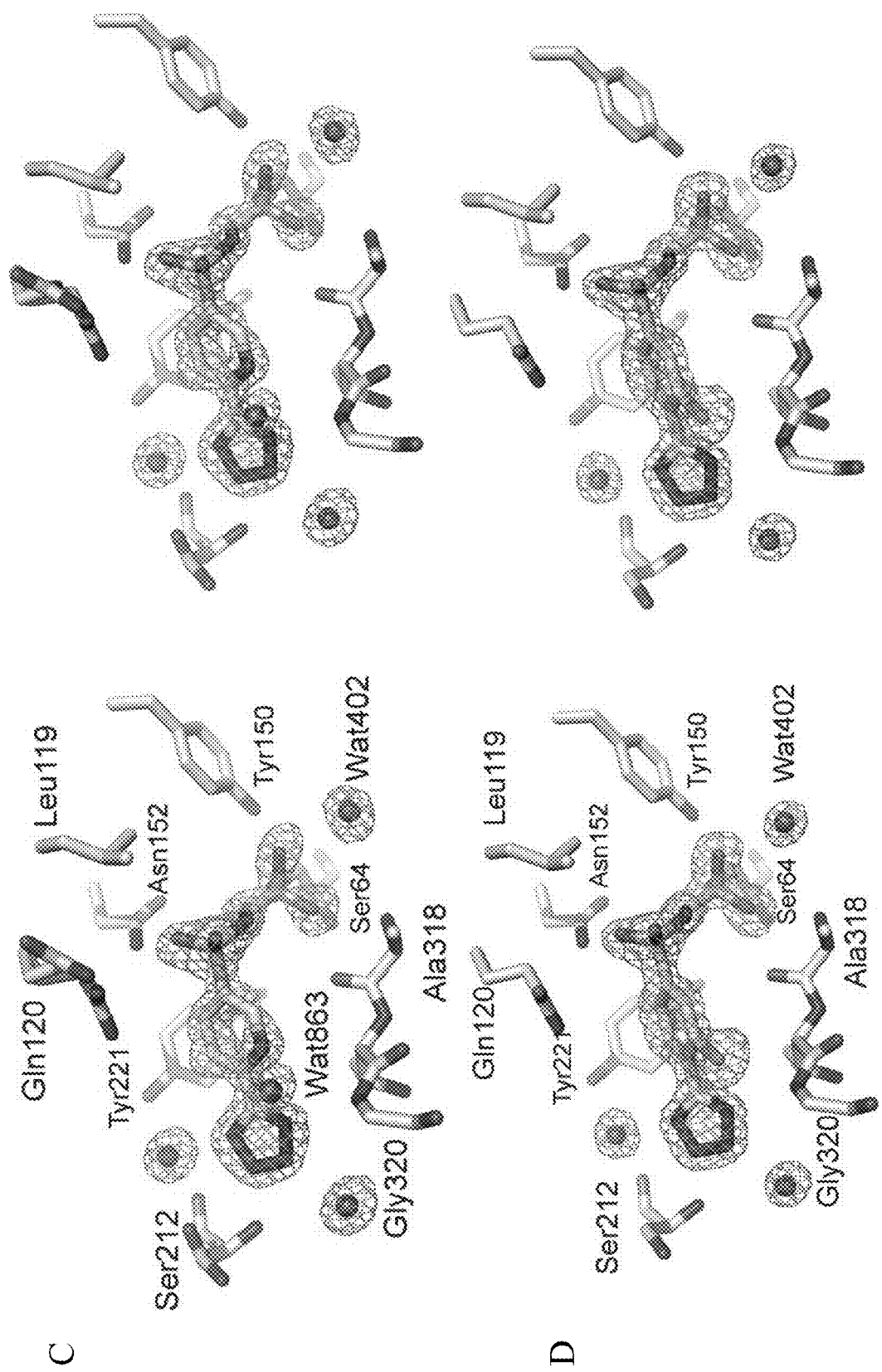
Figure 21:
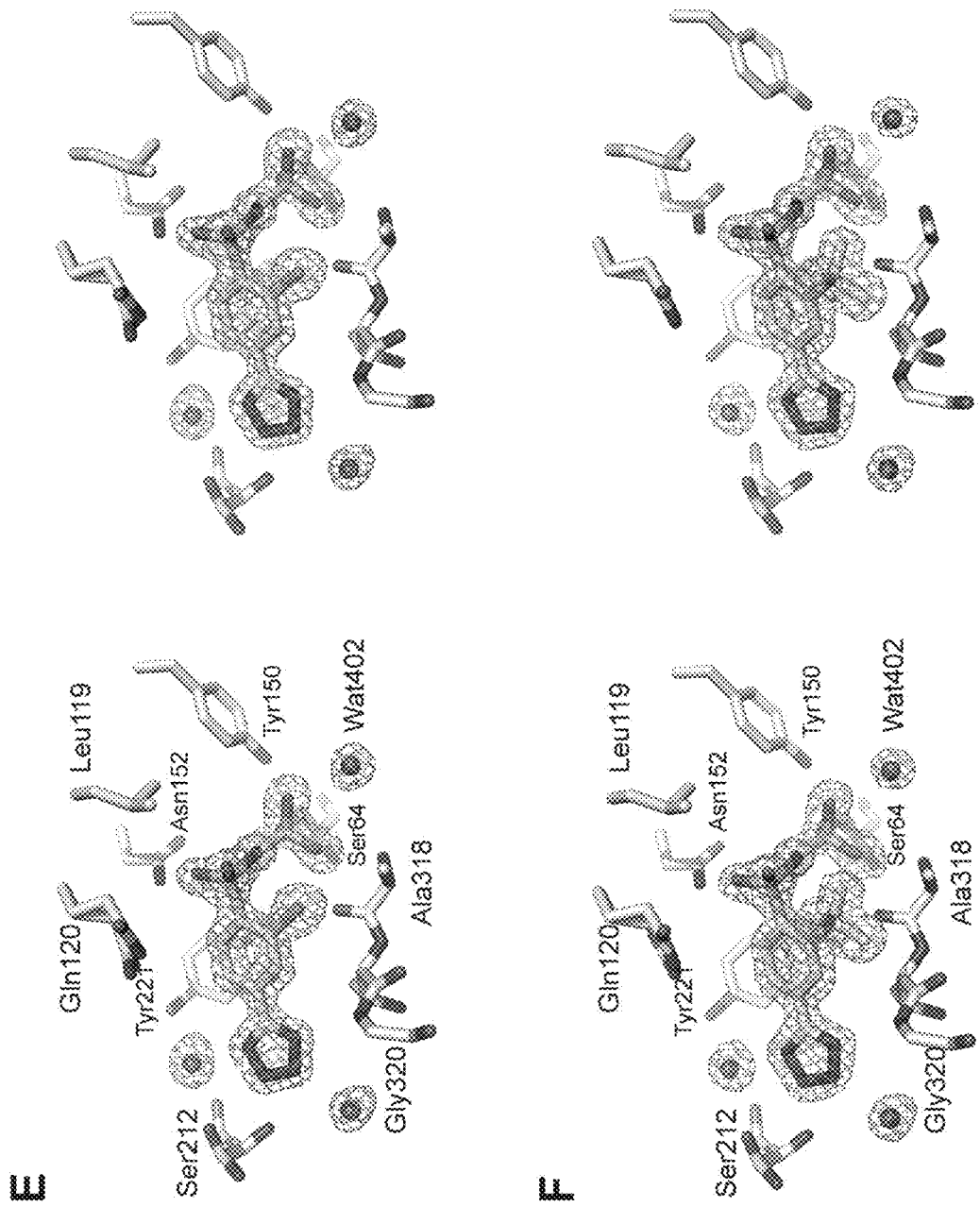
Figure 21:
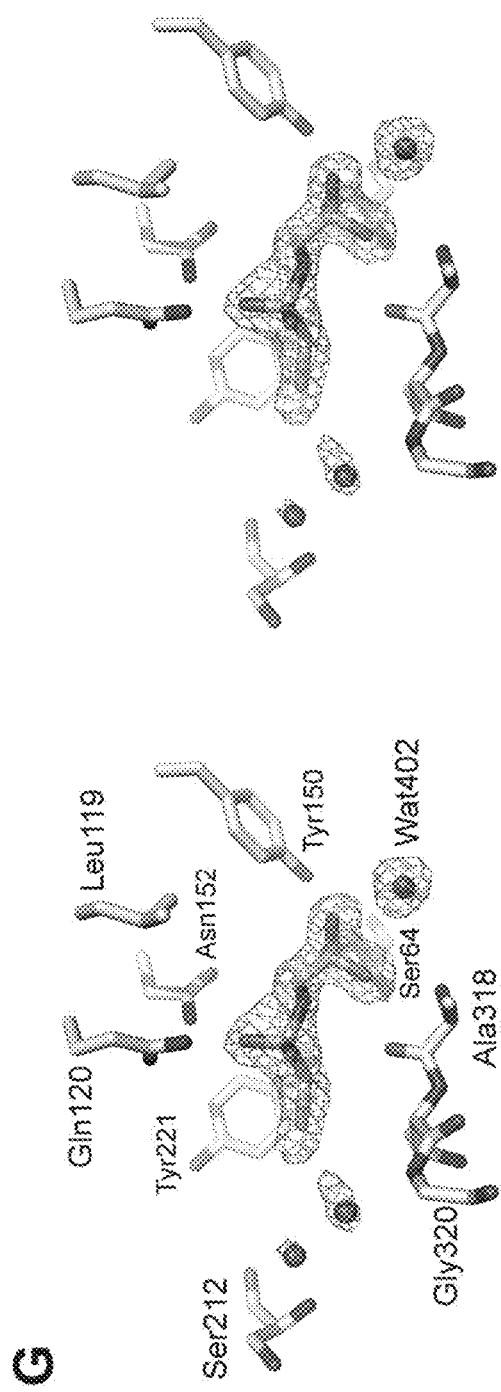

To understand the affinity increase at atomic resolution, we determined the X-ray structures of compounds CR167, CR157, and CR161 in complex with AmpC β-lactamase, to between 1.43 and 1.80 Å resolution (Table 9). Initial $F_o-F_c$ electron density maps allowed all three new inhibitors to be modeled unambiguously (FIG. 21). As expected, the Oγ of the catalytic Ser64 forms a dative covalent bond to the boron atoms of the inhibitors, with the boronic acid adopting a tetrahedral geometry. One boronic oxygen hydrogen bonds with the AmpC oxyanion hole, defined by backbone amides of Ser64 and Ala318, while the other oxygen hydrogen bonds with Tyr150 and the conserved water 402 (Wat402), as observed in earlier boronic acid structures. (Weston G S, et al. (1998), J Med Chem 41:4577-4586, Strynadka N C, et al. (1996), Nat Struct Biol 3:688-695, Chen Y, et al. (2006), J Am Chem Soc 128:2970-2976) Similarly, the key hydrogen bond between a sulfonamide oxygen and Asn152 is conserved (FIG. 15A-F). In the AmpC/CR167 complex an additional hydrogen bond is formed between the sulfonamide nitrogen and the backbone carbonyl of Ala318. The new benzyl ring makes parallel π-π stacking interactions with Tyr221 while the carboxylate hydrogen bonds with backbone amides of Ser212 and Gly320, as intended by design (FIG. 15A). Meanwhile, the conserved moieties of the tetrazole CR157 interact largely as observed in the AmpC/CR167 complex, and though the sulfonamide has shifted, it makes the same crucial hydrogen bond to Asn152 (FIG. 15B). Unlike the benzyl of CR167, the phenyl ring of CR157 makes edge-to-face π-π stacking interactions with Tyr221 at an angle of 55°. The tetrazole ring is almost co-planar with the phenyl ring (angle: 13°) and two nitrogen atoms of the tetrazole ring hydrogen bond with Ser212 and Gly320 backbone amides, also foreseen by design. Compound CR161 differs from CR157 only in the replacement of a phenyl by a pyridine in CR161, which superimposes closely on the CR157 structure; an ordered water (Wat863) is observed to interact with the pyridine nitrogen (as might, too, a protonated form of the tetrazole intramolecularly) (FIG. 15C). Overall, the modeled structures may be superposed with the crystallographic results with little deviation (FIG. 16).

Encouraged by the high affinity of these compounds, we sought derivatives with even further improved affinity. Aware that the tetrazole derivatives might have better cell-penetrance than the carboxylates (Lemke T L & Williams D A (2007) Foye's Principles of Medicinal Chemistry (Lippincott Williams & Wilkins, Philadelphia) Sixth Ed), owing to a higher pKa value, we chose to derivatize CR157. We sought compounds that might improve steric complementarity with the enzyme without disrupting other interactions. Modeling suggested that chloro derivatives ortho- and meta- to the tetrazole were easily accommodated by the site, as was a trifluoromethyl group in the meta position. CR191, CR190, and CR192 were thus synthesized and tested; all three were competitive, slow off-rate inhibitors of AmpC. While the 3-chloro derivative CR191 had a worse $K_i$ of 3 nM, the 2-chloro and 2-trifluoromethyl derivatives CR190 and CR192 showed 6- and 24-fold improved affinities compared to CR157 with $K_i$ values of 200 and 50 picomolar, respectively. X-ray crystal structures of AmpC complexes with CR191, CR190, and CR192, determined at 1.43, 1.44 and 1.49 Å, respectively, confirm that the new substitutions point away from Tyr221 and towards Ala318 as anticipated (FIG. 15D-F). In CR190 and CR192, the derivatives correspond closely to the precursor CR157, while in CR191 the plane of the phenyl is rotated by 20° to avoid a clash between the 3-chloro and backbone atoms of Gly320. In CR190, the 2-chloro is in van der Waals contact with the Cβ and backbone carbonyl atoms of Ala318 (3.8 and 3.6 Å, respectively). Similarly, in CR192 the 2-trifluoromethyl makes comparable interactions and also packs with the backbone of Thr319 (3.2-3.7 Å). The fluorines appear to also interact with the sulfonamide amide hydrogen (F-N distance: 2.8 Å), forming orthogonal multipolar interactions with the sulfonamide oxygen (F-O distance: 2.8 Å). To our knowledge, the 50 pM activity of CR192 makes it the most potent reversible β-lactamase inhibitor described to date, and ranks it among the most potent inhibitors described for most enzymes, having 200-fold better affinity than most drugs for their main targets (Overington J P, et al (2006), Nat Rev Drug Discovery 5:993-996).

Synthesis.

Figure 5:
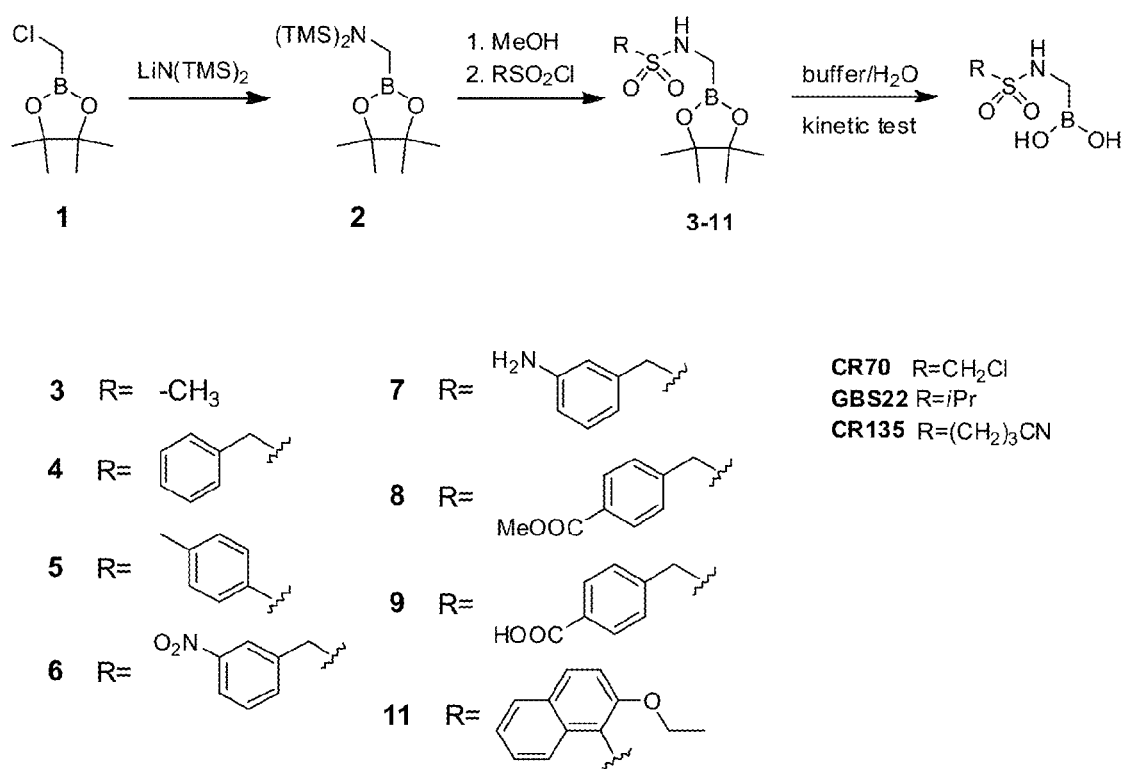
FIG. 5. Scheme 2. General scheme of the synthesis of sulfonamidomethaneboronic acids. Boronic esters convert rapidly to free boronic acids in aqueous solutions. Pinacol boronic esters were hydrolized to free boronic acids during kinetic measurements due to test condition.
Figure 6:
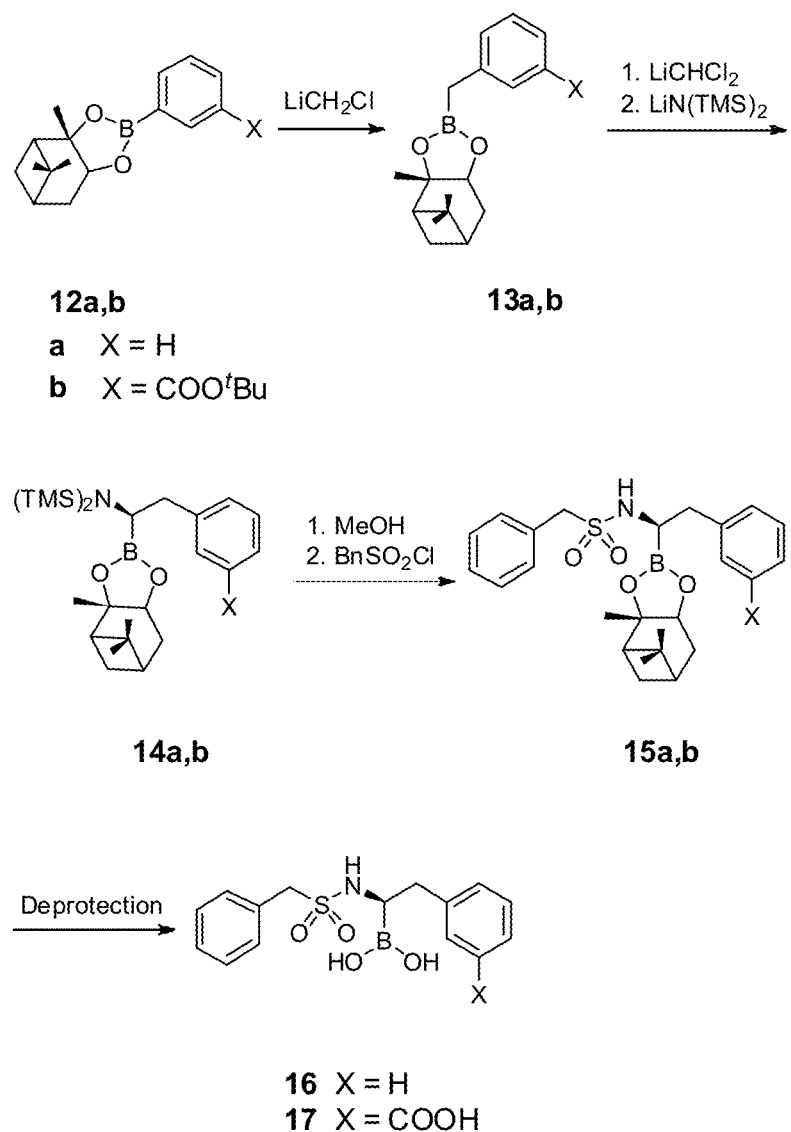
FIG. 6. Scheme 3. Asymmetric synthesis of 1-sulfonamido-2-phenylethaneboronic acids 16 and 17 (Table 1).

The sulfonamidomethaneboronic acids 3-9, 11, CR70, GBS22, CR135 were synthesized through sulfonylation of the aminomethaneboronate 2 (FIG. 5, Scheme 2). The key intermediate 2 was obtained by treating the chloromethylboronic acid pinacol ester 1 with lithium bis(trimethylsilyl) amide. (Caselli, E. et al., Chem. Biol. 2001, 8, 17-31) In situ deprotection of 2 with equimolar methanol, followed by condensation with suitable sulfonyl chlorides, afforded the sulfonamidomethaneboronic acids 3-9 and 11.

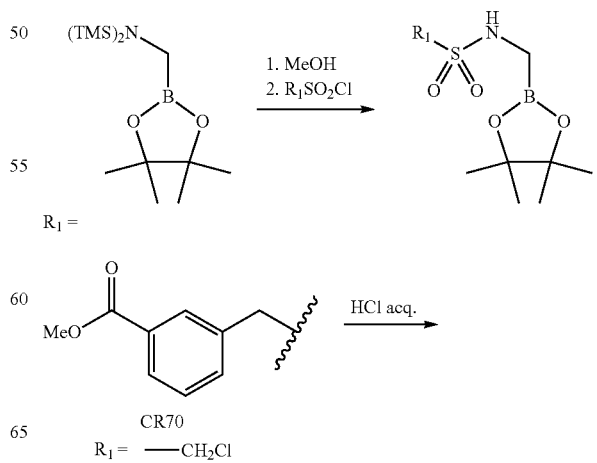

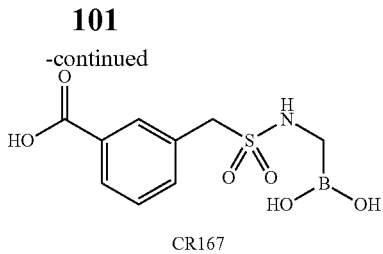

CR167

Compound 10 (Table 1), bearing the cephalothin side chain, could not be obtained because of instability of the suitable sulfonyl chloride. In fact, several attempts to obtain the (thiophene-2-yl)-methanesulfonylchloride lead to the corresponding 2-chloromethyl thiophene instead, as reported for other electron rich phenylmethanesulfonyl chlorides. (Walker, G. and Rana, *Synth. Commun.* 2003, 33, 627-632)

Related sulfonylaminomethaneboronate compounds (Schlapbach, A. and Hoffmann, R. W., *Eur. J. Org. Chem.* 2001, 323-328; Hercouet, A. et al., *Tetrahedron Lett.* 2004, 45, 8749-8751) can also be prepared by alkylation of suitable N-tert-butylsulfonamides with pinacol chloromethaneboronate 1, followed by acidic tert-butyl removal.

Following our previous approach with carboxamides, (Morandi, F. et al., *J. Am. Chem. Soc.* 2003, 125, 685-695) we attempted to synthesize compound 18 (Table 1), but the synthesis failed because of protodeboronation during sulfonylation reaction occurred. The loss of the boronic moiety may occur due to stabilization of the intermediate carbanion formed when a base coordinates to boron. (Matteson, D. S., *J. Organomet. Chem.* 1999, 581, 51-65) Because the presence of the m-carboxyphenyl ring in the present case can account for this stabilization, we decided to add an extra carbon between the boron atom and the phenyl ring (FIG. 6, Scheme 3). Therefore, to build the more elaborated inhibitors 16 and 17, boronates 12a,b were first homologated with chloromethyllithium. (Sadhu, K. M. and Matteson, D. S., *Organometallics* 1985, 4, 1687-1689) Subsequent Matteson stereoselective homologation with dichloromethyllithium, (Matteson, D. S., *J. Organomet. Chem.* 1999, 581, 51-65; Matteson, D. S. et al., *Organometallics* 1983, 2, 1536-1543; Matteson, D. S., *Acc. Chem. Res.* 1988, 21, 294-300; Matteson, D. S., *Chem. Rev.* 1989, 89, 1535-1551) followed by substitution with bis (trimethylsilyl)amide and sulfonylation afforded compounds 15a,b. The use of (+)-pinanediol as chiral auxiliary allowed the formation of the final R configuration, which mimics the stereochemistry of carbon atom C6/7 of penicillin/cephalosporin. The conversion of pinanediol esters 15a,b to free boronic acids 16 and 17 was achieved through transesterification with phenylboronic acid in a biphasic acetonitrile/water system. (Wityak, J.; Earl et al., *J. Org. Chem.* 1995, 60, 3717-3722)

Synthesis and Analysis.

All reactions were performed under argon using oven-dried glassware and dry solvents. Anhydrous tetrahydrofuran (THF) and diethyl ether were obtained by standard methods and freshly distilled under argon from sodium benzophenone ketyl prior to use. All reagents were purchased from Sigma-Aldrich and Fluka. The −100° C. bath was prepared by addition of liquid nitrogen to a pre-cooled (−80° C.) mixture of ethanol/methanol (1:1). Reactions were monitored by TLC, which were visualized by UV fluorescence and by Hanessian's cerium molybdate stain. Chromatographic purification of the compounds was performed on silica gel (particle size 0.05-0.20 mm). Melting points were measured on a Büchi 510 apparatus. Optical rotations were recorded at +20° C. on a Perkin-Elmer 241 polarimeter and are expressed in $10^{-1}$ deg cm$^2$ g$^{-1}$. $^1$H- and $^{13}$C-NMR spectra were recorded on a Bruker DPX-200 or Avance-400 spectrometer; chemical shifts (δ) are reported in ppm downfield from tetramethylsilane (TMS) as internal standard (s singlet, d doublet, t triplet, q quartet, m multiplet, br broad signal); coupling constants (J) are given in Hz. Two-dimensional NMR techniques (COSY, HMBC, HSQC) were used to aid in the assignment of signals in $^1$H and $^{13}$C spectra. Mass spectra were determined on a gas chromatograph HP 5890 with mass spectrometer detector HP 5972 (EI, 70 eV) or on an Agilent Technologies LC-MS(n) Ion Trap 6310A. The purity of all tested compounds was above 95%, determined by elemental analysis performed on a Carlo Erba Elemental Analyzer 1110; elemental analyses for the compounds were within ±0.3% of the theoretical values. MS fragmentation and elemental analyses of free boronic acids were not obtainable, because of the formation of dehydration products. Nevertheless, these boronic acids could be converted into analytically-pure pinacol/pinanediol esters by simple exposure to equimolar amount of pinacol/pinanediol in anhydrous THF.

General Procedure for the Synthesis of Sulfonylaminomethaneboronates (3-6, 8, 11, CR70, GBS22, CR135).

(Matteson, D. S. et al., *Organometallics* 1984, 3, 1284-1288) A solution of 2 (Caselli, E. et al., *Chem. Biol.* 2001, 8, 17-31) (1.00 mmol) in THF (3 mL) was added to a solution of anhydrous methanol in THF (2.5 M, 1.00 mmol) at −10° C. under argon flow. After stirring for 10 min at −10° C., the cooling bath was removed, and the reaction mixture stirred for 1 h at room temperature. Thereafter, the reaction mixture was cooled again to −10° C. and a solution of the selected sulfonyl chloride (1.10 mmol) in THF (2 mL) was slowly added; the resulting mixture was allowed to warm to room temperature overnight. The solvent was evaporated in vacuo and the residue purified by chromatography (dichloromethane/diethyl ether 8:2 to methanol) affording the expected sulfonamides.

Pinacol(methanesulfonylamino)methaneboronate (3)

According to the general procedure described before, the compound was recovered as a colorless oil (78% yield). $^1$H-NMR (200 MHz, CDCl$_3$): δ 1.26 (12H, s, pinacol protons), 2.79 (2H, d, J 4.8, BCH$_2$), 2.91 (3H, s, CH$_3$S), 4.45 (1H, br, SO$_2$NH). $^{13}$C-NMR (100 MHz, CDCl$_3$): δ 24.8, 28.0 (CB), 38.6, 84.8. EI-MS, m/z: 220 (M$^+$−15, 7%), 171 (29), 156 (24), 143 (21), 136 (39), 119 (14), 104 (100), 103 (44), 83 (37), 74 (6). Anal. Calcd. for C$_8$H$_{18}$BNO$_4$S: C, 40.87; H, 7.72; N, 5.96; S, 13.64. Found: C, 41.02; H, 7.55; N, 5.77; S, 13.51.

Pinacol(phenylmethanesulfonylamino)methaneboronate (4)

White solid (84% yield). Mp 138-141° C. $^1$H-NMR (200 MHz, CDCl$_3$): δ 1.27 (12H, s, pinacol protons), 2.71 (2H, s, BCH$_2$), 4.40 (1H, br, SO$_2$NH), 4.27 (2H, s, PhCH$_2$), 7.39 (5H, s, H$_{Arom}$). $^{13}$C-NMR (50 MHz, CDCl$_3$): δ 24.7, 29.6 (CB), 57.3, 84.7, 128.6, 128.7, 129.6, 130.6. EI-MS, m/z: 311 (M$^+$, 2%), 156 (18), 120 (5), 106 (8), 104 (17), 92 (9), 91 (100), 74 (17), 65 (11), 59 (16). Anal. Calcd. for C$_{14}$H$_{22}$BNO$_4$S: C, 54.03; H, 7.13; N, 4.50; S, 10.30. Found: C, 54.32; H, 7.30; N, 4.29; S, 10.55.

Pinacol(4-methylbenzenesulfonylamino)methaneboronate (5)

White solid (84% yield). Mp 103-105° C. $^1$H-NMR (200 MHz, DMSO): δ 1.17 (12H, s, pinacol protons), 2.25 (2H, d, J 5.5, BCH$_2$), 2.38 (3H, s, CH$_3$Ph), 7.06 (1H, t, J 5.5, SO$_2$NH), 7.38 (2H, d, J 8.2, H$_3$, H$_5$), 7.65 (2H, d, J 8.2, H$_2$, H$_6$). $^{13}$C-NMR (50 MHz, CDCl$_3$): δ 21.4, 24.7, 27.6 (CB), 84.6, 127.5, 129.6, 135.8, 143.2. EI-MS, m/z: 296 (M$^+$−15, 15%), 282 (55), 253 (31), 212 (19), 180 (78), 166 (26), 156 (100), 155 (39), 151 (46), 143 (20), 140 (30), 139 (89), 137 (23), 91 (80), 85 (19), 83 (25), 74 (98), 73 (30), 65 (31), 59 (20), 55 (23). Anal. Calcd. for C$_{14}$H$_{22}$BNO$_4$S: C, 54.03; H, 7.13; N, 4.50; S, 10.30. Found: C, 54.26; H, 7.24; N, 4.22; S, 10.38.

Pinacol(3-nitrophenylmethanesulfonylamino)methaneboronate (6)

Yellowish viscous oil (84% yield). $^1$H-NMR (400 MHz, CDCl$_3$): δ 1.29 (12H, s, pinacol protons), 2.80 (2H, d, J 4.4, BCH$_2$), 4.39 (2H, s, PhCH$_2$), 4.44 (1H, t, J 4.4, SO$_2$NH), 7.59 (1H, t, J 8.0, H$_5$), 7.80 (1H, d, J 8.0, H$_6$), 8.23 (1H, d, J 8.0, H$_4$), 8.29 (1H, s, H$_2$). $^{13}$C-NMR (100 MHz, CDCl$_3$): δ 24.8, 28.3 (CB), 56.6, 84.9, 123.5, 125.5, 129.8, 131.8, 136.9, 148.3; EI-MS, m/z: 341 (M$^+$−15, 2%), 327 (2), 240 (8), 165 (8), 156 (24), 137 (11), 136 (100), 129 (8), 104 (54), 103 (14), 90 (52), 89 (32), 83 (36), 74 (34), 59 (38), 43 (15), 41 (19). Anal. Calcd. for C$_{14}$H$_{21}$BN$_2$O$_6$S: C, 47.21; H, 5.94; N, 7.86; S, 9.00. Found: C, 47.35; H, 6.05; N, 7.73; S, 8.74.

Pinacol(3-aminophenylmethanesulfonylamino)methaneboronate hydrochloride (7)

Palladium 10 wt. % on activated carbon (51 mg, 40% w/w) was added to a solution of 6 (128 mg, 0.36 mmol) in ethyl acetate (4 mL), and allowed to react under hydrogen atmosphere for 16 h. The catalyst was filtered off and the solvent was evaporated in vacuo. The crude residue was dissolved in HCl (0.1 M soln in MeOH, 3.6 mL, 0.36 mmol). After 45 min the mixture was concentrated under reduced pressure and the residue repeatedly washed with diethyl ether, affording 7 as a yellowish solid (118 mg, 90% yield). Mp 193-196° C. $^1$H-NMR (400 MHz, DMSO): δ 1.23 (12H, s, pinacol protons), 2.59 (2H, d, J 3.82, BCH$_2$), 4.37 (2H, s, PhCH$_2$), 6.76 (1H, br, SO$_2$NH), 7.30-7.36 (3H, m, H$_{Arom}$), 7.46 (1H, t, J 7.60, H$_{Arom}$), 9.60-10.60 (3H, br, NH$_3$+). $^{13}$C-NMR (100 MHz, DMSO): δ 25.0, 27.5 (CB), 55.9, 84.2, 122.8, 125.3, 130.1, 130.5, 132.7, 133.0. EI-MS, m/z: 326 (M$^+$, 5%), 156 (8), 107 (64), 106 (100), 104 (15), 77 (11), 59 (11), 41 (8). Anal. Calcd. for C$_{14}$H$_{24}$BClN$_2$O$_4$S: C, 46.36; H, 6.67; N, 7.72; S, 8.84. Found: C, 46.41; H, 6.50; N, 7.55; S, 8.68.

Pinacol[4-(methoxycarbonyl)phenylmethanesufonylamino]methaneboronate (8)

According to the general procedure described above, the compound was recovered as a white solid (84% yield). Mp 104-107° C. $^1$H-NMR (400 MHz, CDCl$_3$): δ 1.27 (12H, s, pinacol protons), 2.73 (2H, d, J 4.1, BCH$_2$), 3.93 (3H, s, COOCH$_3$), 4.33 (2H, s, PhCH$_2$), 4.37 (1H, br, SO$_2$NH), 7.49 (2H, d, J 8.3, H$_2$, H$_6$), 8.04 (2H, d, J 8.3, H$_3$, H$_5$); $^{13}$C-NMR (100 MHz, CDCl$_3$): δ 24.8, 28.4 (CB), 52.2, 57.2, 84.8, 129.9, 130.3, 130.7, 134.6, 166.6; EI-MS, m/z: 354 (M$^+$−15, <2%), 338 (2), 311(2), 269 (3), 156 (25), 150 (24), 149 (100), 121 (24), 118 (13), 104 (19), 90 (19), 74 (26), 59 (13), 41 (9). Anal. Calcd. for C$_{16}$H$_{24}$BNO$_6$S: C, 52.04; H, 6.55; N, 3.79; S, 8.68. Found: C, 51.88; H, 6.74; N, 3.56; S, 8.51.

[(4-carboxyphenyl)methanesulfonylamino]methaneboronic acid (9)

A mixture of 8 (67 mg, 0.18 mmol) and HCl 3 N degassed (3 mL) was allowed to react at reflux for 1 h 30 min. After cooling, the reaction mixture was diluted with water (15 mL) and washed twice with diethyl ether (2×20 mL). The aqueous phase was concentrated in vacuo, affording 9 as a yellow solid (42 mg, 86% yield). Mp 118-122° C. (dec). $^1$H-NMR (400 MHz, DMSO): δ 2.5 (2H, d, J 4.9, BCH$_2$), 4.42 (2H, s, PhCH$_2$), 6.22 (1H, t, J 4.9, SO$_2$NH), 7.49 (2H, d, J 8.6, H$_2$, H$_6$), 7.93 (2H, d, J 8.6, H$_3$, H$_5$), 7.94 (1H, s, COOH). $^{13}$C-NMR (100 MHz, DMSO): δ 31.3 (CB), 55.7, 129.7, 130.7, 131.4, 136.0, 167.6. EI-MS and elemental analysis were not obtainable, but exposure of 9 to an equimolar amount of pinacol in anhydrous THF afforded the corresponding pinacol boronate in quantitative yield and satisfactory elemental analysis; Anal. Calcd. for C$_{15}$H$_{22}$BNO$_6$S: C, 50.72; H, 6.24; N, 3.94; S, 9.03. Found: C, 50.88; H, 6.41; N, 3.80; S, 8.77.

(2-Ethoxy-naphthalene-1-sulfonylamino)methaneboronic acid (11)

According to the general procedure described above, reaction of 2 with 2-ethoxy-naphthalene-1-sulfonyl chloride, obtained from 2-ethoxy-naphthalene, (Yekta, S. et al., *J. Fluorine Chem.* 2004, 125, 517-525) afforded 11 as white solid free boronic acid (80% yield). $^1$H-NMR (200 MHz, MeOD): δ 1.46 (3H, t, J 6.9, OCH$_2$CH$_3$), 1.94 (2H, s, BCH$_2$), 4.19 (2H, q, J 6.9, OCH$_2$CH$_3$), 7.24 (1H, dd, J 9.0, 2.0, H$_{Arom}$), 7.29 (1H, s, H$_{Arom}$), 7.70-7.91 (3H, m, H$_{Arom}$), 8.32 (1H, s, H$_{Arom}$). $^{13}$C-NMR (50 MHz, MeOD): δ 13.6, 20.7 (CB), 63.4, 106.2, 120.1, 123.2, 127.3, 127.4, 127.9, 130.1, 133.8, 136.4, 159.0. EI-MS and elemental analysis were not obtainable, but exposure of 11 to an equimolar amount of pinacol in anhydrous THF afforded the corresponding pinacol boronate in quantitative yield and satisfactory elemental analysis; Anal. Calcd. for C$_{19}$H$_{26}$BNO$_5$S: C, 58.32; H, 6.70; N, 3.58; S, 8.19. Found: C, 58.19; H, 6.84; N, 3.40; S, 7.96.

Pinacol(chloromethanesulfonylamino)methaneboronate (CR70)

According to the general procedure the compound was recovered as a cream colored solid (89% yield). Mp 59-61° C. $^1$H-NMR (400 MHz, CDCl$_3$): δ 1.28 (12H, s, pinacol protons), 2.87 (2H, d, J 4.6, CH$_2$B), 4.53 (2H, s, ClCH$_2$), 4.72 (1H, br, NH). $^{13}$C-NMR (100 MHz, CDCl$_3$): δ 24.8, 29.8 (br, CB), 53.9, 85.0. EI-MS: m/z 256 (1%, M$^+$), 254 (4%), 213 (5%), 211 (13%), 191 (6%), 170 (8%), 156 (20%), 127 (6%), 106 (6%), 104 (base peak), 103 (25%), 85 (42%), 74 (21%), 60 (21%), 59 (62%), 55 (14%), 49 (13%), 43 (16%), 41 (21%).

Pinacol(isopropylsulfonylamino)methaneboronate (GBS22)

According to the general procedure the compound was recovered as a white solid (71% yield). Mp 107-108° C. $^1$H-NMR (400 MHz, CDCl$_3$): δ 1.27 (12H, s, pinacol protons), 1.37 (6H, d, J 6.8, (CH$_3$)$_2$CH), 2.83 (2H, s, CH$_2$B), 3.21 (1H, septet, J 6.8, (CH$_3$)$_2$CH), 4.11 (1H, br, NH). $^{13}$C-NMR (100 MHz, CDCl$_3$): δ 16.6, 24.8, 28.3 (br, CB), 52.0, 84.7. EI-MS: m/z 248 (4%, M$^+$−15), 205 (16%), 192 (19%), 156 (20%), 142 (9%), 129 (14%), 105 (60%), 100 (9%), 83 (base peak), 74 (46%), 59 (33%), 43 (43%).

Pinacol(3-cyanopropane-1-sulfonylamino)methaneboronate (CR135)

According to the general procedure the compound was recovered as a white solid (61% yield). Mp 91-93° C.

¹H-NMR (400 MHz, CDCl₃): δ 1.32 (12H, s, pinacol protons), 2.24 (2H, quintet, J 7.1, H₂), 2.66 (2H, t, J 7.1, H₃), 2.87 (2H, d, J 4.4, CH₂B), 3.21 (2H, t, J 7.1, H₁), 4.33 (1H, br, NH). ¹³C-NMR (100 MHz, CDCl₃): δ 16.1, 20.1, 24.8, 28.6 (br, CB), 49.3, 84.9, 118.4. EI-MS: m/z 273 (2.5%, M⁺−15), 230 (2%), 189 (15%), 167 (58%), 156 (23%), 138 (55%), 104 (base peak), 103 (19%), 83 (54%), 74 (45%), 59 (57%), 55 (27%), 41 (71%).

(+)-Pinanediol 3-(tert-butoxycarbonyl)benzeneboronate (12b)

A solution of tert-butyl 3-bromo-benzoate (1.70 g, 6.61 mmol), obtained from 3-bromobenzoic acid, (Wright, S. W. et al., *Tetrahedron Lett.* 1997, 38, 7345-7348) and freshly distilled triisopropyl borate (1.53 mL, 6.61 mmol) in THF (17 mL) was cooled to −100° C. under argon flow and n-butyl-lithium (2.5 M soln in hexane, 2.91 mL, 7.27 mmol) was added dropwise over 15 min, during which the solution turned cherry red. After 1 h at −100° C., trimethylsilyl chloride (0.84 mL, 6.61 mmol) was dropped into the reactor and the resulting colorless solution was allowed to warm to room temperature and stirred overnight. Finally, (+)-pinanediol (1.12 g, 6.61 mmol) was added and the solution stirred 1 h at room temperature. The mixture was partitioned between ethyl acetate (100 mL) and water (40 mL) and the aqueous phase was extracted with ethyl acetate (2×50 mL). The combined organic phases were washed with brine, dried over MgSO₄, filtered and concentrated in vacuo. The crude residue was purified by column chromatography (light petroleum/ethyl ether 95:5), affording 12b as a yellowish solid (2.10 g, 89% yield). Mp 70-71° C. [α]$_D$+7.3 (c 1.1, CHCl₃). ¹H-NMR (400 MHz, CDCl₃): δ 0.94 (3H, s, pinanyl CH₃), 1.24 (1H, d, J 10.9, pinanyl H$_{endo}$), 1.36 (3H, s, pinanyl CH₃), 1.53 (3H, s, pinanyl CH₃), 1.64 (9H, s, t-Bu), 1.98-2.30 (5H, m, pinanyl protons), 4.51 (1H, dd, J 8.5, 2.0, CHOB), 7.46 (1H, t, J 7.6, H₅), 8.0 (1H, d, J 7.6, H₄), 8.12 (1H, d, J 7.6, H₆), 8.45 (1H, s, H₂). ¹³C-NMR (100 MHz, CDCl₃): δ 24.0, 26.5, 27.1, 28.2, 28.7, 35.5, 38.2, 39.5, 51.4, 78.4, 80.9, 86.5, 127.6, 131.5, 132.1, 135.7, 138.7, 169.5, CB not seen. EI-MS: m/z 356 (M⁺, 10%), 300 (36), 283 (41), 231 (50), 204 (38), 83 (65), 67 (59), 57 (100). Anal. Calcd. for C₂₁H₂₉BO₄: C, 70.80; H, 8.20. Found: C, 70.55; H, 8.22.

(+)-Pinanediol phenylmethaneboronate (13a)

n-Butyllithium (2.5 M soln in hexane, 4.66 mL, 11.64 mmol) was added dropwise to a stirred solution of (+)-pinanediol benzeneboronate 12a (Morandi, F. et al., *J. Am. Chem. Soc.* 2003, 125, 685-695) (2.48 g, 9.70 mmol) and bromochloromethane (0.95 mL, 14.55 mmol) in THF (25 mL) at −80° C. under argon atmosphere. The mixture was allowed to reach room temperature overnight. Then the solution was partitioned between light petroleum (80 mL) and water (25 mL), the organic phase was washed with saturated ammonium chloride (20 mL) and the combined aqueous phases were extracted with petroleum ether (2×40 mL). The organic phases were dried, filtered and concentrated and the crude residue was purified by gradient chromatography (light petroleum to light petroleum/ethyl ether 95:5), affording 13a as a colorless oil (2.33 g, 89% yield). [α]$_D$+14.2 (c 2.0, CHCl₃). ¹H-NMR (200 MHz, CDCl₃): δ 0.87 (3H, s, pinanyl CH₃), 1.10 (1H, d, J 10.8, pinanyl H$_{endo}$), 1.30 (3H, s, pinanyl CH₃), 1.41 (3H, s, pinanyl CH₃), 1.62-2.39 (5H, m, pinanyl protons), 2.37 (2H, s, BCH₂), 4.30 (1H, dd, J 8.8, 1.9, CHOB), 7.10-7.31 (5H, m, H$_{Ar}$). ¹³C-NMR (50 MHz, CDCl₃): δ 19.3 (CB), 24.0, 26.4, 27.1, 28.6, 35.5, 38.1, 39.5, 51.3, 78.0, 85.8, 124.8, 128.3, 128.9, 138.8. EI-MS: m/z 217 (M⁺+1, 2%), 270 (M⁺, 81%), 269 (M⁺−1, 21%), 255 (32), 229 (24), 214 (32), 201 (88), 200 (33), 187 (30), 179 (28), 174 (100), 135 (58), 134 (38), 119 (32), 118 (26), 117 (28), 109 (24), 93 (44), 91 (74), 83 (75), 82 (32), 81 (34), 79 (24), 77 (26), 67 (66), 65 (27), 55 (47), 53 (29). Anal. Calcd. for C₁₇H₂₃BO₂: C, 75.57; H, 8.58. Found: C, 75.39; H, 8.44.

(+)-Pinanediol[3-(tert-butoxycarbonyl)phenyl]methaneboronate (13b)

Following the procedure described for the synthesis of 13a, compound 13b was recovered from 12b as a yellow oil (88% yield). [α]$_D$+8.7 (c 1.4, CHCl₃). ¹H-NMR (400 MHz, CDCl₃): δ 0.87 (3H, s, pinanyl CH₃), 1.11 (1H, d, J 11.0, pinanyl H$_{endo}$), 1.32 (3H, s, pinanyl CH₃), 1.43 (3H, s, pinanyl CH₃), 1.63 (9H, s, t-Bu), 1.84-2.39 (5H, m, pinanyl protons), 2.42 (2H, s, BCH₂), 4.32 (1H, dd, J 8.8, 2.0, CHOB), 7.33 (1H, t, J 7.7, H₅), 7.40 (1H, d, J 7.7, H₆), 7.80 (1H, d, J 7.7, H₄), 7.86 (1H, s, H₂). ¹³C-NMR (100 MHz, CDCl₃): δ 19.3 (CB), 24.0, 26.5, 27.1, 28.2, 28.6, 35.4, 38.2, 39.5, 51.3, 78.0, 80.7, 86.0, 126.2, 128.1, 129.9, 132.0, 133.2, 139.0, 166.0; EI-MS: m/z 370 (M⁺, 18%), 314 (71), 297 (59), 135 (55), 57 (100). Anal. Calcd. for C₂₂H₃₁BO₄: C, 71.36; H, 8.44. Found: C, 71.60; H, 8.27.

(+)-Pinanediol (1R)-1-(N-bis(trimethylsilyl)amino)-2-phenylethaneboronate (14a)

n-Butyllithium (2.5 M soln in hexane, 1.78 mL, 4.44 mmol) was added dropwise to a stirred solution of dichloromethane (0.36 mL, 5.55 mmol) in THF (8 mL) at −100° C. under argon atmosphere; at the end of the butyllithium addition, a white microcrystalline precipitate (LiCHCl₂) became evident. After 30 min, a solution of 13a (1.00 g, 3.70 mmol) in THF (8 mL) was slowly added at the same temperature. The white precipitate disappeared and the mixture allowed to gradually reach room temperature overnight. The resulting solution was concentrated under reduced pressure. The crude was treated with petroleum ether (50 mL), and the resulting white inorganic precipitate was filtered off and washed with abundant petroleum ether. Solvent evaporation in vacuo afforded (+)-pinanediol (1S)-1-chloro-2-phenylethaneboronate, used as such for the subsequent reaction.

The above product was dissolved in THF (10 mL) and lithium bis(trimethylsilyl)amide (1.0 M soln in tetrahydrofuran, 3.70 mL, 3.70 mmol) was added dropwise at −100° C. under argon flow. The reaction mixture was allowed to reach room temperature overnight. The resulting solution was concentrated under reduced pressure and the crude was treated with petroleum ether (50 mL); the white inorganic precipitate (LiCl) was filtered off and washed with abundant petroleum ether. The solvent was evaporated in vacuo to give a residue which was subjected to column chromatography (light petroleum/ethyl ether/triethylamine 98:2:5) recovering 14a as a pale yellow oil (837 mg, 51% yield). [α]$_D$−14.8 (c 2.3, CHCl₃). ¹H-NMR (400 MHz, CDCl₃): δ 0.12 (18H, s, 2Si(CH₃)₃), 0.87 (3H, s, pinanyl CH₃), 0.99 (1H, d, J 10.8, pinanyl H$_{endo}$), 1.31 (3H, s, pinanyl CH₃), 1.41 (3H, s, pinanyl CH₃), 1.78-2.36 (5H, m, pinanyl protons), 2.71 (1H, dd, J 13.1, 7.6, CHCH₂), 2.87 (1H, t, J 7.4, BCH), 3.08 (1H, dd, J 13.1, 7.3, CHCH₂), 4.31 (1H, dd, J 8.7, 2.0, CHOB), 7.17-7.31 (5H, m, H$_{Arom}$). ¹³C-NMR (100 MHz, CDCl₃): δ 3.0, 24.0, 26.0, 27.1, 28.4, 35.2, 38.1, 39.5, 42.0, 45.0 (CB), 51.4, 78.2, 85.6, 125.7, 127.8, 129.7, 141.7. Anal. Calcd. for C₂₄H₄₂BNO₂Si₂: C, 64.98; H, 9.54; N, 3.16. Found: C, 65.19; H, 9.46; N, 2.95.

(+)-Pinanediol (1R)-2-(3(tert-butoxycarbonyl)phenyl)-1-(N-bis(trimethylsilyl)-pamino)ethaneboronate (14b)

Following the procedure described for the synthesis of 14a, compound 14b was recovered as a colorless oil (28% yield). $[\alpha]_D$–12.6 (c 3.9, CHCl$_3$). $^1$H-NMR (200 MHz, CDCl$_3$): δ 0.10 (18H, s, 2Si(CH$_3$)$_3$), 0.83 (3H, s, pinanyl CH$_3$), 0.94 (1H, d, J 11.1, pinanyl H$_{endo}$), 1.28 (3H, s, pinanyl CH$_3$), 1.38 (3H, s, pinanyl CH$_3$), 1.61 (9H, s, t-Bu), 1.78-2.35 (5H, m, pinanyl protons), 2.66-2.87 (2H, m, BCH, CHCH$_2$), 3.06-3.15 (1H, m, CHCH$_2$), 4.29 (1H, d, J 8.7, CHOB), 7.29-7.43 (2H, m, H$_5$, H$_6$), 7.82-7.91 (2H, m, H$_2$, H$_4$). $^{13}$C-NMR (50 MHz, CDCl$_3$): δ 3.0, 23.9, 26.2, 27.0, 28.2, 28.4, 35.1, 38.1, 39.5, 41.8, 44.8 (CB), 51.4, 78.3, 80.5, 85.6, 126.9, 127.7, 130.8, 131.5, 133.8, 141.7, 166.0. Anal. Calcd. for C$_{29}$H$_{50}$BNO$_4$Si$_2$: C, 64.06; H, 9.27; N, 2.58. Found: C, 63.84; H, 9.06; N, 2.77.

(+)-Pinanediol (1R)-1-(phenylmethanesulfonylamino)-2-phenylethaneboronate (15a)

A solution of 14a (840 mg, 1.89 mmol) in THF (2 mL) was added to a THF solution of anhydrous methanol (2.5 M, 0.76 mL, 1.89 mmol) at –10° C. under nitrogen and magnetically stirred for 10 min at –10° C. The cooling bath was removed and the solution was stirred at room temperature for an additional hour. Thereafter, the temperature was lowered to –40° C. and phenylmethanesulfonyl chloride (469 mg, 2.46 mmol) in THF (2 mL) was slowly dropped in. The resulting colorless solution was allowed to gradually reach room temperature and stirred overnight. The solution was partitioned between diethyl ether (30 mL) and water (10 mL), the aqueous phase extracted with diethyl ether (2×20 mL) and the combined organic phases were dried (Na$_2$SO$_4$), filtered and concentrated. The crude residue was purified by column chromatography (dichloromethane/diethyl ether 6:4), affording 15a as a thick yellowish oil (343 mg, 40% yield). $[\alpha]_D$+9.7 (c 1.6, CHCl$_3$). $^1$H-NMR (400 MHz, CDCl$_3$): δ 0.85 (3H, s, pinanyl CH$_3$), 1.10 (1H, d, J 10.8, pinanyl H$_{endo}$), 1.31 (3H, s, pinanyl CH$_3$), 1.32 (3H, s, pinanyl CH$_3$), 1.82-2.42 (5H, m, pinanyl protons), 2.90 (1H, dd, J 13.7, 7.1, CHCH$_2$), 3.08 (1H, dd, J 13.7, 5.5, CHCH$_2$), 3.27-3.39 (1H, m, BCH), 4.18 (1H, br, SO$_2$NH), 4.21 (2H, s, CH$_2$SO$_2$), 4.35 (1H, dd, J 8.8, 2.0, CHOB), 7.20-7.34 (10H, m, H$_{Arom}$). $^{13}$C-NMR (100 MHz, CDCl$_3$): δ 23.9, 26.3, 27.0, 28.3, 35.1, 38.1, 38.8, 39.4, 42.5 (CB), 51.2, 59.1, 78.6, 86.9, 126.6, 128.4, 128.5, 128.6, 129.6, 129.7, 130.7, 138.4. Anal. Calcd. for C$_{25}$H$_{32}$BNO$_4$S: C, 66.23; H, 7.11; N, 3.09; S, 7.07. Found: C, 66.04; H, 6.97; N, 2.88; S, 6.91.

Pinanediol (1R)-2-(3(tert-butoxycarbonyl)phenyl)-1-(phenylmethanesulfonylamino)ethaneboronate (15b)

Following the procedure described for 15a, compound 15b was recovered as a yellowish oil (35% yield). $[\alpha]_D$+18.7 (c 0.7, CHCl$_3$). $^1$H-NMR (400 MHz, CDCl$_3$): δ 0.82 (3H, s, pinanyl CH$_3$), 1.00 (1H, d, J 10.9, pinanyl H$_{endo}$), 1.26 (3H, s, pinanyl CH$_3$), 1.28 (3H, s, pinanyl CH$_3$), 1.59 (9H, s, t-Bu), 1.83-2.36 (5H, m, pinanyl protons), 2.95 (1H, dd, J 13.3, 6.4, CHCH$_2$), 3.10 (1H, dd, J 13.3, 5.6, CHCH$_2$), 3.31 (1H, q, J 5.9, BCH), 4.17 (1H, d, J 5.9, SO$_2$NH), 4.23 (2H, s, CH$_2$SO$_2$), 4.37 (1H, d, J 8.7, 2.0, CHOB), 7.32-7.44 (7H, m, H$_{Arom}$), 7.83-7.85 (2H, m, H$_{Arom}$). $^{13}$C-NMR (100 MHz, CDCl$_3$): δ 24.0, 26.3, 27.0, 28.2, 29.7, 35.0, 38.2, 38.7, 39.4, 42.5 (CB), 51.1, 59.1, 78.7, 81.0, 87.1, 127.8, 128.5, 129.0, 129.6, 130.4, 130.8, 132.1, 134.1, 138.5, 165.7. Anal. Calcd. for C$_{30}$H$_{40}$BNO$_6$S: C, 65.10; H, 7.28; N, 2.53; S, 5.79. Found: C, 64.88; H, 7.02; N, 2.29; S, 5.47.

(1R)-1-(phenylmethanesulfonylamino)-2-phenylethaneboronic acid (16)

To a solution of 15a (245 mg, 0.54 mmol) in CH$_3$CN (3 mL), HCl (1M aqueous solution, 350 μL, 0.35 mmol), phenylboronic acid (62 mg, 0.51 mmol) and n-hexane (3 mL) were sequentially added and the resulting biphasic solution was vigorously stirred. After 30 min the n-hexane layer, containing the pinanediol phenylboronate, was removed and fresh n-hexane (3 mL) was added. This last procedure was repeated several times until a TLC analysis revealed no remaining pinanediol boronate. The acetonitrile phase was then concentrated affording 16 as a yellowish solid (159 mg, 92% yield). Mp 107° C. (dec). $[\alpha]_D$+78.0 (c 1.0, MeOH). $^1$H-NMR (400 MHz, MeOD): δ 2.83 (2H, d, J 7.1, CHCH$_2$), 3.05 (1H, t, J 7.1, BCH), 4.20 (2H, s, CH$_2$SO$_2$), 7.16-7.44 (10H, m, H$_{Arom}$). $^{13}$C-NMR (100 MHz, MeOD): δ 38.8, 39.3 (CB), 58.6, 126.1, 127.2, 128.0, 128.2, 129.0, 130.1, 130.6, 133.3. EI-MS and elemental analysis were not obtainable, but exposure of 16 to an equimolar amount of (+)-pinanediol in anhydrous THF afforded compound 15a in quantitative yield and satisfactory elemental analysis; Anal. Calcd. for C$_{25}$H$_{32}$BNO$_4$S: C, 66.23; H, 7.11; N, 3.09; S, 7.07. Found: C, 66.14; H, 6.91; N, 3.32; S, 6.89.

(1R)-2-(3-carboxyphenyl)-1-(phenylmethanesulfonylamino)ethaneboronic acid (17)

A solution of 15b (90 mg, 0.16 mmol) in dichloromethane (2 mL) was cooled to –10° C. and treated with an excess of trifluoroacetic acid (10% v/v soln in dichloromethane, 2 mL). After 10 min at –10° C., the mixture was allowed to react at room temperature for 5 h. The solution was concentrated in vacuo and the residue crystallized from diethyl ether affording (+)-pinanediol (1R)-2-[3-carboxyphenyl]-1-(phenylmethanesulfonylamino)ethaneboronate (79 mg, 100% yield) as a cream coloured solid. Mp 155-158° C. $[\alpha]_D$+25.9 (c 0.6, CHCl$_3$). $^1$H-NMR (400 MHz, CDCl$_3$): δ 0.87 (3H, s, pinanyl CH$_3$), 1.06 (1H, d, J 10.8, pinanyl H$_{endo}$), 1.31 (3H, s, pinanyl CH$_3$), 1.33 (3H, s, pinanyl CH$_3$), 1.88-2.38 (5H, m, pinanyl protons), 2.99 (1H, dd, J 13.7, 6.0, CHCH$_2$), 3.15 (1H, dd, J 13.7, 5.6, CHCH$_2$), 3.37 (1H, br, BCH), 4.31 (2H, s, CH$_2$SO$_2$), 4.40 (1H, d, J 7.7, CHOB), 4.51 (1H, br, SO$_2$NH), 7.30-7.58 (7H, m, H$_{Arom}$), 7.97-8.01 (2H, m, H$_{Arom}$), 10.2 (1H, br, COOH). $^{13}$C-NMR (100 MHz, CDCl$_3$): δ 24.0, 26.3, 27.0, 28.3, 35.0, 38.2, 38.5, 39.4, 42.4 (CB), 51.1, 59.2, 78.8, 87.3, 128.5, 128.6, 128.7, 127.2, 129.3, 129.4, 130.8, 131.2, 135.6, 139.0, 171.8. Anal. Calcd. for C$_{26}$H$_{32}$BNO$_6$S: C, 62.78; H, 6.48; N, 2.82; S, 6.45. Found: C, 62.61; H, 6.72; N, 2.64; S, 6.21.

This compound was then treated according to the procedure described for 16 to recover 17 as a yellowish solid (54 mg, 92% yield). Mp 118-122° C. (dec). $[\alpha]_D$+136.0 (c 0.5, MeOH). $^1$H-NMR (400 MHz, MeOD): δ 2.87 (2H, d, J 7.0, CHCH$_2$), 3.05 (1H, t, J 7.0, BCH), 4.24 (2H, s, CH$_2$SO$_2$), 7.31-7.88 (9H, m, H$_{Arom}$). $^{13}$C-NMR (100 MHz, MeOD): δ 38.4, 42.9 (CB), 58.8, 127.5, 128.0, 128.1, 128.2, 129.6, 130.1, 130.2, 130.6, 133.8, 139.1, 168.4. EI-MS and elemental analysis were not obtainable, but exposure of 11 to an equimolar amount of (+)-pinanediol in anhydrous THF afforded the corresponding pinanediol boronate in quantitative yield and satisfactory elemental analysis; Anal. Calcd. for C$_{26}$H$_{32}$BNO$_6$S: C, 62.78; H, 6.48; N, 2.82; S, 6.45. Found: C, 62.56; H, 6.71; N, 2.59; S, 6.28.

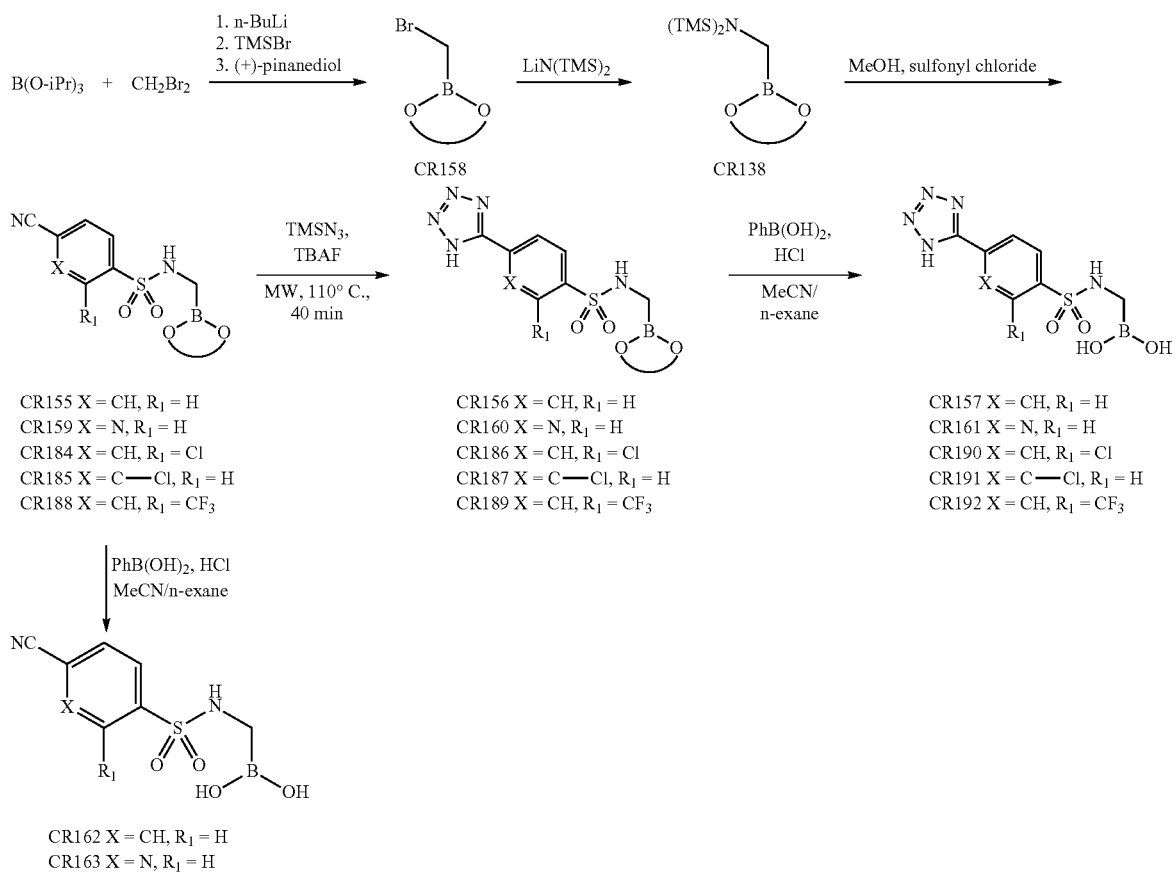

CR155 X = CH, R₁ = H
CR159 X = N, R₁ = H
CR184 X = CH, R₁ = Cl
CR185 X = C—Cl, R₁ = H
CR188 X = CH, R₁ = CF₃

CR156 X = CH, R₁ = H
CR160 X = N, R₁ = H
CR186 X = CH, R₁ = Cl
CR187 X = C—Cl, R₁ = H
CR189 X = CH, R₁ = CF₃

CR157 X = CH, R₁ = H
CR161 X = N, R₁ = H
CR190 X = CH, R₁ = Cl
CR191 X = C—Cl, R₁ = H
CR192 X = CH, R₁ = CF₃

CR162 X = CH, R₁ = H
CR163 X = N, R₁ = H (+)-Pinanediol bromomethaneboronate (CR158)

MW: 272.97. n-Butyllithium (2.5 M solution in n-hexane, 11.75 mL, 29.37 mmol) was added dropwise to a stirred solution of dibromomethane (2.26 mL, 32.45 mmol) and triisopropyl borate (6.5 mL, 27.97 mmol) in THF (20 mL) at −78° C. under argon atmosphere. After one hour bromotrimethylsilane (4.28 mL, 32.45 mmol) was slowly added at the same temperature. The mixture was allowed to gradually reach room temperature overnight. A solution of (1S,2S,3R,5S)-(+)-pinanediol (4.76 g, 27.97 mmol) in dry THF (10 mL) was then added at rt and left to react for 1 h. The reaction mixture was partitioned between ethyl acetate (100 mL) and water (40 mL), and the aqueous phase was extracted with ethyl acetate (2×80 mL). The combined organic phases were washed with brine, dried over Na₂SO₄, filtered and concentrated in vacuo. The crude residue was purified by chromatography (light petroleum/ethyl acetate 9:1), affording CR158 as a colourless oil (6.010 g, 79% yield). $[\alpha]_D$+22.5 (c 2.8, CHCl₃). ¹H-NMR (200 MHz, CDCl₃): δ 0.80 (3H, s, pinanyl CH₃), 1.16 (1H, d, J 11.0, pinanyl H$_{endo}$), 1.25 (3H, s, pinanyl CH₃), 1.37 (3H, s, pinanyl CH₃), 1.71-2.39 (5H, m, pinanyl protons), 2.57 (2H, s, BCH₂), 4.32 (1H, dd, J 8.7, 1.8, CHOB). ¹³C-NMR (50 MHz, CDCl₃): δ 8.2 (br, CB), 23.9, 26.2, 27.0, 28.4, 35.2, 38.2, 39.3, 51.2, 78.5, 86.7. IR (neat): ν$_{max}$ 1242, 1340, 1416. GC-MS, m/z: 272-274 (1:1, M⁺, 11), 257-259 (1:1, 32), 231 (33), 216-218 (1:1, 30), 203-205 (1:1, 52), 189 (25), 176 (26), 152 (25), 134 (74), 119 (30), 109 (30), 96 (80), 83 (100), 81 (66), 67 (62), 55 (51). Anal. Calcd for C₁₁H₁₈BBrO₂: C, 48.40; H, 6.65. Found: C, 48.48; H, 6.71.

(+)-Pinanediol 1-bis(trimethylsilyl)aminomethaneboronate (CR138)

MW: 353.46. A solution of CR158 (1.00 g, 3.66 mmol) in THF (10 mL) was cooled to −78° C. under argon flow and lithium bis(trimethylsilyl)amide (1 M sln in tetrahydrofuran, 4.39 mL, 4.39 mmol) was added dropwise. The reaction mixture was allowed to reach room temperature overnight and then was partitioned between light petroleum (70 mL) and water (10 mL). The organic phase was washed with brine, dried over Na₂SO₄, filtered and concentrated in vacuo, affording CR138 as a yellowish oil (1.07 g, 83% yield). $[\alpha]_D$−15.6 (c 1.1, CHCl₃). ¹H-NMR (400 MHz, CDCl₃): δ 0.12 (18H, s, SiCH₃), 0.88 (3H, s, pinanyl CH₃), 1.19 (1H, d, J 10.9, pinanyl H$_{endo}$), 1.32 (3H, s, pinanyl CH₃), 1.40 (3H, s, pinanyl CH₃), 1.86-2.39 (5H, m, pinanyl protons), 2.53 (2H, s, BCH₂), 4.31 (1H, dd, J 8.8, 1.9, CHOB). ¹³C-NMR (100 MHz, CDCl₃): δ 1.6, 24.0, 26.5, 27.1, 28.6, 29.0 (br, CB), 35.5, 38.2, 39.5, 51.3, 77.9, 85.7. GC-MS, m/z: 353 (M⁺, 2.6), 338 (5), 281 (17), 280 (82), 279 (20), 189 (19), 188 (15), 187 (14), 186 (72), 185 (18), 147 (15), 146 (18), 135 (45), 130 (22), 107 (25), 93 (61), 91 (16), 73 (base peak), 69 (16), 59 (18), 43 (28), 41 (25).

General Procedure for the Synthesis of Sulfonylaminomethaneboronates (CR155, CR159, CR184, CR185, CR188).

A solution of CR138 (1.5 mmol) in THF (2 mL) was added to a solution of anhydrous methanol in THF (2.5 M, 600 μL, 1.5 mmol) at −10° C. under argon flow. After being stirred for 10 min at −10° C., the cooling bath was removed. The reaction mixture was stirred for 1 h at room temperature. Thereafter, the reaction mixture was once cooled again to −10° C. and a solution of selected sulfonyl chloride (1.65 mmol) in THF (2 mL) was slowly added. After 10 min the bath was removed and the resulting mixture was allowed to react at room temperature overnight. The solvent was evaporated in vacuo and the residue purified as described below for single compounds.

(+)-Pinanediol (4-cyanobenzensulfonylamino)methane boronate (CR155)

MW: 374.26. The crude was purified by gradient chromatography (light petroleum/diethyl ether from 7:3 to 3:7). The product was then crystallized from dichloromethane and n-hexane, affording CR155 (53% yield) as a white powder. Mp 118-120° C. $[\alpha]_D$+21.3 (c 0.7, CHCl$_3$). $^1$H-NMR (400 MHz, CDCl$_3$): δ 0.86 (3H, s, pinanyl CH$_3$), 0.98 (1H, d, J 11.0, pinanyl H$_{endo}$), 1.32 (3H, s, pinanyl CH$_3$), 1.40 (3H, s, pinanyl CH$_3$), 1.66-2.38 (5H, m, pinanyl protons), 1.74 (2H, d, J 4.9, BCH$_2$), 4.33 (1H, dd, J 7.3, 1.4, CHOB), 4.69 (1H, br, NH), 7.85 (2H, d, J 8.3, H$_3$, H$_5$), 8.06 (2H, d, J 8.3, H$_2$, H$_6$). $^{13}$C-NMR (100 MHz, CDCl$_3$): δ 23.9, 26.4, 27.0, 27.5 (br, CB), 28.4, 35.0, 38.2, 39.3, 51.1, 78.8, 87.4, 116.3, 117.4, 128.0, 132.9, 143.3. LC-MS (ESI, Ion Trap): m/z 373.3 (M−H)$^+$; MS/MS 373.3: m/z 309.2 (9), 165.9 (base peak), 118.1 (53).

(+)-Pinanediol (6-cyano-pyridin-3-sulfonylamino)methane boronate (CR159)

MW: 375.25. The crude was purified by crystallization from dichloromethane and n-hexane, recovering a white powder (61% yield). Mp 119-121° C. $[\alpha]_D$+7.5 (c 0.9, MeOH). $^1$H-NMR (400 MHz, CDCl$_3$): δ 0.87 (3H, s, pinanyl CH$_3$), 0.97 (1H, d, J 11.0, pinanyl H$_{endo}$), 1.33 (3H, s, pinanyl CH$_3$), 1.40 (3H, s, pinanyl CH$_3$), 1.80-2.39 (5H, m, pinanyl protons), 2.80 (2H, d, J 4.7, BCH$_2$), 4.34 (1H, dd, J 8.7, 3.3, CHOB), 4.82 (1H, br, NH), 7.89 (1H, d, J 8.5, H$_5$), 8.34 (1H, dd, J 8.5, 1.8, H$_4$), 9.19 (1H, d, J 1.8, H$_2$). $^{13}$C-NMR (100 MHz, CDCl$_3$): δ 23.9, 26.4, 26.7, 27.3 (br, CB), 28.4, 35.0, 38.2, 39.3, 51.0, 78.9, 87.6, 116.1, 128.4, 136.2, 136.7, 138.8, 149.3. LC-MS (ESI, Ion Trap): m/z 376.2 (M+H)$^+$.

(+)-Pinanediol (2-chloro-4-cyanobenzensulfonylamino)methane boronate (CR184)

MW: 408.71. The crude was purified by two chromatography (dichloromethane/diethyl ether 8:2, light petroleum/diethyl ether from 7:3 to 3:7). CR184 was recovered (69% yield) as a white rubbery solid. $[\alpha]_D$+15.6 (c 1.6, CHCl$_3$). $^1$H-NMR (400 MHz, CDCl$_3$): δ 0.86 (3H, s, pinanyl CH$_3$), 0.97 (1H, d, J 11.0, pinanyl H$_{endo}$), 1.32 (3H, s, pinanyl CH$_3$), 1.40 (3H, s, pinanyl CH$_3$), 1.80-2.38 (5H, m, pinanyl protons), 2.69 (2H, d, J 4.8, BCH$_2$), 4.34 (1H, dd, J 8.7, 1.7, CHOB), 5.18 (1H, t, J 4.8, NH), 7.74 (1H, dd, J 8.1, 1.5, H$_5$), 7.83 (1H, d, J 1.5, H$_3$), 8.24 (1H, d, J 8.1, H$_6$). $^{13}$C-NMR (100 MHz, CDCl$_3$): δ 23.9, 26.4, 27.0, 27.9 (br, CB), 28.4, 35.0, 38.1, 39.3, 51.1, 78.8, 87.4, 116.2, 117.4, 130.6, 132.5, 132.8, 134.7, 140.8. LC-MS (ESI, Ion Trap): m/z 407.4 (M−H)$^+$.

(+)-Pinanediol(3-chloro-4-cyanobenzensulfonylamino)methane boronate (CR185)

MW: 408.71. The crude was purified by two chromatography (dichloromethane/diethyl ether 8:2, light petroleum/diethyl ether from 7:3 to 3:7). CR185 was recovered (57% yield) as a white rubbery solid. $[\alpha]_D$+14.9 (c 1.6, CHCl$_3$). $^1$H-NMR (400 MHz, CDCl$_3$): δ 0.84 (3H, s, pinanyl CH$_3$), 0.97 (1H, d, J 11.0, pinanyl H$_{endo}$), 1.30 (3H, s, pinanyl CH$_3$), 1.38 (3H, s, pinanyl CH$_3$), 1.78-2.36 (5H, m, pinanyl protons), 2.74 (2H, d, J 4.9, BCH$_2$), 4.32 (1H, dd, J 8.7, 1.6, CHOB), 4.96 (1H, t, J 4.9, NH), 7.86 (1H, d, J 8.1, H$_5$), 7.90 (1H, dd, J 8.1, 1.4, H$_6$), 8.04 (1H, d, J 1.4, H$_2$). $^{13}$C-NMR (100 MHz, CDCl$_3$): δ 23.9, 26.4, 27.0, 27.3 (br, CB), 28.4, 35.0, 38.1, 39.3, 51.1, 78.8, 87.4, 114.8, 116.9, 125.9, 128.7, 134.7, 137.9, 144.7. LC-MS (ESI, Ion Trap): m/z 407.4 (M−H)$^+$.

(+)-Pinanediol (4-cyano-2-trifluoromethyl-benzensulfonylamino)methane boronate (CR188)

MW: 442.26. The crude was purified by chromatography (dichloromethane/diethyl ether 8:2). CR188 was recovered (74% yield) as a white rubbery solid. $[\alpha]_D$+14.5 (c 1.9, CHCl$_3$). $^1$H-NMR (400 MHz, CDCl$_3$): δ 0.82 (3H, s, pinanyl CH$_3$), 0.93 (1H, d, J 11.0, pinanyl H$_{endo}$), 1.28 (3H, s, pinanyl CH$_3$), 1.35 (3H, s, pinanyl CH$_3$), 1.75-2.34 (5H, m, pinanyl protons), 2.73 (2H, d, J 4.6, BCH$_2$), 4.30 (1H, dd, J 8.7, 1.5, CHOB), 5.00 (1H, t, J 4.6, NH), 8.03 (1H, d, J 8.2, H$_5$), 8.14 (1H, s, H$_3$), 8.36 (1H, d, J 8.2, H$_6$). $^{13}$C-NMR (100 MHz, CDCl$_3$): δ 23.9, 26.3, 26.9, 27.5 (br, CB), 28.3, 34.9, 38.1, 39.3, 51.0, 78.7, 87.3, 116.2, 116.7, 121.9 (q, J 274.7, CF$_3$), 129.1 (q, J 34.1, C$_2$), 131.9 (q, J 34.1, C$_3$), 132.9, 135.9, 142.0. LC-MS (ESI, Ion Trap): m/z 441.3.

General Procedure for the Synthesis of Tetrazole Derivatives (CR156, CR160, CR186, CR187, CR189).

The starting cyano derivative described above CR155, CR159, CR184, CR185, CR188 (0.30 mmol), azidotrimethylsilane (4.50 mmol) and tetrabutylammonium fluoride trihydrate (0.30 mmol) were mixed in a microwave glass vial. The vessel was sealed and heated under microwave irradiation at 110° C. for 40 min. The reaction mixture was diluted with ethyl acetate (20 mL) and then washed with 1M HCl (4×7 mL). The organic phase was dried, filtered and concentrated, affording the expected tetrazole derivatives.

(+)-Pinanediol[4-(3-tetrazol-5-yl)benzensulfonylamino]methane boronate (CR156)

MW: 417.29. Gray solid (98% yield). Mp 87-90° C. $[\alpha]_D$+16.0 (c 0.7, CHCl$_3$); $^1$H-NMR (400 MHz, CDCl$_3$): δ 0.83 (3H, s, pinanyl CH$_3$), 0.93 (1H, d, J 7.1, pinanyl H$_{endo}$), 1.29 (3H, s, pinanyl CH$_3$), 1.38 (3H, s, pinanyl CH$_3$), 1.80-2.35 (5H, m, pinanyl protons), 2.75 (2H, d, J 4.4, BCH$_2$), 4.32 (1H, d, J 7.6, CHOB), 4.83 (1H, br, NH), 8.02 (2H, d, J 7.4, H$_2$, H$_6$), 8.38 (2H, d, J 7.4, H$_3$, H$_5$). $^{13}$C-NMR (100 MHz, CDCl$_3$): δ 23.9, 26.4, 26.9, 27.2 (br, CB), 28.4, 35.0, 38.1, 39.3, 51.1, 78.7, 87.3, 128.0, 128.2, 129.1, 141.0, 158.0 (C$_{tetraz}$). LC-MS (ESI, Ion Trap): m/z 418.2 (M+H)$^+$.

(+)-Pinanediol[6-(3-tetrazol-5-yl)pyridin-3-sulfonylamino]methane boronate (CR160)

MW: 418.28. White solid (90% yield). Mp 149-151° C. $[\alpha]_D$+7.27 (c 0.7, MeOH). $^1$H-NMR (400 MHz, CDCl$_3$): δ 0.84 (3H, s, pinanyl CH$_3$), 1.00 (1H, d, J 10.8, pinanyl H$_{endo}$), 1.29 (3H, s, pinanyl CH$_3$), 1.40 (3H, s, pinanyl CH$_3$), 1.80-2.37 (5H, m, pinanyl protons), 2.86 (2H, d, J 4.4, BCH$_2$), 4.36 (1H, d, J 8.4, CHOB), 5.30 (1H, br, NH), 8.44 (1H, d, J 7.8, H$_4$), 8.56 (1H, d, J 7.8, H$_5$), 9.21 (1H, s, H$_2$). $^{13}$C-NMR (100 MHz, CDCl$_3$): δ 23.9, 26.4, 26.9, 27.4 (br, CB), 28.4, 35.0, 38.2, 39.3, 51.0, 78.9, 87.7, 123.2, 137.3, 137.7, 146.5, 148.6, 154.6 ($C_{tetraz}$). LC-MS (ESI, Ion Trap): m/z 419.2 (M+H)$^+$.

(+)-Pinanediol[2-chloro-4-(3-tetrazol-5-yl)benzensulfonylamino]methane boronate (CR186)

MW: 451.74. Gray solid (100% yield). Mp 70-75° C. [α]$_D$+11.0 (c 1.0, CHCl$_3$). $^1$H-NMR (200 MHz, CDCl$_3$): δ 0.83 (3H, s, pinanyl CH$_3$), 0.98 (1H, d, J 10.9, pinanyl H$_{endo}$), 1.28 (3H, s, pinanyl CH$_3$), 1.39 (3H, s, pinanyl CH$_3$), 1.77-2.39 (5H, m, pinanyl protons), 2.69 (2H, d, J 4.7, BCH$_2$), 4.33 (1H, dd, J 8.6, 1.7, CHOB), 5.16 (1H, t, J 4.7, NH), 8.15-8.27 (2H, m, H$_5$, H$_6$), 8.35 (1H, d, J 1.4, H$_3$). $^{13}$C-NMR (100 MHz, CDCl$_3$): δ 23.9, 26.4, 26.9, 27.4 (br, CB), 28.3, 35.0, 38.1, 39.3, 51.1, 78.8, 87.4, 125.8, 130.3, 130.6, 132.66, 132.7, 137.7, 157.6 ($C_{tetraz}$). LC-MS (ESI, Ion Trap): m/z 450.3 (M−H)$^+$.

(+)-Pinanediol[3-chloro-4-(3-tetrazol-5-yl)benzensulfonylamino]methane boronate (CR187)

MW: 451.74. Gray solid (95% yield). Mp 73-78° C. [α]$_D$+12.9 (c 1.1, CHCl$_3$). $^1$H-NMR (200 MHz, CDCl$_3$): δ 0.83 (3H, s, pinanyl CH$_3$), 0.98 (1H, d, J 10.9, pinanyl H$_{endo}$), 1.28 (3H, s, pinanyl CH$_3$), 1.38 (3H, s, pinanyl CH$_3$), 1.78-2.39 (5H, m, pinanyl protons), 2.77 (2H, d, J 2.8, BCH$_2$), 4.32 (1H, dd, J 8.7, 1.6, CHOB), 4.74 (1H, br, NH), 7.94 (1H, d, J 8.2, H$_5$), 8.07 (1H, s, H$_2$), 8.40 (1H, d, J 8.2, H$_6$). $^{13}$C-NMR (100 MHz, CDCl$_3$): δ 23.9, 26.4, 26.9, 27.4 (br, CB), 28.4, 35.0, 38.1, 39.3, 51.0, 78.7, 87.4, 126.1, 127.4, 129.4, 132.5, 133.6, 142.6, 153.5 ($C_{tetraz}$). LC-MS (ESI, Ion Trap): m/z 450.3 (M−H)$^+$.

(+)-Pinanediol[4-(3-tetrazol-5-yl)-2-trifluoromethyl-benzensulfonylamino]methane boronate (CR189)

MW: 485.29. Gray solid (100% yield). Mp 63-67° C. [α]$_D$+11.3 (c 1.3, CHCl$_3$). $^1$H-NMR (400 MHz, CDCl$_3$): δ 0.85 (3H, s, pinanyl CH$_3$), 0.98 (1H, d, J 11.1, pinanyl H$_{endo}$), 1.30 (3H, s, pinanyl CH$_3$), 1.40 (3H, s, pinanyl CH$_3$), 1.81-2.38 (5H, m, pinanyl protons), 2.80 (2H, d, J 4.7, BCH$_2$), 4.34 (1H, dd, J 8.7, 1.6, CHOB), 4.99 (1H, t, J 4.4, NH), 8.41 (1H, d, J 8.2, H$_6$), 8.52 (1H, d, J 8.2, H$_5$), 8.72 (1H, s, H$_3$). $^{13}$C-NMR (100 MHz, CDCl$_3$): δ 23.9, 26.3, 26.9, 27.5 (br, CB), 28.3, 35.0, 38.1, 39.3, 51.0, 78.8, 87.5, 122.6 (q, J 274.7, CF$_3$), 127.3 (q, J 6.3, C$_3$), 128.9 (q, J 33.4, C$_2$), 130.4 (2C), 133.2, 139.0, 159.5 ($C_{tetraz}$). LC-MS (ESI, Ion Trap): m/z 484.2 (M−H)$^+$.

General Procedure for the Synthesis of Boronic Acids (CR157, CR161, CR190, CR191, CR192).

To a solution of (+)-pinanediolboronic ester described above CR156, CR160, CR186, CR187, CR189 (0.30 mmol) in acetonitrile (3 mL) were sequentially added phenylboronic acid (0.30 mmol), n-hexane (3 mL) and 3N HCl (0.90 mmol). The resulting biphasic solution was vigorously stirred at room temperature. After 30 min the n-hexane layer, containing the pinanediol phenylboronate, was removed and fresh n-hexane (3 mL) was added. This last procedure was repeated several times until a TLC analysis revealed no remaining pinanediol boronate. The acetonitrile phase was concentrated and the residue crystallized from diethyl ether, affording the expected boronic acids.

[4-(3-tetrazol-5-yl)benzensulfonylamino]methaneboronic acid (CR157)

MW: 283.07. Cream-colored solid (100% yield). Mp 146-148° C. dec. $^1$H-NMR (400 MHz, MeOD): δ 2.59 (2H, s, BCH$_2$), 8.07 (2H, d, J 8.4, H$_2$, H$_6$), 8.26 (2H, d, J 8.4, H$_3$, H$_5$). $^{13}$C-NMR (100 MHz, MeOD): δ 28.9 (br, CB), 127.3, 128.0, 128.5, 141.7, 156.5 ($C_{tetraz}$). LC-MS (ESI, Ion Trap): m/z 284.1 (M+H)$^+$.

[6-(3-tetrazol-5-yl)pyridin-3-sulfonylamino]methaneboronic acid hydrocloride (CR161)

MW: 284.06. White solid (90% yield). Mp>250° C. dec. $^1$H-NMR (400 MHz, MeOD): δ 2.65 (2H, s, BCH$_2$), 8.43-8.48 (2H, m, H$_4$, H$_5$), 9.17 (1H, s, H$_2$). $^{13}$C-NMR (100 MHz, MeOD): δ 29.2 (br, CB), 122.3, 136.7, 137.8, 146.7, 148.4, 154.9 ($C_{tetraz}$). LC-MS (ESI, Ion Trap): m/z 285.1 (M+H)$^+$.

[2-chloro-4-(3-tetrazol-5-yl)benzensulfonylamino]methaneboronic acid (CR190)

MW: 317.52. White solid (80% yield). Mp 110-113° C. dec. $^1$H-NMR (400 MHz, MeOD): δ 2.58 (2H, s, BCH$_2$), 8.16 (1H, d, J 8.2, H$_5$), 8.22 (1H, d, J 8.2, H$_6$), 8.29 (1H, s, H$_3$). $^{13}$C-NMR (100 MHz, MeOD): δ 28.5 (br, CB), 125.2, 129.6, 130.4, 132.2, 132.5, 138.6, 156.6 ($C_{tetraz}$). LC-MS (ESI, Ion Trap): m/z 316.4 (M−H)$^+$.

[3-chloro-4-(3-tetrazol-5-yl)benzensulfonylamino]methaneboronic acid (CR191)

MW: 317.52. Cream-colored solid (89% yield). Mp 195-198° C. dec. $^1$H-NMR (400 MHz, MeOD): δ 2.60 (2H, s, BCH$_2$), 7.98 (1H, d, J 8.1, H$_6$), 8.08 (1H, d, J 8.41, H$_5$), 8.12 (1H, s, H$_2$). $^{13}$C-NMR (100 MHz, MeOD): δ 28.8 (br, CB), 125.9, 127.8, 128.9, 132.1, 133.3, 143.4, 153.8 ($C_{tetraz}$). LC-MS (ESI, Ion Trap): m/z 316.3 (M−H)$^+$.

[4-(3-tetrazol-5-yl)-2-trifluoromethyl-benzensulfonylamino]methaneboronic acid (CR192)

MW: 351.07. Yellowish solid (90% yield). Mp 195-198° C. dec. $^1$H-NMR (400 MHz, MeOD): δ 2.69 (2H, s, BCH$_2$), 8.36 (1H, d, J 8.3, H$_6$), 8.50 (1H, dd, J 8.3, 1.4, H$_5$), 8.64 (1H, s, H$_3$). $^{13}$C-NMR (100 MHz, MeOD): δ 28.9 (br, CB), 122.7 (q, J 273.6, CF$_3$), 126.4 (q, J 6.5, C$_3$), 128.6 (q, J 33.5, C$_2$), 129.6, 130.3, 132.2, 140.1, 157.0 ($C_{tetraz}$). LC-MS (ESI, Ion Trap): m/z 350.1 (M−H)$^+$.

[4-cyanobenzensulfonylamino]methaneboronic acid (CR162)

MW: 240.04. According to the general procedure described for the synthesis of boronic acids, transesterification of CR155 afforded CR162 as a white solid (83% yield). Mp 142-144° C. dec. $^1$H-NMR (400 MHz, MeOD): δ 2.56 (2H, s, BCH$_2$), 7.95 (2H, d, J 8.3, H$_2$, H$_6$), 8.03 (2H, d, J 8.3, H$_3$, H$_5$). $^{13}$C-NMR (100 MHz, MeOD): δ 28.3 (br, CB), 115.6, 117.2, 127.7, 132.7, 143.7. LC-MS (ESI, Ion Trap): m/z 239.2 (M−H)$^+$.

[6-cyanopyridin-3-sulfonylamino]methaneboronic acid hydrocloride (CR163)

MW: 241.03. According to the general procedure described for the synthesis of boronic acids, transesterification of CR159 afforded CR163 as a white solid (100% yield). Mp 154-159° C. dec. $^1$H-NMR (400 MHz, MeOD): δ 2.62 (2H, s, BCH$_2$), 8.07 (1H, d, J 7.9, H$_5$), 8.40 (1H, dd, J 7.9, 1.3, H$_4$), 9.10 (1H, d, J 1.3, H$_2$). $^{13}$C-NMR (100 MHz, MeOD): δ

28.3 (br, CB), 116.1, 128.7, 135.8, 136.4, 139.3, 148.9. LC-MS (ESI, Ion Trap): m/z 242.0 (M+H)+.

Pinacol[3-(methoxycarbonyl)phenylmethanesulfonylamino]methaneboronate (CR166)

MW: 369.24. A solution of CR99 (300 mg, 1.00 mmol) in THF (3 mL) was added to a solution of anhydrous methanol in THF (2.5 M, 400 μL, 1.00 mmol) at −10° C. under nitrogen. After stirring for 10 min at −10° C., the cooling bath was removed, and the reaction mixture was stirred for 1 h at room temperature. The reaction mixture was once again cooled to −10° C. A solution of methyl 3-[(chlorosulfonyl)methyl]benzoate (274 mg, 1.10 mmol) in THF (2 mL) was slowly added and allowed to react for 16 h. The solvent was evaporated in vacuo and the residue purified by gradient chromatography (dichloromethane/diethyl ether 8:2 to methanol; 10×2 cm Ø), affording CR166 (269 mg, 73%) as a yellowish oil. $^1$H-NMR (400 MHz, CDCl$_3$): δ 1.27 (12H, s, pinacol protons), 2.75 (2H, d, J 2.8, BCH$_2$), 3.92 (3H, s, OCH$_3$), 4.33 (3H, br, CH$_2$S, NH), 7.47 (1H, t, J 7.7, H$_5$), 7.65 (1H, d, J 7.7, H$_6$), 8.04-8.09 (2H, m, H$_2$, H$_4$). $^{13}$C-NMR (100 MHz, CDCl$_3$): δ 24.7, 28.2 (br, CB), 52.2, 57.0, 84.8, 128.9, 129.8, 130.1, 130.8, 131.7, 135.1, 166.5. EI-MS, m/z: 354 (<2%, M$^+$−15), 160 (43%), 150 (20%), 146 (base peak), 119 (14%), 104 (20%), 91 (14%), 90 (16%), 74 (26%), 59 (16%).

[3-(Carboxyphenyl)methanesulfonylamino]methaneboronic acid (CR167)

MW: 273.07. A mixture of CR166 (105 mg, 0.28 mmol) and HCl 3N degassed (5 mL) was allowed to react at reflux temperature for 3 h. After cooling, the reaction mixture was diluted with water (15 mL) and washed twice with diethyl ether (2×20 mL). Then the aqueous phase was concentrated in vacuo, affording CR167 (38 mg, 51%) as a yellow solid. Mp 90-93° C. dec. $^1$H-NMR (400 MHz, MeOD): δ 2.71 (2H, s, BCH$_2$), 4.42 (2H, s, CH$_2$S), 7.50 (1H, t, J 7.7, H$_5$), 7.68 (1H, d, J 7.7, H$_6$), 8.03 (1H, d, J 7.7, H$_4$), 8.11 (1H, s, H$_2$). $^{13}$C-NMR (100 MHz, DMSO): δ 29.0 (br, CB), 55.7, 128.3, 129.2, 130.8, 130.9, 131.8, 135.1, 167.9. LC-MS (ESI, Ion Trap): m/z 272.2 (M−H)+.

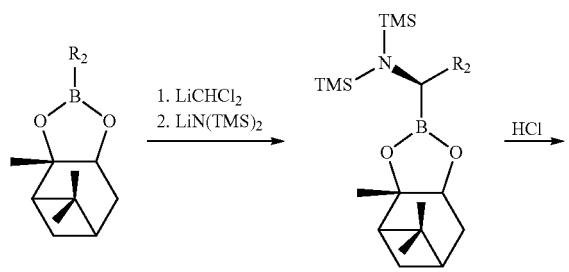

GBS27 R$_2$ = Me
CR168 R$_2$ = iPr

GBS29 R$_2$ = Me
CR170 R$_2$ = iPr

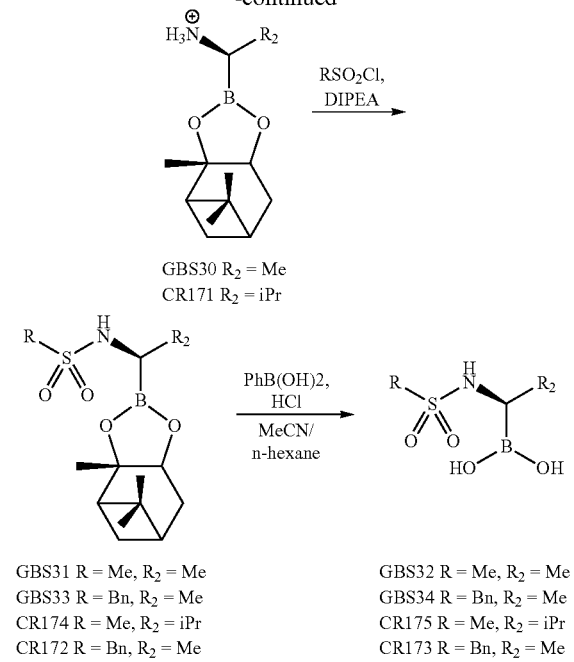

GBS30 R$_2$ = Me
CR171 R$_2$ = iPr

GBS31 R = Me, R$_2$ = Me
GBS33 R = Bn, R$_2$ = Me
CR174 R = Me, R$_2$ = iPr
CR172 R = Bn, R$_2$ = Me

GBS32 R = Me, R$_2$ = Me
GBS34 R = Bn, R$_2$ = Me
CR175 R = Me, R$_2$ = iPr
CR173 R = Bn, R$_2$ = Me

(+)-Pinanediol methaneboronate (GBS27)

A solution of (+)-pinanediol (2.845 g, 16.71 mmol) and methylboronic acid (1.00 g, 16.71 mmol) in THF (15 mL) was stirred for 20 min, concentrated, and then purified by chromatography (light petroleum/diethyl ether 9:1), affording GBS27 as a colourless oil (3.07 g, 95% yield). [α]$_D$+31.3 (c 1.1, MeOH). $^1$H-NMR (400 MHz, CDCl$_3$): δ 0.31 (3H, s, BCH3), 0.87 (3H, s, pinanyl CH$_3$), 1.15 (1H, d, J 10.9, pinanyl H$_{endo}$), 1.32 (3H, s, pinanyl CH$_3$), 1.47 (3H, s, pinanyl CH$_3$), 1.85-2.39 (5H, m, pinanyl protons), 4.28 (1H, dd, J 8.7, 1.8, CHOB). $^{13}$C-NMR (100 MHz, CDCl$_3$): δ −6.2 (br, CB), 24.0, 26.3, 26.5, 27.1, 28.7, 35.5, 38.1, 39.5, 51.3, 85.4. GC-MS, m/z: 194 (9%, M$^+$), 179 (59%), 153 (30%), 137 (27%), 125 (base peak), 119 (15.5%), 111 (59%), 98 (71%), 91 (17.5%), 83 (92%), 77 (19%), 67 (57%), 55 (45%), 43 (57%).

(+)-Pinanediol 1-methylethaneboronate (CR168)

Following the procedure described for the synthesis of GBS27, compound CR168 was recovered starting from 1-methylethaneboronic acid as a colorless oil (85% yield). [α]$_D$+28.3 (c 1.4, CHCl$_3$). $^1$H-NMR (400 MHz, CDCl$_3$): δ 0.88 (3H, s, pinanyl CH$_3$), 1.04 (6H, d, J 6.9, CH(CH$_3$)$_2$), 1.13 (1H, d, J 10.9, pinanyl H$_{endo}$), 1.11-1.18 (1H, m, CH(CH$_3$)$_2$), 1.32 (3H, s, pinanyl CH$_3$), 1.41 (3H, s, pinanyl CH$_3$), 1.85-2.40 (5H, m, pinanyl protons), 4.28 (1H, dd, J 8.7, 1.6, CHOB). $^{13}$C-NMR (100 MHz, CDCl$_3$): δ 10.5 (br, CB), 18.2, 24.0, 26.4, 27.1, 28.7, 35.6, 38.2, 39.5, 51.3, 77.6, 85.2. GC-MS, m/z: 222 (7%, M$^+$), 207 (38%), 181 (22%), 179 (19%), 166 (19%), 153 (base peak), 152 (48%), 139 (31%), 135 (20%), 134 (33%), 126 (72%), 125 (25%), 111 (20%), 109 (25%), 93 (22%), 86 (66%), 82 (31%), 81 (25%), 67 (47%), 55 (36%), 53 (22%), 43 (42%), 41 (41%).

(+)-Pinanediol (1R)-1-(N-bis(trimethylsilyl)amino)-1-ethaneboronate (GBS29)

n-Butyllithium (2.5 M solution in hexane, 7.41 mL, 18.53 mmol) was added dropwise to a stirred solution of dichloromethane (1.48 mL, 23.16 mmol) in THF (24 mL) at −100° C. under argon atmosphere; at the end of the butyllithium addition, a white microcrystalline precipitate (LiCHCl$_2$) became evident. After 30 min, a solution of GBS27 (3.00 g, 15.44 mmol) in THF (20 mL) was slowly added at the same temperature. The white precipitate disappeared and the mixture allowed to gradually reach room temperature overnight. The resulting solution was concentrated under reduced pressure. The crude was treated with petroleum ether (50 mL), and the resulting white inorganic precipitate was filtered off and washed with abundant petroleum ether. Solvent evaporation in vacuo afforded (+)-pinanediol (1S)-1-chloro-1-ethaneboronate, used as such for the subsequent reaction.

The above product was dissolved in THF (10 mL) and lithium bis(trimethylsilyl)amide (1.0 M solution in tetrahydrofuran, 15.44 mL, 15.44 mmol) was added dropwise at −100° C. under argon flow. The reaction mixture was allowed to reach room temperature overnight. The resulting solution was concentrated under reduced pressure and the crude was treated with petroleum ether (50 mL); the white inorganic precipitate (LiCl) was filtered off and washed with abundant petroleum ether. The solvent was evaporated in vacuo to give a residue which was subjected to column chromatography (light petroleum/ethyl ether/triethylamine 98:2:5) recovering GBS29 as a pale yellow oil (3.52 g, 62% yield). [α]$_D$+5.5 (c 0.9, MeOH). $^1$H-NMR (400 MHz, CDCl$_3$): δ 0.13 (21H, s, 2Si(CH$_3$)$_3$), 0.87 (3H, s, pinanyl CH$_3$), 1.17 (1H, d, J 10.9, pinanyl H$_{endo}$), 1.22 (3H, d, J 7.6, CHCH$_3$), 1.31 (3H, s, pinanyl CH$_3$), 1.42 (3H, s, pinanyl CH$_3$), 1.86-2.39 (5H, m, pinanyl protons), 2.77 (1H, q, J 7.6, CHB), 4.33 (1H, d, J 8.6, CHOB). $^{13}$C-NMR (100 MHz, CDCl$_3$): δ 2.7, 21.3, 24.0, 26.3, 27.1, 28.4, 35.5, 37.0 (br, CB), 38.2, 39.5, 51.5, 78.3, 85.7. GC-MS, m/z: 367 (0.3%, M$^+$), 352 (5.5%), 294 (base peak), 200 (26%), 135 (16%), 93 (11%), 73 (29%).

(+)-Pinanediol (1R)-1-(N-bis(trimethylsilyl)amino)-2-methylpropaneboronate (CR170)

Following the procedure described for the synthesis of GBS29, compound CR170 was recovered from CR168 as a yellowish oil (82% yield). [α]$_D$−7.5 (c 1.4, CHCl$_3$). $^1$H-NMR (400 MHz, CDCl$_3$): δ 0.16 (21H, s, 2Si(CH$_3$)$_3$), 0.88 (3H, s, pinanyl CH$_3$), 0.94 (3H, d, J 6.5, CH(CH$_3$)$_2$), 0.95 (3H, d, J 6.5, CH(CH$_3$)$_2$), 1.21 (1H, d, J 10.8, pinanyl H$_{endo}$), 1.32 (3H, s, pinanyl CH$_3$), 1.41 (3H, s, pinanyl CH$_3$), 1.86-2.39 (6H, m, pinanyl protons, CH(CH$_3$)$_2$), 2.19 (1H, d, J 11.2, CHB), 4.30 (1H, dd, J 8.7, 1.6, CHOB). $^{13}$C-NMR (100 MHz, CDCl$_3$): δ 3.4, 21.0, 21.7, 24.0, 26.6, 27.1, 28.5, 30.5, 35.4, 38.1, 39.5, 49.4 (br, CB), 51.4, 77.8, 85.2. GC-MS, m/z: 322 (32%, M$^+$−TMS), 228 (11%), 218 (16%), 200 (11%), 172 (8%), 148 (11%), 147 (14%), 135 (24%), 128 (13%), 107 (9%), 93 (27%), 73 (base peak), 59 (11%), 43 (17%), 41 (13%).

(+)-Pinanediol (1R)-1-amino-1-ethaneboronate hydrocloride (GBS30)

A solution of chloric acid in dioxane (3.9M, 4.10 mL, 15.96 mmol) was added dropwise to a stirred solution of GBS29 (1.67 g, 4.56 mmol) in THF (20 mL) at −20° C. After 30 min the reaction was allowed to reach room temperature and furtherly stirred for 3 h. The resulting mixture was concentrated under reduced pressure and subsequent washing with diethyl ether afforded GBS30 as a yellow solid (1.14 g, 96% yield). Mp 100-110° C. [α]$_D$+14.5 (c 1.0, MeOH). $^1$H-NMR (400 MHz, MeOD): δ 0.90 (3H, s, pinanyl CH$_3$), 1.18 (1H, d, J 11.0, pinanyl H$_{endo}$), 1.34 (3H, s, pinanyl CH$_3$), 1.38 (3H, d, J 7.8, CHCH$_3$), 1.46 (3H, s, pinanyl CH$_3$), 1.83- 2.47 (5H, m, pinanyl protons), 2.98 (1H, q, J 7.8, CHB), 4.50 (1H, dd, J 9.0, 1.7, CHOB). $^{13}$C-NMR (100 MHz, MeOD): δ 13.5, 22.9, 25.8, 26.1, 27.4, 32.6 (br, CB), 34.6, 37.9, 39.4, 51.1, 78.9, 87.5.

(+)-Pinanediol (1R)-1-amino-2-methylpropaneboronate hydrocloride (CR171)

Following the procedure described for the synthesis of GBS30, compound CR171 was recovered from CR170 as a white solid (74% yield). Mp 148-150° C. [α]$_D$+17.0 (c 1.4, MeOH). $^1$H-NMR (400 MHz, MeOD): δ 0.91 (3H, s, pinanyl CH$_3$), 1.09 (3H, d, J 6.5, CH(CH$_3$)$_2$), 1.10 (3H, d, J 6.3, CH(CH$_3$)$_2$), 1.22 (1H, d, J 11.0, pinanyl H$_{endo}$), 1.34 (3H, s, pinanyl CH$_3$), 1.47 (3H, s, pinanyl CH$_3$), 1.89-2.49 (6H, m, pinanyl protons, CH(CH$_3$)$_2$), 2.80 (1H, d, J 5.1, CHB), 4.51 (1H, dd, J 8.8, 1.6, CHOB). $^{13}$C-NMR (100 MHz, MeOD): δ 18.3, 18.9, 22.9, 26.0, 26.1, 27.6, 29.0, 34.7, 37.9, 39.4, 43.7 (br, CB), 51.1, 78.7, 87.6.

General Procedure for the Synthesis of Sulfonylaminomethaneboronates (GBS31, GBS33, CR174, CR172).

A solution of DIPEA in CH$_2$Cl$_2$ 50% v/v (2.20 mmol) was slowly added to a solution of suitable aminoboronate hydrochloride (1.00 mmol) and sulfonylchloride (2 mmol) in CH$_2$Cl$_2$ (10 mL). The reaction mixture was stirred at room temperature for 6 h. Then the solution was partitioned between dichloromethane (20 mL) and water (10 mL) and the aqueous phase was extracted with dichloromethane (3×20 mL). The combined organic phases were washed with brine, dried over MgSO$_4$, filtered and concentrated in vacuo. The crude residue was purified by gradient chromatography (from light petroleum/ethyl ether 8:8 to 1:1), affording the expected sulfonamides.

(+)-Pinanediol (1R)-1-(methylsulfonylamino)-1-ethaneboronate (GBS31)

According to the general procedure described above GBS31 was recovered as a white solid (75% yield). Mp 105-110° C. [α]$_D$+8.7 (c 0.4, MeOH). $^1$H-NMR (400 MHz, CDCl$_3$): δ 0.88 (3H, s, pinanyl CH$_3$), 1.08 (1H, d, J 11.0, pinanyl H$_{endo}$), 1.34 (3H, s, pinanyl CH$_3$), 1.38 (3H, d, J 7.5, CH$_3$CH), 1.45 (3H, s, pinanyl CH$_3$), 1.87-2.43 (5H, m, pinanyl protons), 3.02 (3H, s, CH$_3$SO$_2$), 3.26-3.32 (1H, m, CHB), 4.39 (1H, dd, J 8.8, 1.8, CHOB), 4.50 (1H, d, J 4.8, NH). $^{13}$C-NMR (100 MHz, CDCl$_3$): δ 18.3, 24.0, 26.4, 27.0, 28.5, 35.2, 35.5 (br, CB), 38.2, 39.4, 41.8, 51.2, 78.7, 87.2. EI-MS: m/z 301 (1%, M$^+$), 286 (2%), 232 (19%), 222 (20%), 216 (13%), 173 (13%), 150 (base peak), 143 (12.5%), 137 (41%), 125 (31%), 119 (37.5%), 107 (20%), 97 (27%), 88 (39%), 79 (31%), 67 (23%), 55 (23%), 44 (44%).

(+)-Pinanediol (1R)-1-(phenylmethanesulfonylamino)-1-ethaneboronate (GBS33)

According to the general procedure described above GBS33 was recovered as a colorless viscous oil (82% yield). [α]$_D$+3.9 (c 1.0, MeOH). $^1$H-NMR (200 MHz, CDCl$_3$): δ 0.88 (3H, s, pinanyl CH$_3$), 1.13 (1H, d, J 11.0, pinanyl H$_{endo}$), 1.30 (3H, d, J 7.4, CHCH$_3$), 1.33 (3H, s, pinanyl CH$_3$), 1.44 (3H, s, pinanyl CH$_3$), 1.86-2.40 (5H, m, pinanyl protons), 3.10 (1H, q, J 7.4, CHB), 4.27 (1H, d, J 13.8, PhCH$_2$), 4.32 (1H, d, J 13.8, PhCH$_2$), 4.36 (1H, dd, J 8.7, 1.7, CHOB), 4.44 (1H, br, NH), 7.37-7.45 (5H, m, Ph). $^{13}$C-NMR (100 MHz, CDCl$_3$): δ 18.8, 24.0, 26.4, 27.0, 28.5, 35.2, 36.0 (br, CB), 38.2, 39.4, 51.2, 59.4, 78.6, 87.0, 128.5, 128.6, 129.8, 130.8. LC-MS (ESI, Ion Trap): m/z 378 (M+H)+. MS/MS 378: m/z 314 (100%), 226 (27%).

(+)-Pinanediol (1R)-1-(methylsulfonylamino)-2-methylpropaneboronate (CR174)

According to the general procedure described above CR174 was recovered as a yellowish oil (85% yield). $[\alpha]_D$+25.0 (c 1.2, CHCl$_3$). $^1$H-NMR (400 MHz, CDCl$_3$): δ 0.88 (3H, s, pinanyl CH$_3$), 1.01 (3H, d, J 6.9, CH(CH$_3$)$_2$), 1.03 (3H, d, J 6.5, CH(CH$_3$)$_2$), 1.15 (1H, d, J 10.9, pinanyl H$_{endo}$), 1.33 (3H, s, pinanyl CH$_3$), 1.43 (3H, s, pinanyl CH$_3$), 1.85-2.42 (6H, m, pinanyl protons, CH(CH$_3$)$_2$), 2.97 (3H, s, CH$_3$SO$_2$), 3.07 (1H, t, J 5.7, CHB), 4.40 (1H, dd, J 8.8, 1.9, CHOB), 4.47 (1H, d, J 7.1, NH). $^{13}$C-NMR (100 MHz, CDCl$_3$): δ 19.57, 19.62, 24.0, 26.5, 27.0, 28.7, 30.9, 35.3, 38.2, 39.5, 40.9, 47.3 (br, CB), 51.1, 78.6, 87.0. EI-MS: m/z 329 (1%, M+), 286 (26%), 259 (12%), 250 (32%), 178 (56%), 177 (15%), 162 (18%), 152 (29%), 136 (47%), 135 (base peak), 146 (76%), 133 (18%), 125 (21%), 122 (25%), 119 (29%), 116 (22%), 109 (18%), 107 (32%), 93 (74%), 91 (28%), 81 (21%), 79 (32%), 72 (29%), 69 (22%), 67 (26%), 55 (38%), 43 (62%), 41 (49%).

(+)-Pinanediol (1R)-1-(phenylmethanesulfonylamino)-2-methylpropaneboronate (CR172)

According to the general procedure described above CR172 was recovered as a yellowish viscous oil (88% yield). $[\alpha]_D$+36.0 (c 1.7, CHCl$_3$). $^1$H-NMR (400 MHz, CDCl$_3$): δ 0.89 (3H, s, pinanyl CH$_3$), 0.98 (3H, d, J 6.9, CH(CH$_3$)$_2$), 1.00 (3H, d, J 6.5, CH(CH$_3$)$_2$), 1.21 (1H, d, J 10.9, pinanyl H$_{endo}$), 1.34 (3H, s, pinanyl CH$_3$), 1.45 (3H, s, pinanyl CH$_3$), 1.86-2.43 (6H, m, pinanyl protons, CH(CH$_3$)$_2$), 3.03 (1H, t, J 5.2, CHB), 4.27 (1H, d, J 13.8, PhCH$_2$), 4.32 (1H, d, J 13.8, PhCH$_2$), 4.37 (1H, br, NH), 4.38 (1H, dd, J 8.8, 1.9, CHOB), 7.39-7.51 (5H, m, Ph). $^{13}$C-NMR (100 MHz, CDCl$_3$): δ 19.4, 19.7, 24.0, 26.6, 27.0, 28.8, 31.4, 35.3, 38.2, 39.5, 47.5 (br, CB), 51.1, 59.1, 78.5 87.0, 128.5, 128.6, 129.7, 130.8. LC-MS (ESI, Ion Trap): m/z 406.2 (M+H)+. MS/MS 378: m/z 250.2 (12%), 342.3 (27%).

General Procedure for the Synthesis of Boronic Acids (GBS32, GBS34, CR175, CR173).

To a solution of (+)-pinanediolboronic ester described above GBS31, GBS33, CR174, CR172 (0.30 mmol) in acetonitrile (3 mL) were sequentially added phenylboronic acid (0.30 mmol), n-hexane (3 mL) and 3N HCl (0.90 mmol). The resulting biphasic solution was vigorously stirred at room temperature. After 30 min the n-hexane layer, containing the pinanediol phenylboronate, was removed and fresh n-hexane (3 mL) was added. This last procedure was repeated several times until a TLC analysis revealed no remaining pinanediol boronate. The acetonitrile phase was concentrated and the residue crystallized from diethyl ether, affording the expected boronic acids.

(1R)-1-(Methylsulfonylamino)-1-ethaneboronic acid (GBS31)

Yellowish oil (100% yield). $[\alpha]_D$+30.4 (c 0.4, MeOH). $^1$H-NMR (400 MHz, MeOD): δ 1.24 (2H, d, J 7.4, CHCH$_3$), 2.94 (3H, s, CH$_3$SO$_2$), 2.99 (1H, q, J 7.4, CHCH$_3$). $^{13}$C-NMR (100 MHz, MeOD): δ16.4, 39.7, CB not seen.

(1R)-1-(Phenylmethanesulfonylamino)-1-ethaneboronic acid (GBS33)

White solid (88% yield). Mp 82-84° C. $[\alpha]_D$+21.1 (c 0.9, MeOH). $^1$H-NMR (400 MHz, MeOD): δ 1.15 (3H, d, J 7.2, CHCH$_3$), 2.89 (1H, q, J 7.2, CHCH$_3$), 4.30 (1H, d, J 13.6, PhCH$_2$), 4.35 (1H, d, J 13.6, PhCH$_2$), 7.34-7.46 (5H, m, Ph). $^{13}$C-NMR (100 MHz, MeOD): δ16.8, 58.8, 128.97, 128.08, 128.13, 130.6, CB not seen.

(1R)-1-(Methylsulfonylamino)-2-methylpropaneboronic acid (CR175)

White solid (66% yield). $[\alpha]_D$+26.3 (c 0.6, MeOH). $^1$H-NMR (400 MHz, MeOD): δ 0.97 (3H, d, J 6.8, CH(CH$_3$)$_2$), 0.99 (3H, d, J 6.8, CH(CH$_3$)$_2$), 1.90 (3H, septet, J 6.8, CH(CH$_3$)$_2$), 2.84 (1H, d, J 7.5, CHB), 2.91 (3H, s, CH$_3$SO$_2$). $^{13}$C-NMR (100 MHz, MeOD): δ19.0, 29.7, 39.1, 46.8 (br, CB). LC-MS (ESI, Ion Trap): m/z 406.2 (M+H)+. LC-MS (ESI, Ion Trap): m/z 196.0 (M+H)+.

(1R)-1-(Phenylmethanesulfonylamino)-2-methylpropaneboronic acid (CR173)

White solid (62% yield). $[\alpha]_D$+33.0 (c 0.7, MeOH). $^1$H-NMR (400 MHz, MeOD): δ 0.91 (3H, d, J 6.8, CH(CH$_3$)$_2$), 1.77 (3H, d, J 6.8, CH(CH$_3$)$_2$), 2.64 (1H, d, J 6.7, CHB), 4.29 (1H, d, J 13.8, PhCH$_2$), 4.34 (1H, d, J 13.8, PhCH$_2$), 7.36-7.44 (5H, m, Ph). $^{13}$C-NMR (100 MHz, MeOD): δ18.9, 19.1, 30.2, 46.2 (br, CB), 58.6, 128.0, 128.1, 130.2, 130.6. LC-MS (ESI, Ion Trap): m/z 254.1 (M+H−18)+.

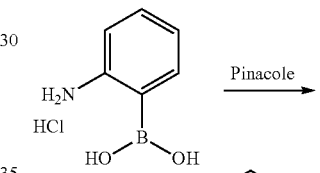

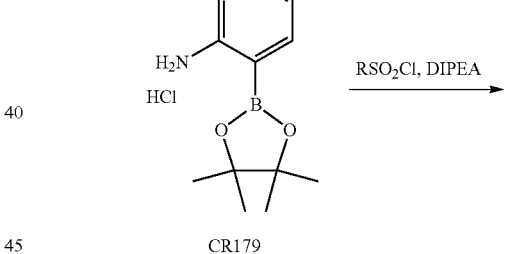

CR179

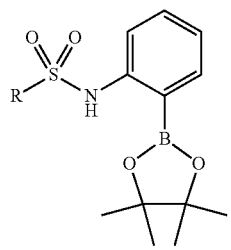

CR180 R = Bn
CR181 R = Me

Pinacol 2-aminophenylboronate (CR179)

A solution of pinacole (137 mg, 1.16 mmol) and 2-aminophenylboronic acid hidrochloride (200 mg, 1.16 mmol) in THF (7 mL) was stirred for 20 min and then concentrated. The crude was washed with diethyl ether, affording CR179 as a cream colored solid (291 mg, 98% yield). Mp 185-188° C. $^1$H-NMR (200 MHz, CDCl$_3$): δ 1.38 (12H, s, pinacol protons), 7.40 (1H, t, J 7.4, $H_4$), 7.57 (1H, dt, J 7.4, 1.4, $H_5$), 7.83-7.89 (2H, m, $H_3$, $H_6$), 10.05 (3H, br, $NH_3$). $^{13}$C-NMR (50 MHz, CDCl$_3$): δ 24.8, 85.5, 121.7 (br, CB), 124.2, 128.3, 133.3, 136.3, 136.6. GC-MS, m/z: 219 (38%, M$^+$−1), 162 (65%), 161 (16%), 146 (44%), 145 (11%), 137 (12%), 120 (36%) 119 (base peak), 118 (24%), 92 (1%), 77 (13%), 43 (12%), 41 (14%).

Pinacol 2-(phenylmethanesulfonylamino)phenylboronate (CR180)

Triethylamine (120 μL, 0.86 mmol) was slowly added to a solution of CR179 (100 mg, 0.39 mmol) in CHCl$_3$ (2 mL) at −10° C. Then phenylmethanesulfonyl chloride (112 mg, 0.59 mmol) was added and after 15 min the reaction mixture was allowed to warm to room temperature and finally stirred at reflux (85° C.) for 4 h. Then the solution was partitioned between dichloromethane (30 mL) and HCl 1 N (10 mL) and the aqueous phase was extracted with dichloromethane (20 mL). The combined organic phases were washed with brine, dried over MgSO$_4$, filtered and concentrated in vacuo. The crude residue was purified by column chromatography (light petroleum/ethyl acetate 9:1), affording CR180 as a white solid (79 mg, 55% yield). Mp 86-88° C. $^1$H-NMR (400 MHz, CDCl$_3$): δ 1.26 (12H, s, pinacol protons), 4.41 (2H, s, PhCH$_2$), 7.14 (1H, t, J 7.7, $H_5$), 7.18-7.36 (5H, m, PhCH$_2$), 7.51 (1H, t, J 7.7, $H_4$), 7.70 (1H, d, J 7.7, $H_3$), 7.80 (1H, d, J 7.7, $H_6$), 8.55 (1H, br, NH). $^{13}$C-NMR (100 MHz, CDCl$_3$): δ 24.8, 56.8, 84.6, 116.4, 122.9, 128.7 (3C), 128.8, 130.8 (2C), 133.3, 137.0, 144.2, CB not seen. LC-MS (ESI, Ion Trap): m/z 374.2 (M+H)$^+$.

Pinacol 2-(methylsulfonylamino)phenylboronate (CR181)

Following the procedure described for the synthesis of CR180, compound CR181 was recovered as a white solid (64% yield). Mp 130-132° C. $^1$H-NMR (400 MHz, CDCl$_3$): δ 1.41 (12H, s, pinacol protons), 3.00 (3H, s, CH$_3$S), 7.17 (1H, dt, J 7.6, 1.0, $H_5$), 7.51 (1H, dt, J 7.6, 1.5, $H_4$), 7.63 (1H, d, J 7.6, $H_3$), 7.83 (1H, dd, J 7.6, 1.5, $H_6$), 8.68 (1H, br, NH). $^{13}$C-NMR (100 MHz, CDCl$_3$): δ 24.9, 39.1, 84.8, 118.7, 123.8, 133.3, 136.9, 143.8, CB not seen. LC-MS (ESI, Ion Trap): m/z 298.1 (M+H)$^+$.

C. Example 3

Enzymology and Binding Affinities

Except for those binding in the low nanomolar range, all previously studied boronic acids inhibitors of AmpC β-lactamase have been reversible, competitive inhibitors with fast-on, fast-off rates. (Powers, R. A. et al., *Protein Sci.* 1999, 8, 2330-2337; Weston, G. S. et al., *J. Med. Chem.* 1998, 41, 4577-4586) The same was found for the new sulfonamide boronic acid series as no incubation effect were detected for any of the compounds.

To investigate the effect of the carboxamide replacement with a sulfonamide we first measured the potency of methanesulfonamide boronic acid 3 (Table 1). Compound 3 inhibits AmpC with a $K_i$ of 789 nM, a 23-fold improvement of potency compared to the carboxamide analog 3c ($K_i$ 18.5 μM). The high affinity of this molecules prompted us to study additional derivatives. Compound 4, bearing the penicillin G side chain has a $K_i$ of 70 nM, a 10-fold improvement over the initial sulfonamide 3 and an eight-fold improvement compared to its exact carboxamide analog 4c ($K_i$ 570 nM) (Table 1). (Caselli, E. et al., *Chem. Biol.* 2001, 8, 17-31) Because compound 5, isomer of compound 4, has a $K_i$ of 210 nM, we decided to focus on benzylic derivatives and synthesized compounds 6-9, for which required sulfonylchlorides were commercially available or the final products easily accessible. Although most of those derivatives have a lower potency than 4, compound 9 has a $K_i$ of 25 nM, a three-fold improvement versus compound 4. We tried to synthesize compound 10, the exact analog of the carboxamide 10c, but found that the required (thiophene-2-yl)-methanesulfonyl-chloride was unstable. Unexpectedly, compound 11, bearing the nafcillin side chain, inhibits AmpC with a $K_i$ of 670 nM, 20-fold weaker than the carboxamide analog 11c ($K_i$ 33 nM). This was another indicator that the SAR changes substantially in the sulfonamide series.

In the carboxamide series, addition of a m-carboxybenzyl group to 10c had resulted in a seven-fold improvement of potency for compound 17c. We decided to investigate the same modification for the sulfonamide 4 and synthesized the chiral compound 17. This latter has a $K_i$ of 430 nM, thus rather than a seven-fold improvement, adding a m-carboxybenzyl to compound 4 lead to a six-fold decrease in inhibition. Compound 16, only with a benzyl as $R^b$ group, has an even worse $K_i$ of 3.7 μM. The weaker potency of compounds 16 and 17 further demonstrate the changed SAR resulting from the carboxamide to sulfonamide conversion.

Sulfonamidomethaneboronic acids were dissolved in 100% DMSO at a concentration of 100 mM; more diluted stocks were prepared as necessary. AmpC activity was determined by monitoring the change of absorbance at 405 nm due to hydrolyzed substrate CENTA ($K_m$ 15 μM) by an HP5453 UV-vis spectrophotometer. The enzyme was expressed and purified as described (Usher, K. C. et al., *Biochemistry* 1998, 37, 16082-16092) and CENTA was purchased from Tydock Pharma.

Kinetic measurements were run at room temperature in 50 mM sodium-cacodylate pH 6.5 in the presence of 0.01% Triton-X to prevent non-specific inhibition via compound aggregation. (Feng, B. Y. et al., *Nat. Chem. Biol.* 2005, 1, 146-148; Feng, B. Y. et al., *J. Med. Chem.* 2007, 50, 2385-2390) These conditions also ensure the hydrolysis of pinacol esters to free boronic acids. (Kettner, C. A. and Shenvi, A. B., *J. Biol. Chem.* 1984, 259, 15106-15114) Reactions were performed in 1 mL cuvettes with 60 μM CENTA and initiated by adding 1.2 nM enzyme. No incubation effect was detected for any compound, consistent with earlier studies. (Weston, G. S. et al., *J. Med. Chem.* 1998, 41, 4577-4586) The first 180 sec of each reaction were used to measure initial rates. IC$_{50}$ values were obtained by fitting binding data to a sigmoidal dose-response equation using GraphPad Prism (GraphPad software, Inc). $K_i$ values were determined by the use of Cheng-Prusoff equation. (Cheng, Y. and Prusoff, W. H., *Biochem. Pharmacol.* 1973, 22, 3099-3108)

D. Example 4

Structural Analysis

Figure 7:
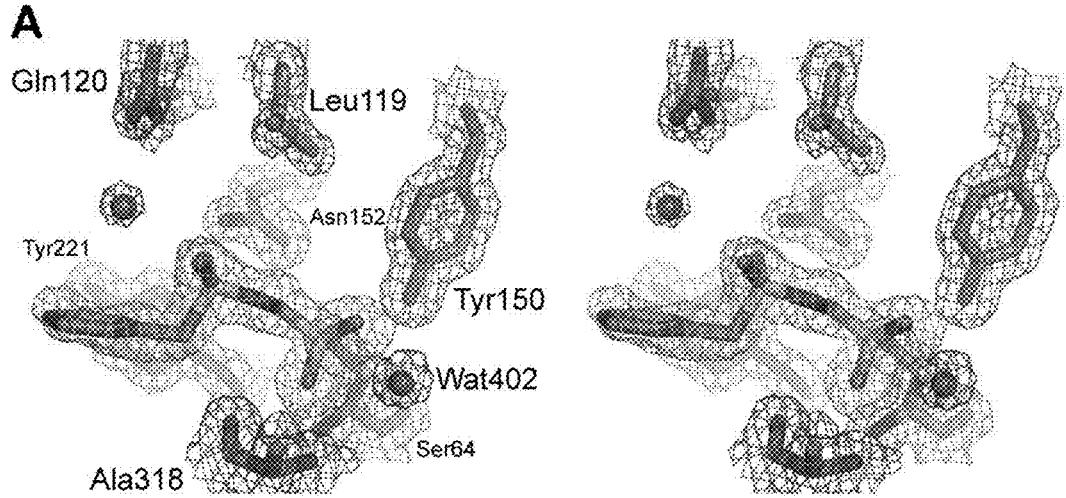
FIG. 7. Stereo views of initial $F_o$-$F_c$ electron densities (2.5σ contour level) of sulfonamide boronic acids and final $2F_o$-$F_c$ densities (1σ contour level) of AmpC and conserved water molecules. A) Compound 4 in chain A. B) Compound 9. C) Compound 17 (Table 1). Inhibitor carbons in light gray, enzyme carbons in light gray, oxygens dark gray, nitrogens dark gray, sulfurs dark gray, borons dark gray.
Figure 7:
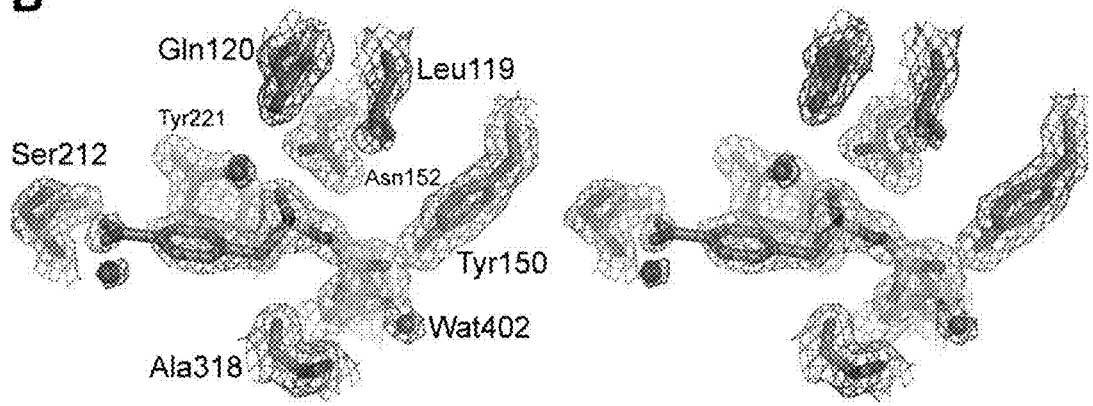
Figure 7:
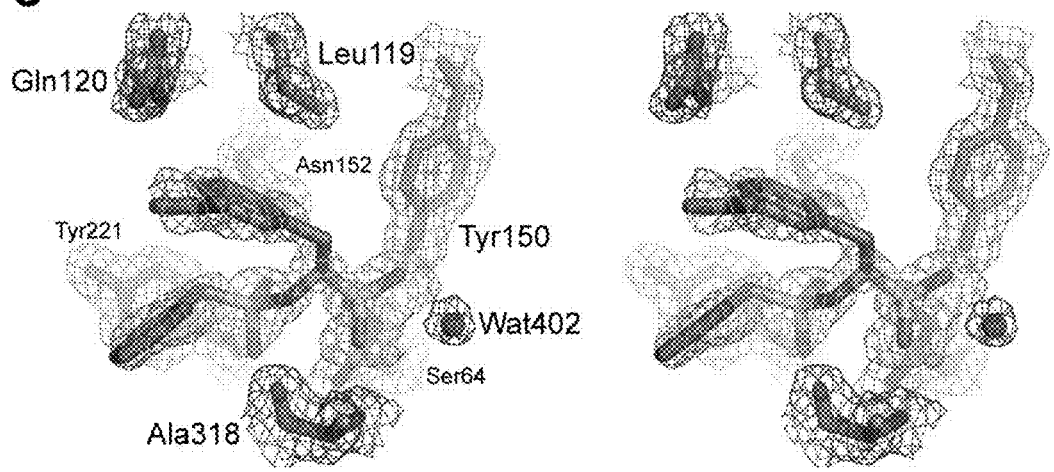

To investigate the structural basis of the carboxamide to sulfonamide conversion, we determined co-crystal structures of AmpC in complex with 4, 9 and 17 (Table 2). All complexes were obtained from the same crystallization condition yielding centered monoclinic C2 crystals with two AmpC complexes in the asymmetric unit. The positions of the inhibitors in the active site were unambiguously identified in both chains in the initial $F_o$-$F_c$ difference density maps (FIG. 7).

With exception of the complex with compound 4, the conformations of the inhibitors were very similar in both monomers.

Figure 8:
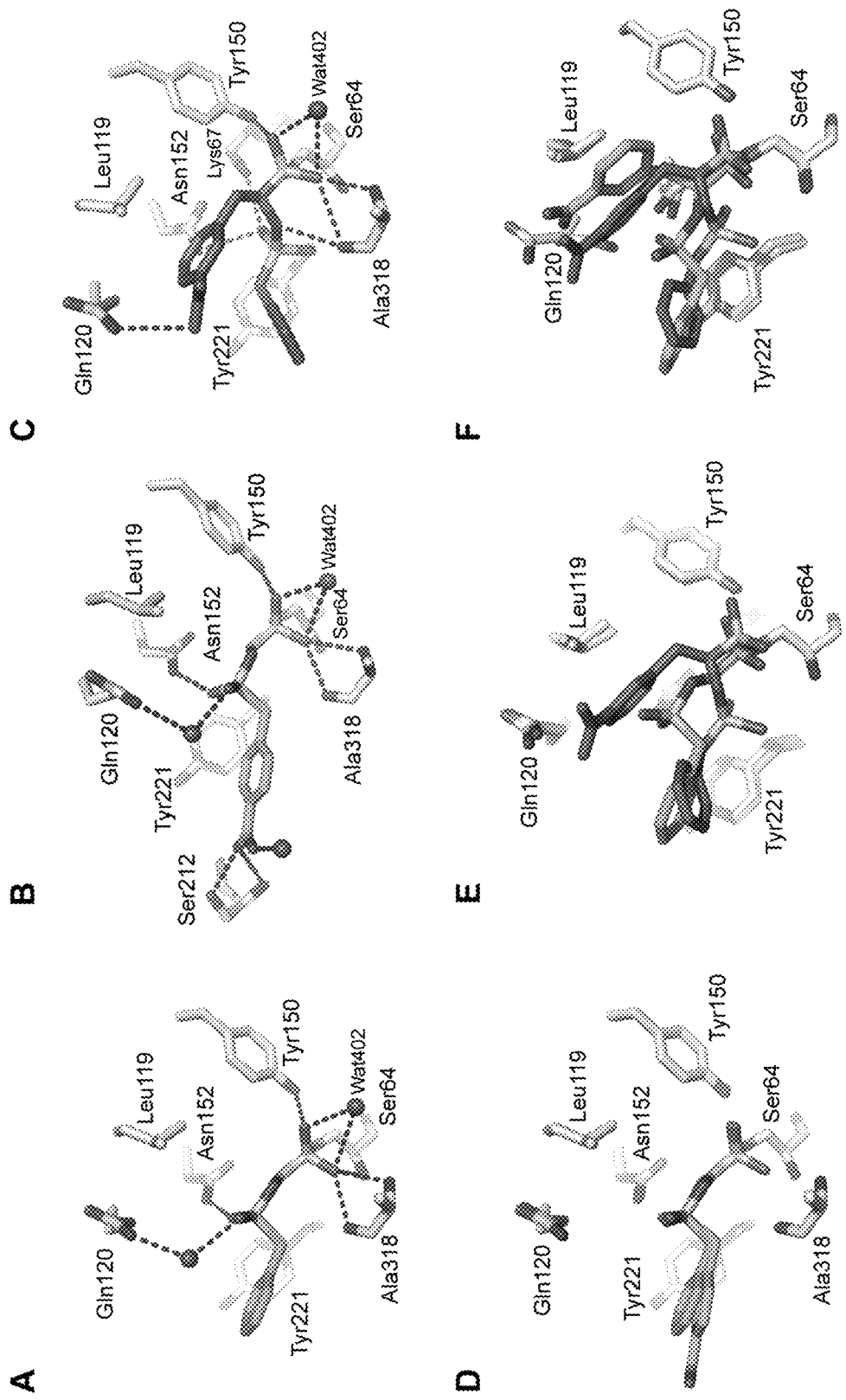
FIG. 8. Polar interactions of sulfonamide boronic acids with AmpC and comparison of conformations. Enzyme residues depicted in atom-colors (light grey carbons, red dark grey, dark grey nitrogens), hydrogen bonds shown as dashes, water molecules as spheres. A) Compound 4 in chain A. B) Compound 9. C) Compound 17. D) Superposition of compound 9 on compound 4. E) Superposition of compound 17 on compound 4. F) Superposition of a model of 17 on its actual crystal structure. (compound numbering as in Table 1)

For all three inhibitors, electron density connected the Oγ of the catalytic Ser64 to the boron atoms of the inhibitors. The boron geometry was tetrahedral, as expected, and key hydrogen bond interactions in the active site closely resembled those typically observed in β-lactamase structures with transition-state analogs and with β-lactams (FIG. 8A-C). (Strynadka, N. C. et al., *Nat. Struct. Biol.* 1996, 3, 688-695; Caselli, E. et al., *Chem. Biol.* 2001, 8, 17-31; Morandi, F. et al., *J. Am. Chem. Soc.* 2003, 125, 685-695; Morandi, S. et al., *Bioorg. Med. Chem.* 2008, 16, 1195-1205) One oxygen atom of the boronic acid is placed in the "oxyanion hole" formed by the backbone amide groups of Ser64 and Ala318. The other oxygen atom of the boronic acid interacts with the conserved Tyr150, which contributes to activating the deacylating water Wat402 for attack on the acyl-intermediate. (Lobkovsky, E. et al., *Biochemistry* 1994, 33, 6762-6772; Chen, Y. et al., *Protein Sci.* 2009, 18, 662-669; Bulychev, A. and Mobashery, S., *Antimicrob. Agents Chemother.* 1999, 43, 1743-1746; Patera, A. et al., *J. Am. Chem. Soc.* 2000, 122, 10504-10512; Galleni, M. et al., *Biochem. Pharmacol.* 1995, 49, 1171-1178; Rahil, J. and Pratt, R. F., *Biochemistry* 1994, 33, 116-125) Both oxygen atoms are also within hydrogen bonding distance to the conserved water molecule Wat402.

The crystal structure of compound 4 ($K_i$ 70 nM) in complex with AmpC was determined at 1.60 Å (FIG. 8A). Whereas there were several differences between the two monomers in the asymmetric unit, such as the rotation of the benzyl ring to stack with Tyr221 in either a parallel or herringbone conformation, we will focus on the interaction in chain A. Here, one oxygen atom of the sulfonamide hydrogen bonds to Asn152 (nitrogen-oxygen distance: 2.6 Å). The other sulfonamide oxygen atom hydrogen bonds with a water molecule bridging to Gln120. The benzyl group makes a T-shaped π-π interaction (90° angle) with Tyr221. The sulfonamide nitrogen interacts neither with the protein nor with a well-ordered water molecule.

To understand the influence of the p-carboxylate group, responsible for a three-fold increase affinity of compound 9 ($K_i$ 25 nM) compared to compound 4, we determined the crystal structure of the AmpC/9 complex to 1.78 Å resolution (FIG. 8B). The conformation of 9 is similar in both monomers and resembles the conformation of 4 observed in chain A, except that the plane of its phenyl ring is slightly off-set relative to that of 4 (FIG. 8D). The slightly altered conformation allows the p-carboxylate group to hydrogen bond with the side chain hydroxyl and amide nitrogen of Ser212. The other carboxylate oxygen atom hydrogen bonds with an ordered water molecule.

To understand the reduced activity of 17 ($K_i$ 430 nM) against AmpC relative to compounds 4 and 9, we determined its crystal structure in complex with AmpC at 1.64 Å resolution (FIG. 8C). In this complex, the boron-carbon bond is rotated by 90° compared to the conformation adopted by compound 4. This is necessary to accommodate the additional m-carboxybenzyl $R^b$ group of 17. Consequently, the sulfonamide is reoriented in the active site placing the benzyl sulfonamide in a totally different location relative to compounds 4 and 9 (FIG. 8E). One sulfonamide oxygen of compound 17 makes stretched hydrogen bonds with Asn152 and Lys67 (3.2 and 3.1 Å, respectively) and the nitrogen atom of the sulfonamide hydrogen bonds with the backbone amide of Ala318 (3.1 Å), an interaction missed in the other two structures. Conversely, the second oxygen atom now abuts the backbone carbonyl of Ala318 (2.8 Å) and the quality of the other sulfonamide hydrogen bonds, as judged by distance and angle, has deteriorated substantially. The R phenyl group makes a T-shaped π-π interaction with Tyr221, but in a different conformation than observed in the AmpC/4 and AmpC/9 complex structures.

Modeling.

Compound 17 was modeled in complex with AmpC by superposing 17 on the crystal structure of compound 4 in chain A. To remove clashes of the additional m-carboxybenzyl group with the protein, we minimized 17 in the AmpC active site by an all-atom energy minimization using PLOP. (Kalyanaraman, C. et al., *Biochemistry* 2005, 44, 2059-2071) The oxygen atom of Ser64 was allowed to move while the rest of the enzyme was kept rigid during the minimization. This resulted in a model with the phenylmethanesulfonamide conformation resembling the conformation observed for compounds 4 and 9, in which the sulfonamide oxygen atoms pointed in the direction of the m-carboxybenzyl group.

Modeling of distal site binders. Fifteen boronic acids were modeled manually in their tetrahedral adduct state into the AmpC active site using Coot. Small molecule coordinates and restraints were generated using eLBOW. Chain A of the AmpC structure in complex with 10 (Supporting Results, PDB code 4E3O) was used as the receptor. Care was taken to keep the sulfonamide conformation similar to the one observed in 10: molecules were checked for their capability to hydrogen bond with the peptide nitrogens of Ser212 and Gly320. Subsequently, the ligand conformations were minimized using the Protein Local Optimization Program (PLOP) to remove clashes and optimize electrostatic interactions with the protein. In the minimization, we used the oxygen and C-beta atom coordinates of Ser64 to create an artificial methylated tetrahedral boronic acid. An artificial Ser64Gly mutant of the AmpC/70 structure served as the receptor, which was kept rigid during the minimization. All ligand atoms were subjected to minimization, except for the artificial methyl (C-beta of Ser64), thereby mimicking the covalent bond between the ligand and the protein. Molecules having a linker with the right length and good geometry allowing for distal site binding were suggested for synthesis.

Crystal Growth and Structure Determination.

Co-crystals of AmpC in complex with compound 4, 9 and 17 were grown by vapour diffusion in hanging drop vapor diffusion experiments equilibrated over 1.7 M potassium phosphate buffer (pH 8.7-8.9) using microseeding technique. The initial concentration of the protein was 3.9 mg/ml, and the concentrations of the compounds were 625 μM, the DMSO concentration was 1.25%. Crystals appeared 4-7 days after equilibration at 20° C. Before data collection, crystals were immersed in a cryoprotectant solution of 25% sucrose, 1.7 M potassium phosphate, pH 8.7, for about 30 sec, and were flash cooled in liquid nitrogen.

Diffraction data were measured at beamline 8.3.1 of the Advance Light Source (ALS, Lawrence Berkeley Lab, CA). Reflections were indexed, integrated and scaled using the XDS package. (Kabsch, W., *J. Appl. Crystallogr.* 1993, 26, 795-800) The space group was C2 with two molecules in the asymmetric unit. The initial phasing model was an apo AmpC model (PDB entry 1KE4), with water molecules and ions removed. The model was positioned initially by rigid body refinement and further refined with L-BFGS minimization, simulated annealing, individual B-factor refinement and water picking using PHENIX. (Adams, P. D. et al., *Acta Crystallogr., Sect. D: Biol. Crystallogr.* 2010, 66, 213-221) Coot was used for model building and the PRODRG server was used to generate ligand restraints. (Emsley, P. and Cowtan, K., *Acta Crystallogr., Sect. D: Biol. Crystallogr.* 2004, 60, 2126-2132; Schuttelkopf, A. W. and van Aalten, D.

M., *Acta Crystallogr., Sect. D: Biol. Crystallogr.* 2004, 60, 1355-1363) Ligand restraints were modified manually because the PRODRG server does not support boron atoms.

E. Example 5

Antimicrobial Activity

The anti-resistance activity of inhibitors 4 and 9 was investigated against clinical bacteria exhibiting high level of resistance against third-generation cephalosporins, such as ceftazidime, via expression of class A or class C β-lactamases. When the compounds were administrated alone in a disk diffusion assay they had little or no detectable activity on bacteria growth, as expected. However, in combination with ceftazidime the compounds produced a large inhibition halo surrounding the disk (FIG. 6A). This inhibition of the bacterial growth revealed clear synergy between these compounds. The size of the inhibition zone was similar for both compounds and showed improved inhibition of bacterial growth compared to ceftazidime alone.

Antimicrobial activity was investigated quantitatively to determine the minimum inhibitory concentrations (MICs) of the β-lactam/inhibitor combination necessary to inhibit the bacterial growth (Table 3). The MICs of β-lactams alone against the strains corresponded to a high level of resistance according to Clinical and Laboratory Standards Institute (CLSI) standards. (Clinical and Laboratory Standards Institute, Performance standards for antimicrobial susceptibility testing, 20*th Informational Supplement, M*100-*S*20 2010) The compounds had no measurable antibiotic activity when used alone. In combination with β-lactams, the compounds decreased MIC values by eight-fold on average. Interestingly, even larger relative decreases in MIC values were observed for an *E. coli* strain producing the plasmid-mediated class A β-lactamase CTX-M-14 (16 to 32-fold). This offers preliminary evidence that the sulfonamide boronic acids may inhibit both class C β-lactamases and class A enzymes, consistent with studies revealing activity against this class of enzymes in the low μM range described in this study (Table 4).

A traditional β-lactam resistance mechanism is the upregulation of β-lactamase-encoding gene transcription caused by β-lactams such as cefoxitin and the β-lactamase inhibitor clavulanate. To test the role of compounds on the induction of AmpC expression, we investigated their ability to potentiate the action of the β-lactam ceftazidime. We compared the potentiation effect of compounds with that of cefoxitin (FIGS. 9B and 9C). Agar plates were inoculated with *K. pneumoniae* and *E. cloacae* strains in which AmpC expression is inducible. A ceftazidime-containing disk and a disk containing the inhibitors (cefoxitin or compounds 4 and 9) were placed on each plate. As ceftazidime diffuses from disks into the agar, a clear zone is created around the ceftazidime-containing disk, indicating where bacteria are unable to grow. The shape of this halo in the vicinity of the inhibitor-containing disk indicated the effect of these compounds on the induction of AmpC. The inhibition halos normally surrounding ceftazidime were substantially diminished in the regions nearest to the cefoxitin disk. This well-known antagonist picture is characteristic of the ampC gene induction by cefoxitin. The antagonist picture was replaced by a synergic picture with compounds 4 and 9; the inhibition halos of ceftazidime were dramatically increased in the region near the compound disks. This result indicates that the compounds inhibit AmpC and do not induce significant upregulation of AmpC-encoding genes in contrast to β-lactams such as cefoxitin.

Figure 23:
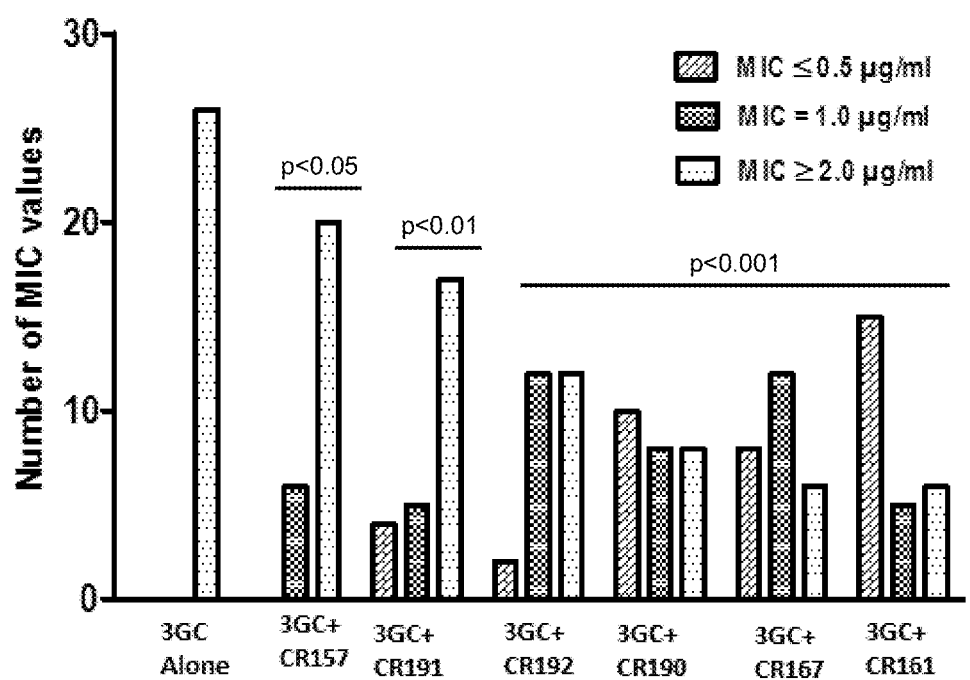
FIG. 23. MIC distribution for clinical strains resistant to third-generation cephalosporins (3GC). p values refer to the comparisons of the MICs of 3GC alone with the MICs of 3GC-compound combinations.

The anti-resistance activity of inhibitors was investigated by the determination of the minimum inhibitory concentrations (MICs) of the β-lactam/inhibitor combination necessary to inhibit the growth of clinically-isolated bacteria resistant to third-generation cephalosporins via expression of class A or class C β-lactamases (Table 6). Used by themselves, the antibiotics cefotaxime and ceftazidime had high MIC values, often greater than 64 μg/mL, certainly much higher than the break point for empirical resistance levels ≥2 μg/mL (Clinical and Laboratory Standards Institute (2010) Performance standards for antimicrobial susceptibility testing. 20th Informational Supplement, M100-S20). Conversely, in combination with the new inhibitors, the MIC values of these third-generation cephalosporins improved substantially, typically by 64-fold or more. For 75% of the clinical isolates measured, MICs dropped into the susceptible range (MICs≤1 μg/mL) with compounds CR167 and CR161, for 50% with compounds CR190 and CR192, and for 25% of those treated with the cephalosporins and CR157 or CR191 (Table 11). For many clinical isolates, MIC values for ceftazidime and cefotaxime combined with CR161 and CR190 dropped to 0.5 μg/mL and below (FIG. 23), which represents an 8- to 16-fold improvement of MIC values compared to previously tested boronic acids (Caselli E, et al. (2001), Chem Biol 8:17-31, Morandi F, et al. (2003), J Am Chem Soc 125:685-695, Eidam O, et al. (2010), J Med Chem 53:7852-7863).

Intriguingly, substantial decreases in MIC values were observed for a strain producing the plasmid-mediated class A β-lactamase CTX-M-14 (8 to 64-fold), especially for compounds CR167 and CR157, which had the broadest spectrums of activity. This offers preliminary evidence that the sulfonamide boronic acids may inhibit both class C and class A β-lactamases, consistent with their in vitro activity against this class of enzymes.

Microbiology.

Susceptibility testing was performed and interpreted following the guidelines of CLSI. (Clinical and Laboratory Standards Institute, Performance standards for antimicrobial susceptibility testing, 20*th Informational Supplement, M*100-*S*20 2010) The compounds were dissolved in 50% DMSO, and dilutions were performed using Muller-Hinton medium. An adequate final concentration was obtained to determine the minimum inhibitory concentrations (MICs). The concentration of DMSO was maintained below 5%. The inhibitors were tested for synergy with the third-generation β-lactams ceftazidime and cefotaxime against several clinical bacteria. The ratio of β-lactams to inhibitors was 1:4. Each value reported reflects the average of three independent experiments. The bacteria exhibited high level of resistance to β-lactams because of the expression of class C or class A β-lactamases. Six *Escherichia coli* strains showed an AmpC-overproduced phenotype and the last one produced the plasmid-mediated class A β-lactamase CTX-M-14. *Citrobacter freundii, Enterobacter cloacae,* and *Pseudomas aeruginosa* strains showed AmpC-derepressed phenotype. A *Klebsiella pneumoniae* isolate produced the inducible plasmid-mediated class C enzyme DHA-1. The Friedman's test and the Wilcoxon signed rank test were used to compare MIC values. Statistical significance was established at p<0.05.

For disk diffusion plate assays, bacterial strains were diluted in sterile water to a turbidity equivalent to 0.5 McFarland turbidity standards. After a subsequent 10-fold dilution, the bacterial suspensions were inoculated on Mueller Hinton agar. The plates were dried for 10 min before applying the disks containing cefotaxime or ceftazidime antibiotics (30

μg) or the inhibitor (30 μg) or both. After overnight incubation at 37° C., the zones of bacterial-growth inhibition were measured.

For the β-lactamase induction experiments, plates of Mueller Hinton agar were inoculated with two clinical strains (*E. cloacae* and *K. pneumoniae*) in which production of AmpC-type enzyme is inducible by β-lactam antibiotics. Inhibitors were added to blank disks, and the final content of inhibitor per disk was 64 μg of compounds and 32 μg cefoxitin. Disks of ceftazidime contained 30 μg of antibiotic.

F. Example 6

Selectivity

To investigate the selectivity of sulfonamide boronic acids, compounds 4 and 9 were tested against the serine protease α-chymotrypsin, the cysteine protease cruzain, and against the class A β-lactamase CTX-M-9, that is structurally different from AmpC (Table 4a). Compounds 4 and 9 showed no measurable inhibition at 100 μM against cruzain and α-chymotrypsin. Interestingly, the compounds are active against CTX-M-9 with $IC_{50}$s in the low micromolar range. The $K_i$ values corresponding to the $IC_{50}$ values are 2.529 and 0.552 μM, respectively, indicating 36-fold and 22-fold selectivity towards AmpC versus CTX-M-9 β-lactamase.

The selectivity of compounds 4 and 9 was tested by determining their activity against CTX-M-9 β-lactamase, α-chymotrypsin (bovine pancreatic) and cruzain. α-Chymotrypsin and all necessary assay components were purchased from Sigma-Aldrich.

CTX-M-9 activity was measured under the same conditions as with AmpC, with 60 μM CENTA ($K_m$ 35 μM) as substrate. Reactions were initiated by the addition of 0.3 nM enzyme and monitored at 405 nm.

α-Chymotrypsin assays were performed in 50 mM Tris buffer pH 7.5 with 0.01% Triton-X. Inhibitor and 0.001 mg/mL enzyme were incubated at their final concentration for 10 min before the reaction was initiated by the addition of 200 μM N-succinyl-Ala-Ala-Pro-Phe p-nitroanilide and monitored at 410 nm.

Cruzain assays were performed in 100 mM sodium acetate pH 5.5 with 0.01% Triton-X and 5 mM dithiothreitol. Cruzain activity was measured in a 96-well format fluorimetric assay, monitoring the cleavage of the substrate Z-Phe-Arg-aminomethylcoumarin (Z-FR-AMC), in a SpectraMax M5, Molecular Devices spectrofluorimeter. Inhibitor and 0.4 nM enzyme were incubated at their final concentration for 10 min before the reactions was initiated by the addition of 2.5 μM Z-FR-AMC ($K_m$ 2 μM) and monitored for five minutes, determining activity based on initial rates.

Figure 22:
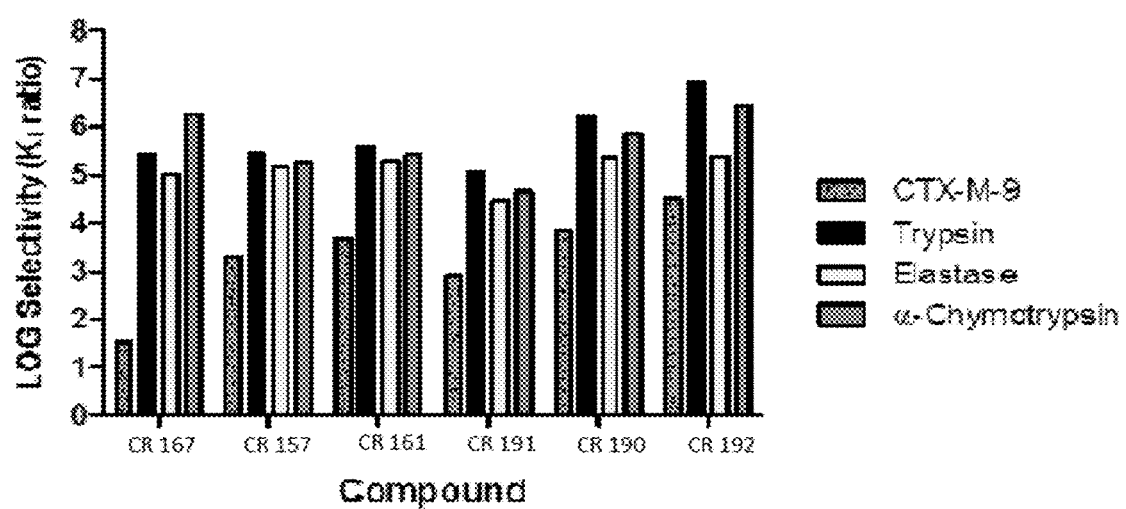
FIG. 22. Selectivity for AmpC. Comparison of $K_i$ values from Table 6 shows that all compounds (except CR191) are at least $10^5$ times more selective for AmpC (see dashed black line at the LOG (10)$^5$ mark) over the tested serine proteases (Trypsin, Elastase, α-Chymotrypsin). The tetrazoles are ~$10^3$ times more selective for AmpC over CTX-M-9 exhibiting $K_i$ values in the single digit micromolar range. Compound CR167 is ~30-times more selective for AmpC compared to CTX-M-9, with $K_i$ values of 1.3 nM and 45 nM, respectively.

To assess the selectivity of the new molecules we determined Ki values against three common serine proteases, Trypsin, Elastase and α-Chymotrypsin, as well as that of a class A β-lactamase, CTX-M-9 (Table 10) (Pouvreau L, et al. (1998), FEBS Lett 423:167-172; Del Mar E G, et al. (1980), Biochemistry 19:468-472; Rodriguez-Martinez J A, et al. (2009), Biotechnol Lett 31:883-887; Chen Y, et al. (2005), J Mol Biol 348:349-362). Affinity for AmpC was typically 105 to 106-fold better than for the serine proteases (FIG. 22). Notwithstanding the boronic acid warhead shared by these inhibitors, the compounds show clear specificity for their target over protease off-targets. Affinity was also substantially better for AmpC than CTX-M-9, which, though speaking to specificity, may portend difficulties for clinical relevance, as one would ideally prefer a compound active against both class C and class A enzymes. Still, several of the analogs retained substantial affinity for CTX-M-9, especially CR167, which was a 45 nM inhibitor of CTX-M-9.

G. Example 7

Figure 17:
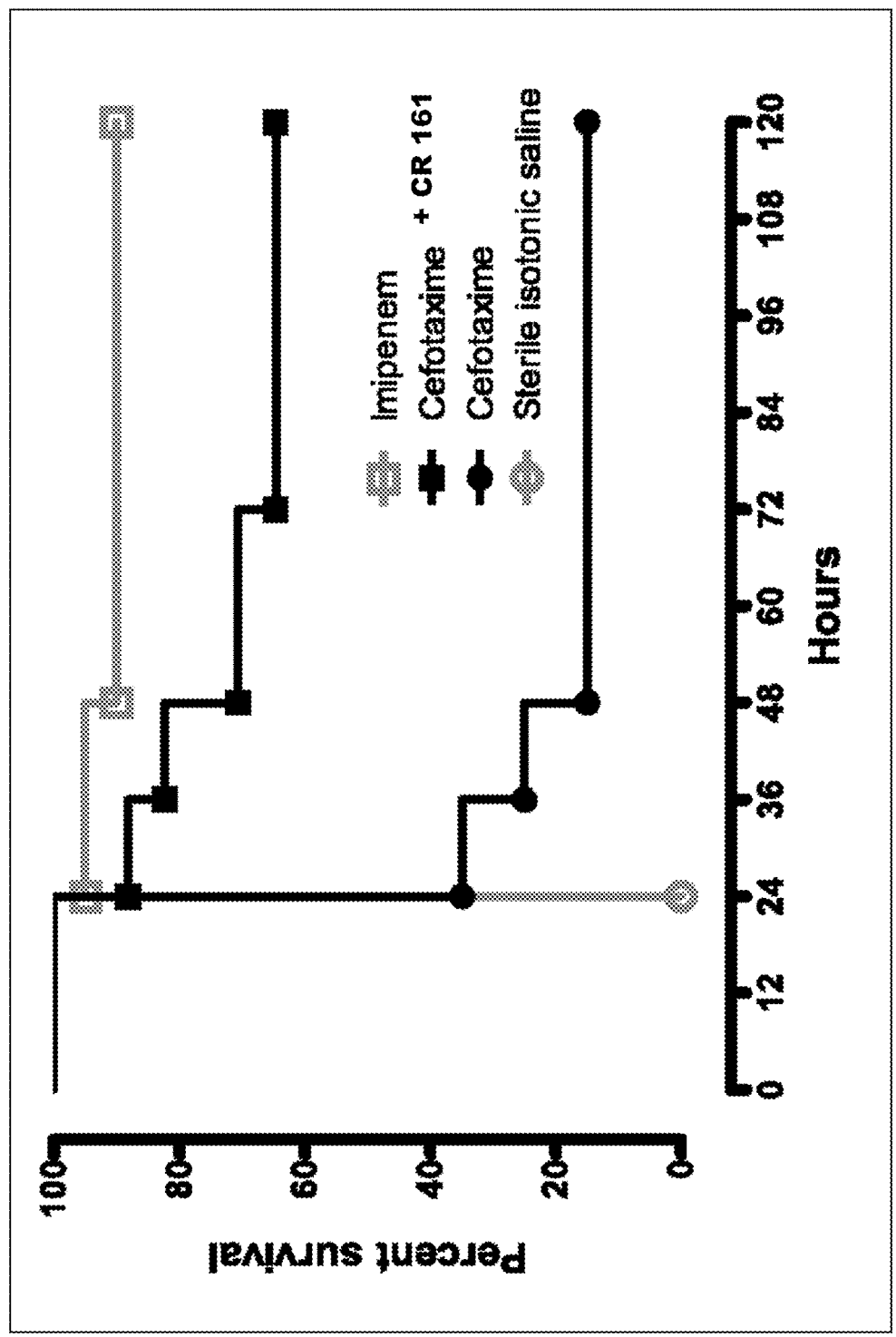
FIG. 17. Percentage of survival of mice infected with AmpC-overproducing *Escherichia coli* over the course of 5 days (120 h). Mice were inoculated by intraperitoneal injection with AmpC-overproducing *Escherichia coli* strain 4 (1±0.5 $10^9$ colony-forming units) and treated at 0.5, 3.5, 6.5 h after infection by intraperitoneal injection of 50 mg/kg imipenem (□, n=20), 50:200 mg/kg cefotaxime:CR161 combination (■, n=17), 50 mg/kg cefotaxime (●, n=20) or sterile isotonic saline (○, n=20).
Figure 18:
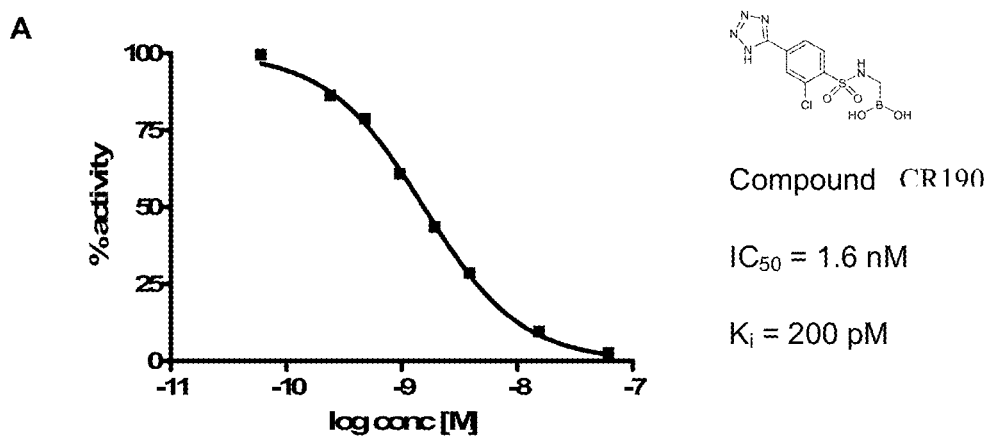
FIG. 18. Representative $IC_{50}$ curves. $IC_{50}$ curves of inhibitors CR190 (A) and CR192 (B), which had $K_i$ values of 200 pM and 50 pM, respectively. $IC_{50}$ curves were obtained by measuring rates (in duplicates) at different inhibitor concentrations (x-axis) and by determining the residual activity (y-axis, in percentage). $IC_{50}$ values were determined by non-linear regression and $K_i$ values calculated using GraphPad software assuming competitive inhibition. The substrate (CENTA) concentration was 105 µM. The 95% confidence interval was usually ±10% around the $K_i$, and the Hill-slope was always close to −1, indicating that one molecule binds at a time.
Figure 18:
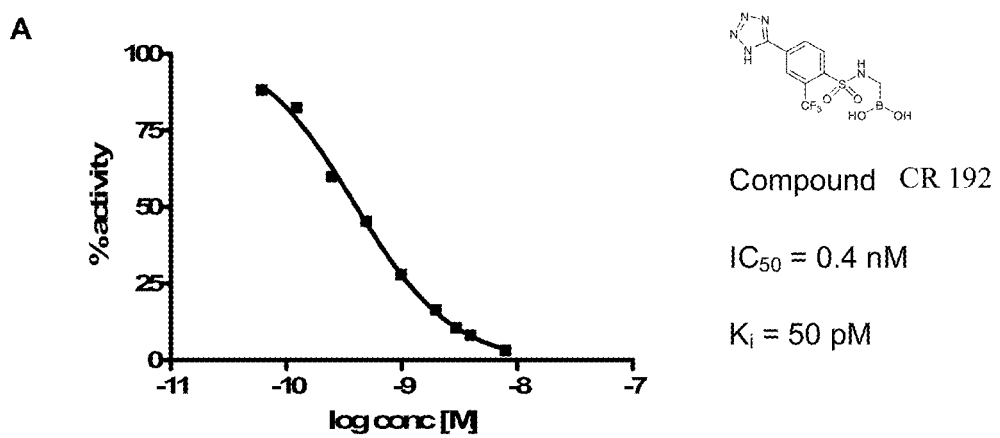
Figure 19:
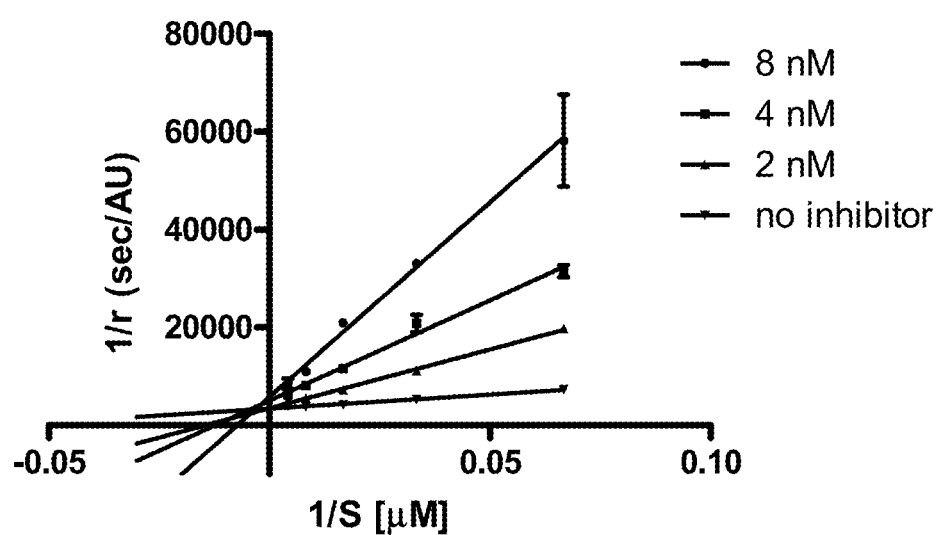
FIG. 19. Example of a Lineweaver-Burk plot. Depicted is the Lineweaver-Burk analysis for compound CR161, which indicates competitive enzyme inhibition as all curves have the same y-intercept at 1/[S]=0. Enzymatic rates for substrate hydrolysis were determined at four different inhibitor CR161 concentrations (0, 2, 4 and 8 nM of CR161) and at five different substrate [S] concentrations (15, 30, 60, 120 and 240 µM). AmpC concentration was 100 pM.
Figure 24:
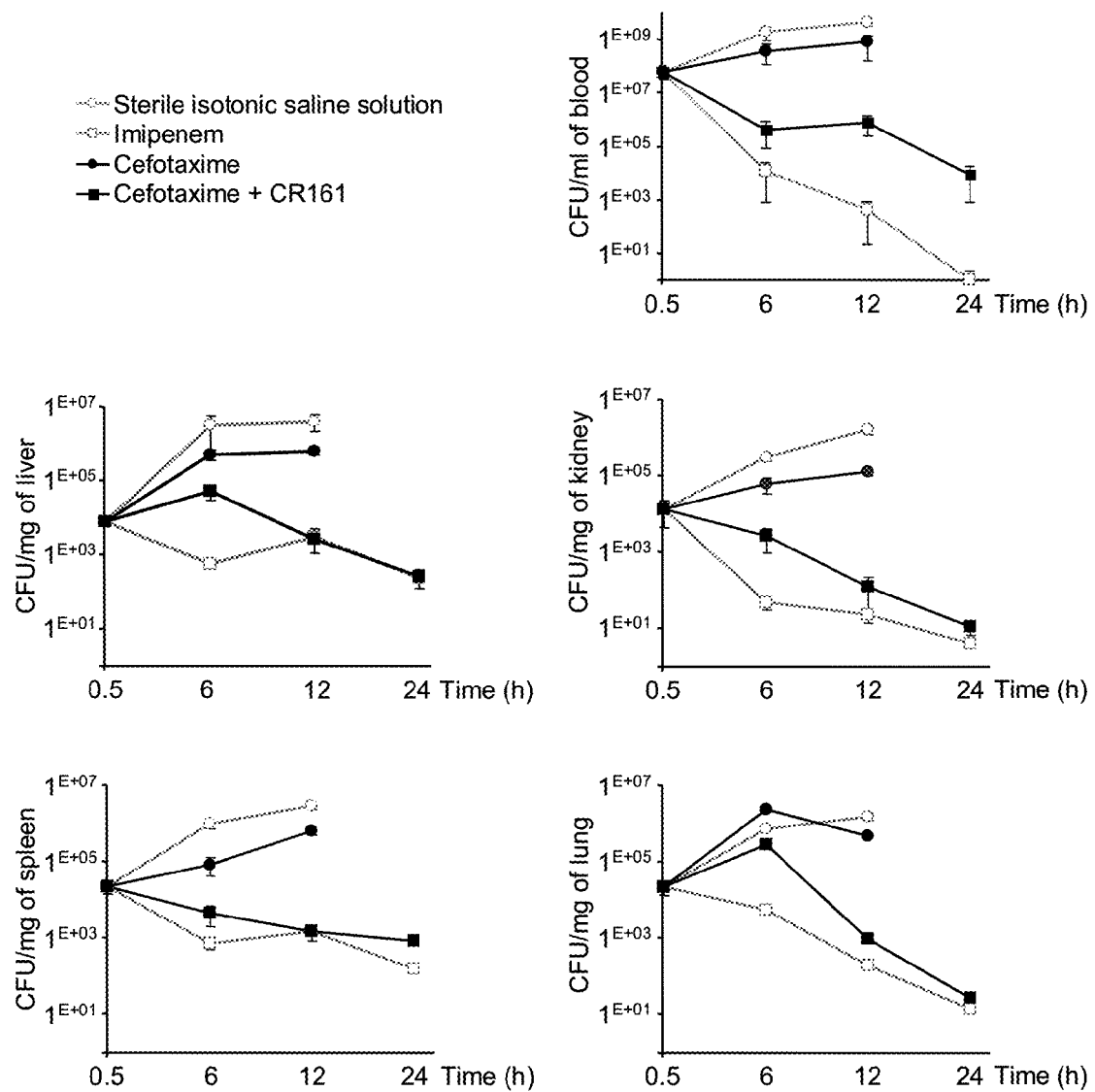
FIG. 24. Bacterial counts (CFUs) in liver, spleen, blood, kidney and lung measured during the first 24 hours. The points on the graphs represent the average and standard deviation of colony forming units (CFUs) often mice on a log scale. Mice were inoculated by intraperitoneal injection with AmpC-overproducing *Escherichia coli* (1±0.5 $10^9$ colony-forming units) and treated at 0.5, 3.5, 6.5 h after infection by intraperitoneal injection of 50 mg/kg imipenem (□), 50:200 mg/kg cefotaxime:CR161 combination (■), 50 mg/kg cefotaxime (●) or sterile isotonic saline (○).
Figure 25:
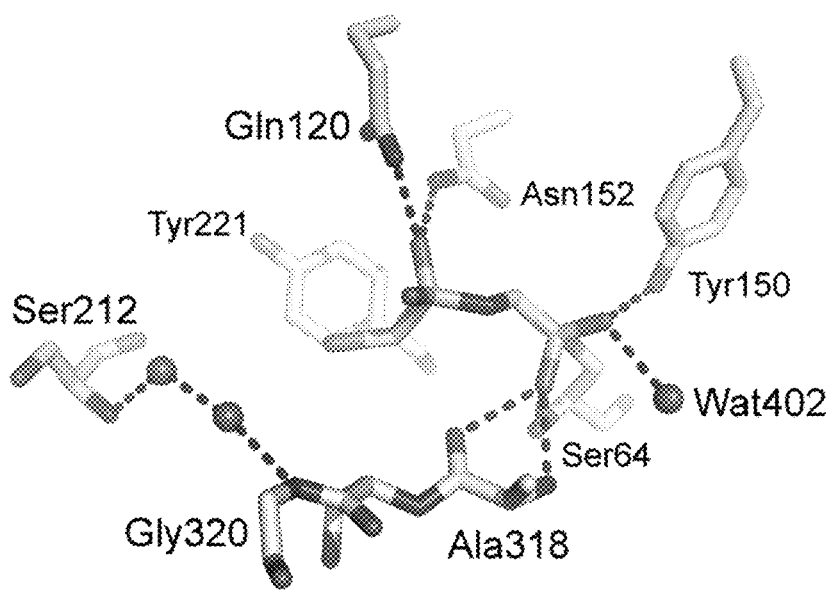
FIG. 25. Active site of AmpC/CR70 X-ray structure. AmpC carbon atoms are depicted in grey, carbons in light gray, oxygens dark gray, nitrogens dark gray, sulfurs light gray, borons light gray, chlorides in medium gray, fluorides in light gray. Dashes represent hydrogen bonds with AmpC and selected water molecules (spheres).
Figure 26:
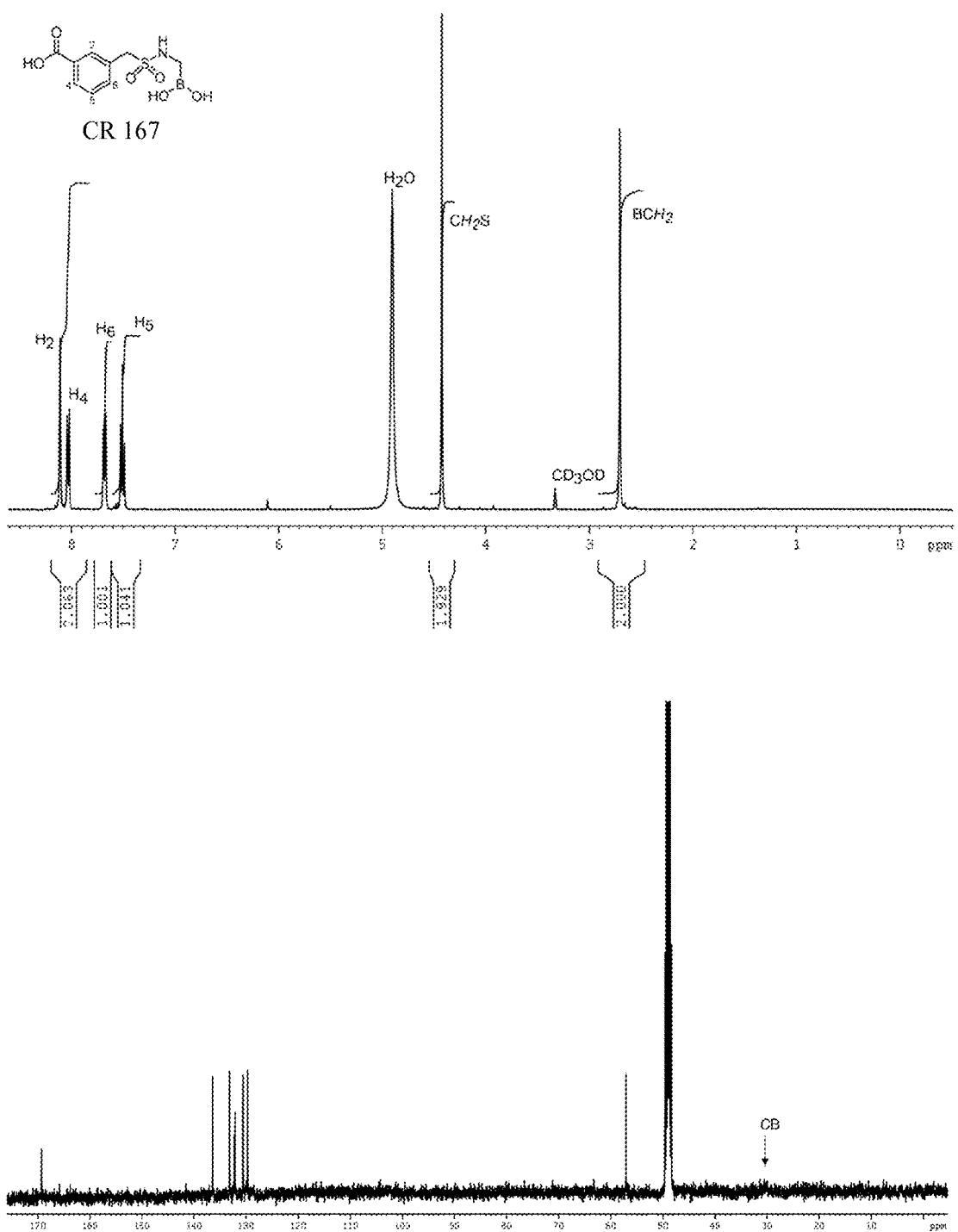
FIG. 26. Spectral data of compound CR167. $^1$H NMR (400 MHz, $CD_3OD$) and $^{13}C$ NMR (100 MHz, $CD_3OD$).
Figure 27:
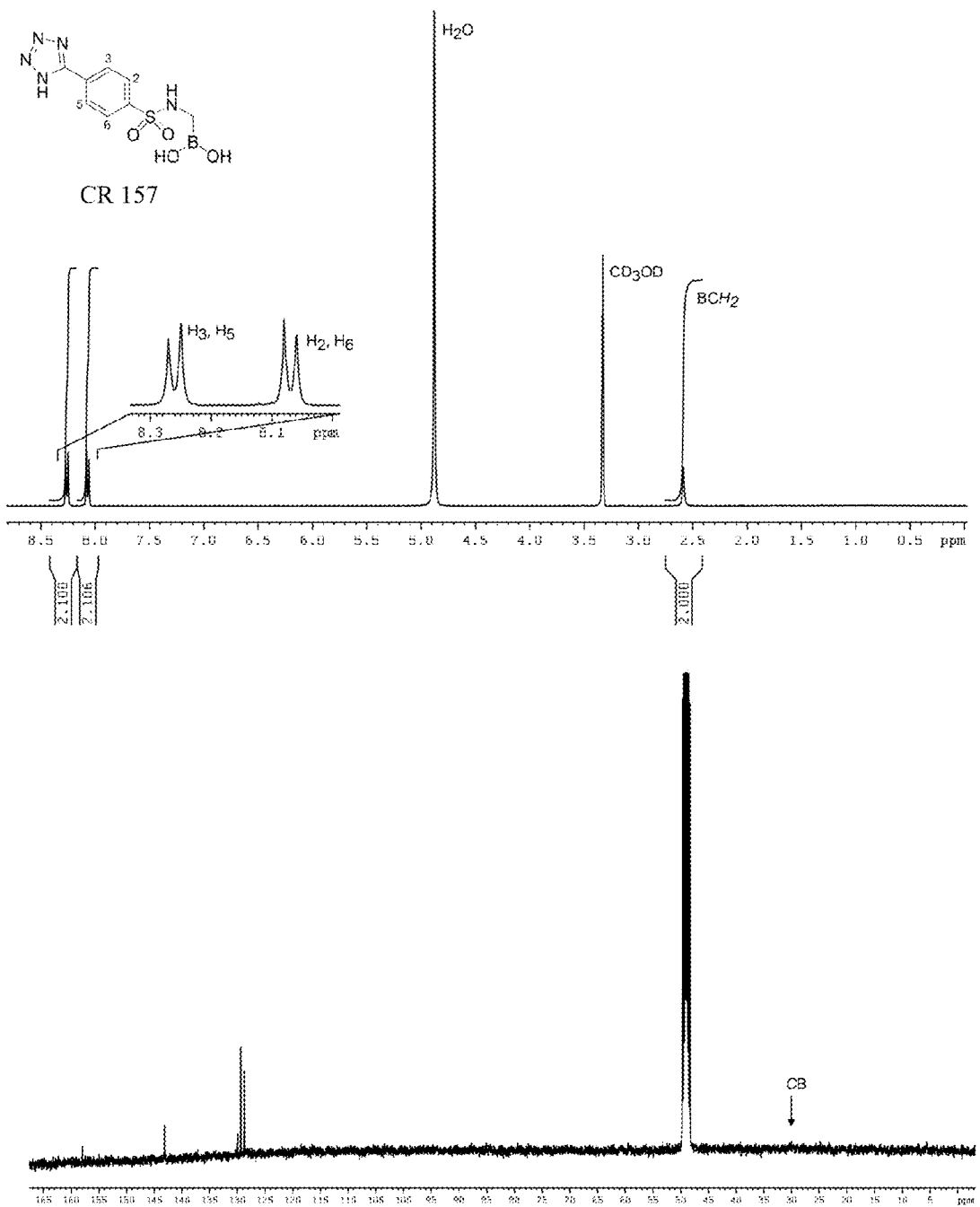
FIG. 27. Spectral data of compound CR157. $^1$H NMR (400 MHz, $CD_3OD$) and $^{13}C$ NMR (100 MHz, $CD_3OD$).
Figure 28:
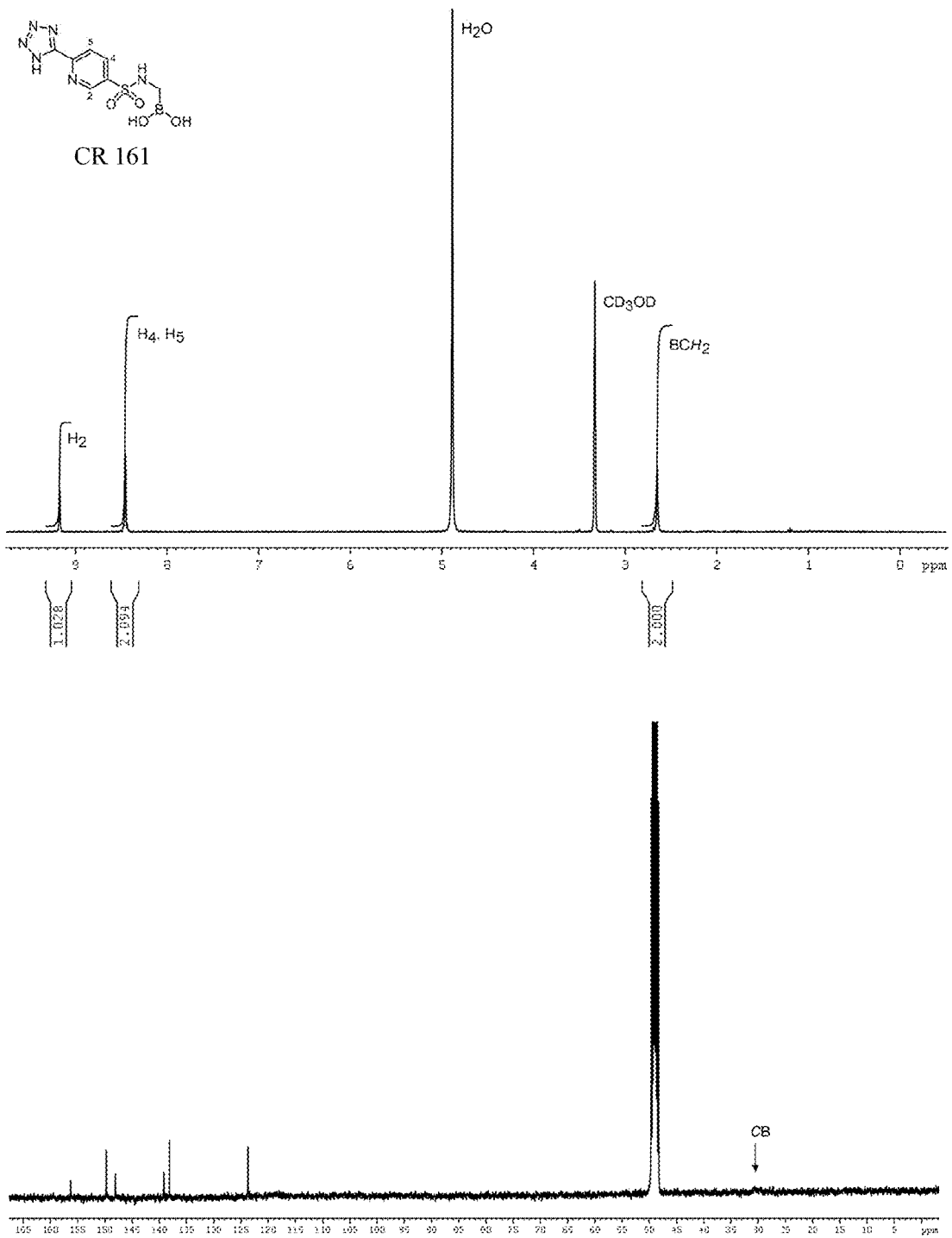
FIG. 28. Spectral data of compound CR161. $^1$H NMR (400 MHz, $CD_3OD$) and $^{13}C$ NMR (100 MHz, $CD_3OD$).
Figure 29:
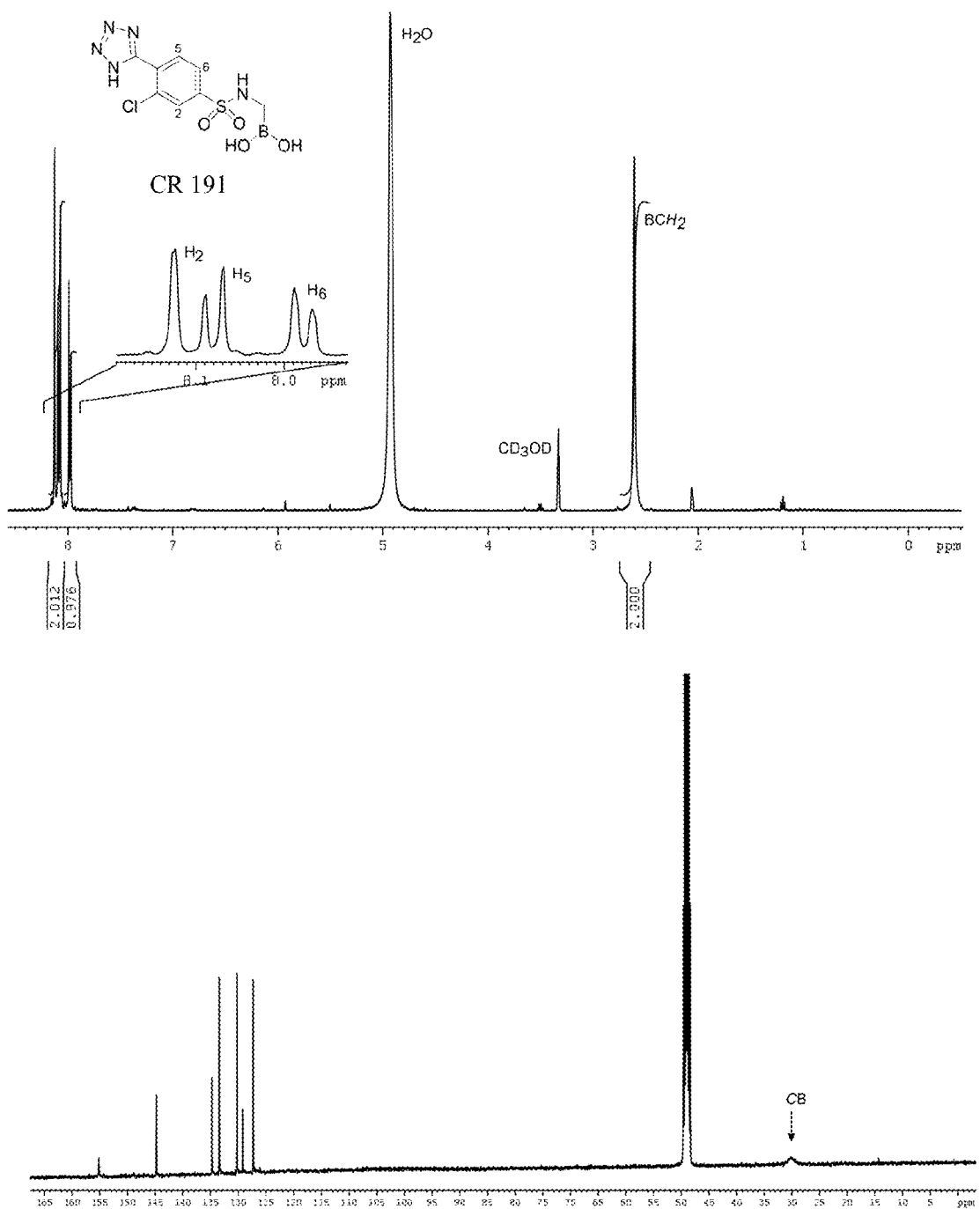
FIG. 29. Spectral data of compound CR191. $^1$H NMR (400 MHz, $CD_3OD$) and $^{13}C$ NMR (100 MHz, $CD_3OD$).
Figure 30:
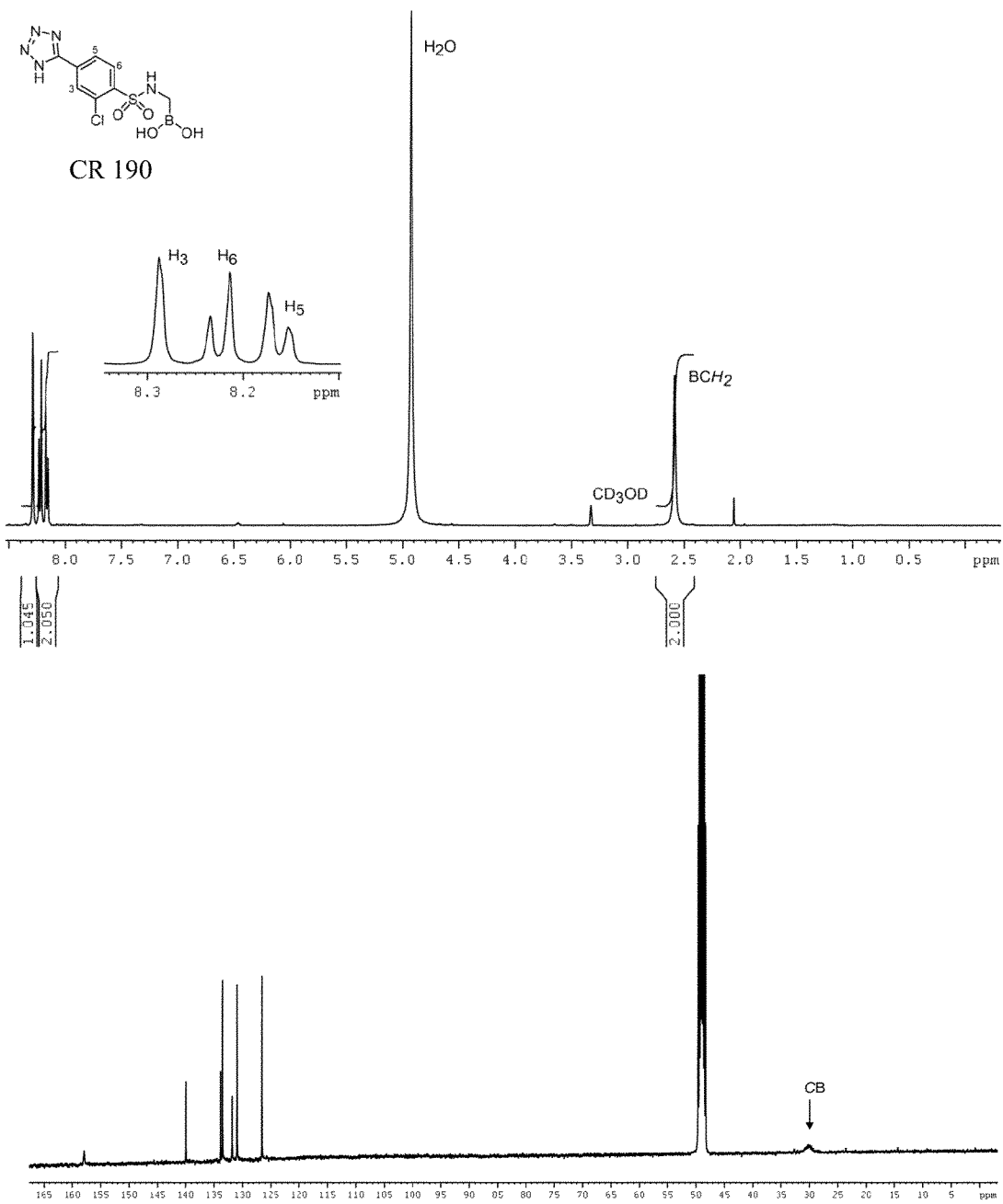
FIG. 30. Spectral data of compound CR190. $^1$H NMR (400 MHz, $CD_3OD$) and $^{13}C$ NMR (100 MHz, $CD_3OD$).
Figure 31:
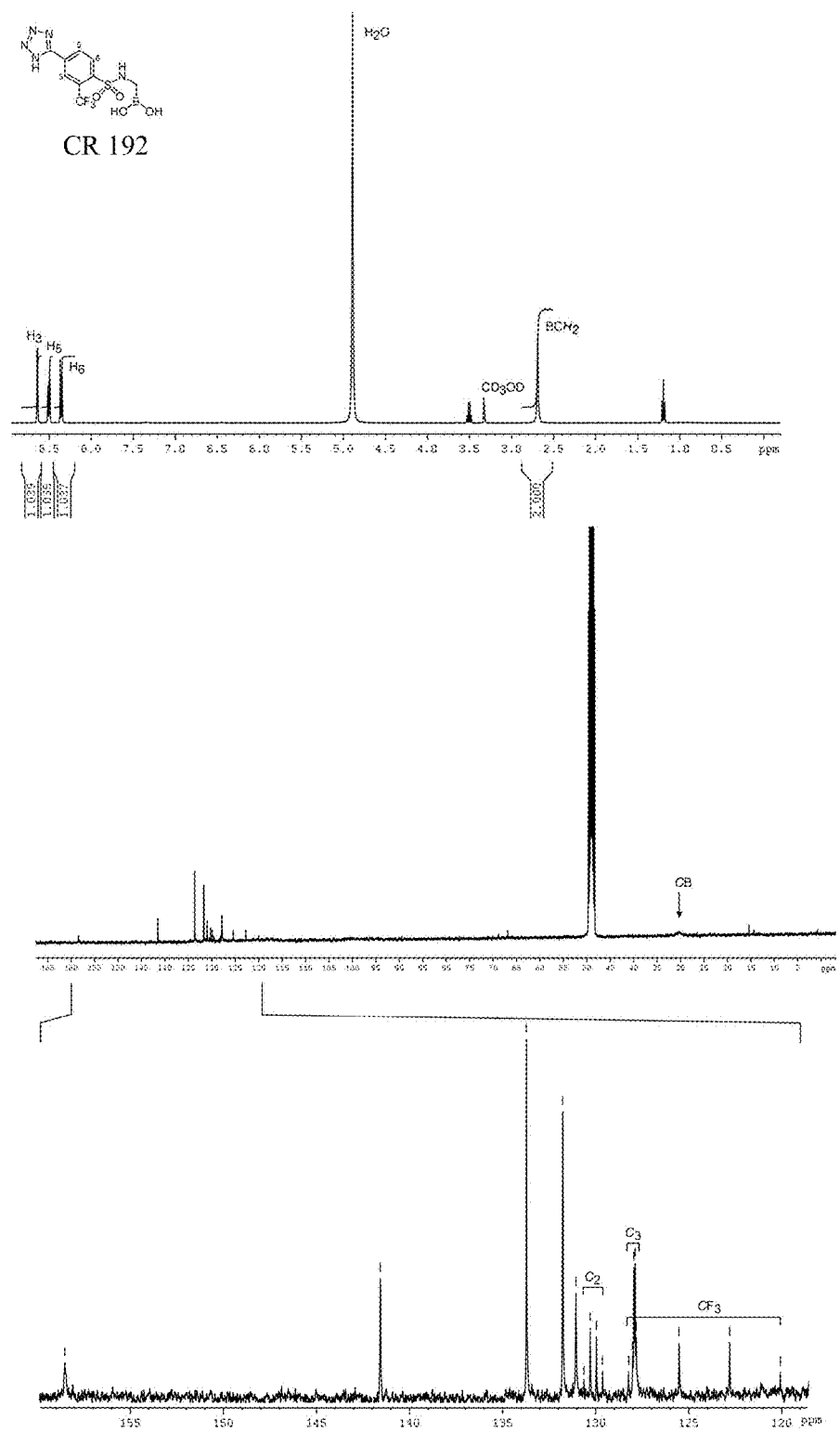
FIG. 31. Spectral data of compound CR192. $^1$H NMR (400 MHz, $CD_3OD$) and $^{13}C$ NMR (100 MHz, $CD_3OD$).

Efficacy in a mouse model of infection. We had not observed such substantial reversal of bacterial resistance to β-lactams, across such a broad spectrum of clinical isolates, for previous series of boronic acid inhibitors of β-lactamase; indeed, this lack of efficacy had motivated this study. These new cell-culture MIC values inspired us to investigate the efficacy of one of these compounds in a mouse model of bacteremia and sepsis. OF1 mice were infected with a hospital-derived strain of *E. coli* that overproduces AmpC and is highly resistant to cefotaxime (MIC, 32 μg/mL). Mice were treated with cefotaxime alone, cefotaxime combined with compound CR161, with sterile isotonic saline, and with imipenem as a reference treatment of systemic infections by cephalosporin-resistant enterobacteriaceae (FIG. 17); 20 mice were used in each clade. The animals became severely sick 5 h after infection and all untreated animals (sterile isotonic saline) died within 12-24 h. With a clinical dose of 50 mg/kg, imipenem was almost fully active (90% survival at 120 h postinfection). Only 15% of mice treated with cefotaxime alone survived by at 120 h post infection. Cefotaxime: CR161 treatment, conversely, rescued 65% of animals at the 120 h post infection timepoint, and those mice that did die did so later than with cefotaxime alone. Statistical analysis confirms a significant increase in the percent survival for the combination of CR161 with cefotaxime (p≤0.0005 versus cefotaxime alone). No significant difference was observed with imipenem treatment (p≥0.1148 for the comparison cefotaxime:CR161 versus imipenem). Consistent with the expectation that the cefotaxime:CR161 treatment has a direct effect on bacteria, the colony forming unit (CFU) counts of imipenem- and cefotaxime:CR161-treated mice showed reductions in all organs and blood compared to treatment with cefotaxime alone and to untreated controls (FIG. 24 and Table 12).

In Vivo Efficacy Studies.

OF1 mice 4-5 weeks of age and weighing 20-25 g were used in this study. All animals were obtained from Charles River Laboratories, Inc. (Wilmington, Mass., USA). They were maintained in accordance with the recommendations of the Guidelines for the Care and Use of Laboratory Animals, and the experiments were approved by the Animal Care Committee of Auvergne University, Clermont-Ferrand, France. Infection was induced by the intraperitoneal (ip) administration of $1.0 \pm 0.5 \times 10^9$ CFUs (colony forming units) AmpC-overproducing *E. coli* strain 4 inoculum in 0.4 mL PBS buffer. After bacterial challenge, mice were either administered a 50 mg/kg dose of imipenem, 50 mg/kg dose of cefotaxime, 50:200 mg/kg of cefotaxime:CR161 combination or sterile isotonic saline by ip injection at 0.5, 3.5, and 6.5 h after infection. Prior to drug administration, 10 μL blood was collected by retro-orbital sinus puncture to determine blood bacterial counts. The survival of mice in each group was monitored every 6 h for 5 days after infection. To determine bacterial loads in blood, kidney, liver, spleen and lung, 10 mice from each group were sacrificed by cervical dislocation at 30 min, 6 h, and 12 h post-infection (24 h: only imipenem- and cefotaxime:CR161-treated animals). The organs were dissected, weighed, homogenized in PBS, serially diluted in 0.85% NaCl and then plated on Drigalski agar plates. Blood was extracted from the mice using cardiac puncture, diluted in 0.85% NaCl and plated onto Drigalski agar plates. Plates were incubated for 24 hours under aerobic conditions at 37°

C. for counts of remaining colony forming units (CFU). The Mantel-Cox's test and the Gehan-Breslow-Wilcoxon's test were used to compare the resulting survival curves. Student's t test was used to compare paired data.

H. Example 8

Table 1. $K_i$ values (μM) of sulfonamide and carboxamide boronic acids. Compounds 3c-11c have been published in ref. (Caselli, E. et al., *Chem. Biol.* 2001, 8, 17-31) and 18c in ref. (Morandi, F. et al., *J. Am. Chem. Soc.* 2003, 125, 685-695). Compound 17c has been synthesized and tested in this study. N.A. means Not applicable.[‡] Compounds 17c and 18c have a thiophene in the $R^a$ side chain and are therefore not exact analogs of 17 and 18, respectively.

Table 2. Data collection and refinement statistics.[a] Values in parentheses represent highest resolution shells. [b] Calculated for both molecules in asymmetric unit.

Table 3. Minimum inhibitory concentrations (MIC) of third-generation cephalosporins alone and in association with compounds 4 or 9 (ratio 1:1) for clinical bacteria exhibiting a high level of resistance. [a] Bacteria overproducing chromosomally-mediated class C β-lactamase; [b] *K. pneumoniae* producing the plasmid-mediated class C β-lactamase DHA-1; c *E. coli* producing plasmid-mediated class A β-lactamase CTX-M-14.

Table 4. (4a) Selectivity of 4 and 9 for AmpC versus other amide hydrolases. [a] No inhibition was observed at 100 μM. The $IC_{50}$ values assume that inhibition was no greater than 20% at this concentration (4b) Percentage activity with 100 μM inhibitor (4c) Percentage inhibition with 100 μM inhibitor (4d) Percentage inhibition with 16 μM inhibitor (4e) IC50 [μM](Estimated from single concentration measurement) (4f) IC50 [μuM](from multi- or single concentration measurements) Single concentration measurements underlined. (4g) $K_i$ [μM](from multi- or single concentration measurements) Single concentration measurements underlined. (4h) Selectivity vs AmpC (comparison of IC50 values).

Table 5. Structures and $K_i$ values of sulfonamide boronic acids. The carboxamide SM23 is shown as reference.

Table 6. MICs (μg/ml) of third-generation cephalosporins alone and in association with the compounds (ratio 1/4) for clinical bacteria. CTX, cefotaxime and CAZ, ceftazidime. [1], AmpC-overproducing bacteria; [2], CTX-M-14-producing *E. coli*; [3], KPC-2-producing *K. pneumoniae*; [4], OXA-48-producing *K. pneumoniae*; [5], NDM-1-producing *C. freundii*.

Table 7 showing inhibition by select sulfonamide boronic acids.

Table 8 showing inhibition by select sulfonamide boronic acids.

Table 9. Data collection and refinement statistics. One crystal was used for each structure. [a] Values in parentheses represent highest resolution shells. [b] Calculated for both molecules in asymmetric unit.

Table 10. $K_i$ values (M) for AmpC, CTX-M-9 and selected serine proteases.

Table 11. MIC median, 25th and 75th percentile for clinical strains resistant to third-generation cephalosporins.

Table 12. Statistical analysis (p values) of tissue colonization using Student's t-test.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

TABLE 1

Sulfonamide boronic acids

| ID | Structure | $K_i$ (μM) |
| --- | --- | --- |
| 3 | 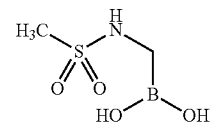 | 0.789 |
| 4 | 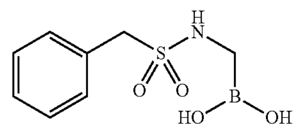 [SMILES: O=S(=O)(Cc1ccccc1)NCB(O)O] | 0.070 |
| 5 | 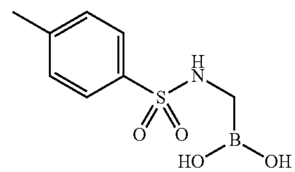 | 0.210 |
| 6 | 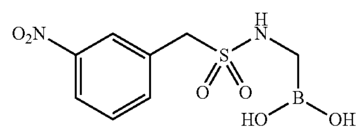 [SMILES: O=[N+]([O-])c1cccc(CS(=O)(=O)NCB(O)O)c1] | 0.189 |
| 7 | 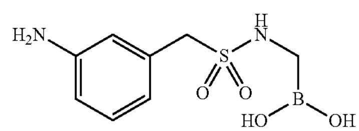 | 0.106 |
| 8 | 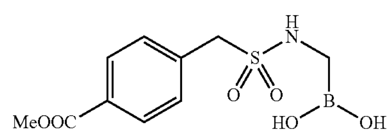 [SMILES: COC(=O)c1ccc(CS(=O)(=O)NCB(O)O)cc1] | 0.120 |
| 9 | 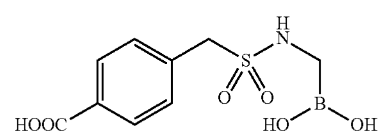 [SMILES: O=C(O)c1ccc(CS(=O)(=O)NCB(O)O)cc1] | 0.025 |
| 10 | 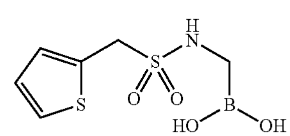 [SMILES: O=S(=O)(Cc1cccs1)NCB(O)O] | N.A.[#] |
| 11 | 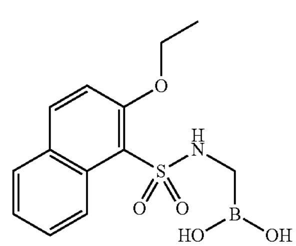 [SMILES: CCOc1ccc2ccccc2c1S(=O)(=O)NCB(O)O] | 0.670 |

TABLE 1-continued

| ID | Structure* | $K_i$ (μM) |
|---|---|---|
| 16 | [benzyl-sulfonamide with CH2-phenyl and B(OH)2] | 3.723 |
| 17 | [benzyl-sulfonamide with CH2-(3-COOH-phenyl) and B(OH)2] | 0.430 |
| 18 | [benzyl-sulfonamide with CH-(3-COOH-phenyl) and B(OH)2] | N.A.# |

| Carboxamide boronic acids | | |
|---|---|---|
| ID | Structure* | $K_i$ (μM) |
| 3c | [H3C-C(O)-NH-CH2-B(OH)2] | 18.5 |
| 4c | [phenyl-CH2-C(O)-NH-CH2-B(OH)2] | 0.570 |
| 10c | [thiophene-CH2-C(O)-NH-CH2-B(OH)2] | 0.320 |
| 11c | [2-ethoxy-naphthalene-C(O)-NH-CH2-B(OH)2] | 0.033 |
| 17c‡ | [thiophene-CH2-C(O)-NH-CH(CH2-3-COOH-phenyl)-B(OH)2] | 0.039 |
| 18c‡ | [thiophene-CH2-C(O)-NH-CH(3-COOH-phenyl)-B(OH)2] | 0.001 |

TABLE 2

| | AmpC/4 | AmpC/9 | AmpC/17 |
|---|---|---|---|
| PDB ID | 3O86 | 3O87 | 3O88 |
| Data collection | | | |
| Space group | C2 | C2 | C2 |
| Cell dimensions | | | |
| a, b, c (Å) | 118.34, 76.88, 97.76 | 118.13, 76.19, 97.38 | 118.03, 77.39, 97.41 |
| α, β, γ (°) | 90.00, 116.11, 90.00 | 90.00, 116.16, 90.00 | 90.00, 115.90, 90.00 |
| Resolution (Å) | 30-1.60 (1.69-1.60)$^a$ | 40-1.78 (1.88-1.78)$^a$ | 30-1.64 (1.72-1.64)$^a$ |
| $R_{merge}$ (%) | 4.5 (44.0)$^a$ | 5.8 (45.5)$^a$ | 4.4 (44.8)$^a$ |
| Completeness (%) | 99.0 (98.6)$^a$ | 97.5 (95.7)$^a$ | 98.5 (99.5)$^a$ |
| I/σI | 16.4 (3.1)$^a$ | 12.6 (2.7)$^a$ | 15.3 (2.6)$^a$ |
| Redundancy | 3.85 (3.81)$^a$ | 2.95 (2.95)$^a$ | 3.05 (3.05)$^a$ |
| Refinement | | | |
| Resolution (Å) | 29.58-1.60 | 38.43-1.78 | 29.54-1.64 |
| No. reflections | 102732 | 72662 | 95179 |
| $R_{work}/R_{free}$ (%) | 16.7/19.3 | 18.8/23.2 | 18.1/21.0 |
| No. atoms | | | |
| Protein$^b$ | 5540 | 5448 | 5595 |
| Ligand$^b$ | 30 | 36 | 50 |
| Water | 819 | 519 | 744 |
| B-factors (Å$^2$) | | | |
| Protein$^b$ | 20.97 | 22.31 | 24.59 |
| Ligand$^b$ | 26.41 | 26.32 | 32.02 |
| Water | 33.62 | 31.03 | 35.15 |

TABLE 2-continued

|  | AmpC/4 | AmpC/9 | AmpC/17 |
|---|---|---|---|
| R.m.s. deviations |  |  |  |
| bond lengths (Å) | 0.010 | 0.011 | 0.011 |
| bond angles (°) | 1.323 | 1.355 | 1.374 |

TABLE 3

|  | Ceftazidime (µg/mL) | Ceftazidime Compound 4 (µg/mL) | Ceftazidime Compound 9 (µg/mL) | Cefotaxime (µg/mL) | Cefotaxime Compound 4 (µg/mL) | Cefotaxime Compound 9 (µg/mL) |
|---|---|---|---|---|---|---|
| E. coli[a] | 64 | 4 | 8 | 8 | 1 | 2 |
| E. cloacae[a] | 64 | 4 | 4 | 64 | 4 | 8 |
| C. freundii[a] | 64 | 4 | 4 | 16 | 2 | 4 |
| P. aeruginosa[a] | 32 | 4 | 8 | >128 | 16 | 32 |
| K. pneumoniae[b] | 32 | 8 | 4 | 8 | 4 | 2 |
| E. coli[c] | 2 | 2 | 1 | 256 | 16 | 8 |

TABLE 4

Table 4a

| Enzyme | $IC_{50}$ (µM) for 4 | $IC_{50}$ (µM) for 9 |
|---|---|---|
| AmpC | 0.38 | 0.13 |
| CTX-M-9 | 6.87 | 1.50 |
| α-Chymotrypsin | >500[a] | >500[a] |
| Cruzain | >500[a] | >500[a] |

Table 4b: Percentage activity with 100 µM inhibitor

|  | CR70 | CR157 | CR161 | CR167 | CR190 | CR191 | CR192 |
|---|---|---|---|---|---|---|---|
| Trypsin | 97 | 95 | 95 | 95 | 95 | 95 | 96 |
| Elastase | 10 | 66 | 63 | 59 | 33 | 50 | 12 |
| Chymotrypsin | 90 | 90 | 90 | 99 | 85 | 85 | 85 |

Table 4c: Percentage inhibtion with 100 µM inhibitor

|  | CR70 | CR157 | CR161 | CR167 | CR190 | CR191 | CR192 |
|---|---|---|---|---|---|---|---|
| Trypsin | 3 | 5 | 5 | 5 | 5 | 5 | 4 |
| Elastase | 90 | 34 | 37 | 41 | 67 | 50 | 88 |
| Chymotrypsin | 10 | 10 | 10 | 1 | 15 | 15 | 15 |

Table 4d: Percentage inhibtion with 16 µM inhibitor

|  | CR70 | CR157 | CR161 | CR167 | CR190 | CR191 | CR192 |
|---|---|---|---|---|---|---|---|
| CTX-M-9 | 50 | 73 | 66 | 99 | 81 | 70 | 77 |

Table 4e: IC50 [µM] (Estimated from single concentration measurement)

|  | CR70 | CR157 | CR161 | CR167 | CR190 | CR191 | CR192 |
|---|---|---|---|---|---|---|---|
| Trypsin | 3233 | 1900 | 1900 | 1900 | 1900 | 1900 | 2400 |
| Elastase | 11 | 194 | 170 | 144 | 49 | 100 | 14 |
| Chymotrypsin | 900 | 900 | 900 | 9900 | 567 | 567 | 567 |
| CTX-M-9 | 16 | 6 | 8 | 0.162 | 4 | 7 | 5 |

Table 4f: IC50 [µM] (from multi- or single concentration measurements)

|  | CR70 | CR157 | CR161 | CR167 | CR190 | CR191 | CR192 |
|---|---|---|---|---|---|---|---|
| CTX-M-9 | 16 | 10.5 | 6.7 | 0.125 | 4 | 7 | 5 |
| AmpC | 1.55 | 0.0062 | 0.0066 | 0.0065 | 0.0016 | 0.0016 | 0.0004 |

TABLE 4-continued

Table 4g: Ki [μM] (from multi- or single concentration measurements)

|  | CR70 | CR157 | CR161 | CR167 | CR190 | CR191 | CR192 |
|---|---|---|---|---|---|---|---|
| CTX-M-9 | <u>5.9</u> | 2.5 | 3.9 | 0.045 | <u>1.4</u> | <u>2.5</u> | <u>1.8</u> |
| AmpC | 0.3 | 0.0012 | 0.0008 | 0.0013 | 0.0002 | 0.003 | 0.00005 |

$$IC50 = [I]^* \quad \frac{100-}{\%(inhibition)/\%(inhibition)} \quad Ki = \frac{IC50}{1+[S]/Km}$$

Table 4h: Selectivity vs AmpC (comparison of IC50 values)

|  | CR70 | CR157 | CR161 | CR167 | CR190 | CR191 | CR192 |
|---|---|---|---|---|---|---|---|
| Trypsin | 2086 | 306452 | 287879 | 292308 | 1187500 | 1187500 | 6000000 |
| Elastase | 7 | 31309 | 25799 | 22139 | 30784 | 62500 | 34091 |
| Chymotrypsin | 581 | 145161 | 136364 | 1523077 | 354167 | 354167 | 1416667 |
| CTX-M-9 | 10 | 1694 | 1015 | 19 | 2346 | 4286 | 11948 |
| AmpC | 1 | 1 | 1 | 1 | 1 | 1 | 1 |

TABLE 5

| ID | Structure | $K_i$ (nM) | Ligand efficiency |
|---|---|---|---|
| SM23 | [structure] | 1.0 | 0.55 |
| CR23 (4) | [structure] | 70 | 0.64 |
| CR107 (9) | [structure] | 25 | 0.57 |
| CR167 | [structure] | 1.3 | 0.66 |
| CR157 | [structure] | 1.2 | 0.63 |

TABLE 5-continued

| ID | Structure | $K_i$ (nM) | Ligand efficiency |
|---|---|---|---|
| CR161 | 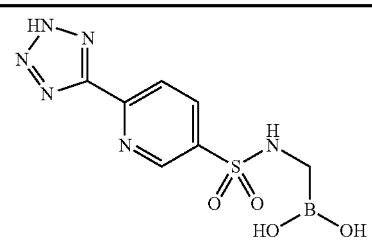 | 0.8 | 0.64 |
| CR190 | 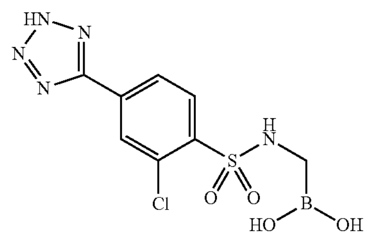 [SMILES: O=S(=O)(NCB(O)O)c1ccc(-c2nn[nH]n2)cc1Cl] | 0.2 | 0.65 |
| CR191 | 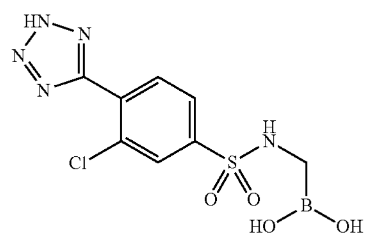 [SMILES: O=S(=O)(NCB(O)O)c1ccc(-c2nn[nH]n2)c(Cl)c1] | 3.0 | 0.57 |
| CR192 | 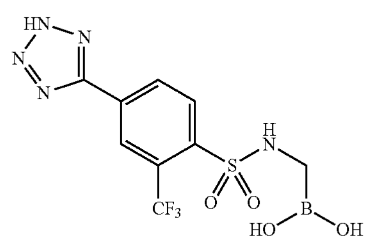 | 0.05 | 0.60 |

TABLE 6

| | CAZ | CR157 | CR161 | CR167 | CR190 | CR191 | CR192 |
|---|---|---|---|---|---|---|---|
| E. coli[1] | 128 | 4 | 0.5 | 1 | 0.5 | 1 | 1 |
| E. coli 145[1] | 128 | 4 | 1 | 2 | 1 | 2 | 1 |
| E. coli 146[1] | 64 | 2 | 0.5 | 1 | 0.5 | 0.5 | 1 |
| E. coli 144[1] | 64 | 2 | 1 | 1 | 1 | 2 | 1 |
| E. coli 142[1] | 32 | 1 | 0.5 | 1 | 0.5 | 1 | 1 |
| E. coli R1[1] | 8 | 1 | 0.5 | 0.5 | 0.5 | 0.5 | 1 |
| E. cloacae[1] | 64 | 2 | 0.5 | 1 | 1 | 4 | 2 |
| E. cloacae 135[1] | 128 | 4 | 4 | 4 | 1 | 2 | 2 |
| C. freundii[1] | 64 | 2 | 0.5 | 1 | 1 | 1 | 2 |
| C. freundii 101[1] | 128 | 4 | 2 | 1 | 2 | 2 | 2 |
| P. aeruginosa[1] | 32 | 2 | 2 | 2 | 2 | 4 | 2 |
| K. pneumoniae[1] | 32 | 2 | 0.5 | 1 | 1 | 4 | 2 |
| E. coli[2] | 2 | 2 | 1 | 0.25 | 2 | 4 | 4 |
| K. pneumoniae[3] | 512 | 32 | 16 | 4 | — | — | — |
| K. pneumoniae[4] | 256 | 32 | 16 | 16 | — | — | — |
| C. freundii[5] | 512 | 512 | 512 | 512 | — | — | — |

| | CTX | CR157 | CR161 | CR167 | CR190 | CR191 | CR192 |
|---|---|---|---|---|---|---|---|
| E. coli[1] | 8 | 2 | 0.25 | 0.5 | 0.5 | 1 | 1 |
| E. coli 145[1] | 16 | 2 | 0.5 | 0.5 | 0.5 | 2 | 1 |
| E. coli 146[1] | 8 | 1 | 0.5 | 0.5 | 0.25 | 0.5 | 0.5 |

TABLE 6-continued
| | | | | | | | |
|---|---|---|---|---|---|---|---|
| E. coli 144[1] | 16 | 2 | 0.5 | 1 | 0.5 | 1 | 0.5 |
| E. coli 142[1] | 4 | 1 | 0.5 | 0.5 | 0.5 | 2 | 1 |
| E. coli R1[1] | 4 | 1 | 0.5 | 0.25 | 0.25 | 0.5 | 1 |
| E. cloacae[1] | 64 | 4 | 1 | 1 | 1 | 2 | 1 |
| E. cloacae 135[1] | 128 | 4 | 4 | 4 | 2 | 4 | 2 |
| C. freundii[1] | 16 | 1 | 0.5 | 0.5 | 1 | 2 | 1 |
| C. freundii 101[1] | 64 | 2 | 1 | 1 | 2 | 4 | 2 |
| P. aeruginosa[1] | >128 | 16 | 8 | 8 | 16 | 16 | 16 |
| K. pneumoniae[1] | 8 | 2 | 0.5 | 1 | 4 | 4 | 8 |
| E. coli[2] | 256 | 16 | 32 | 4 | 8 | 8 | 16 |
| K. pneumoniae[3] | 512 | 4 | 4 | 0.5 | — | — | — |
| K. pneumoniae[4] | 256 | 32 | 16 | 16 | — | — | — |
| C. freundii[5] | 512 | 512 | 512 | 512 | — | — | — |
TABLE 7
| Compound | Structure | $K_i$ (μM) Vs AmpC |
|---|---|---|
| FP100707 | 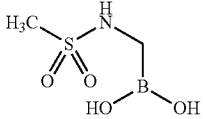 | 0.789 |
| CR23 | 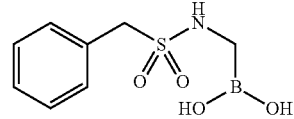 | 0.070 |
| CR20 | 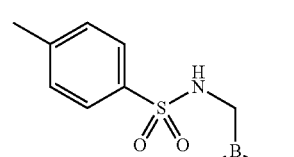 | 0.210 |
| CR104 | 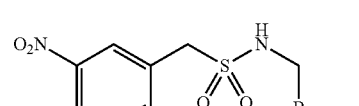 | 0.189 |
| CR106 | 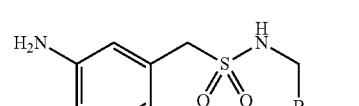 | 0.106 |
| CR105 | 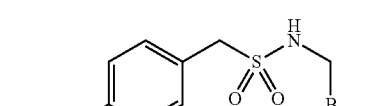 | 0.120 |
| CR107 | 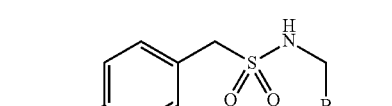 | 0.025 |
| | 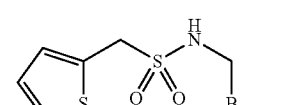 | |
TABLE 7-continued
| Compound | Structure | $K_i$ (μM) Vs AmpC |
|---|---|---|
| CR57 | 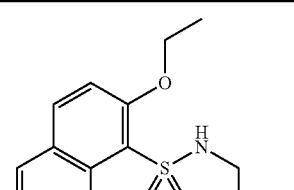 | 0.670 |
| ECS06 | 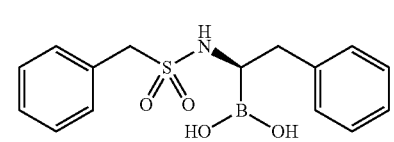 [SMILES: O=S(=O)(Cc1ccccc1)N[C@@H](Cc1ccccc1)B(O)O] | 3.723 |
| CR100 | 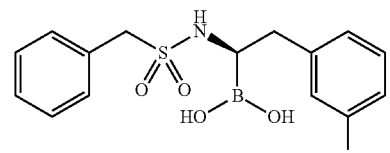 | 0.430 |
| | 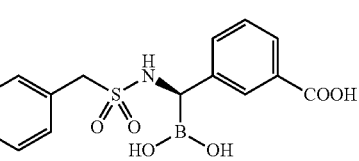 | |
| CR14 | 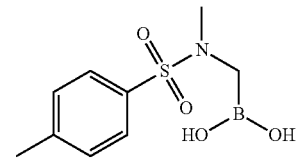 [SMILES: Cc1ccc(S(=O)(=O)N(C)CB(O)O)cc1] | 0.630 |
| CR17 | 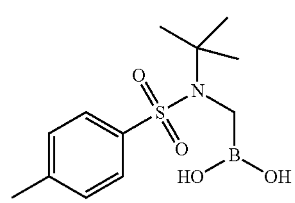 [SMILES: Cc1ccc(S(=O)(=O)N(CB(O)O)C(C)(C)C)cc1] | 2.5 |

TABLE 7-continued

| Compound | Structure | $K_i$ (μM) Vs AmpC |
|---|---|---|
| CR22 | | 5.1 |
| CR70 | | 0.310 |
| GBS22 | | 0.100 |
| | | |
| | | |
| | | |
| CR73 | | |
| CR75 | | |
| CR141 | | |

TABLE 7-continued

| Compound | Structure | $K_i$ (μM) Vs AmpC |
|---|---|---|
| CR135 | 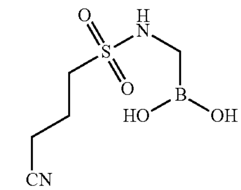 [SMILES: N#CCCCS(=O)(=O)NCB(O)O] | 0.200 |
| CR162 | 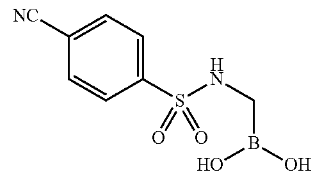 [SMILES: N#Cc1ccc(S(=O)(=O)NCB(O)O)cc1] | 0.310 |
| CR163 | 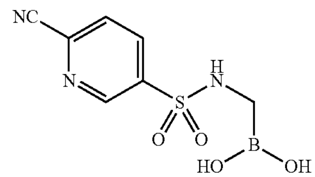 [SMILES: N#Cc1ccc(S(=O)(=O)NCB(O)O)cn1] | 0.270 |
| CR157 | 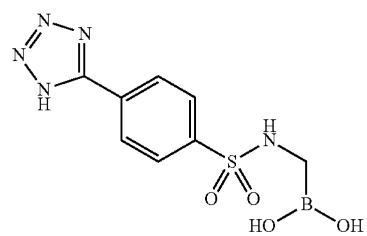 [SMILES: O=S(=O)(NCB(O)O)c1ccc(-c2nnn[nH]2)cc1] | 0.0012 |
| CR161 | 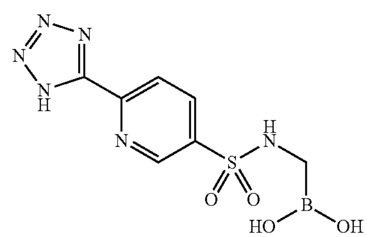 [SMILES: O=S(=O)(NCB(O)O)c1ccc(-c2nnn[nH]2)nc1] | 0.0008 |
| CR190 | 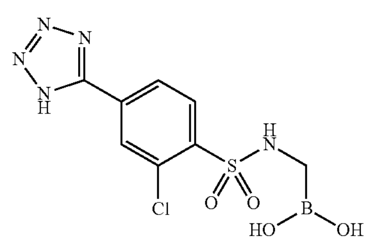 [SMILES: O=S(=O)(NCB(O)O)c1ccc(-c2nnn[nH]2)cc1Cl] | 0.0002 |
| CR191 | 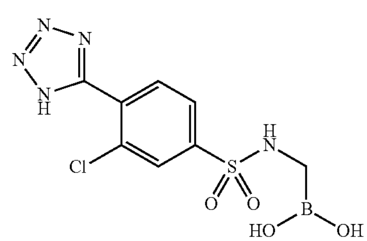 [SMILES: O=S(=O)(NCB(O)O)c1ccc(-c2nnn[nH]2)c(Cl)c1] | 0.003 |

TABLE 7-continued

| Compound | Structure | $K_i$ (μM) Vs AmpC |
|---|---|---|
| CR192 | 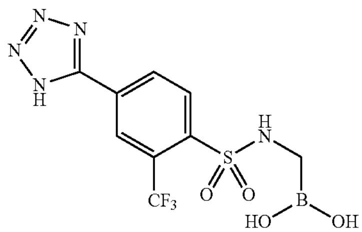 [SMILES: O=S(=O)(NCB(O)O)c1ccc(-c2nnn[nH]2)cc1C(F)(F)F] | 0.00005 |
| CR167 | 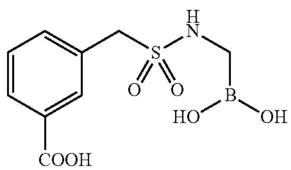 [SMILES: O=C(O)c1cccc(CS(=O)(=O)NCB(O)O)c1] | 0.0013 |
| GBS32 | 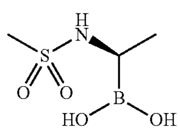 | 0.650 |
| GBS34 | 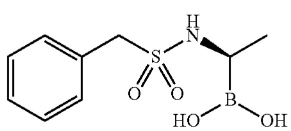 [SMILES: C[C@H](NS(=O)(=O)Cc1ccccc1)B(O)O] | 0.310 |
| CR175 | 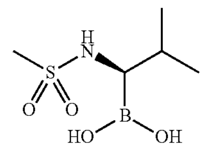 | 100.0 |
| CR173 | 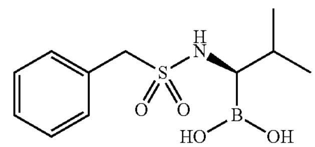 [SMILES: CC(C)[C@H](NS(=O)(=O)Cc1ccccc1)B(O)O] | 13.0 |
| CR181 | 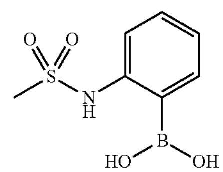 | 0.400 |
| CR180 | 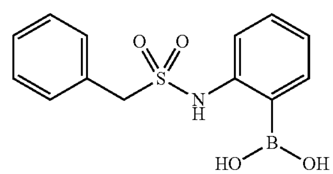 [SMILES: O=S(=O)(Cc1ccccc1)Nc1ccccc1B(O)O] | 0.200 |
| CR88 | 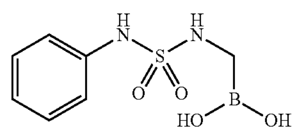 [SMILES: O=S(=O)(NCB(O)O)Nc1ccccc1] | |

TABLE 8

| ID | Structure | $K_i$ vs AmpC (nM) | $K_i$ vs CTX-M-9 (nM) |
|---|---|---|---|
| FP100707 | 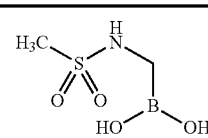 | 800 | n.d. |
| CR70 | 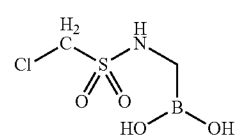 | 310 | 5900 |
| CR23 | 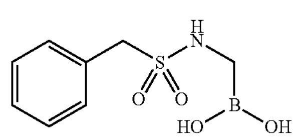 [SMILES: O=S(=O)(Cc1ccccc1)NCB(O)O] | 70 | 2500 |
| CR107 | 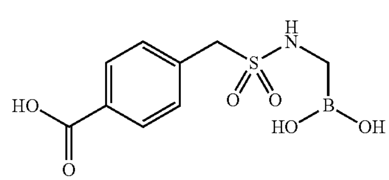 [SMILES: O=C(O)c1ccc(CS(=O)(=O)NCB(O)O)cc1] | 25 | 550 |

TABLE 8-continued

| ID | Structure | K_i vs AmpC (nM) | K_i vs CTX-M-9 (nM) |
|---|---|---|---|
| CR167 | (3-carboxybenzyl sulfonamide methylboronic acid) | 1.3 | 45 |
| CR20 | (4-methylphenyl sulfonamide methylboronic acid) | 210 | n.d. |
| CR162 | (4-cyanophenyl sulfonamide methylboronic acid) | 310 | n.d. |
| CR163 | (6-cyanopyridin-3-yl sulfonamide methylboronic acid) | 270 | n.d. |
| CR157 | (4-(tetrazol-5-yl)phenyl sulfonamide methylboronic acid) | 1.2 | 2500 |
| CR161 | (6-(tetrazol-5-yl)pyridin-3-yl sulfonamide methylboronic acid) | 0.8 | 3900 |
| CR190 | (2-chloro-4-(tetrazol-5-yl)phenyl sulfonamide methylboronic acid) | 0.2 | 1400 |

TABLE 8-continued

| ID | Structure | $K_i$ vs AmpC (nM) | $K_i$ vs CTX-M-9 (nM) |
|---|---|---|---|
| CR191 | 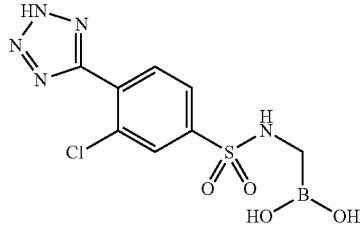 [SMILES: O=S(=O)(NCB(O)O)c1ccc(-c2nn[nH]n2)c(Cl)c1] | 3.0 | 2500 |
| CR192 | 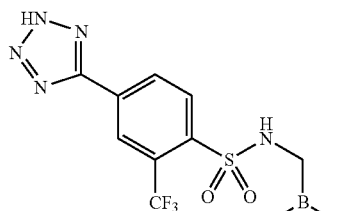 | 0.05 | 1800 |

TABLE 9

Data collection and refinement statistics.

|  | AmpC/CR167 | AmpC/CR157 | AmpC/CR161 | AmpC/CR191 | AmpC/CR190 | AmpC/CR192 | AmpC/CR70 |
|---|---|---|---|---|---|---|---|
| PDB code | 4E3I | 4E3J | 4E3K | 4E3L | 4E3M | 4E3N | 4E3O |
| Data collection |  |  |  |  |  |  |  |
| Space group | C2 | C2 | C2 | C2 | C2 | C2 | C2 |
| Cell dimensions |  |  |  |  |  |  |  |
| a, b, c (Å) | 118.46, 77.14, 97.75 | 118.44, 76.54, 97.74 | 119.12, 76.82, 97.84 | 117.65, 77.22, 97.69 | 118.12, 76.92, 97.60 | 118.16, 76.73, 97.90 | 118.54, 76.74, 97.88 |
| α, β, χ (°) | 90.00, 116.67, 90.00 | 90.00, 116.88, 90.00 | 90.00, 116.25, 90.00 | 90.00, 116.42, 90.00 | 90.00, 116.37, 90.00 | 90.00, 116.58, 90.00 | 90.00, 116.60, 90.00 |
| Resolution (Å) | 30-1.60 (1.64-1.60)[a] | 30-1.80 (1.85-1.80)[a] | 30-1.43 (1.47-1.43)[a] | 30-1.43 (1.47-1.43)[a] | 30-1.44 (1.48-1.44)[a] | 30-1.49 (1.53-1.49r | 30-1.60 (1.69-1.60r |
| $R_{merge}$ (%) | 3.8 (54.0)[a] | 5.8 (41.4)[a] | 3.6 (44.5)[a] | 4.2 (67.8)[a] | 3.1 (53.7)[a] | 4.0 (66.6)[a] | 4.0 (50.3)[a] |
| Completeness (%) | 94.4 (93.4)[a] | 95.3 (90.6)[a] | 95.3 (90.6)[a] | 97.6 (96.3)[a] | 96.6 (95.3)[a] | 99.6 (99.7)[a] | 99.2 (99.7)[a] |
| I/σ| | 14.7 (2.0)[a] | 11.9 (2.0)[a] | 15.2 (2.0)[a] | 16.5 (2.1)[a] | 18.8 (2.0)[a] | 18.1 (2.1)[a] | 16.4 (2.4)[a] |
| Redundancy | 2.6 (2.6)[a] | 2.8 (2.3)[a] | 2.8 (2.2)[a] | 4.1 (4.1)[a] | 2.7 (2.6)[a] | 4.0 (3.9)[a] | 3.3 (3.2)[a] |
| Refinement |  |  |  |  |  |  |  |
| Resolution (Å) | 29.6-1.60 | 29.5-1.80 | 29.6-1.43 | 29.6-1.43 | 29.5-1.44 | 29.6-1.49 | 29.6-1.60 |
| No. of reflections (test set) | 98110 (3603) | 68932 (2559) | 139944 (5339) | 141064 (5308) | 136573 (5177) | 127104 (4760) | 102678 (3799) |
| $R_{work}/R_{free}$ (%) | 16.4/18.9 | 17.6/22.1 | 16.6/19.9 | 15.9/18.5 | 16.1/19.3 | 15.4/18.8 | 16.1/18.6 |
| No. atoms |  |  |  |  |  |  |  |
| Protein[b] | 5642 | 5472 | 5580 | 5602 | 5606 | 5620 | 5556 |
| Ligand[b] | 36 | 38 | 38 | 60 | 60 | 46 | 20 |
| Water | 633 | 446 | 719 | 589 | 577 | 549 | 691 |
| B-factors (Å$^2$) |  |  |  |  |  |  |  |
| Protein[b] | 24.1 | 23.8 | 21.2 | 20.0 | 20.3 | 21.0 | 23.6 |
| Ligand[b] | 23.8 | 23.3 | 24.0 | 23.1 | 21.5 | 20.8 | 35.4 |
| Water | 34.6 | 32.5 | 33.9 | 30.9 | 29.4 | 31.4 | 35.9 |
| R.m.s. deviations |  |  |  |  |  |  |  |
| bond lengths (Å) | 0.010 | 0.010 | 0.011 | 0.010 | 0.010 | 0.010 | 0.011 |
| bond angles (°) | 1.3 | 1.3 | 1.3 | 1.3 | 1.3 | 1.4 | 1.4 |

One crystal was used for each structure.
[a]Values in parentheses represent highest resolution shells.
[b]Calculated for both molecules in asymmetric unit.

TABLE 10

$K_i$ values (μM) for AmpC, CTX-M-9 and selected serine proteases.

| Targets | $K_i$ values (μM) | | | | | |
|---|---|---|---|---|---|---|
| | CR167 | CR157 | CR161 | CR190 | CR191 | CR192 |
| AmpC | 0.0013 | 0.0012 | 0.0008 | 0.0002 | 0.003 | 0.00005 |
| CTX-M-9 | 0.045 | 2.5 | 3.9 | 1.4 | 2.5 | 1.8 |
| Trypsin | 350 | 350 | 350 | 350 | 350 | 442 |
| Elastase | 136 | 183 | 161 | 47 | 95 | 13 |
| α-Chymotrypsin | 2463 | 224 | 224 | 141 | 141 | 141 |

TABLE 11

MIC median, 25th and 75th percentile for clinical strains resistant to third-generation cephalosporins.

| | MICs (μg/mL) of third-generation cephalosporins alone or in combination | | | | | | |
|---|---|---|---|---|---|---|---|
| | Alone | CR157 | CR161 | CR167 | CR190 | CR191 | CR192 |
| MIC 25% percentile | 12 | 1.5 | 0.5 | 0.5 | 0.5 | 1.0 | 1.0 |
| MIC median | 64 | 2.0 | 0.5 | 1.0 | 1.0 | 2.0 | 1.0 |
| MIC 75% percentile | 128 | 4.0 | 1.5 | 1.5 | 2.0 | 4.0 | 2.0 |

TABLE 12

Statistical analysis (p values) of tissue colonization using Student's t-test.

| | 6 h | | | | 12 h | | | | 24 h | |
|---|---|---|---|---|---|---|---|---|---|---|
| | Saline solution | Imipenem | CTX | CTX + I | Saline solution | Imipenem | CTX | CTX + I | | CTX + I |
| Blood | | | | | | | | | | |
| Saline solution | — | 0.0002 | 0.203 | 0.0009 | Saline solution | — | <0.0001 | 0.0062 | <0.0001 | Imipenem | 0.0056 |
| Imipenem | 0.0002 | — | 0.0003 | 0.0016 | Imipenem | <0.0001 | — | 0.0001 | 0.0702 | | |
| CTX | 0.203 | 0.0003 | — | <0.0001 | CTX | 0.0062 | 0.0001 | — | 0.0001 | | |
| Spleen | | | | | | | | | | |
| Saline solution | — | 0.0036 | 0.0454 | 0.007 | Saline solution | — | 0.0004 | 0.0026 | 0.0003 | Imipenem | 0.854 |
| Imipenem | 0.0036 | — | <0.0001 | 0.356 | Imipenem | 0.0004 | — | 0.0001 | 0.9048 | | |
| CTX | 0.0454 | <0.0001 | — | 0.003 | CTX | 0.0026 | 0.0001 | — | <0.0001 | | |
| Liver | | | | | | | | | | |
| Saline solution | — | <0.0001 | 0.515 | 0.0044 | Saline solution | — | <0.0001 | 0.0013 | <0.0001 | Imipenem | 1 |
| Imipenem | <0.0001 | — | <0.0001 | 0.0021 | Imipenem | <0.0001 | — | 0.0001 | 0.327 | | |
| CTX | 0.515 | <0.0001 | — | 0.0007 | CTX | 0.0013 | 0.0001 | — | <0.0001 | | |
| Kidney | | | | | | | | | | |
| Saline solution | — | 0.0008 | 0.0079 | 0.0029 | Saline solution | — | <0.0001 | 0.0033 | <0.0001 | Imipenem | 0.244 |
| Imipenem | 0.0008 | — | <0.0001 | 0.0133 | Imipenem | <0.0001 | — | 0.0001 | 0.905 | | |
| CTX | 0.0079 | <0.0001 | — | 0.0001 | CTX | 0.0033 | 0.0001 | — | <0.0001 | | |
| Lung | | | | | | | | | | |
| Saline solution | ND | 0.001 | 0.237 | 0.0155 | Saline solution | ND | <0.0001 | 0.0276 | <0.0001 | Imipenem | 0.364 |
| Imipenem | 0.001 | ND | <0.0001 | 0.0172 | Imipenem | <0.0001 | ND | 0.0001 | 0.72 | | |
| CTX | 0.237 | <0.0001 | ND | 0.0068 | CTX | 0.0276 | 0.0001 | ND | <0.0001 | | |

Legend:
CTX: Cefotaxime
I: Inhibitor CR161

TABLE 13

Amide compound substituents that will be combined with a sulfonamide scaffold.

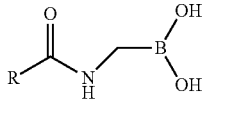

| compound | β-lactam analog | side chain | $K_i$ (μM) vs AmpC |
|---|---|---|---|
| | penicillin G | 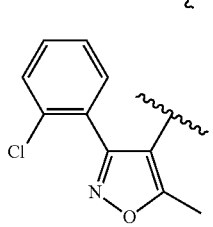 | 0.57 |
| | cloxacillin | 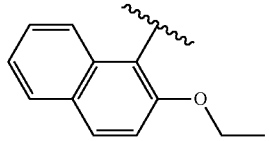 [SMILES: *c1c(OCC)ccc2ccccc12] | 0.150 |
| | nafcillin | 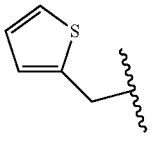 [SMILES: *Cc1cccs1] | 0.033 |
| | cephalothin | 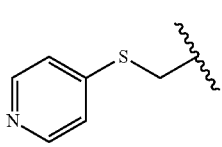 [SMILES: *CSc1ccncc1] | 0.32 |
| | — | —CH$_2$Cl | 0.24 |
| | cephapirin | 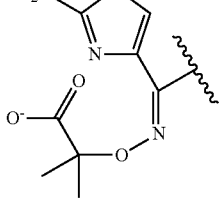 | 0.175 |
| | ceftazidime | 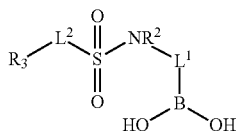 | 0.020 |

What is claimed is:

1. A compound of the formula:

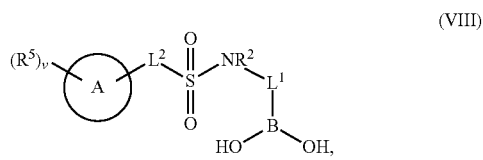

(I)

wherein, $L^1$ is unsubstituted alkylene;

$L^2$ is a bond, substituted or unsubstituted alkylene or substituted or unsubstituted heteroalkylene;

$R^2$ is hydrogen or substituted or unsubstituted $C_1$-$C_5$ alkyl;

$R^3$ is substituted or unsubstituted aryl.

2. The compound of claim 1, of the formula:

(VIII)

$$(R^5)_v - A - L^2 - \underset{\underset{O}{\|}}{\overset{\underset{O}{\|}}{S}} - NR^2 - L^1 - B(OH)(OH)$$

wherein ring A is, substituted or unsubstituted aryl;

$R^5$ is independently hydrogen, halogen, $CX^a{}_3$, —CN, —SO$_2$Cl, —SO$_p$R$^{14}$, —SO$_q$NR$^{11}$R$^{12}$, —NHNH$_2$, —ONR$^{11}$R$^{12}$, —NHC=(O)NHNH$_2$, —NHC=(O)NR$^{11}$R$^{12}$, —N(O)$_r$, —NR$^{11}$R$^{12}$, —C(O)R$^{13}$, —C(O)—OR$^{13}$, —C(O)NR$^{11}$R$^{12}$, —OR$^{14}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

wherein two adjacent $R^5$ substituents are optionally joined to form a substituted or unsubstituted cycloalkyl, substituted or unsubstituted heterocycloalkyl, substituted or unsubstituted aryl, or substituted or unsubstituted heteroaryl;

v is an integer from 0 to 7;

$R^{11}$, $R^{12}$, $R^{13}$, and $R^{14}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

q and r are independently 1 or 2;

p is independently an integer from 0 to 4;

$X^a$ is —Cl, —Br, —I, or —F.

3. The compound of claim 1, having the formula:

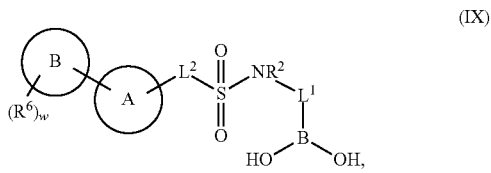

(IX)

wherein ring A is substituted or unsubstituted arylene;

wherein ring B are independently substituted or unsubstituted cycloalkyl, substituted or unsubstituted heterocycloalkyl, substituted or unsubstituted aryl, or substituted or unsubstituted heteroaryl;

$R^6$ is independently hydrogen, halogen, —CX$^a{}_3$, —CN, —SO$_2$Cl, —SO$_{p1}$R$^{18}$, —SO$_{q1}$NR$^{15}$R$^{16}$, —NHNH$_2$, —ONR$^{15}$R$^{16}$, —NHC=(O)NHNH$_2$, —NHC=(O)NR$^{15}$R$^{16}$, —N(O)$_{r1}$, —NR$^{15}$R$^{16}$, —C(O)R$^{17}$, —C(O)—OR$^{17}$, —C(O)NR$^{15}$R$^{16}$, —OR$^{18}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

wherein two adjacent $R^6$ substituents are optionally joined to form a substituted or unsubstituted cycloalkyl, substituted or unsubstituted heterocycloalkyl, substituted or unsubstituted aryl, or substituted or unsubstituted heteroaryl;

$R^{15}$, $R^{16}$, $R^{17}$, and $R^{18}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

q1 and r1 are independently 1 or 2;

p1 is an integer from 0 to 4;

$X^{a1}$ is —Cl, —Br, —I, or —F;

w is an integer from 0 to 7.

4. The compound of claim 1, of the formula:

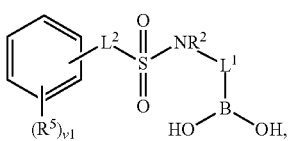

(XI)

wherein, $R^5$ is independently hydrogen, halogen, —$CX^a{}_3$, —CN, —$SO_2Cl$, —$SO_pR^{14}$, —$SO_qNR^{11}R^{12}$, —$NHNH_2$, —$ONR^{11}R^{12}$, —$NHC$=(O)$NHNH_2$, —$NHC$=(O)$NR^{11}R^{12}$, —$N(O)_r$, —$NR^{11}R^{12}$, —$C(O)R^{13}$, —$C(O)$—$OR^{13}$, —$C(O)NR^{11}R^{12}$, —$OR^{14}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

wherein two adjacent $R^5$ substituents are optionally joined to form a substituted or unsubstituted cycloalkyl, substituted or unsubstituted heterocycloalkyl, substituted or unsubstituted aryl, or substituted or unsubstituted heteroaryl;

$R^{11}$, $R^{12}$, $R^{13}$, and $R^{14}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

q and r are independently 1 or 2;

p is independently an integer from 0 to 4;

$X^a$ is —Cl, —Br, —I, or —F;

v1 is an integer from 0 to 5.

5. The compound of claim 1, having the formula:

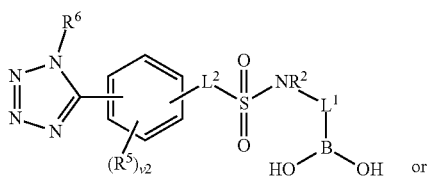

(XIII)

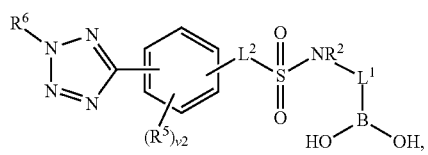

(XIV)

wherein, $R^5$ is independently hydrogen, halogen, —$CX^a{}_3$, —CN, —$SO_2Cl$, —$SO_pR^{14}$, —$SO_qNR^{11}R^{12}$, —$NHNH_2$, —$ONR^{11}R^{12}$, —$NHC$=(O)$NHNH_2$, —$NHC$=(O)$NR^{11}R^{12}$, —$N(O)_r$, —$NR^{11}R^{12}$, —$C(O)R^{13}$, —$C(O)$—$OR^{13}$, —$C(O)NR^{11}R^{12}$, —$OR^{14}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

wherein two adjacent $R^5$ substituents are optionally joined to form a substituted or unsubstituted cycloalkyl, substituted or unsubstituted heterocycloalkyl, substituted or unsubstituted aryl, or substituted or unsubstituted heteroaryl;

$R^6$ is independently hydrogen, halogen, —$CX^{a1}{}_3$, —CN, —$C(O)R^{17}$, —$C(O)$—$OR^{17}$, —$C(O)NR^{15}R^{16}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{11}$, $R^{12}$, $R^{13}$, and $R^{14}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

q and r are independently 1 or 2;

p is independently an integer from 0 to 4;

$X^a$ is —Cl, —Br, —I, or —F;

$R^{15}$, $R^{16}$, and $R^{17}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$X^{a1}$ is —Cl, —Br, —I, or —F; and v2 is an integer from 0 to 4.

6. The compound of claim 1, having the formula:

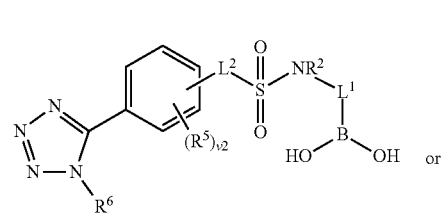

(XVII)

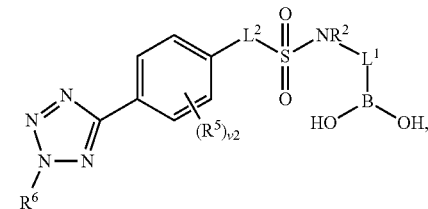

(XVIII)

wherein, $R^5$ is independently hydrogen, halogen, —$CX^a{}_3$, —CN, —$SO_2Cl$, —$SO_pR^{14}$, —$SO_qNR^{11}R^{12}$, —$NHNH_2$, —$ONR^{11}R^{12}$, —$NHC$=(O)$NHNH_2$, —$NHC$=(O)$NR^{11}R^{12}$, —$N(O)_r$, —$NR^{11}R^{12}$, —$C(O)R^{13}$, —$C(O)$—$OR^{13}$, —$C(O)NR^{11}R^{12}$, —$OR^{14}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

wherein two adjacent $R^5$ substituents are optionally joined to form a substituted or unsubstituted cycloalkyl, substituted or unsubstituted heterocycloalkyl, substituted or unsubstituted aryl, or substituted or unsubstituted heteroaryl;

$R^6$ is independently hydrogen, halogen, —$CX^{a1}_3$, —CN, —$C(O)R^{17}$, —$C(O)$—$OR^{17}$, —$C(O)NR^{15}R^{16}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{11}$, $R^{12}$, $R^{13}$, and $R^{14}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

q and r are independently 1 or 2;

p is independently an integer from 0 to 4;

$X^a$ is —Cl, —Br, —I, or —F;

$R^{15}$, $R^{16}$, and $R^{17}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$X^{a1}$ is —Cl, —Br, —I, or —F;

v2 is an integer from 0 to 4.

7. The compound of claim 1, having the formula:

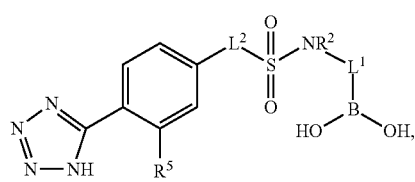
(XXIa)

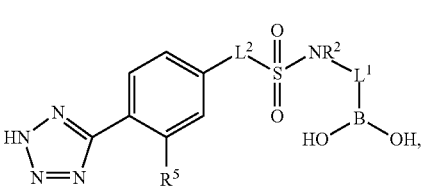
(XXIb)

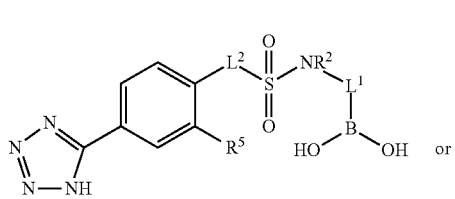
(XXIIIa)

or

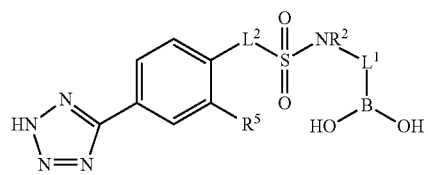
(XXIIIb)

wherein, $R^5$ is independently hydrogen, halogen, —$CX^a_3$, —CN, —$SO_2Cl$, —$SO_pR^{14}$, —$SO_qNR^{11}R^{12}$, —$NHNH_2$, —$ONR^{11}R^{12}$, —$NHC=(O)NHNH_2$, —$NHC=(O)NR^{11}R^{12}$, —$N(O)_r$, —$NR^{11}R^{12}$, —$C(O)R^{13}$, —$C(O)$—$OR^{13}$, —$C(O)NR^{11}R^{12}$, —$OR^{14}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{11}$, $R^{12}$, $R^{13}$, and $R^{14}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

q and r are independently 1 or 2;

p is independently an integer from 0 to 4;

$X^a$ is —Cl, —Br, —I, or —F.

8. The compound of claim 7, wherein $R^5$ is halogen.

9. The compound of claim 7, wherein $R^5$ is —Cl.

10. The compound of claim 7, wherein $R^5$ is —$CF_3$.

11. A compound selected from

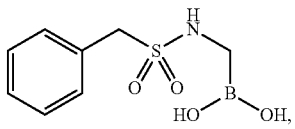

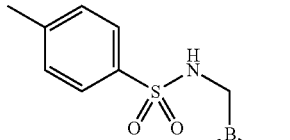

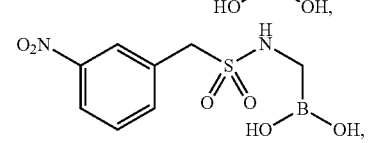

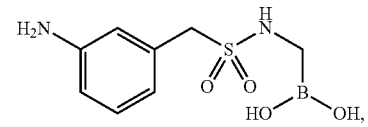

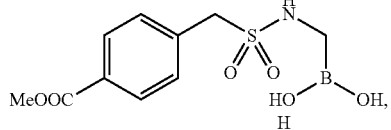

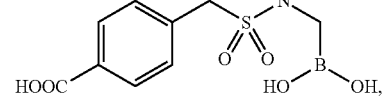

-continued
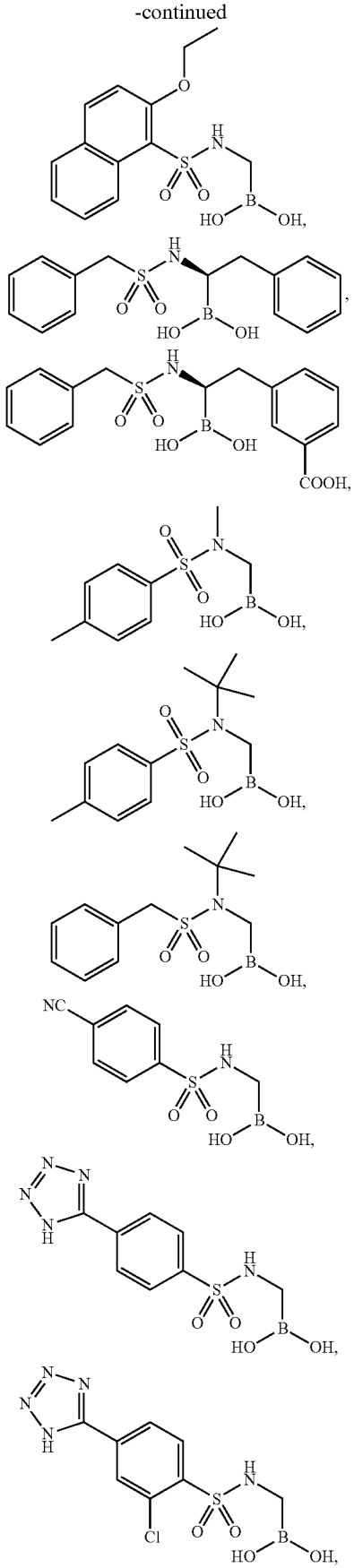
-continued
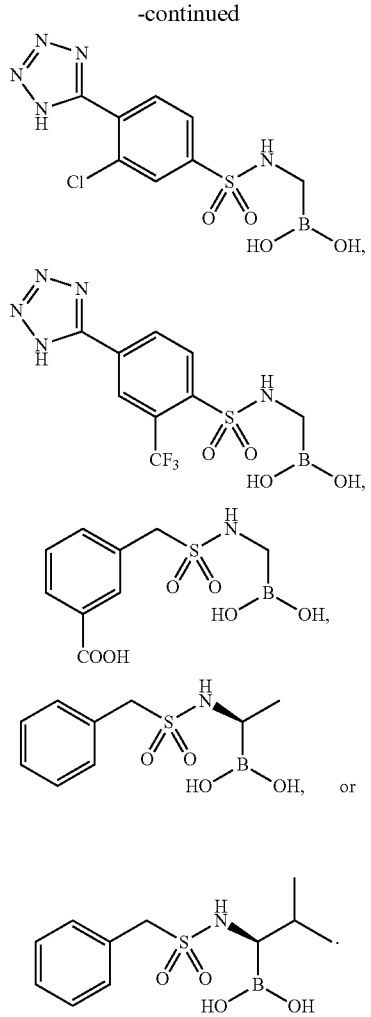
12. A compound selected from
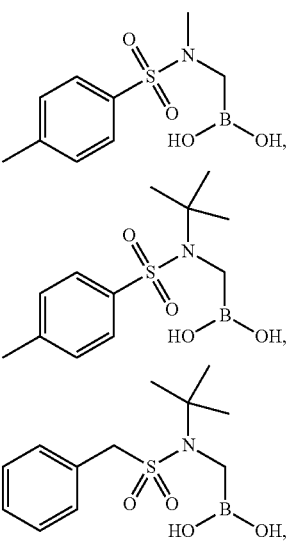

-continued
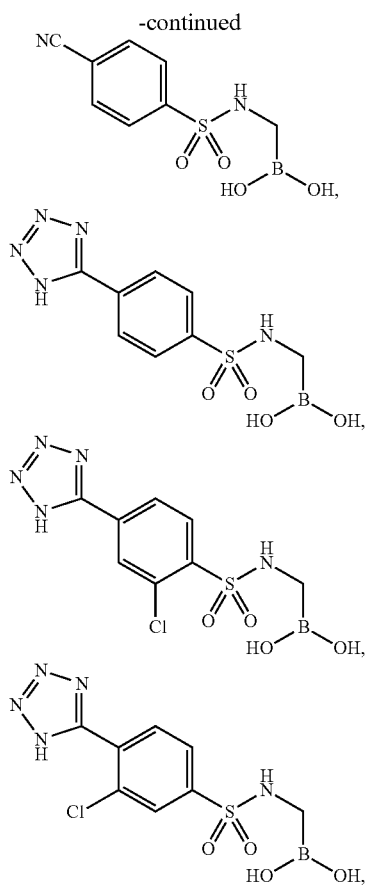
-continued
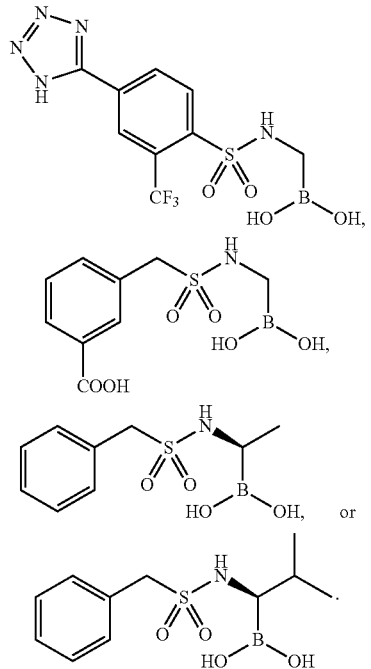
13. A pharmaceutical composition comprising a pharmaceutically acceptable excipient and a compound of claim 1.
* * * * *